United States Patent
Bertin et al.

(10) Patent No.: US 7,034,135 B2
(45) Date of Patent: Apr. 25, 2006

(54) MOLECULES OF THE NBS/LRR PROTEIN FAMILY AND USES THEREOF

(75) Inventors: John Bertin, Watertown, MA (US); Weiye Wang, Plainsboro, NJ (US); Maria Blatcher, Moorestown, NJ (US)

(73) Assignees: Millennium Pharmaceuticals, Inc., Cambridge, MA (US); Wyeth, Madison, NJ (US)

( * ) Notice: Subject to any disclaimer, the term of this patent is extended or adjusted under 35 U.S.C. 154(b) by 536 days.

(21) Appl. No.: 10/116,422

(22) Filed: Apr. 4, 2002

(65) Prior Publication Data

US 2005/0191624 A1     Sep. 1, 2005

Related U.S. Application Data

(63) Continuation-in-part of application No. 09/986,224, filed on Oct. 22, 2001, now abandoned, which is a continuation-in-part of application No. 09/848,035, filed on May 3, 2001, now abandoned.

(60) Provisional application No. 60/201,464, filed on May 3, 2000.

(51) Int. Cl.
  C07H 21/04   (2006.01)
  C07H 21/02   (2006.01)
  C12P 21/06   (2006.01)
  C12P 21/04   (2006.01)

(52) U.S. Cl. .................. 536/23.4; 536/23.1; 536/23.5; 435/69.1; 435/69.7; 435/252.3; 435/320.1

(58) Field of Classification Search ............... 435/69.1, 435/69.7, 252.3, 320, 320.1; 536/23.1, 23.5, 536/23.4
See application file for complete search history.

(56) References Cited

FOREIGN PATENT DOCUMENTS

| | | |
|---|---|---|
| WO | WO 99/09169 | 2/1999 |
| WO | WO 99/58675 | 11/1999 |
| WO | WO 00/58473 | 10/2000 |
| WO | WO 00/61620 | 10/2000 |
| WO | WO 01/42467 A2 | 6/2001 |
| WO | WO 01/61005 A2 | 8/2001 |

OTHER PUBLICATIONS

Birren et al., docment #1.*
Birren et al., document #2.*
DOE Joint Genome Institute and Stanford Human Genome Center, document #3.*
Birren et al., "Human DNA clone RP11-45K21", Mar. 28, 2000, Alignment result 4, SEQ ID No: 18, Database: GenEmbl, Accession No; AC012107, docment #1.*
Birren et al., "Human DNA clone RP11-45K21", Mar. 28, 2000, Alignment result 3, SEQ ID No: 19, Database: GenEmbl, Accession No; AC012107, docment #2.*
DOE Joint Genome Institute and Stanford Human Genome Center, Jul. 15, 2000, Alignment result 3, SEQ ID No: 19, aa211-532, Database: GenEmbl, Accession No: AC011470, document #3.*
Bertin et al. (1999) J. Biol. Chem. 274:12955.
GenBank™ Accession No. AA075860 (Dec. 23, 1997).
GenBank™ Accession No. AA421452 (Nov. 9, 1997).
GenBank™ Accession No. AC008749 (Aug. 4, 1999).
GenBank™ Accession No. AC011470 (Oct. 8, 1999).
GenBank™ Accession No. AC011476 (Oct. 8, 1999).
GenBank™ Accession No. AC011501 (Oct. 8, 1999).
GenBank™ Accession No. AC012107 (Oct. 21, 1999).
GenBank™ Accession No. AC012310 (Oct. 25, 1999).
GenBank™ Accession No. AC019238 (Jan. 2, 2000).
GenBank™ Accession No. AC022066 (Jan. 26, 2000).
GenBank™ Accession No. AF298547 (Sep. 20, 2000).
GenBank™ Accession No. AK000517 (Feb. 22, 2000).
GenBank™ Accession No. AX186665 (Aug. 6, 2001).

(Continued)

*Primary Examiner*—Jon Weber
*Assistant Examiner*—Rita Mitra
(74) *Attorney, Agent, or Firm*—Millennium Pharmaceuticals, Inc.

(57) ABSTRACT

Novel NBS-2, NBS-3, PYRIN-12/NBS-4, and NBS-5 polypeptides, proteins, and nucleic acid molecules are disclosed. In addition to isolated NBS-2, NBS-3, PYRIN-12/NBS-4, and NBS-5 proteins, the invention further provides NBS-2, NBS-3, PYRIN-12/NBS-4, and NBS-5 fusion proteins, antigenic peptides and anti-NBS-2, anti-NBS-3, anti-PYRIN-12/NBS-4, and anti-NBS-5 antibodies. The invention also provides NBS-2, NBS-3, PYRIN-12/NBS-4, and NBS-5 nucleic acid molecules, recombinant expression vectors containing a nucleic acid molecule of the invention, host cells into which the expression vectors have been introduced and non-human transgenic animals in which a NBS-2, NBS-3, PYRIN-12/NBS-4, or NBS-5 gene has been introduced or disrupted. Diagnostic, screening and therapeutic methods utilizing compositions of the invention are also provided.

24 Claims, 45 Drawing Sheets

OTHER PUBLICATIONS

GenBank™ Accession No. AX186810 (Aug. 6, 2001).
GenBank™ Accession No. AX187729 (Aug. 6, 2001).
GenBank™ Accession No. AX187888 (Aug. 6, 2001).
GenBank™ Accession No. BF797150 (Jan. 12, 2001).
Koonin et al. (2000) Trends Biochem. Sci. 25:223.
van der Bizen and Jones (1999) Current Biology 8:226-228.

* cited by examiner

| | |
|---|---|
| atg aca tcg ccc cag cta gag tgg act ctg cag acc ctt ctg gag cag<br>Met Thr Ser Pro Gln Leu Glu Trp Thr Leu Gln Thr Leu Leu Glu Gln<br>1                         5                          10                       15 | 48 |
| ctg aac gag gat gaa tta aag agt ttc aaa tcc ctt tta tgg gct ttt<br>Leu Asn Glu Asp Glu Leu Lys Ser Phe Lys Ser Leu Leu Trp Ala Phe<br>                  20                         25                       30 | 96 |
| ccc ctc gaa gac gtg cta cag aag acc cca tgg tct gag gtg gaa gag<br>Pro Leu Glu Asp Val Leu Gln Lys Thr Pro Trp Ser Glu Val Glu Glu<br>        35                       40                       45 | 144 |
| gct gat ggc aag aaa ctg gca gaa att ctg gtc aac acc tcc tca gaa<br>Ala Asp Gly Lys Lys Leu Ala Glu Ile Leu Val Asn Thr Ser Ser Glu<br>     50                       55                      60 | 192 |
| aat tgg ata agg aat gcg act gtg aac atc ttg gaa gag atg aat ctc<br>Asn Trp Ile Arg Asn Ala Thr Val Asn Ile Leu Glu Glu Met Asn Leu<br>65                       70                       75                   80 | 240 |
| acg gaa ttg tgt aag atg gca aag gct gag atg atg gag gac gga cag<br>Thr Glu Leu Cys Lys Met Ala Lys Ala Glu Met Met Glu Asp Gly Gln<br>                  85                       90                       95 | 288 |
| gtg caa gaa ata gat aat cct gag ctg gga gat gca gaa gaa gac tcg<br>Val Gln Glu Ile Asp Asn Pro Glu Leu Gly Asp Ala Glu Glu Asp Ser<br>             100                      105                     110 | 336 |
| gag tta gca aag cca ggt gaa aag gaa gga tgg aga aat tca atg gag<br>Glu Leu Ala Lys Pro Gly Glu Lys Glu Gly Trp Arg Asn Ser Met Glu<br>         115                      120                     125 | 384 |
| aaa caa tct ttg gtc tgg aag aac acc ttt tgg caa gga gac att gac<br>Lys Gln Ser Leu Val Trp Lys Asn Thr Phe Trp Gln Gly Asp Ile Asp<br>     130                       135                      140 | 432 |
| aat ttc cat gac gac gtc act ctg aga aac caa cgg ttc att cca ttc<br>Asn Phe His Asp Asp Val Thr Leu Arg Asn Gln Arg Phe Ile Pro Phe<br>145                     150                      155                     160 | 480 |
| ttg aat ccc aga aca ccc agg aag cta aca cct tac acg gtg gtg ctg<br>Leu Asn Pro Arg Thr Pro Arg Lys Leu Thr Pro Tyr Thr Val Val Leu<br>             165                      170                     175 | 528 |
| cac ggc ccc gca ggc gtg ggg aaa acc acg ctg gcc aaa aag tgt atg<br>His Gly Pro Ala Gly Val Gly Lys Thr Thr Leu Ala Lys Lys Cys Met<br>         180                      185                     190 | 576 |
| ctg gac tgg aca gac tgc aac ctc agc ccg acg ctc aga tac gcg ttc<br>Leu Asp Trp Thr Asp Cys Asn Leu Ser Pro Thr Leu Arg Tyr Ala Phe<br>     195                       200                     205 | 624 |

FIG. 1A

```
tac ctc agc tgc aag gag ctc agc cgc atg ggc ccc tgc agt ttt gca      672
Tyr Leu Ser Cys Lys Glu Leu Ser Arg Met Gly Pro Cys Ser Phe Ala
    210             215                 220 gag ctg atc tcc aaa gac tgg cct gaa ttg cag gat gac att cca agc      720
Glu Leu Ile Ser Lys Asp Trp Pro Glu Leu Gln Asp Asp Ile Pro Ser
225             230                 235                 240 atc cta gcc caa gca cag aga atc ctg ttc gtg gtc gat ggc ctt gat      768
Ile Leu Ala Gln Ala Gln Arg Ile Leu Phe Val Val Asp Gly Leu Asp
                245                 250                 255 gag ctg aaa gtc cca cct ggg gcg ctg atc cag gac atc tgc ggg gac      816
Glu Leu Lys Val Pro Pro Gly Ala Leu Ile Gln Asp Ile Cys Gly Asp
            260                 265                 270 tgg gag aag aag aag ccg gtg ccc gtc ctc ctg ggg agt ttg ctg aag      864
Trp Glu Lys Lys Lys Pro Val Pro Val Leu Leu Gly Ser Leu Leu Lys
        275                 280                 285 agg aag atg tta ccc agg gca gcc ttg ctg gtc acc acg cgg ccc agg      912
Arg Lys Met Leu Pro Arg Ala Ala Leu Leu Val Thr Thr Arg Pro Arg
    290                 295                 300 gca ctg agg gac ctc cag ctc ctg gcg cag cag ccg atc tac ata agg      960
Ala Leu Arg Asp Leu Gln Leu Leu Ala Gln Gln Pro Ile Tyr Ile Arg
305             310                 315                 320 gtg gag ggc ttc ctg gag gag gac agg agg gcc tat ttc ctg aga cac     1008
Val Glu Gly Phe Leu Glu Glu Asp Arg Arg Ala Tyr Phe Leu Arg His
                325                 330                 335 ttt gga gac gag gac caa gcc atg cgt gcc ttt gag cta atg agg agc     1056
Phe Gly Asp Glu Asp Gln Ala Met Arg Ala Phe Glu Leu Met Arg Ser
            340                 345                 350 aac gcg gcc ctg ttc cag ctg ggc tcg gcc ccc gcg gtg tgc tgg att     1104
Asn Ala Ala Leu Phe Gln Leu Gly Ser Ala Pro Ala Val Cys Trp Ile
        355                 360                 365 gtg tgc acg act ctg aag ctg cag atg gag aag ggg gag gac ccg ccg     1152
Val Cys Thr Thr Leu Lys Leu Gln Met Glu Lys Gly Glu Asp Pro Pro
    370                 375                 380 gtt ccc gca ggg cgc aca gct gcg ggg cgc gct gcg gac gct gag cct     1200
Val Pro Ala Gly Arg Thr Ala Ala Gly Arg Ala Ala Asp Ala Glu Pro
385             390                 395                 400 cct ggc cgc gca ggg ctg tgg gcg cag atg tcc gtg ttc cac cga gag     1248
Pro Gly Arg Ala Gly Leu Trp Ala Gln Met Ser Val Phe His Arg Glu
                405                 410                 415
```

FIG. 1B

```
gac ctg gaa agg ctc ggg gtg cag gag tcc gac ctc cgt ctg ttc ctg      1296
Asp Leu Glu Arg Leu Gly Val Gln Glu Ser Asp Leu Arg Leu Phe Leu
            420                 425                 430 gac gga gac atc ctc cgc cag gac aga gtc tcc aaa ggc tgc tac tcc      1344
Asp Gly Asp Ile Leu Arg Gln Asp Arg Val Ser Lys Gly Cys Tyr Ser
            435                 440                 445 ttc atc cac ctc agc ttc cag cag ttt ctc act gcc ctg ttc tac gcc      1392
Phe Ile His Leu Ser Phe Gln Gln Phe Leu Thr Ala Leu Phe Tyr Ala
        450                 455                 460 ctg gag aag gag gag gag gag gac agg gac ggc cac gcc tgg gac att      1440
Leu Glu Lys Glu Glu Glu Glu Asp Arg Asp Gly His Ala Trp Asp Ile
465                 470                 475                 480 ggg gac gta cag aag ctg ctt tcc gga gaa gaa aga ctc aag aac ccc      1488
Gly Asp Val Gln Lys Leu Leu Ser Gly Glu Glu Arg Leu Lys Asn Pro
                485                 490                 495 gac ctg att caa gta gga cac ttc tta ttc ggc ctc gct aac gag aag      1536
Asp Leu Ile Gln Val Gly His Phe Leu Phe Gly Leu Ala Asn Glu Lys
            500                 505                 510 aga gcc aag gag ttg gag gcc act ttt ggc tgc cgg atg tca ccg gac      1584
Arg Ala Lys Glu Leu Glu Ala Thr Phe Gly Cys Arg Met Ser Pro Asp
            515                 520                 525 atc aaa cag gaa ttg ctg caa tgc aaa gca cat ctt cat gca aat aag      1632
Ile Lys Gln Glu Leu Leu Gln Cys Lys Ala His Leu His Ala Asn Lys
        530                 535                 540 ccc tta tcc gtg acc gac ctg aag gag gtc ttg ggc tgc ctg tat gag      1680
Pro Leu Ser Val Thr Asp Leu Lys Glu Val Leu Gly Cys Leu Tyr Glu
545                 550                 555                 560 tct cag gag gag gag ctg gcg aag gtg gtg gtg gcc ccg ttc aag gaa      1728
Ser Gln Glu Glu Glu Leu Ala Lys Val Val Val Ala Pro Phe Lys Glu
                565                 570                 575 att tct att cac ctg aca aat act tct gaa gtg atg cat tgt tcc ttc      1776
Ile Ser Ile His Leu Thr Asn Thr Ser Glu Val Met His Cys Ser Phe
            580                 585                 590 agc ctg aag cat tgt caa gac ttg cag aaa ctc tca ctg cag gta gca      1824
Ser Leu Lys His Cys Gln Asp Leu Gln Lys Leu Ser Leu Gln Val Ala
        595                 600                 605 aag ggg gtg ttc ctg gag aat tac acg gat ttt gaa ctg gac att gaa      1872
Lys Gly Val Phe Leu Glu Asn Tyr Met Asp Phe Glu Leu Asp Ile Glu
    610                 615                 620
```

FIG. 1C

```
ttt gaa agc tca aac agc aac ctc aag ttt ctg gaa gtg aaa caa agc      1920
Phe Glu Ser Ser Asn Ser Asn Leu Lys Phe Leu Glu Val Lys Gln Ser
625             630                 635                 640 ttc ctg agt gac tct tct gtg cgg att ctt tgt gac cac gta acc cgt      1968
Phe Leu Ser Asp Ser Ser Val Arg Ile Leu Cys Asp His Val Thr Arg
            645                 650                 655 agc acc tgt cat ctg cag aaa gtg gag att aaa aac gtc acc cct gac      2016
Ser Thr Cys His Leu Gln Lys Val Glu Ile Lys Asn Val Thr Pro Asp
                660                 665                 670 acc gcg tac cgg gac ttc tgt ctt gct ttc att ggg aag aag acc ctc      2064
Thr Ala Tyr Arg Asp Phe Cys Leu Ala Phe Ile Gly Lys Lys Thr Leu
            675                 680                 685 acg cac ctg acc ctg gca ggg cac atc gag tgg gaa cgc acg atg atg      2112
Thr His Leu Thr Leu Ala Gly His Ile Glu Trp Glu Arg Thr Met Met
690                 695                 700 ctg atg ctg tgt gac ctg ctc aga aat cat aaa tgc aac ctg cag tac      2160
Leu Met Leu Cys Asp Leu Leu Arg Asn His Lys Cys Asn Leu Gln Tyr
705                 710                 715                 720 ctg agg ttg gga ggt cac tgt gcc acc ccg gag cag tgg gct gaa ttc      2208
Leu Arg Leu Gly Gly His Cys Ala Thr Pro Glu Gln Trp Ala Glu Phe
                725                 730                 735 ttc tat gtc ctc aaa gcc aac cag tcc ctg aag cac ctg cgt ctc tca      2256
Phe Tyr Val Leu Lys Ala Asn Gln Ser Leu Lys His Leu Arg Leu Ser
            740                 745                 750 gcc aat gtg ctc ctg gat gag ggt gcc atg ttg ctg tac aag acc atg      2304
Ala Asn Val Leu Leu Asp Glu Gly Ala Met Leu Leu Tyr Lys Thr Met
            755                 760                 765 aca cgc cca aaa cac ttc ctg cag atg ttg tcg ttg gaa aac tgt cgt      2352
Thr Arg Pro Lys His Phe Leu Gln Met Leu Ser Leu Glu Asn Cys Arg
770                 775                 780 ctt aca gaa gcc agt tgc aag gac ctt gct gct gtc ttg gtt gtc agc      2400
Leu Thr Glu Ala Ser Cys Lys Asp Leu Ala Ala Val Leu Val Val Ser
785                 790                 795                 800 aag aag ctg aca cac ctg tgc ttg gcc aag aac ccc att ggg gat aca      2448
Lys Lys Leu Thr His Leu Cys Leu Ala Lys Asn Pro Ile Gly Asp Thr
                805                 810                 815 ggg gtg aag ttt ctg t                                                 2464
Gly Val Lys Phe Leu
            820
```

FIG. 1D

NB-ARC: domain 1 of 1, from 176 to 190: score 11.4, E = 0.033
(SEQ ID NO: 9)   *->ivGMGGiGKTTLakq<-*
                   ++G++G+GKTTLak+
        NBS-2  176 LHGPAGVGKTTLAKK 190

FIG. 4A

LRR_RI_2: domain 1 of 2, from 743 to 770: score 13.4, E = 0.57
(SEQ ID NO:10)  *->npsLreLdLsnNklgdeGaraLaeaLks<-*
                   n+sL+ L+Ls N l deGa+ L ++ +
        NBS-2  743 NQSLKHLRLSANVLLDEGAMLLYKTMTR 770

FIG. 4B

LRR_RI_2: domain 2 of 2, from 772 to 799: score 18.2, E = 0.12
(SEQ ID NO:10)  *->npsLreLdLsnNklgdeGaraLaeaLks<-*
                   ++ L+ L+L+n+ l+++ ++ La++L
        NBS-2  772 KHFLQMLSLENCRLTEASCKDLAAVLVV 799

FIG. 4C

LRR_RI_2: domain 1 of 1, from 596 to 623: score 11.0, E = 1.2
(SEQ ID NO:10)  *->npsLreLdLsnNklgdeGaraLaeaLks<-*
                   ++sLreL++     +N+l     L ++sL++
        NBS-3  596 NKSLRELHIFDNDLNGISRILSKALEH 623

FIG. 8

```
atg gca gaa tcg gat tct act gac ttt gac ctg ctg tgg tat cta gag       48
Met Ala Glu Ser Asp Ser Thr Asp Phe Asp Leu Leu Trp Tyr Leu Glu
 1               5                  10                  15 aat ctc agt gac aag gaa ttt cag agt ttt aag aag tat ctg gca cgc       96
Asn Leu Ser Asp Lys Glu Phe Gln Ser Phe Lys Lys Tyr Leu Ala Arg
                20                  25                  30 aag att ctt gat ttc aaa ctg cca cag ttt cca ctg ata cag atg aca      144
Lys Ile Leu Asp Phe Lys Leu Pro Gln Phe Pro Leu Ile Gln Met Thr
             35                  40                  45 aaa gaa gaa ctg gct aac gtg ttg cca atc tct tat gag gga cag tat      192
Lys Glu Glu Leu Ala Asn Val Leu Pro Ile Ser Tyr Glu Gly Gln Tyr
         50                  55                  60 ata tgg aat atg ctc ttc agc ata ttt tca atg atg cgt aag gaa gat      240
Ile Trp Asn Met Leu Phe Ser Ile Phe Ser Met Met Arg Lys Glu Asp
 65                  70                  75                  80 ctt tgt agg aag atc att ggc aga cga aac cat gtg ttc tac ata ctt      288
Leu Cys Arg Lys Ile Ile Gly Arg Arg Asn His Val Phe Tyr Ile Leu
                 85                  90                  95 caa tta gcc tat gat tct acc agc tat tat tca gca aac aat ctc aat      336
Gln Leu Ala Tyr Asp Ser Thr Ser Tyr Tyr Ser Ala Asn Asn Leu Asn
            100                 105                 110 gtg ttc ctg atg gga gag aga gca tct gga aaa act att gtt ata aat      384
Val Phe Leu Met Gly Glu Arg Ala Ser Gly Lys Thr Ile Val Ile Asn
        115                 120                 125 ctg gct gtg ttg agg tgg atc aag ggt gag atg tgg cag aac atg atc      432
Leu Ala Val Leu Arg Trp Ile Lys Gly Glu Met Trp Gln Asn Met Ile
130                 135                 140 tcg tac gtc gtt cac ctc act gct cac gaa ata aac cag atg acc aac      480
Ser Tyr Val Val His Leu Thr Ala His Glu Ile Asn Gln Met Thr Asn
145                 150                 155                 160 agc agc ttg gct gag cta atc gcc aag gac tgg cct gac ggc cag gct      528
Ser Ser Leu Ala Glu Leu Ile Ala Lys Asp Trp Pro Asp Gly Gln Ala
                165                 170                 175 ccc att gca gac atc ctg tct gat ccc aag aaa ctc ctt ttc atc ctc      576
Pro Ile Ala Asp Ile Leu Ser Asp Pro Lys Lys Leu Leu Phe Ile Leu
            180                 185                 190 gag gac ttg gac aac ata aga ttc gag tta aat gtc aat gaa agt gct      624
Glu Asp Leu Asp Asn Ile Arg Phe Glu Leu Asn Val Asn Glu Ser Ala
        195                 200                 205
```

FIG. 5A

```
ttg tgt agt aac agc acc cag aaa gtt ccc att cca gtt ctc ctg gtc        672
Leu Cys Ser Asn Ser Thr Gln Lys Val Pro Ile Pro Val Leu Leu Val
    210                 215                 220 agt ttg ctg aag aga aaa atg gct cca ggc tgc tgg ttc ctc atc tcc        720
Ser Leu Leu Lys Arg Lys Met Ala Pro Gly Cys Trp Phe Leu Ile Ser
225                 230                 235                 240 tca agg ccc aca cgt ggg aat aat gta aaa acg ttc ttg aaa gag gta        768
Ser Arg Pro Thr Arg Gly Asn Asn Val Lys Thr Phe Leu Lys Glu Val
                245                 250                 255 gat tgc tgc acg acc ttg cag ctg tcg aat ggg aag agg gag ata tat        816
Asp Cys Cys Thr Thr Leu Gln Leu Ser Asn Gly Lys Arg Glu Ile Tyr
            260                 265                 270 ttt aac tct ttc ttt aaa gac cgc cag agg gcg tcg gca gcc ctc cag        864
Phe Asn Ser Phe Phe Lys Asp Arg Gln Arg Ala Ser Ala Ala Leu Gln
        275                 280                 285 ctt gta cat gag gat gaa ata ctc gtg ggt ctg tgc cga gtc gcc atc        912
Leu Val His Glu Asp Glu Ile Leu Val Gly Leu Cys Arg Val Ala Ile
    290                 295                 300 tta tgc tgg atc acg tgt act gtc ctg aag cgg cag atg gac aag ggg        960
Leu Cys Trp Ile Thr Cys Thr Val Leu Lys Arg Gln Met Asp Lys Gly
305                 310                 315                 320 cgt gac ttc cag ctc tgc tgc caa aca ccc act gat cta cat gcc cac       1008
Arg Asp Phe Gln Leu Cys Cys Gln Thr Pro Thr Asp Leu His Ala His
                325                 330                 335 ttt ctt gct gat gcg ttg aca tca gag gct gga ctt act gcc aat cag       1056
Phe Leu Ala Asp Ala Leu Thr Ser Glu Ala Gly Leu Thr Ala Asn Gln
            340                 345                 350 tat cac cta ggt ctc cta aaa cgt ctg tgt ttg ctg gct gca gga gga       1104
Tyr His Leu Gly Leu Leu Lys Arg Leu Cys Leu Leu Ala Ala Gly Gly
        355                 360                 365 ctg ttt ctg agc acc ctg aat ttc agt ggt gaa gac ctc aga tgt gtt       1152
Leu Phe Leu Ser Thr Leu Asn Phe Ser Gly Glu Asp Leu Arg Cys Val
    370                 375                 380 ggg ttt act gag gct gat gtc tct gtg ttg cag gcc gcg aat att ctt       1200
Gly Phe Thr Glu Ala Asp Val Ser Val Leu Gln Ala Ala Asn Ile Leu
385                 390                 395                 400 ttg ccg agc aac act cat aaa gac cgt tac aag ttc ata cac ttg aac       1248
Leu Pro Ser Asn Thr His Lys Asp Arg Tyr Lys Phe Ile His Leu Asn
                405                 410                 415
```

FIG. 5B

```
gtc cag gag ttt tgt aca gcc att gca ttt ctg atg gca gta ccc aac     1296
Val Gln Glu Phe Cys Thr Ala Ile Ala Phe Leu Met Ala Val Pro Asn
            420                 425                 430 tat ctg atc ccc tca ggc agc aga gag tat aaa gag aag aga gaa caa     1344
Tyr Leu Ile Pro Ser Gly Ser Arg Glu Tyr Lys Glu Lys Arg Glu Gln
            435                 440                 445 tac tct gac ttt aat caa gtg ttt act ttc att ttt ggt ctt cta aat     1392
Tyr Ser Asp Phe Asn Gln Val Phe Thr Phe Ile Phe Gly Leu Leu Asn
            450                 455                 460 gca aac agg aga aag att ctt gag aca tcc ttt gga tac cag cta ccg     1440
Ala Asn Arg Arg Lys Ile Leu Glu Thr Ser Phe Gly Tyr Gln Leu Pro
465                 470                 475                 480 atg gta gac agc ttc aag tgg tac tcg gtg gga tac atg aaa cat ttg     1488
Met Val Asp Ser Phe Lys Trp Tyr Ser Val Gly Tyr Met Lys His Leu
                    485                 490                 495 gac cgt gac ccg gaa aag ttg acg cac cat atg cct ttg ttt tac tgt     1536
Asp Arg Asp Pro Glu Lys Leu Thr His His Met Pro Leu Phe Tyr Cys
            500                 505                 510 ctc tat gag aat cgg gaa gaa gaa ttt gtg aag acg att gtg gat gct     1584
Leu Tyr Glu Asn Arg Glu Glu Glu Phe Val Lys Thr Ile Val Asp Ala
            515                 520                 525 ctc atg gag gtt aca gtt tac ctt caa tca gac aag gat atg atg gtc     1632
Leu Met Glu Val Thr Val Tyr Leu Gln Ser Asp Lys Asp Met Met Val
            530                 535                 540 tca tta tac tgt ctg gat tac tgc tgt cac ctg agg aca ctt aag ttg     1680
Ser Leu Tyr Cys Leu Asp Tyr Cys Cys His Leu Arg Thr Leu Lys Leu
545                 550                 555                 560 agt gtt cag cgc atc ttt caa aac aaa gag cca ctt ata agg cca act     1728
Ser Val Gln Arg Ile Phe Gln Asn Lys Glu Pro Leu Ile Arg Pro Thr
                    565                 570                 575 gct agt caa atg aag agc ctt gtc tac tgg aga gag atc tgc tct ctt     1776
Ala Ser Gln Met Lys Ser Leu Val Tyr Trp Arg Glu Ile Cys Ser Leu
            580                 585                 590 ttt tat aca atg gag agc ctc cgg gag ctg cat atc ttt gac aat gac     1824
Phe Tyr Thr Met Glu Ser Leu Arg Glu Leu His Ile Phe Asp Asn Asp
            595                 600                 605 ctt aat ggt att tca gaa agg att ctg tct aaa gcc ctg gag cat tct     1872
Leu Asn Gly Ile Ser Glu Arg Ile Leu Ser Lys Ala Leu Glu His Ser
610                 615                 620
```

FIG. 5C

```
agc tgt aaa ctt cgc aca ctc aa
Ser Cys Lys Leu Arg Thr Leu
625             630
```

FIG. 5D

```
atg aag gct gaa cta ctg gag aca tgg gac aac atc agt tgg cct aaa      48
Met Lys Ala Glu Leu Leu Glu Thr Trp Asp Asn Ile Ser Trp Pro Lys
 1               5                  10                  15 gac cac gta tat atc cgt aat aca tca aag gac gaa cat gag gaa ctg      96
Asp His Val Tyr Ile Arg Asn Thr Ser Lys Asp Glu His Glu Glu Leu
             20                  25                  30 cag cgc cta ctg gat cct aat agg act aga gcc cag gcc cag acg ata     144
Gln Arg Leu Leu Asp Pro Asn Arg Thr Arg Ala Gln Ala Gln Thr Ile
         35                  40                  45 gtc ttg gtg ggg agg gca ggg gtt ggg aag acc acc ttg gca atg cag     192
Val Leu Val Gly Arg Ala Gly Val Gly Lys Thr Thr Leu Ala Met Gln
 50                  55                  60 gct atg ctg cac tgg gca aat gga gtt ctc ttt cag caa agg ttc tcc     240
Ala Met Leu His Trp Ala Asn Gly Val Leu Phe Gln Gln Arg Phe Ser
 65                  70                  75                  80 tat gtt ttc tat ctc agc tgc cat aaa ata agg tac atg aag gaa act     288
Tyr Val Phe Tyr Leu Ser Cys His Lys Ile Arg Tyr Met Lys Glu Thr
             85                  90                  95 acc ttt gct gaa ttg att tct ttg gat tgg ccc gat ttt gat gcc ccc     336
Thr Phe Ala Glu Leu Ile Ser Leu Asp Trp Pro Asp Phe Asp Ala Pro
                100                 105                 110 att gaa gag ttc atg tct caa cca gag aag ctc ctg ttt att att gat     384
Ile Glu Glu Phe Met Ser Gln Pro Glu Lys Leu Leu Phe Ile Ile Asp
                115                 120                 125 ggc ttt gag gaa ata atc ata tct gag tca cgc tct gag agc ttg gat     432
Gly Phe Glu Glu Ile Ile Ile Ser Glu Ser Arg Ser Glu Ser Leu Asp
 130                 135                 140 gat ggc tcg cca tgt aca gac tgg tac cag gag ctc cca gtg acc aaa     480
Asp Gly Ser Pro Cys Thr Asp Trp Tyr Gln Glu Leu Pro Val Thr Lys
145                 150                 155                 160 atc cta cac agc ttg ttg aag aaa gaa ttg gtt ccc ctg gct acc tta     528
Ile Leu His Ser Leu Leu Lys Lys Glu Leu Val Pro Leu Ala Thr Leu
                165                 170                 175 ctg atc acg atc aag acc tgg ttt gtg aga gat ctt aag gcc tca tta     576
Leu Ile Thr Ile Lys Thr Trp Phe Val Arg Asp Leu Lys Ala Ser Leu
                180                 185                 190 gtg aat cca tgc ttt gta caa att aca ggg ttc aca ggg gac gac cta     624
Val Asn Pro Cys Phe Val Gln Ile Thr Gly Phe Thr Gly Asp Asp Leu
                195                 200                 205
```

FIG. 9A

```
cgg gta tat ttc atg aga cac ttt gat gac tca agt gaa gtt gag aaa    672
Arg Val Tyr Phe Met Arg His Phe Asp Asp Ser Ser Glu Val Glu Lys
    210             215             220 atc ctg cag cag cta aga aaa aac gaa act ctc ttt cat tcc tgc agt    720
Ile Leu Gln Gln Leu Arg Lys Asn Glu Thr Leu Phe His Ser Cys Ser
225             230             235             240 gcc ccc atg gtg tgt tgg acc gta tgt tcc tgt ctg aag cag ccg aag    768
Ala Pro Met Val Cys Trp Thr Val Cys Ser Cys Leu Lys Gln Pro Lys
            245             250             255 gtg agg tat tac gat ctc cag tca atc act cag act acc acc agt ctg    816
Val Arg Tyr Tyr Asp Leu Gln Ser Ile Thr Gln Thr Thr Thr Ser Leu
        260             265             270 tat gcc tat ttt ttc tcc aac ttg ttc tcc aca gca gag gta gat ttg    864
Tyr Ala Tyr Phe Phe Ser Asn Leu Phe Ser Thr Ala Glu Val Asp Leu
    275             280             285 gca gat gac agc tgg cca gga caa tgg agg gcc ctc tgc agt ctg gcc    912
Ala Asp Asp Ser Trp Pro Gly Gln Trp Arg Ala Leu Cys Ser Leu Ala
290             295             300 ata gaa ggg ctg tgg tct atg aac ttc acg ttt aac aaa gaa gac act    960
Ile Glu Gly Leu Trp Ser Met Asn Phe Thr Phe Asn Lys Glu Asp Thr
305             310             315             320 gag atc gag ggc ctg gaa gtg cct ttc att gat tct ctc tac gag ttc   1008
Glu Ile Glu Gly Leu Glu Val Pro Phe Ile Asp Ser Leu Tyr Glu Phe
            325             330             335 aat att ctt caa aag atc aat gac tgt ggg ggt tgc act act ttc acc   1056
Asn Ile Leu Gln Lys Ile Asn Asp Cys Gly Gly Cys Thr Thr Phe Thr
        340             345             350 cac cta agt ttc cag gag ttt ttt gca gcc atg tcc ttt gtg cta gag   1104
His Leu Ser Phe Gln Glu Phe Phe Ala Ala Met Ser Phe Val Leu Glu
    355             360             365 gaa cct aga gaa ttc cct ccc cat tcc aca aag cca caa gag atg aag   1152
Glu Pro Arg Glu Phe Pro Pro His Ser Thr Lys Pro Gln Glu Met Lys
370             375             380 atg tta ctg caa cac gtc ttg ctt gac aaa gaa gcc tac tgg act cca   1200
Met Leu Leu Gln His Val Leu Leu Asp Lys Glu Ala Tyr Trp Thr Pro
385             390             395             400 gtg gtt ctg ttc ttc ttt ggt ctt tta aat aaa aac ata gca aga gaa   1248
Val Val Leu Phe Phe Phe Gly Leu Leu Asn Lys Asn Ile Ala Arg Glu
            405             410             415
```

FIG. 9B

```
ctg gaa gat act ttg cat tgt aaa ata tct ccc agg gta atg gag gaa      1296
Leu Glu Asp Thr Leu His Cys Lys Ile Ser Pro Arg Val Met Glu Glu
            420                 425                 430 tta tta aag tgg gga gaa gag tta ggt aag gct gaa agt gcc tct ctc      1344
Leu Leu Lys Trp Gly Glu Glu Leu Gly Lys Ala Glu Ser Ala Ser Leu
        435                 440                 445 caa ttt cac att cta cga ctt ttt cac tgc cta cac gag tcc cag gag      1392
Gln Phe His Ile Leu Arg Leu Phe His Cys Leu His Glu Ser Gln Glu
    450                 455                 460 gaa gac ttc aca aag aag atg ttg ggt cgt atc ttt gaa gtt gac ctt      1440
Glu Asp Phe Thr Lys Lys Met Leu Gly Arg Ile Phe Glu Val Asp Leu
465                 470                 475                 480 aat att ttg gag gac gaa gaa ctc caa gct tct tca ttt tgc cta aag      1488
Asn Ile Leu Glu Asp Glu Glu Leu Gln Ala Ser Ser Phe Cys Leu Lys
                485                 490                 495 cac tgt aaa agg tta aat aag cta agg ctt tct gtt agc agt cac atc      1536
His Cys Lys Arg Leu Asn Lys Leu Arg Leu Ser Val Ser Ser His Ile
            500                 505                 510 ctt gaa agg gac ttg gaa att ctg gag tga                              1566
Leu Glu Arg Asp Leu Glu Ile Leu Glu
        515                 520
```

FIG. 9C

NB-ARC: domain 1 of 1, from 50 to 79: score 9.4, E = 0.12
(SEQ ID NO:11)    *->ivGMGGiGKTTLakqiyndes..qevqrhF<-*
                     +vG++G+GKTTLa q+   ++++  ++q  +F
NBS-4     50       LVGRAGVGKTTLAMQAMLHWAngVLFQQRF    79

```
  c agc cgc tta tgg tcc agc aag tct gtc act gag att cac cta tac ttt      49
    Ser Arg Leu Trp Ser Ser Lys Ser Val Thr Glu Ile His Leu Tyr Phe
    1               5                   10                  15 gag gag gaa gtc aag caa gaa gaa tgt gac cat ttg gac cgc ctt ttt        97
  Glu Glu Glu Val Lys Gln Glu Glu Cys Asp His Leu Asp Arg Leu Phe
                  20                  25                  30 gct ccc aag gaa gct ggg aaa cag cca cgt aca gtg atc att caa gga       145
  Ala Pro Lys Glu Ala Gly Lys Gln Pro Arg Thr Val Ile Ile Gln Gly
          35                  40                  45 cca caa gga att gga aaa acg aca ctc ctg atg aag ctg atg atg gcc       193
  Pro Gln Gly Ile Gly Lys Thr Thr Leu Leu Met Lys Leu Met Met Ala
      50                  55                  60 tgg tcg gac aac aag atc ttt cgg gat agg ttc ctg tac acg ttc tat       241
  Trp Ser Asp Asn Lys Ile Phe Arg Asp Arg Phe Leu Tyr Thr Phe Tyr
  65                  70                  75                  80 ttc tgc tgc aga gaa ctg agg gag ttg ccg cca acg agt ttg gct gac       289
  Phe Cys Cys Arg Glu Leu Arg Glu Leu Pro Pro Thr Ser Leu Ala Asp
                  85                  90                  95 ttg att tcc aga gag tgg cct gac ccc gct gct cct ata aca gag atc       337
  Leu Ile Ser Arg Glu Trp Pro Asp Pro Ala Ala Pro Ile Thr Glu Ile
              100                 105                 110 gtg tct caa ccg gag aga ctc ttg ttc gtc atc gac agc ttc gaa gag       385
  Val Ser Gln Pro Glu Arg Leu Leu Phe Val Ile Asp Ser Phe Glu Glu
          115                 120                 125 ctg cag ggc ggc ttg aac gaa ccc gat tcg gat ctg tgt ggt gac ttg       433
  Leu Gln Gly Gly Leu Asn Glu Pro Asp Ser Asp Leu Cys Gly Asp Leu
      130                 135                 140 atg gag aaa cgg ccg gtg cag gtg ctt ctg agc agt ttg ctg agg aag       481
  Met Glu Lys Arg Pro Val Gln Val Leu Leu Ser Ser Leu Leu Arg Lys
  145                 150                 155                 160 aag atg ctc ccg gag gcc tcc ctg ctc atc gct atc aaa ccc gtg tgc       529
  Lys Met Leu Pro Glu Ala Ser Leu Leu Ile Ala Ile Lys Pro Val Cys
                  165                 170                 175 ccg aag gag ctc cgg gat cag gtg acg atc tca gaa atc tac cag ccc       577
  Pro Lys Glu Leu Arg Asp Gln Val Thr Ile Ser Glu Ile Tyr Gln Pro
              180                 185                 190 cgg gga ttc aac gag agt gat agg tta gtg tat ttc tgc tgt ttc ttc       625
  Arg Gly Phe Asn Glu Ser Asp Arg Leu Val Tyr Phe Cys Cys Phe Phe
          195                 200                 205
```

FIG. 13A

```
aaa gac ccg aaa aga gcc atg gaa gcc ttc aat ctt gta aga gaa agt        673
Lys Asp Pro Lys Arg Ala Met Glu Ala Phe Asn Leu Val Arg Glu Ser
        210             215                 220 gaa cag ctg ttt tcc ata tgc caa atc ccg ctc ctc tgc tgg atc ctg        721
Glu Gln Leu Phe Ser Ile Cys Gln Ile Pro Leu Leu Cys Trp Ile Leu
225             230                 235                 240 tgt acc agt ctg aag caa gag atg cag aaa gga aaa gac ctg gcc ctg        769
Cys Thr Ser Leu Lys Gln Glu Met Gln Lys Gly Lys Asp Leu Ala Leu
                245                 250                 255 acc tgc cag agc act acc tct gtg tac tcc tct ttc gtc ttt aac ctg        817
Thr Cys Gln Ser Thr Thr Ser Val Tyr Ser Ser Phe Val Phe Asn Leu
            260                 265                 270 ttc aca cct gag ggt gcc gag ggc ccg act ccg caa acc cag cac cag        865
Phe Thr Pro Glu Gly Ala Glu Gly Pro Thr Pro Gln Thr Gln His Gln
        275                 280                 285 ctg aag gcc ctg tgc tcc ctg gct gca gag ggt atg tgg aca gac aca        913
Leu Lys Ala Leu Cys Ser Leu Ala Ala Glu Gly Met Trp Thr Asp Thr
    290                 295                 300 ttt gag ttt tgt gaa gac gac ctc cgg aga aat ggg gtt gtt gac gct        961
Phe Glu Phe Cys Glu Asp Asp Leu Arg Arg Asn Gly Val Val Asp Ala
305             310                 315                 320 gac atc cct gcg ctg ctg ggc acc aag ata ctt ctg aag tac ggg gag       1009
Asp Ile Pro Ala Leu Leu Gly Thr Lys Ile Leu Leu Lys Tyr Gly Glu
                325                 330                 335 cgt gag agc tcc tac gtg ttc ctc cac gtg tgt atc cag gag ttc tgt       1057
Arg Glu Ser Ser Tyr Val Phe Leu His Val Cys Ile Gln Glu Phe Cys
            340                 345                 350 gcc gcc ttg ttc tat ttg ctc aag agc cac ctt gat cat cct cac cca       1105
Ala Ala Leu Phe Tyr Leu Leu Lys Ser His Leu Asp His Pro His Pro
        355                 360                 365 gct gtg aga tgt gta cag gaa ttg cta gtt gcc aat ttt gaa aaa gca       1153
Ala Val Arg Cys Val Gln Glu Leu Leu Val Ala Asn Phe Glu Lys Ala
    370                 375                 380 agg aga gca cat tgg att ttt ttg ggg tgt ttt cta act ggc ctt tta       1201
Arg Arg Ala His Trp Ile Phe Leu Gly Cys Phe Leu Thr Gly Leu Leu
385                 390                 395                 400 aat aaa aag gaa caa gaa aaa ctg gat gcg ttt ttt ggc ttc caa ctg       1249
Asn Lys Lys Glu Gln Glu Lys Leu Asp Ala Phe Phe Gly Phe Gln Leu
                405                 410                 415
```

FIG. 13B

```
tcc caa gag ata aag cag caa att cac cag tgc ctg aag agc tta ggg    1297
Ser Gln Glu Ile Lys Gln Gln Ile His Gln Cys Leu Lys Ser Leu Gly
            420             425                 430 gag cgt ggc aat cct cag gga cag gtg gat tcc ttg gcg ata ttt tac    1345
Glu Arg Gly Asn Pro Gln Gly Gln Val Asp Ser Leu Ala Ile Phe Tyr
        435                 440                 445 tgt ctc ttt gaa atg cag gat cct gcc ttt gtg aag cag gca gtg aac    1393
Cys Leu Phe Glu Met Gln Asp Pro Ala Phe Val Lys Gln Ala Val Asn
    450                 455                 460 ctc ctc caa gaa gct aac ttt cat att att gac aac gtg gac ttg gtg    1441
Leu Leu Gln Glu Ala Asn Phe His Ile Ile Asp Asn Val Asp Leu Val
465                 470                 475                 480 gtt tct gcc tac tgc tta aaa tac tgc tcc agc ttg agg aaa ctc tgt    1489
Val Ser Ala Tyr Cys Leu Lys Tyr Cys Ser Ser Leu Arg Lys Leu Cys
            485                 490                 495 ttt tcc gtt caa aat gtc ttt aag aaa gag gat gaa cac agc tct acg    1537
Phe Ser Val Gln Asn Val Phe Lys Lys Glu Asp Glu His Ser Ser Thr
        500                 505                 510 tcg gat tac agc ctc atc tgt tgg cat cac atc tgc tct gtg ctc acc    1585
Ser Asp Tyr Ser Leu Ile Cys Trp His His Ile Cys Ser Val Leu Thr
    515                 520                 525 acc agc ggg cac ctc aga gag ctc cag gtg cag gac agc acc ctc agc    1633
Thr Ser Gly His Leu Arg Glu Leu Gln Val Gln Asp Ser Thr Leu Ser
530                 535                 540 gag tcg acc ttt gtg acc tgg tgt aac cag ctg agg cat ccc agc tgt    1681
Glu Ser Thr Phe Val Thr Trp Cys Asn Gln Leu Arg His Pro Ser Cys
545                 550                 555                 560 cgc ctt cag aag ctt gga ata aat aac gtt tcc ttt tct ggc cag agt    1729
Arg Leu Gln Lys Leu Gly Ile Asn Asn Val Ser Phe Ser Gly Gln Ser
            565                 570                 575 gtt ctg ctc ttt gag gtg ctc ttt tat cag cca gac ttg aaa tac ctg    1777
Val Leu Leu Phe Glu Val Leu Phe Tyr Gln Pro Asp Leu Lys Tyr Leu
        580                 585                 590 agc ttc acc ctc acg aaa ctc tct cgt gat gac atc agg tcc ctc tgt    1825
Ser Phe Thr Leu Thr Lys Leu Ser Arg Asp Asp Ile Arg Ser Leu Cys
    595                 600                 605 gat gcc ttg aac tac cca gca ggc aac gtc aaa gag cta gcg ctg gta    1873
Asp Ala Leu Asn Tyr Pro Ala Gly Asn Val Lys Glu Leu Ala Leu Val
610                 615                 620
```

FIG. 13C

```
aat tgt cac ctc tca ccc att gat tgt gaa gtc ctt gct ggc ctt cta    1921
Asn Cys His Leu Ser Pro Ile Asp Cys Glu Val Leu Ala Gly Leu Leu
625                 630                 635                 640 acc aac aac aag aag ctg acg tat ctg aat gta tcc tgc aac cag tta    1969
Thr Asn Asn Lys Lys Leu Thr Tyr Leu Asn Val Ser Cys Asn Gln Leu
                645                 650                 655 gac aca ggc gtg ccc ctt ttg tgt gaa gcc ctg tgc agc cca gac acg    2017
Asp Thr Gly Val Pro Leu Leu Cys Glu Ala Leu Cys Ser Pro Asp Thr
            660                 665                 670 gtc ctg gta tac ctg atg ttg gct ttc tgc cac ctc agc gag cag tgc    2065
Val Leu Val Tyr Leu Met Leu Ala Phe Cys His Leu Ser Glu Gln Cys
        675                 680                 685 tgc gaa tac atc tct gaa atg ctt ctg cgt aac aag agc gtg cgc tat    2113
Cys Glu Tyr Ile Ser Glu Met Leu Leu Arg Asn Lys Ser Val Arg Tyr
    690                 695                 700 cta gac ctc agt gcc aat gtc ctg aag gac gaa gga ctg aaa act ctc    2161
Leu Asp Leu Ser Ala Asn Val Leu Lys Asp Glu Gly Leu Lys Thr Leu
705                 710                 715                 720 tgc gag gcc ttg aaa cat ccg gac tgc tgc ctg gat tca ctg tgt ttg    2209
Cys Glu Ala Leu Lys His Pro Asp Cys Cys Leu Asp Ser Leu Cys Leu
                725                 730                 735 gta aaa tgt ttt atc act gct gct ggc tgt gaa gac ctc gcc tct gct    2257
Val Lys Cys Phe Ile Thr Ala Ala Gly Cys Glu Asp Leu Ala Ser Ala
            740                 745                 750 ctc atc agc aat caa aac ctg aag att ctg caa att ggg tgc aat gaa    2305
Leu Ile Ser Asn Gln Asn Leu Lys Ile Leu Gln Ile Gly Cys Asn Glu
        755                 760                 765 atc gga gat gtg ggt gtg cag ctg ttg tgt cgg gct ctg acg cat acg    2353
Ile Gly Asp Val Gly Val Gln Leu Leu Cys Arg Ala Leu Thr His Thr
    770                 775                 780 gat tgc cgc tta gag att ctt ggg ttg gaa gaa tgt ggg tta acg agc    2401
Asp Cys Arg Leu Glu Ile Leu Gly Leu Glu Glu Cys Gly Leu Thr Ser
785                 790                 795                 800 acc tgc tgt aag gat ctc gcg tct gtt ctc acc tgc agt aag acc ctg    2449
Thr Cys Cys Lys Asp Leu Ala Ser Val Leu Thr Cys Ser Lys Thr Leu
                805                 810                 815 cag cag ctc aac ctg acc ttg aac acc ttg gac cac aca ggg gtg gtt    2497
Gln Gln Leu Asn Leu Thr Leu Asn Thr Leu Asp His Thr Gly Val Val
            820                 825                 830
```

FIG. 13D

```
gta ctc tgt gag gcc ctg aga cac cca gag tgt gcc ctg cag gtg ctc      2545
Val Leu Cys Glu Ala Leu Arg His Pro Glu Cys Ala Leu Gln Val Leu
        835                 840                 845 ggg gtt gtt gca gga gta aga acc aag cag                              2575
Gly Val Val Ala Gly Val Arg Thr Lys Gln
        850                 855
```

FIG. 13E

LRR_RI_2: domain 1 of 8, from 530 to 557: score 6.4, E = 5.6
(SEQ ID NO:10) *->npsLreLdLsnNklgdeGaraLaeaLks<-*
                 + +LreL++++ +l ++      ++-L++
NBS-5    530    SGHLRELQVQDSTLSESTFVTWCNQLRH    557

FIG. 16A

LRR_RI_2: domain 2 of 8, from 615 to 642: score 5.2, E = 8.4
(SEQ ID NO:10) *->npsLreLdLsnNklgdeGaraLaeaLks<-*
                   +eL L n++l +   + +La +L+
NBS-5    615    AGNVKELALVNCHLSPIDCEVLAGLLTN    642

FIG. 16B

LRR_RI_2: domain 3 of 8, from 643 to 669: score 9.3, E = 2.2
(SEQ ID NO:10) *->npsLreLdLsnNklgdeGaraLaeaLks<-*
                   n++L  L++s+N l d G+  L+eaL s
NBS-5    643    NKKLTYLNVSCNQL-DTGVPLLCEALCS    669

FIG. 16C

LRR_RI_2: domain 4 of 8, from 699 to 726: score 32.8, E = 7.9e-06
(SEQ ID NO:10) *->npsLreLdLsnNklgdeGaraLaeaLks<-*
                   n+s  r LdLs N l deG + L+eaLk+
NBS-5    699    NKSVRYLDLSANVLKDEGLKTLCEALKH    726

FIG. 16D

LRR_RI_2: domain 5 of 8, from 728 to 755: score 10.0, E = 1.8
(SEQ ID NO:10) *->npsLreLdLsnNklgdeGaraLaeaLks<-*
                   ++L  L L  + ++++G+  La+aL s
NBS-5    728    DCCLDSLCLVKCFITAAGCEDLASALIS    755

FIG. 16E

LRR_RI_2: domain 6 of 8, from 756 to 783: score 30.9, E = 3e-05
(SEQ ID NO:10) *->npsLreLdLsnNklgdeGaraLaeaLks<-*
                   n++L+ L++++N +gd G++ L+ aL++
NBS-5    756    NQNLKILQIGCNEIGDVGVQLLCRALTH    783

FIG. 16F

LRR_RI_2: domain 7 of 8, from 785 to 812: score 8.0, E = 3.3
(SEQ ID NO:10) *->npsLreLdLsnNklgdeGaraLaeaLks<-*
                   ++L+ L L+ ++l+   ++ La++L+
NBS-5    785    DCRLEILGLEECGLTSTCCKDLASVLTC    812

FIG. 16G

LRR_RI_2: domain 8 of 8, from 813 to 840: score 17.6, E = 0.14
(SEQ ID NO:10) *->npsLreLdLsnNklgdeGaraLaeaLks<-*
                   +++L+ L+L  N+l   G+ +L+eaL++
NBS-5    813    SKFLQQLNLTLNTLDHTGVVVLCEALRH    840

FIG. 16H

```
gaattcgaat tcggggaagt tcttcagcct taacctaagg tctcatactc ggagcact         58
atg aca tcg ccc cag cta gag tgg act ctg cag acc ctt ctg gag cag        106
Met Thr Ser Pro Gln Leu Glu Trp Thr Leu Gln Thr Leu Leu Glu Gln
 1               5                  10                  15 ctg aac gag gat gaa tta aag agt ttc aaa tcc ctt tta tgg gct ttt        154
Leu Asn Glu Asp Glu Leu Lys Ser Phe Lys Ser Leu Leu Trp Ala Phe
             20                  25                  30 ccc ctc gaa gac gtg cta cag aag acc cca tgg tct gag gtg gaa gag        202
Pro Leu Glu Asp Val Leu Gln Lys Thr Pro Trp Ser Glu Val Glu Glu
         35                  40                  45 gct gat ggc aag aaa ctg gca gaa att ctg gtc aac acc tcc tca gaa        250
Ala Asp Gly Lys Lys Leu Ala Glu Ile Leu Val Asn Thr Ser Ser Glu
     50                  55                  60 aat tgg ata agg aat gcg act gtg aac atc ttg gaa gag atg aat ctc        298
Asn Trp Ile Arg Asn Ala Thr Val Asn Ile Leu Glu Glu Met Asn Leu
 65                  70                  75                  80 acg gaa ttg tgt aag atg gca aag gct gag atg atg gag gac gga cag        346
Thr Glu Leu Cys Lys Met Ala Lys Ala Glu Met Met Glu Asp Gly Gln
                 85                  90                  95 gtg caa gaa ata gat aat cct gag ctg gga gat gca gaa gaa gac tcg        394
Val Gln Glu Ile Asp Asn Pro Glu Leu Gly Asp Ala Glu Glu Asp Ser
            100                 105                 110 gag tta gca aag cca ggt gaa aag gaa gga tgg aga aat tca atg gag        442
Glu Leu Ala Lys Pro Gly Glu Lys Glu Gly Trp Arg Asn Ser Met Glu
        115                 120                 125 aaa cag tct ttg gtc tgg aag aac acc ttt tgg caa gga gac att gac        490
Lys Gln Ser Leu Val Trp Lys Asn Thr Phe Trp Gln Gly Asp Ile Asp
    130                 135                 140 aat ttc cat gac gac gtc act ctg aga aac caa cgg ttc att cca ttc        538
Asn Phe His Asp Asp Val Thr Leu Arg Asn Gln Arg Phe Ile Pro Phe
145                 150                 155                 160 ttg aat ccc aga aca ccc agg aag cta aca cct tac acg gtg gtg ctg        586
Leu Asn Pro Arg Thr Pro Arg Lys Leu Thr Pro Tyr Thr Val Val Leu
                165                 170                 175 cac ggc ccc gca ggc gtg ggg aaa acc acg ctg gcc aaa aag tgt atg        634
His Gly Pro Ala Gly Val Gly Lys Thr Thr Leu Ala Lys Lys Cys Met
            180                 185                 190 ctg gac tgg aca gac tgc aac ctc agc ccg acg ctc aga tac gcg ttc        682
Leu Asp Trp Thr Asp Cys Asn Leu Ser Pro Thr Leu Arg Tyr Ala Phe
        195                 200                 205 tac ctc agc tgc aag gag ctc agc cgc atg ggc ccc tgc agt ttt gca        730
Tyr Leu Ser Cys Lys Glu Leu Ser Arg Met Gly Pro Cys Ser Phe Ala
    210                 215                 220
```

FIG. 17A

```
gag ctg atc tcc aaa gac tgg cct gaa ttg cag gat gac att cca agc     778
Glu Leu Ile Ser Lys Asp Trp Pro Glu Leu Gln Asp Asp Ile Pro Ser
225             230                 235                 240 atc cta gcc caa gca cag aga atc ctg ttc gtg gtc gat ggc ctt gat     826
Ile Leu Ala Gln Ala Gln Arg Ile Leu Phe Val Val Asp Gly Leu Asp
                245                 250                 255 gag ctg aaa gtc cca cct ggg gcg ctg atc cag gac atc tgc ggg gac     874
Glu Leu Lys Val Pro Pro Gly Ala Leu Ile Gln Asp Ile Cys Gly Asp
                260                 265                 270 tgg gag aag aag aag ccg gtg ccc gtc ctc ctg ggg agt ttg ctg aag     922
Trp Glu Lys Lys Lys Pro Val Pro Val Leu Leu Gly Ser Leu Leu Lys
            275                 280                 285 agg aag atg tta ccc agg gca gcc ttg ctg gtc acc acg cgg ccc agg     970
Arg Lys Met Leu Pro Arg Ala Ala Leu Leu Val Thr Thr Arg Pro Arg
290                 295                 300 gca ctg agg gac ctc cag ctc ctg gcg cag cag ccg atc tac gta agg    1018
Ala Leu Arg Asp Leu Gln Leu Leu Ala Gln Gln Pro Ile Tyr Val Arg
305                 310                 315                 320 gtg gag ggc ttc ctg gag gag gac agg agg gcc tat ttc ctg aga cac    1066
Val Glu Gly Phe Leu Glu Glu Asp Arg Arg Ala Tyr Phe Leu Arg His
                325                 330                 335 ttt gga gac gag gac caa gcc atg cgt gcc ttt gag cta atg agg agc    1114
Phe Gly Asp Glu Asp Gln Ala Met Arg Ala Phe Glu Leu Met Arg Ser
                340                 345                 350 aac gcg gcc ctg ttc cag ctg ggc tcg gcc ccc gcg gtg tgc tgg att    1162
Asn Ala Ala Leu Phe Gln Leu Gly Ser Ala Pro Ala Val Cys Trp Ile
            355                 360                 365 gtg tgc acg act ctg aag ctg cag atg gag aag ggg gag gac ccg gtc    1210
Val Cys Thr Thr Leu Lys Leu Gln Met Glu Lys Gly Glu Asp Pro Val
            370                 375                 380 ccc acc tgc ctc acc cgc acg ggg ctg ttc ctg cgt ttc ctc tgc agc    1258
Pro Thr Cys Leu Thr Arg Thr Gly Leu Phe Leu Arg Phe Leu Cys Ser
385                 390                 395                 400 cgg ttc ccg cag ggc gca cag ctg cgg ggc gcg ctg cgg acg ctg agc    1306
Arg Phe Pro Gln Gly Ala Gln Leu Arg Gly Ala Leu Arg Thr Leu Ser
                405                 410                 415 ctc ctg gcc gcg cag ggc ctg tgg gcg cag atg tcc gtg ttc cac cga    1354
Leu Leu Ala Ala Gln Gly Leu Trp Ala Gln Met Ser Val Phe His Arg
                420                 425                 430 gag gac ctg gaa agg ctc ggg gtg cag gag tcc gac ctc cgt ctg ttc    1402
Glu Asp Leu Glu Arg Leu Gly Val Gln Glu Ser Asp Leu Arg Leu Phe
                435                 440                 445
```

FIG. 17B

```
ctg gac gga gac atc ctc cgc cag gac aga gtc tcc aaa ggc tgc tac    1450
Leu Asp Gly Asp Ile Leu Arg Gln Asp Arg Val Ser Lys Gly Cys Tyr
    450             455             460 tcc ttc atc cac ctc agc ttc cag cag ttt ctc act gcc ctg ttc tac    1498
Ser Phe Ile His Leu Ser Phe Gln Gln Phe Leu Thr Ala Leu Phe Tyr
465             470             475             480 gcc ctg gag aag gag gag ggg gag gac agg gac ggc cac gcc tgg gac    1546
Ala Leu Glu Lys Glu Glu Gly Glu Asp Arg Asp Gly His Ala Trp Asp
                485             490             495 atc ggg gac gta cag aag ctg ctt tcc gga gaa gaa aga ctc aag aac    1594
Ile Gly Asp Val Gln Lys Leu Leu Ser Gly Glu Glu Arg Leu Lys Asn
            500             505             510 ccc gac ctg att caa gta gga cac ttc tta ttc ggc ctc gct aac gag    1642
Pro Asp Leu Ile Gln Val Gly His Phe Leu Phe Gly Leu Ala Asn Glu
        515             520             525 aag aga gcc aag gag ttg gag gcc act ttt ggc tgc cgg atg tca ccg    1690
Lys Arg Ala Lys Glu Leu Glu Ala Thr Phe Gly Cys Arg Met Ser Pro
    530             535             540 gac atc aaa cag gaa ttg ctg caa tgc aaa gca cat ctt cat gca aat    1738
Asp Ile Lys Gln Glu Leu Leu Gln Cys Lys Ala His Leu His Ala Asn
545             550             555             560 aag ccc tta tcc gtg acc gac ctg aag gag gtc ttg ggc tgc ctg tat    1786
Lys Pro Leu Ser Val Thr Asp Leu Lys Glu Val Leu Gly Cys Leu Tyr
                565             570             575 gag tct cag gag gag gag ctg gcg aag gtg gtg gtg gcc ccg ttc aag    1834
Glu Ser Gln Glu Glu Glu Leu Ala Lys Val Val Val Ala Pro Phe Lys
            580             585             590 gaa att tct att cac ctg aca aat act tct gaa gtg atg cat tgt tcc    1882
Glu Ile Ser Ile His Leu Thr Asn Thr Ser Glu Val Met His Cys Ser
        595             600             605 ttc agc ctg aag cat tgt caa gac ttg cag aaa ctc tca ctg cag gta    1930
Phe Ser Leu Lys His Cys Gln Asp Leu Gln Lys Leu Ser Leu Gln Val
    610             615             620 gca aag ggg gtg ttc ctg gag aat tac atg gat ttt gaa ctg gac att    1978
Ala Lys Gly Val Phe Leu Glu Asn Tyr Met Asp Phe Glu Leu Asp Ile
625             630             635             640 gaa ttt gaa agg tgc act tac cta acc att ccg aac tgg gct cgg cag    2026
Glu Phe Glu Arg Cys Thr Tyr Leu Thr Ile Pro Asn Trp Ala Arg Gln
                645             650             655 gat ctt cgc tct ctt cgc ctc tgg aca gat ttc tgc tct ctc ttc agc    2074
Asp Leu Arg Ser Leu Arg Leu Trp Thr Asp Phe Cys Ser Leu Phe Ser
            660             665             670
```

FIG. 17C

```
tca aac agc aac ctc aag ttt ctg gaa gtg aaa caa agc ttc ctg agt         2122
Ser Asn Ser Asn Leu Lys Phe Leu Glu Val Lys Gln Ser Phe Leu Ser
            675                 680                 685 gac tct tct gtg cgg att ctt tgt gac cac gta acc cgt agc acc tgt         2170
Asp Ser Ser Val Arg Ile Leu Cys Asp His Val Thr Arg Ser Thr Cys
            690                 695                 700 cat ctg cag aaa gtg gag att aaa aac gtc acc cct gac acc gcg tac         2218
His Leu Gln Lys Val Glu Ile Lys Asn Val Thr Pro Asp Thr Ala Tyr
705                 710                 715                 720 cgg gac ttc tgt ctt gct ttc att ggg aag aag acc ctc acg cac ctg         2266
Arg Asp Phe Cys Leu Ala Phe Ile Gly Lys Lys Thr Leu Thr His Leu
            725                 730                 735 acc ctg gca ggg cac atc gag tgg gaa cgc acg atg atg ctg atg ctg         2314
Thr Leu Ala Gly His Ile Glu Trp Glu Arg Thr Met Met Leu Met Leu
            740                 745                 750 tgt gac ctg ctc aga aat cat aaa tgc aac ctg cag tac ctg agg ttg         2362
Cys Asp Leu Leu Arg Asn His Lys Cys Asn Leu Gln Tyr Leu Arg Leu
            755                 760                 765 gga ggt cac tgt gcc acc ccg gag cag tgg gct gaa ttc ttc tat gtc         2410
Gly Gly His Cys Ala Thr Pro Glu Gln Trp Ala Glu Phe Phe Tyr Val
            770                 775                 780 ctc aaa gcc aac cag tcc ctg aag cac ctg cgt ctc tca gcc aat gtg         2458
Leu Lys Ala Asn Gln Ser Leu Lys His Leu Arg Leu Ser Ala Asn Val
785                 790                 795                 800 ctc ctg gat gag ggt gcc atg ttg ctg tac aag acc atg aca cgc cca         2506
Leu Leu Asp Glu Gly Ala Met Leu Leu Tyr Lys Thr Met Thr Arg Pro
            805                 810                 815 aaa cac ttc ctg cag atg ttg tcg ttg gaa aac tgt cgt ctt aca gaa         2554
Lys His Phe Leu Gln Met Leu Ser Leu Glu Asn Cys Arg Leu Thr Glu
            820                 825                 830 gcc agt tgc aag gac ctt gct gct gtc ttg gtt gtc agc aag aag ctg         2602
Ala Ser Cys Lys Asp Leu Ala Ala Val Leu Val Val Ser Lys Lys Leu
            835                 840                 845 aca cac ctg tgc ttg gcc aag aac ccc att ggg gat aca ggg gtg aag         2650
Thr His Leu Cys Leu Ala Lys Asn Pro Ile Gly Asp Thr Gly Val Lys
850                 855                 860 ttt ctg tgt gag ggc ttg agt tac cct gat tgt aaa ctg cag acc ttg         2698
Phe Leu Cys Glu Gly Leu Ser Tyr Pro Asp Cys Lys Leu Gln Thr Leu
865                 870                 875                 880 gtg tta cag caa tgc agc ata acc aag ctt ggc tgt aga tat ctc tca         2746
Val Leu Gln Gln Cys Ser Ile Thr Lys Leu Gly Cys Arg Tyr Leu Ser
            885                 890                 895
```

FIG. 17D

```
gag gcg ctc caa gaa gcc tgc agc ctc aca aac ctg gac ttg agt atc        2794
Glu Ala Leu Gln Glu Ala Cys Ser Leu Thr Asn Leu Asp Leu Ser Ile
            900                 905                 910 aac cag ata gct cgt gga ttg tgg att ctc tgt cag gca tta gag aat        2842
Asn Gln Ile Ala Arg Gly Leu Trp Ile Leu Cys Gln Ala Leu Glu Asn
            915                 920                 925 cca aac tgt aac cta aaa cac cta cgg ttg aag acc tat gaa act aat        2890
Pro Asn Cys Asn Leu Lys His Leu Arg Leu Lys Thr Tyr Glu Thr Asn
        930                 935                 940 ttg gaa atc aag aag ctg ttg gag gaa gtg aaa gaa aag aat ccc aag        2938
Leu Glu Ile Lys Lys Leu Leu Glu Glu Val Lys Glu Lys Asn Pro Lys
945                 950                 955                 960 ctg act att gat tgc aat gct tcc ggg gca acg gca cct ccg tgc tgt        2986
Leu Thr Ile Asp Cys Asn Ala Ser Gly Ala Thr Ala Pro Pro Cys Cys
                965                 970                 975 gac ttt ttt tgc tgagcagcct gggatcgctc tacgaattac acaggaagcg           3038
Asp Phe Phe Cys
            980 ggattcgggt ctctaagatg tcttatgaat gcaggtcaga gggtcacatg ttaacactag      3098
agtctgtcga gaggtaggat ttgacactgg ttttctcact attttggga gattctgcac      3158
gagtcacgca ccccttcac atgacgctat gtactttctc acagggataa taaagttaga      3218
gcactctcaa aaaaaaaaaa aaaaaaaaaa aaaaaaaaaa aaaaa                      3263
```

FIG. 17E

```
atg gca gaa tcg gat tct act gac ttt gac ctg ctg tgg tat cta gag      48
Met Ala Glu Ser Asp Ser Thr Asp Phe Asp Leu Leu Trp Tyr Leu Glu
 1               5                  10                  15 aat ctc agt gac aag gaa ttt cag agt ttt aag aag tat ctg gca cgc      96
Asn Leu Ser Asp Lys Glu Phe Gln Ser Phe Lys Lys Tyr Leu Ala Arg
            20                  25                  30 aag att ctt gat ttc aaa ctg cca cag ttt cca ctg ata cag atg aca     144
Lys Ile Leu Asp Phe Lys Leu Pro Gln Phe Pro Leu Ile Gln Met Thr
        35                  40                  45 aaa gaa gaa ctg gct aac gtg ttg cca atc tct tat gag gga cag tat     192
Lys Glu Glu Leu Ala Asn Val Leu Pro Ile Ser Tyr Glu Gly Gln Tyr
50                  55                  60 ata tgg aat atg ctc ttc agc ata ttt tca atg atg cgt aag gaa gat     240
Ile Trp Asn Met Leu Phe Ser Ile Phe Ser Met Met Arg Lys Glu Asp
65                  70                  75                  80 ctt tgt agg aag atc att ggc aga cga aac cat gtg ttc tac ata ctt     288
Leu Cys Arg Lys Ile Ile Gly Arg Arg Asn His Val Phe Tyr Ile Leu
                85                  90                  95 caa tta gcc tat gat tct acc agc tat tat tca gca aac aat ctc aat     336
Gln Leu Ala Tyr Asp Ser Thr Ser Tyr Tyr Ser Ala Asn Asn Leu Asn
            100                 105                 110 gtg ttc ctg atg gga gag aga gca tct gga aaa act att gtt ata aat     384
Val Phe Leu Met Gly Glu Arg Ala Ser Gly Lys Thr Ile Val Ile Asn
        115                 120                 125 ctg gct gtg ttg agg tgg atc aag ggt gag atg tgg cag aac atg atc     432
Leu Ala Val Leu Arg Trp Ile Lys Gly Glu Met Trp Gln Asn Met Ile
130                 135                 140 tcg tac gtc gtt cac ctc act tct cac gaa ata aac cag atg acc aac     480
Ser Tyr Val Val His Leu Thr Ser His Glu Ile Asn Gln Met Thr Asn
145                 150                 155                 160 agc agc ttg gct gag cta atc gcc aag gac tgg cct gac ggc cag gct     528
Ser Ser Leu Ala Glu Leu Ile Ala Lys Asp Trp Pro Asp Gly Gln Ala
                165                 170                 175 ccc att gca gac atc ctg tct gat ccc aag aaa ctc ctt ttc att ctc     576
Pro Ile Ala Asp Ile Leu Ser Asp Pro Lys Lys Leu Leu Phe Ile Leu
            180                 185                 190 gag gac ttg gac aac ata aga ttc gag tta aat gtc aat gaa agt gct     624
Glu Asp Leu Asp Asn Ile Arg Phe Glu Leu Asn Val Asn Glu Ser Ala
        195                 200                 205 ttg tgt agt aac agc acc cag aaa gtt ccc att cca gtt ctc ctg gtc     672
Leu Cys Ser Asn Ser Thr Gln Lys Val Pro Ile Pro Val Leu Leu Val
210                 215                 220
```

FIG. 18A

```
agt ttg ctg aag aga aaa atg gct cca ggc tgc tgg ttc ctc atc tcc    720
Ser Leu Leu Lys Arg Lys Met Ala Pro Gly Cys Trp Phe Leu Ile Ser
225                 230                 235                 240 tca agg ccc aca cgt ggg aat aat gta aaa acg ttc ttg aaa gag gta    768
Ser Arg Pro Thr Arg Gly Asn Asn Val Lys Thr Phe Leu Lys Glu Val
                245                 250                 255 gat tgc tgc acg acc ttg cag ctg tcg aat ggg aag agg gag ata tat    816
Asp Cys Cys Thr Thr Leu Gln Leu Ser Asn Gly Lys Arg Glu Ile Tyr
            260                 265                 270 ttt aac tct ttc ttt aaa gac cgc cag agg gcg tcg gca gcc ctc cag    864
Phe Asn Ser Phe Phe Lys Asp Arg Gln Arg Ala Ser Ala Ala Leu Gln
        275                 280                 285 ctt gta cat gag gat gaa ata ctc gtg ggt ctg tgc cga gtc gcc atc    912
Leu Val His Glu Asp Glu Ile Leu Val Gly Leu Cys Arg Val Ala Ile
    290                 295                 300 tta tgc tgg atc acg tgt act gtc ctg aag cgg cag atg gac aag ggg    960
Leu Cys Trp Ile Thr Cys Thr Val Leu Lys Arg Gln Met Asp Lys Gly
305                 310                 315                 320 cgt gac ttc cag ctc tgc tgc caa aca ccc act gat cta cat gcc cac   1008
Arg Asp Phe Gln Leu Cys Cys Gln Thr Pro Thr Asp Leu His Ala His
                325                 330                 335 ttt ctt gct gat gcg ttg aca tca gag gct gga ctt act gcc aat cag   1056
Phe Leu Ala Asp Ala Leu Thr Ser Glu Ala Gly Leu Thr Ala Asn Gln
            340                 345                 350 tat cac cta ggt ctc cta aaa cgt ctg tgt ttg ctg gct gca gga gga   1104
Tyr His Leu Gly Leu Leu Lys Arg Leu Cys Leu Leu Ala Ala Gly Gly
        355                 360                 365 ctg ttt ctg agc acc ctg aat ttc agt ggt gaa gac ctc aga tgt gtt   1152
Leu Phe Leu Ser Thr Leu Asn Phe Ser Gly Glu Asp Leu Arg Cys Val
370                 375                 380 ggg ttt act gag gct gat gtc tct gtg ttg cag gcc gcg aat att ctt   1200
Gly Phe Thr Glu Ala Asp Val Ser Val Leu Gln Ala Ala Asn Ile Leu
385                 390                 395                 400 ttg ccg agc aac act cat aaa gac cgt tac aag ttc ata cac ttg aac   1248
Leu Pro Ser Asn Thr His Lys Asp Arg Tyr Lys Phe Ile His Leu Asn
                405                 410                 415 gtc cag gag ttt tgt aca gcc att gca ttt ctg atg gca gta ccc aac   1296
Val Gln Glu Phe Cys Thr Ala Ile Ala Phe Leu Met Ala Val Pro Asn
            420                 425                 430 tat ctg atc ccc tca ggc agc aga gag tat aaa gag aag aga gaa caa   1344
Tyr Leu Ile Pro Ser Gly Ser Arg Glu Tyr Lys Glu Lys Arg Glu Gln
        435                 440                 445
```

FIG. 18B

```
tac tct gac ttt aat caa gtg ttt act ttc att ttt ggt ctt cta aat     1392
Tyr Ser Asp Phe Asn Gln Val Phe Thr Phe Ile Phe Gly Leu Leu Asn
    450                 455                 460 gca aac agg aga aag att ctt gag aca tcc ttt gga tac cag cta ccg     1440
Ala Asn Arg Arg Lys Ile Leu Glu Thr Ser Phe Gly Tyr Gln Leu Pro
465                 470                 475                 480 atg gta gac agc ttc aag tgg tac tcg gtg gga tac atg aaa cat ttg     1488
Met Val Asp Ser Phe Lys Trp Tyr Ser Val Gly Tyr Met Lys His Leu
                485                 490                 495 gac cgt gac ccg gaa aag ttg acg cac cat atg cct ttg ttt tac tgt     1536
Asp Arg Asp Pro Glu Lys Leu Thr His His Met Pro Leu Phe Tyr Cys
            500                 505                 510 ctc tat gag aat cgg gaa gaa gaa ttt gtg aag acg att gtg gat gct     1584
Leu Tyr Glu Asn Arg Glu Glu Glu Phe Val Lys Thr Ile Val Asp Ala
        515                 520                 525 ctc atg gag gtt aca gtt tac ctt caa tca gac aag gat atg atg gtc     1632
Leu Met Glu Val Thr Val Tyr Leu Gln Ser Asp Lys Asp Met Met Val
    530                 535                 540 tca tta tac tgt ctg gat tac tgc tgt cac ctg agg aca ctt aag ttg     1680
Ser Leu Tyr Cys Leu Asp Tyr Cys Cys His Leu Arg Thr Leu Lys Leu
545                 550                 555                 560 agt gtt cag cgc atc ttt caa aac aaa gag cca ctt ata agg cca act     1728
Ser Val Gln Arg Ile Phe Gln Asn Lys Glu Pro Leu Ile Arg Pro Thr
                565                 570                 575 gct agt caa atg aag agc ctt gtc tac tgg aga gag atc tgc tct ctt     1776
Ala Ser Gln Met Lys Ser Leu Val Tyr Trp Arg Glu Ile Cys Ser Leu
            580                 585                 590 ttt tat aca atg gag agc ctc cgg gag ctg cat atc ttt gac aat gac     1824
Phe Tyr Thr Met Glu Ser Leu Arg Glu Leu His Ile Phe Asp Asn Asp
        595                 600                 605 ctt aat ggt att tca gaa agg att ctg tct aaa gcc ctg gag cat tct     1872
Leu Asn Gly Ile Ser Glu Arg Ile Leu Ser Lys Ala Leu Glu His Ser
    610                 615                 620 agc tgt aaa ctt cgc aca ctc aag ttg tcc tat gtc tcg act gct tct     1920
Ser Cys Lys Leu Arg Thr Leu Lys Leu Ser Tyr Val Ser Thr Ala Ser
625                 630                 635                 640 ggt ttt gaa gac tta ctc aag gct ttg gct cgt aat cgg agc ctg aca     1968
Gly Phe Glu Asp Leu Leu Lys Ala Leu Ala Arg Asn Arg Ser Leu Thr
                645                 650                 655 tac ctg agt atc aac tgt acg tcc att tcc cta aat atg ttt tca ctt     2016
Tyr Leu Ser Ile Asn Cys Thr Ser Ile Ser Leu Asn Met Phe Ser Leu
            660                 665                 670
```

FIG. 18C

```
ctg cat gac atc ctg cac gag ccc aca tgc caa ata agt cat ctg agc    2064
Leu His Asp Ile Leu His Glu Pro Thr Cys Gln Ile Ser His Leu Ser
        675                 680                 685 ttg atg aaa tgt gat ttg cga gcc agc gaa tgc gaa gaa atc gcc tct    2112
Leu Met Lys Cys Asp Leu Arg Ala Ser Glu Cys Glu Glu Ile Ala Ser
        690                 695                 700 ctc ctc atc agt ggc ggg agt ctg aga aaa ctg acc tta tcc agc aat    2160
Leu Leu Ile Ser Gly Gly Ser Leu Arg Lys Leu Thr Leu Ser Ser Asn
705                 710                 715                 720 ccg ctg agg agc gac ggg atg aac ata ctg tgt gat gcc ttg ctt cat    2208
Pro Leu Arg Ser Asp Gly Met Asn Ile Leu Cys Asp Ala Leu Leu His
        725                 730                 735 ccc aac tgc act ctt ata tca ctg gtt ctg tct ggc tgt ttc ttt agc    2256
Pro Asn Cys Thr Leu Ile Ser Leu Val Leu Ser Gly Cys Phe Phe Ser
        740                 745                 750 agc gat atc tgt caa tat att gcc ata gtt att gct act aat gaa aaa    2304
Ser Asp Ile Cys Gln Tyr Ile Ala Ile Val Ile Ala Thr Asn Glu Lys
        755                 760                 765 ctg agg agc ctg gag att ggg agc aac aaa ata gaa gat gca gga atg    2352
Leu Arg Ser Leu Glu Ile Gly Ser Asn Lys Ile Glu Asp Ala Gly Met
770                 775                 780 cag ctg cta tgt ggt ggt ttg aga cat ccc aac tgc atg ttg gtg aat    2400
Gln Leu Leu Cys Gly Gly Leu Arg His Pro Asn Cys Met Leu Val Asn
785                 790                 795                 800 att ggg cta gaa gag tgc atg tta acc agt gcc tgc tgt cga tct ctt    2448
Ile Gly Leu Glu Glu Cys Met Leu Thr Ser Ala Cys Cys Arg Ser Leu
                805                 810                 815 gcc tct gtt ctt acc acc aac aaa aca cta gaa aga ctc aac ttg ctt    2496
Ala Ser Val Leu Thr Thr Asn Lys Thr Leu Glu Arg Leu Asn Leu Leu
        820                 825                 830 caa aat cac ttg ggc aat gat gga gtt gca aaa ctt ctt gag agc ttg    2544
Gln Asn His Leu Gly Asn Asp Gly Val Ala Lys Leu Leu Glu Ser Leu
        835                 840                 845 atc agc cca gat tgt gta ctt aag gta gtt ggc ttg atg gct gct gag    2592
Ile Ser Pro Asp Cys Val Leu Lys Val Val Gly Leu Met Ala Ala Glu
        850                 855                 860 aac atg gag tcc ctc att ccc agg cca gca cgc tga                    2628
Asn Met Glu Ser Leu Ile Pro Arg Pro Ala Arg
865                 870                 875
```

FIG. 18D

```
atg tat gag ttt tat att cac aaa ggt tat gat gat gtg tct tca gac      48
Met Tyr Glu Phe Tyr Ile His Lys Gly Tyr Asp Asp Val Ser Ser Asp
 1               5                  10                  15 aac agc aga gag aaa atc aaa ggt gaa ccc tct gaa tgt gag ttg ggg      96
Asn Ser Arg Glu Lys Ile Lys Gly Glu Pro Ser Glu Cys Glu Leu Gly
             20                  25                  30 cac ttc ccg cgt atc ccc tgg gca aac ttg aga gct gcc gac cct ttg     144
His Phe Pro Arg Ile Pro Trp Ala Asn Leu Arg Ala Ala Asp Pro Leu
         35                  40                  45 aat ctg tcc ttt ctt ttg gat gaa cac ttc cca aaa ggt cag gca tgg     192
Asn Leu Ser Phe Leu Leu Asp Glu His Phe Pro Lys Gly Gln Ala Trp
     50                  55                  60 aaa gtg gtc ctc ggc atc ttc cag aca atg aat ctg acc tca ctg tgt     240
Lys Val Val Leu Gly Ile Phe Gln Thr Met Asn Leu Thr Ser Leu Cys
 65                  70                  75                  80 gag aaa gtt aga gcc gag atg aaa gag aat gtg cag acc caa gag ctg     288
Glu Lys Val Arg Ala Glu Met Lys Glu Asn Val Gln Thr Gln Glu Leu
                 85                  90                  95 caa gat cca acc cag gaa gat cta gag atg cta gaa gca gca gca ggg     336
Gln Asp Pro Thr Gln Glu Asp Leu Glu Met Leu Glu Ala Ala Ala Gly
             100                 105                 110 aat atg cag acc cag gga tgc caa gat cca aac caa gaa gaa cta gac     384
Asn Met Gln Thr Gln Gly Cys Gln Asp Pro Asn Gln Glu Glu Leu Asp
         115                 120                 125 gag cta gaa gaa gaa aca ggg aat gta cag gcc cag gga tgc caa gat     432
Glu Leu Glu Glu Glu Thr Gly Asn Val Gln Ala Gln Gly Cys Gln Asp
     130                 135                 140 cca aac caa gaa gaa cca gag atg cta gag gaa gca gac cac aga aga     480
Pro Asn Gln Glu Glu Pro Glu Met Leu Glu Glu Ala Asp His Arg Arg
145                 150                 155                 160 aaa tac aga gag aac atg aag gct gaa cta ctg gag aca tgg gac aac     528
Lys Tyr Arg Glu Asn Met Lys Ala Glu Leu Leu Glu Thr Trp Asp Asn
                 165                 170                 175 atc agt tgg cct aaa gac cac gta tat atc cgt aat aca tca aag gac     576
Ile Ser Trp Pro Lys Asp His Val Tyr Ile Arg Asn Thr Ser Lys Asp
             180                 185                 190 gaa cat gag gaa ctg cag cgc cta ctg gat cct aat agg act aga gcc     624
Glu His Glu Glu Leu Gln Arg Leu Leu Asp Pro Asn Arg Thr Arg Ala
         195                 200                 205
```

FIG. 19A

```
cag gcc cag acg ata gtc ttg gtg ggg agg gca ggg gtt ggg aag acc        672
Gln Ala Gln Thr Ile Val Leu Val Gly Arg Ala Gly Val Gly Lys Thr
    210             215                 220 acc ttg gca atg cgg gct atg ctg cac tgg gca aat gga gtc ctc ttt        720
Thr Leu Ala Met Arg Ala Met Leu His Trp Ala Asn Gly Val Leu Phe
225             230                 235                 240 cag caa agg ttc tcc tat gtt ttc tat ctc agc tgc cat aaa ata agg        768
Gln Gln Arg Phe Ser Tyr Val Phe Tyr Leu Ser Cys His Lys Ile Arg
                245                 250                 255 tac atg aag gaa act acc ttt gct gaa ttg att tct ttg gat tgg ccc        816
Tyr Met Lys Glu Thr Thr Phe Ala Glu Leu Ile Ser Leu Asp Trp Pro
            260                 265                 270 gat ttt gat gcc ccc att gaa gag ttc atg tct caa cca gag aag ctc        864
Asp Phe Asp Ala Pro Ile Glu Glu Phe Met Ser Gln Pro Glu Lys Leu
        275                 280                 285 ctg ttt att att gat ggc ttt gag gaa ata atc ata tct gag tca cgc        912
Leu Phe Ile Ile Asp Gly Phe Glu Glu Ile Ile Ile Ser Glu Ser Arg
    290                 295                 300 tct gag agc ttg gat gat ggc tcg cca tgt aca gac tgg tac cag gag        960
Ser Glu Ser Leu Asp Asp Gly Ser Pro Cys Thr Asp Trp Tyr Gln Glu
305             310                 315                 320 ctc cca gtg acc aaa atc cta cac agc ttg ttg aag aaa gaa ttg gtt       1008
Leu Pro Val Thr Lys Ile Leu His Ser Leu Leu Lys Lys Glu Leu Val
                325                 330                 335 ccc ctg gct acc tta ctg atc acg atc aag acc tgg ttt gtg aga gat       1056
Pro Leu Ala Thr Leu Leu Ile Thr Ile Lys Thr Trp Phe Val Arg Asp
            340                 345                 350 ctt aag gcc tca tta gtg aat cca tgc ttt gta caa att aca ggg ttc       1104
Leu Lys Ala Ser Leu Val Asn Pro Cys Phe Val Gln Ile Thr Gly Phe
        355                 360                 365 aca ggg gac gac cta cgg gta tat ttc atg aga cac ttt gat gac tca       1152
Thr Gly Asp Asp Leu Arg Val Tyr Phe Met Arg His Phe Asp Asp Ser
    370                 375                 380 agt gaa gtt gag aaa atc ctg cag cag cta aga aaa aac gaa act ctc       1200
Ser Glu Val Glu Lys Ile Leu Gln Gln Leu Arg Lys Asn Glu Thr Leu
385             390                 395                 400 ttt cat tcc tgc agt gcc ccc atg gtg tgt tgg act gta tgt tcc tgt       1248
Phe His Ser Cys Ser Ala Pro Met Val Cys Trp Thr Val Cys Ser Cys
                405                 410                 415
```

FIG. 19B

```
ctg aag cag ccg aag gtg agg tat tac gat ctc cag tca atc act cag    1296
Leu Lys Gln Pro Lys Val Arg Tyr Tyr Asp Leu Gln Ser Ile Thr Gln
        420                 425                 430 act acc acc agt ctg tat gcc tat ttt ttc tcc aac ttg ttc tcc aca    1344
Thr Thr Thr Ser Leu Tyr Ala Tyr Phe Phe Ser Asn Leu Phe Ser Thr
        435                 440                 445 gca gag gta gat ttg gca gat gac agc tgg cca gga caa tgg agg gcc    1392
Ala Glu Val Asp Leu Ala Asp Asp Ser Trp Pro Gly Gln Trp Arg Ala
        450                 455                 460 ctc tgc agc ctg gcc ata gaa ggg ctg tgg tct atg aac ttc aca ttt    1440
Leu Cys Ser Leu Ala Ile Glu Gly Leu Trp Ser Met Asn Phe Thr Phe
465                 470                 475                 480 aac aaa gaa gac act gag att gag ggc ctg gaa gtg cct ttc att gat    1488
Asn Lys Glu Asp Thr Glu Ile Glu Gly Leu Glu Val Pro Phe Ile Asp
                485                 490                 495 tct ctc tac gag ttc aat att ctt caa aag atc aat gac tgt ggg ggt    1536
Ser Leu Tyr Glu Phe Asn Ile Leu Gln Lys Ile Asn Asp Cys Gly Gly
            500                 505                 510 tgc act act ttc acc cac cta agt ttc cag gag ttt ttt gca gcc atg    1584
Cys Thr Thr Phe Thr His Leu Ser Phe Gln Glu Phe Phe Ala Ala Met
        515                 520                 525 tcc ttt gtg cta gag gaa cct aga gaa ttc cct ccc cat tcc aca aag    1632
Ser Phe Val Leu Glu Glu Pro Arg Glu Phe Pro Pro His Ser Thr Lys
        530                 535                 540 cca caa gag atg aag atg tta ctg caa cac gtc ttg ctt gac aaa gaa    1680
Pro Gln Glu Met Lys Met Leu Leu Gln His Val Leu Leu Asp Lys Glu
545                 550                 555                 560 gcc tac tgg act cca gtg gtt ctg ttc ttc ttt ggt ctt tta aat aaa    1728
Ala Tyr Trp Thr Pro Val Val Leu Phe Phe Phe Gly Leu Leu Asn Lys
                565                 570                 575 aac ata gca aga gaa ctg gaa gat act ttg cat tgt aaa ata tct ccc    1776
Asn Ile Ala Arg Glu Leu Glu Asp Thr Leu His Cys Lys Ile Ser Pro
            580                 585                 590 agg gta atg gag gaa tta tta aag tgg gga gaa gag tta ggt aag gct    1824
Arg Val Met Glu Glu Leu Leu Lys Trp Gly Glu Glu Leu Gly Lys Ala
        595                 600                 605 gaa agt gcc tct ctc caa ttt cac att cta cga ctt ttt cac tgc cta    1872
Glu Ser Ala Ser Leu Gln Phe His Ile Leu Arg Leu Phe His Cys Leu
610                 615                 620
```

FIG. 19C

```
cac gag tcc cag gag gaa gac ttc aca aag aag atg ttg ggt cgt atc    1920
His Glu Ser Gln Glu Glu Asp Phe Thr Lys Lys Met Leu Gly Arg Ile
625                 630                 635                 640 ttt gaa gtt gac ctt aat att ttg gag gac gaa gaa ctc caa gct tct    1968
Phe Glu Val Asp Leu Asn Ile Leu Glu Asp Glu Glu Leu Gln Ala Ser
                645                 650                 655 tca ttt tgc cta aag cac tgt aaa agg tta aat aag cta agg ctt tct    2016
Ser Phe Cys Leu Lys His Cys Lys Arg Leu Asn Lys Leu Arg Leu Ser
            660                 665                 670 gtt agc agt cac atc ctt gaa agg gac ttg gaa att ctg gag tgc aaa    2064
Val Ser Ser His Ile Leu Glu Arg Asp Leu Glu Ile Leu Glu Cys Lys
        675                 680                 685 tcg gta act cct gag tgg gtt ctg cag gac ctc att att gcc ctt cag    2112
Ser Val Thr Pro Glu Trp Val Leu Gln Asp Leu Ile Ile Ala Leu Gln
    690                 695                 700 ggt aac agc aag ctg acc cat ctg aac ttc agc tct aac aag ctg gga    2160
Gly Asn Ser Lys Leu Thr His Leu Asn Phe Ser Ser Asn Lys Leu Gly
705                 710                 715                 720 atg act gtc ccc ctg att ctt aaa gct ttg aga cac tca gct tgc aac    2208
Met Thr Val Pro Leu Ile Leu Lys Ala Leu Arg His Ser Ala Cys Asn
                725                 730                 735 ctc aag tat ctg tgc ctg gag aaa tgc aac ttg tcg gca gcc agc tgt    2256
Leu Lys Tyr Leu Cys Leu Glu Lys Cys Asn Leu Ser Ala Ala Ser Cys
            740                 745                 750 cag gac cta gcc ttg ttt ctc acc agc atc caa cac gta act cga ttg    2304
Gln Asp Leu Ala Leu Phe Leu Thr Ser Ile Gln His Val Thr Arg Leu
        755                 760                 765 tgc ctg gga ttt aat cgg ctc caa gat gat ggc ata aag cta ttg tgt    2352
Cys Leu Gly Phe Asn Arg Leu Gln Asp Asp Gly Ile Lys Leu Leu Cys
    770                 775                 780 gcg gcc ctg act cac ccc aag tgt gcc tta gag aga ctg gag ctc tgg    2400
Ala Ala Leu Thr His Pro Lys Cys Ala Leu Glu Arg Leu Glu Leu Trp
785                 790                 795                 800 ttt tgc cag ctg gca gca ccc gct tgc aag cac ttg tca gat gct ctc    2448
Phe Cys Gln Leu Ala Ala Pro Ala Cys Lys His Leu Ser Asp Ala Leu
                805                 810                 815 ctg cag aac agg agc ctg aca cac ctg aat ctg agc aag aac agc ctg    2496
Leu Gln Asn Arg Ser Leu Thr His Leu Asn Leu Ser Lys Asn Ser Leu
            820                 825                 830
```

FIG. 19D

```
aga gac gag gga gtc aag ttc ctg tgt gag gcc ttg ggt cgc cca gat    2544
Arg Asp Glu Gly Val Lys Phe Leu Cys Glu Ala Leu Gly Arg Pro Asp
            835                 840                 845 ggt aac ctg cag agc ctg aat ttg tca ggt tgt tct ttc aca aga gag    2592
Gly Asn Leu Gln Ser Leu Asn Leu Ser Gly Cys Ser Phe Thr Arg Glu
        850                 855                 860 ggc tgt gga gag ctg gct aat gcc ctc agc cat aat cat aat gtg aaa    2640
Gly Cys Gly Glu Leu Ala Asn Ala Leu Ser His Asn His Asn Val Lys
865                 870                 875                 880 atc ttg gat ttg gga gaa aat gat ctt cag gat gat gga gtg aag cta    2688
Ile Leu Asp Leu Gly Glu Asn Asp Leu Gln Asp Asp Gly Val Lys Leu
                885                 890                 895 ctg tgt gag gct ctg aaa cca cat cgt gca ttg cac aca ctt ggg ttg    2736
Leu Cys Glu Ala Leu Lys Pro His Arg Ala Leu His Thr Leu Gly Leu
            900                 905                 910 gcg aaa tgc aat ctg aca act gct tgc tgc cag cat ctc ttc tct gtt    2784
Ala Lys Cys Asn Leu Thr Thr Ala Cys Cys Gln His Leu Phe Ser Val
        915                 920                 925 ctc agc agc agt aag agc ctg gtc aat ctg aac ctt cta ggc aat gaa    2832
Leu Ser Ser Ser Lys Ser Leu Val Asn Leu Asn Leu Leu Gly Asn Glu
930                 935                 940 ttg gat act gat ggt gtc aag atg cta tcc tct atc ctc gtg tct tta    2880
Leu Asp Thr Asp Gly Val Lys Met Leu Ser Ser Ile Leu Val Ser Leu
945                 950                 955                 960 gat tta gac ccc ttg ttc ttc gag cca ctt ccg gac tgc caa att aga    2928
Asp Leu Asp Pro Leu Phe Phe Glu Pro Leu Pro Asp Cys Gln Ile Arg
                965                 970                 975 ctt cag tta aaa gac ttt agc tcc tgg ccc ccc gtc agc ccc tcc ggt    2976
Leu Gln Leu Lys Asp Phe Ser Ser Trp Pro Pro Val Ser Pro Ser Gly
            980                 985                 990 gat gtg cag gac atg gag gta gaa tgg gac cct gtt tac agg aat aat    3024
Asp Val Gln Asp Met Glu Val Glu Trp Asp Pro Val Tyr Arg Asn Asn
        995                 1000                1005 att cag gtt aat aca aaa cca tcg taa                                3051
Ile Gln Val Asn Thr Lys Pro Ser  *
1010                1015
```

FIG. 19E

```
ccacgcgtcc ggccaaggag acctggtggc agggttgatc tcatatttct tgtgcctcaa      60
aatcccttct ctgaagtctg ccttccctgg agaagcaag atg gca gaa tcg gat        114
                                           Met Ala Glu Ser Asp
                                            1               5 tct act gac ttt gac ctg ctg tgg tat cta gag aat ctc agt gac aag        162
Ser Thr Asp Phe Asp Leu Leu Trp Tyr Leu Glu Asn Leu Ser Asp Lys
             10                  15                  20 gaa ttt cag agt ttt aag aag tat ctg gca cgc aag att ctt gat ttc        210
Glu Phe Gln Ser Phe Lys Lys Tyr Leu Ala Arg Lys Ile Leu Asp Phe
             25                  30                  35 aaa ctg cca cag ttt cca ctg ata cag atg aca aaa gaa gaa ctg gct        258
Lys Leu Pro Gln Phe Pro Leu Ile Gln Met Thr Lys Glu Glu Leu Ala
             40                  45                  50 aac gtg ttg cca atc tct tat gag gga cag tat ata tgg aat atg ctc        306
Asn Val Leu Pro Ile Ser Tyr Glu Gly Gln Tyr Ile Trp Asn Met Leu
 55                  60                  65 ttc agc ata ttt tca atg atg cgt aag gaa gat ctt tgt agg aag atc        354
Phe Ser Ile Phe Ser Met Met Arg Lys Glu Asp Leu Cys Arg Lys Ile
 70                  75                  80                  85 att ggc aga cga aac cgc aat cag gag gca tgc aaa gct gtc atg agg        402
Ile Gly Arg Arg Asn Arg Asn Gln Glu Ala Cys Lys Ala Val Met Arg
             90                  95                 100 aga aaa ttc atg ctg caa tgg gaa agt cac act ttt gga aaa ttt cat        450
Arg Lys Phe Met Leu Gln Trp Glu Ser His Thr Phe Gly Lys Phe His
            105                 110                 115 tat aaa ttt ttt cgt gac gtt tcg tca gat gtg ttc tac ata ctt caa        498
Tyr Lys Phe Phe Arg Asp Val Ser Ser Asp Val Phe Tyr Ile Leu Gln
            120                 125                 130 tta gcc tat gat tct acc agc tat tat tca gca aac aat ctc aat gtg        546
Leu Ala Tyr Asp Ser Thr Ser Tyr Tyr Ser Ala Asn Asn Leu Asn Val
            135                 140                 145 ttc ctg atg gga gag aga gca tct gga aaa act att gtt ata aat ctg        594
Phe Leu Met Gly Glu Arg Ala Ser Gly Lys Thr Ile Val Ile Asn Leu
150                 155                 160                 165 gct gtg ttg agg tgg atc aag ggt gag atg tgg cag aac atg atc tcg        642
Ala Val Leu Arg Trp Ile Lys Gly Glu Met Trp Gln Asn Met Ile Ser
            170                 175                 180 tac gtc gtt cac ctc act tct cac gaa ata aac cag atg acc aac agc        690
Tyr Val Val His Leu Thr Ser His Glu Ile Asn Gln Met Thr Asn Ser
            185                 190                 195
```

FIG. 20A

```
agc ttg gct gag cta atc gcc aag gac tgg cct gac ggc cag gct ccc      738
Ser Leu Ala Glu Leu Ile Ala Lys Asp Trp Pro Asp Gly Gln Ala Pro
        200                 205                 210 att gca gac atc ctg tct gat ccc aag aaa ctc ctt ttc atc ctc gag      786
Ile Ala Asp Ile Leu Ser Asp Pro Lys Lys Leu Leu Phe Ile Leu Glu
        215                 220                 225 gac ttg gac aac ata aga ttc gag tta aat gtc aat gaa agt gct ttg      834
Asp Leu Asp Asn Ile Arg Phe Glu Leu Asn Val Asn Glu Ser Ala Leu
230                 235                 240                 245 tgt agt aac agc acc cag aaa gtt ccc att cca gtt ctc ctg gtc agt      882
Cys Ser Asn Ser Thr Gln Lys Val Pro Ile Pro Val Leu Leu Val Ser
                250                 255                 260 ttg ctg aag aga aaa atg gct cca ggc tgc tgg ttc ctc atc tcc tca      930
Leu Leu Lys Arg Lys Met Ala Pro Gly Cys Trp Phe Leu Ile Ser Ser
                265                 270                 275 agg ccc aca cgt ggg aat aat gta aaa acg ttc ttg aaa gag gta gat      978
Arg Pro Thr Arg Gly Asn Asn Val Lys Thr Phe Leu Lys Glu Val Asp
            280                 285                 290 tgc tgc acg acc ttg cag ctg tcg aat ggg aag agg gag ata tat ttt     1026
Cys Cys Thr Thr Leu Gln Leu Ser Asn Gly Lys Arg Glu Ile Tyr Phe
295                 300                 305 aac tct ttc ttt aaa gac cgc cag agg gcg tcg gca gcc ctc cag ctt     1074
Asn Ser Phe Phe Lys Asp Arg Gln Arg Ala Ser Ala Ala Leu Gln Leu
310                 315                 320                 325 gta cat gag gat gaa ata ctc gtg ggt ctg tgc cga gtc gcc atc tta     1122
Val His Glu Asp Glu Ile Leu Val Gly Leu Cys Arg Val Ala Ile Leu
                330                 335                 340 tgc tgg atc acg tgt act gtc ctg aag cgg cag atg gac aag ggg cgt     1170
Cys Trp Ile Thr Cys Thr Val Leu Lys Arg Gln Met Asp Lys Gly Arg
                345                 350                 355 gac ttc cag ctc tgc tgc caa aca ccc act gat cta cat gcc cac ttt     1218
Asp Phe Gln Leu Cys Cys Gln Thr Pro Thr Asp Leu His Ala His Phe
            360                 365                 370 ctt gct gat gcg ttg aca tca gag gct gga ctt act gcc aat cag tat     1266
Leu Ala Asp Ala Leu Thr Ser Glu Ala Gly Leu Thr Ala Asn Gln Tyr
375                 380                 385 cac cta cgt ctc cta aaa cgt ctg tgt ttg ctg gct gca gga gga ctg     1314
His Leu Gly Leu Leu Lys Arg Leu Cys Leu Leu Ala Ala Gly Gly Leu
390                 395                 400                 405
```

FIG. 20B

```
ttt ctg agc acc ctg aat ttc agt ggt gaa gac ctc aga tgt gtt ggg    1362
Phe Leu Ser Thr Leu Asn Phe Ser Gly Glu Asp Leu Arg Cys Val Gly
            410                 415                 420 ttt act gag gct gat gtc tct gtg ttg cag gcc gcg aat att ctt ttg    1410
Phe Thr Glu Ala Asp Val Ser Val Leu Gln Ala Ala Asn Ile Leu Leu
            425                 430                 435 ccg agc aac act cat aaa gac cgt tac aag ttc ata cac ttg aac gtc    1458
Pro Ser Asn Thr His Lys Asp Arg Tyr Lys Phe Ile His Leu Asn Val
            440                 445                 450 cag gag ttt tgt aca gcc att gca ttt ctg atg gca gta ccc aac tat    1506
Gln Glu Phe Cys Thr Ala Ile Ala Phe Leu Met Ala Val Pro Asn Tyr
            455                 460                 465 ctg atc ccc tca ggc agc aga gag tat aaa gag aag aga gaa caa tac    1554
Leu Ile Pro Ser Gly Ser Arg Glu Tyr Lys Glu Lys Arg Glu Gln Tyr
470                 475                 480                 485 tct gac ttt aat caa gtg ttt act ttc att ttt ggt ctt cta aat gca    1602
Ser Asp Phe Asn Gln Val Phe Thr Phe Ile Phe Gly Leu Leu Asn Ala
            490                 495                 500 aac agg aga aag att ctt gag aca tcc ttt gga tac cag cta ccg atg    1650
Asn Arg Arg Lys Ile Leu Glu Thr Ser Phe Gly Tyr Gln Leu Pro Met
            505                 510                 515 gta gac agc ttc aag tgg tac tcg gtg gga tac atg aaa cat ttg gac    1698
Val Asp Ser Phe Lys Trp Tyr Ser Val Gly Tyr Met Lys His Leu Asp
            520                 525                 530 cgt gac ccg gaa aag ttg acg cac cat atg cct ttg ttt tac tgt ctc    1746
Arg Asp Pro Glu Lys Leu Thr His His Met Pro Leu Phe Tyr Cys Leu
535                 540                 545 tat gag aat cgg gaa gaa gaa ttt gtg aag acg att gtg gat gct ctc    1794
Tyr Glu Asn Arg Glu Glu Glu Phe Val Lys Thr Ile Val Asp Ala Leu
550                 555                 560                 565 atg gag gtt aca gtt tac ctt caa tca gac aag gat atg atg gtc tca    1842
Met Glu Val Thr Val Tyr Leu Gln Ser Asp Lys Asp Met Met Val Ser
            570                 575                 580 tta tac tgt ctg gat tac tgc tgt cac ctg agg aca ctt aag ttg agc    1890
Leu Tyr Cys Leu Asp Tyr Cys Cys His Leu Arg Thr Leu Lys Leu Ser
            585                 590                 595 gtt cag cgc atc ttt caa aac aaa gag cca ctt ata agg cca act gct    1938
Val Gln Arg Ile Phe Gln Asn Lys Glu Pro Leu Ile Arg Pro Thr Ala
            600                 605                 610
```

FIG. 20C

```
agt caa atg aag agc ctt gtc tac tgg aga gag atc tgc tct ctt ttt    1986
Ser Gln Met Lys Ser Leu Val Tyr Trp Arg Glu Ile Cys Ser Leu Phe
    615             620             625 tat aca atg gag agc ctc cgg gag ctg cat atc ttt gac aat gac ctt    2034
Tyr Thr Met Glu Ser Leu Arg Glu Leu His Ile Phe Asp Asn Asp Leu
630             635             640             645 aat ggt att tca gaa agg att ctg tct aaa gcc ctg gag cat tct agc    2082
Asn Gly Ile Ser Glu Arg Ile Leu Ser Lys Ala Leu Glu His Ser Ser
            650             655             660 tgt aaa ctt cgc aca ctc aag ttg tcc tat gtc tcg act gct tct ggt    2130
Cys Lys Leu Arg Thr Leu Lys Leu Ser Tyr Val Ser Thr Ala Ser Gly
        665             670             675 ttt gaa gac tta ctc aag gct ttg gct cgt aat cgg agc ctg aca tac    2178
Phe Glu Asp Leu Leu Lys Ala Leu Ala Arg Asn Arg Ser Leu Thr Tyr
    680             685             690 ctg agt atc aac tgt acg tcc att tcc cta aat atg ttt tca ctt ctg    2226
Leu Ser Ile Asn Cys Thr Ser Ile Ser Leu Asn Met Phe Ser Leu Leu
695             700             705 cat gac atc ctg cac gag ccc aca tgc caa ata agt cat ctg agc ttg    2274
His Asp Ile Leu His Glu Pro Thr Cys Gln Ile Ser His Leu Ser Leu
710             715             720             725 atg aaa tgt gat ttg cga gcc agc gaa tgc gaa gaa atc gcc tct ctc    2322
Met Lys Cys Asp Leu Arg Ala Ser Glu Cys Glu Glu Ile Ala Ser Leu
        730             735             740 ctc atc agt ggc ggg agt ctg aga aaa ctg acc tta tcc agc aat ccg    2370
Leu Ile Ser Gly Gly Ser Leu Arg Lys Leu Thr Leu Ser Ser Asn Pro
    745             750             755 ctg agg agc gac ggg atg aac ata ctg tgt gat gcc ttg ctt cat ccc    2418
Leu Arg Ser Asp Gly Met Asn Ile Leu Cys Asp Ala Leu Leu His Pro
760             765             770 aac tgc act ctt ata tca ctg gtg tta gtc ttc tgc tgt ctc act gaa    2466
Asn Cys Thr Leu Ile Ser Leu Val Leu Val Phe Cys Cys Leu Thr Glu
775             780             785 aat tgc tgc agc gcc ctt gga aga gtg ctt ctg ttc agc cca act cta    2514
Asn Cys Cys Ser Ala Leu Gly Arg Val Leu Leu Phe Ser Pro Thr Leu
790             795             800             805 aga caa cta gac ctg tgt gtg aat cgc tta aaa aat tac gga gtg ttg    2562
Arg Gln Leu Asp Leu Cys Val Asn Arg Leu Lys Asn Tyr Gly Val Leu
            810             815             820
```

FIG. 20D

```
cat gtg acg ttt ccc ttg ctg ttt cca acc tgt cag tta gag gag ctt      2610
His Val Thr Phe Pro Leu Leu Phe Pro Thr Cys Gln Leu Glu Glu Leu
            825                 830                 835 cat ctg tct ggc tgt ttc ttt agc agc gat atc tgt caa tat att gcc      2658
His Leu Ser Gly Cys Phe Phe Ser Ser Asp Ile Cys Gln Tyr Ile Ala
            840                 845                 850 ata gtt att gct act aat gaa aaa ctg agg agc ctg gag att ggg agc      2706
Ile Val Ile Ala Thr Asn Glu Lys Leu Arg Ser Leu Glu Ile Gly Ser
            855                 860                 865 aac aaa ata gaa gat gca gga atg cag ctg cta tgt ggt ggt ttg aga      2754
Asn Lys Ile Glu Asp Ala Gly Met Gln Leu Leu Cys Gly Gly Leu Arg
870                 875                 880                 885 cat ccc aac tgc atg ttg gtg aat att ggg cta gaa gag tgc atg tta      2802
His Pro Asn Cys Met Leu Val Asn Ile Gly Leu Glu Glu Cys Met Leu
                890                 895                 900 acc agt gcc tgc tgt cga tct ctt gcc tct gtt ctt acc acc aac aaa      2850
Thr Ser Ala Cys Cys Arg Ser Leu Ala Ser Val Leu Thr Thr Asn Lys
            905                 910                 915 aca cta gaa aga ctc aac ttg ctt caa aat cac ttg ggc aat gat gga      2898
Thr Leu Glu Arg Leu Asn Leu Leu Gln Asn His Leu Gly Asn Asp Gly
            920                 925                 930 gtt gca aaa ctt ctt gag agc ttg atc agc cca gat tgt gta ctt aag      2946
Val Ala Lys Leu Leu Glu Ser Leu Ile Ser Pro Asp Cys Val Leu Lys
            935                 940                 945 gta gtt ggg ctt cca tta act ggc ctg aac aca caa acc cag cag ttg      2994
Val Val Gly Leu Pro Leu Thr Gly Leu Asn Thr Gln Thr Gln Gln Leu
950                 955                 960                 965 ctg atg act gta aag gaa aga aaa ccc agt ttg atc ttt ctg tct gaa      3042
Leu Met Thr Val Lys Glu Arg Lys Pro Ser Leu Ile Phe Leu Ser Glu
            970                 975                 980 act tgg tct tta aag gaa ggc aga gaa att ggt gtg aca cct gct tct      3090
Thr Trp Ser Leu Lys Glu Gly Arg Glu Ile Gly Val Thr Pro Ala Ser
            985                 990                 995 cag cca ggt tca ata ata cct aat tct aat ttg gat tac atg ttt ttc      3138
Gln Pro Gly Ser Ile Ile Pro Asn Ser Asn Leu Asp Tyr Met Phe Phe
            1000                1005                1010 aaa ttt ccc aga atg tct gca gcc atg aga acg tca aat aca gca tct      3186
Lys Phe Pro Arg Met Ser Ala Ala Met Arg Thr Ser Asn Thr Ala Ser
            1015                1020                1025
```

FIG. 20E

```
agg caa ccc ctt tgatcatgtt gtacgtaaac agtatttatt ataaattact         3238
Arg Gln Pro Leu
1030 accgtgactg ggatgcaaga gaattaggac tataattttc ctatttgatg tgtgtgtgtg    3298
tgtgtgtgtg tgtgtgtgtg tgtgtgtgtg tgtgtgacct tgatccagtc aaccacttca    3358
aattcctaca ctgtctcaag agtattaaaa ggattatatg aagtaataaa ggataaaatg    3418
cattggaaaa aaaaaaaaaa a                                              3439
```

FIG. 20F

MOLECULES OF THE NBS/LRR PROTEIN FAMILY AND USES THEREOF

RELATED APPLICATION INFORMATION

This application is a continuation-in-part of application Ser. No. 09/986,224, filed Oct. 22, 2001, now abandoned, which is a continuation-in-part of application Ser. No. 09/848,035, filed May 3, 2001, now abandoned, which claims priority from provisional application Ser. No. 60/201, 464 filed May 3, 2000. The entire content of each of these applications is herein incorporated by reference.

BACKGROUND OF THE INVENTION

Many cytoplasmic plant proteins involved in plant resistance to pathogens, generally referred to as "R" proteins, possess both a nucleotide binding site (NBS) and a leucine rich repeat (LRR). R proteins are involved in both a rapid defense response (hypersensitive response) and more long-term nonspecific resistance (systemic acquired resistance). The hypersensitive response involves a form of programmed death localized to the site of infection and changes in gene expression that are thought to prevent further infection. The LRR of the R proteins is believed to recognize and bind to pathogen-derived proteins, triggering the defensive responses and resulting in a rapid and localized host cell death. Many R proteins have an amino terminal effector domain (e.g., a TIR domain or a leucine zipper domain) that is thought to play a role in downstream signaling of events triggered by infection and, possibly, other stresses.

The R proteins are structurally similar to APAF-1, which mediates the activation of caspases, the proteases directly responsible for the degradation of cellular proteins that leads to the morphological changes seen in cells undergoing apoptosis. A domain, designated the NB-ARC domain ("nucleotide-binding adaptor shared by APAF-1, certain R gene products and CED-4"), contains a series of motifs and residues that are conserved among plant resistance proteins (e.g., R proteins) and regulators of cell death (e.g., APAF-1 and CED-4) (van der Bizen and Jones (1999) Current Biology 8:226–228). In addition to the NBS, APAF-1 has a CARD domain, functionally analogous to the effector domain of R proteins, and a WD-40 domain, functionally analogous to the LRR domain of R proteins.

The mechanisms that mediate apoptosis have been intensively studied. These mechanisms involve the activation of endogenous proteases, loss of mitochondrial function, and structural changes such as disruption of the cytoskeleton, cell shrinkage, membrane blebbing, and nuclear condensation due to degradation of DNA.

The various signals that trigger apoptosis are thought to bring about these events by converging on a common cell death pathway, the core components of which are highly conserved from worms, such as *C. elegans*, to humans. In fact, invertebrate model systems have been invaluable tools in identifying and characterizing the genes that control apoptosis. Despite this conservation of certain core components, apoptotic signaling in mammals is much more complex than in invertebrates. For example, in mammals there are multiple homologues of the core components in the cell death signaling pathway.

Caspases, a class of proteins central to the apoptotic program, are responsible for the degradation of cellular proteins that leads to the morphological changes seen in cells undergoing apoptosis. Caspases (cysteinyl aspartate-specific proteinases) are cysteine proteases having specificity for aspartate at the substrate cleavage site. Generally, caspases are classified as either initiator caspases or effector caspases, both of which are zymogens that are activated by proteolysis that generates an active species. An effector caspase is activated by an initiator caspase which cleaves the effector caspase. Initiator caspases are activated by an autoproteolytic mechanism that is often dependent upon oligomerization directed by association of the caspase with an adapter molecule.

CARD-4 is a member of the CED-4/Apaf-1 family that interacts with RICK, a serine threonine kinase, and induces NF-κB via the signaling protein TRAF-6 and NIK (Bertin et al. (1999) J. Biol. Chem. 274:12955). CARD-4 includes domains that are similar to the nucleotide binding site domain (NBS) and leucine rich repeat (LRR) domains found in plant R proteins that mediate resistance to pathogens.

SUMMARY OF THE INVENTION

The invention features nucleic acid molecules encoding human NBS-2, human NBS-3, human PYRIN-12/NBS-4, and human NBS-5. Each of NBS-2, NBS-3, PYRIN-12/NBS-4, and NBS-5 has a nucleotide binding site (NBS) domain, which is present in a number of proteins that transmit signals which activate apoptotic and inflammatory pathways in response to stress and other stimuli. NBS-2, NBS-3, PYRIN-12/NBS-4, and NBS-5 each contain a leucine rich repeat domain (LRR) domain, another domain present in a number of proteins involved in apoptotic and inflammatory pathways. NBS-2, NBS-3, and PYRIN-12/NBS-4 each contain a pyrin domain, so-named for its homology to a portion of pyrin (marenostrin). Mutations in the pyrin gene are associated with familial Mediterranean fever (FMF), an inherited inflammatory disease. The predicted cDNA described herein encoding NBS-5 is truncated in the homologous regions of NBS-2, NBS-3, and PYRIN-12/NBS-4 that encode a pyrin domain. The full length NBS-5 cDNA is predicted to encode a pyrin domain.

NBS-2, NBS-3, PYRIN-12/NBS-4, and NBS-5 nucleic acids and polypeptides, as well as modulators of NBS-2, NBS-3, PYRIN-12/NBS-4, or NBS-5 activity or expression, are expected to be useful in the modulation of stress-related, apoptotic and inflammatory responses, e.g., for the treatment of apoptotic and inflammatory disorders. In addition, NBS-2, NBS-3, PYRIN-12/NBS-4, and NBS-5 nucleic acids and polypeptides are expected to be useful in the diagnosis of apoptotic and inflammatory disorders as well as in screening assays which can be used to identify compounds which can be used to modulate stress-related, apoptotic and inflammatory responses.

CARD-4, CARD-7, and CARD-12 have both an NBS domain and an LRR domain as well as a CARD domain (detailed information concerning CARD-4, CARD-7, and CARD-12 can be found in U.S. application Ser. No. 09/245, 281, filed Feb. 5, 1999, U.S. application Ser. No. 09/207, 359, filed Dec. 8, 1998, U.S. application Ser. No. 09/099, 041, filed Jun. 17, 1998, U.S. application Ser. No. 09/019, 942, filed Feb. 6, 1998, U.S. application Ser. No. 09/428, 252, filed Oct. 27, 1999, U.S. application Ser. No. 60/161, 822, filed Oct. 27, 1999, and U.S. application Ser. No. 09/841,739, filed Apr. 24, 2001, all of which are incorporated herein by reference). The CARD domain, which is present in a number of apoptotic signaling molecules, is an effector domain that is thought to be involved in homophilic protein—protein interactions, e.g., with downstream CARD-containing signaling molecules. For example, the CARD domain of CARD-4 interacts with the CARD domain of RICK (RIP2, CARDIAK), a serine-threonine kinase that activates NF-κB signaling pathways.

NBS-1 and Pyrin-1 have both a NBS domain and a LRR domain, as well as a pyrin domain. As described herein, the pyrin domain is an effector domain thought to be involved in homophilic protein—protein interactions. Detailed information concerning NBS-1 and Pyrin-1 can be found in U.S. application Ser. No. 09/506,067, filed Feb. 17, 2000, and U.S. application Ser. No. 09/506,067, filed Sep. 1, 2000, both of which are incorporated herein by reference.

In general, an NBS domain includes a kinase 1a domain (P-loop), a kinase 2 domain (Walker B box) and a kinase 3a domain. NBS-2, NBS-3, PYRIN-12/NBS-4, and NBS-5 belong to the NACHT (NAIP, CIIA, HET-E and TP1) subfamily of NBS-domain containing proteins. Members of the NACHT subfamily contain additional motifs common among subfamily members (see, e.g., Koonin et al. (2000) Trends Biochem. Sci. 25:223). NACHT NTPase subfamily members have been implicated in apoptosis and MHC transcription activation. Other members of the NACHT NTPase subfamily include CARD-4, CARD-7, and NAIP.

An LRR domain usually is composed of several leucine rich repeats.

Without being bound by a particular theory, it is possible that the LRR domain of NBS-2, NBS-3, or PYRIN-12/NBS-4 interacts with an upstream signaling molecule that is associated with stress, infection, and/or inflammation. This interaction triggers a conformational change in NBS-2, NBS-3, or PYRIN-12/NBS-4 that exposes an effector domain, e.g., the pyrin domain of NBS-2, NBS-3, or PYRIN-12/NBS-4. The exposed effector domain then mediates interaction with a downstream signaling molecule or molecules to transmit a stress-related, apoptotic or inflammatory signal. In this model, the conformational change is dependent upon hydrolysis of a nucleotide triphosphate (ATP or GTP) bound to the NBS domain. Based on this model, full-length NBS-5 is expected to include an N-terminal effector domain (e.g., a pyrin domain) and act in a similar manner.

NBS-2, NBS-3, PYRIN-12/NBS-4, and NBS-5 molecules are useful as modulating agents in regulating a variety of cellular processes including cell growth and cell death. In one aspect, this invention provides isolated nucleic acid molecules encoding NBS-2, NBS-3, PYRIN-12/NBS-4, or NBS-5 proteins or biologically active portions thereof, as well as nucleic acid fragments suitable as primers or hybridization probes for the detection of NBS-2, NBS-3, PYRIN-12/NBS-4, or NBS-5 encoding nucleic acids.

NBS-2, NBS-3, PYRIN-12/NBS-4, or NBS-5 polypeptides, nucleic acids and modulators of NBS-2, NBS-3, PYRIN-12/NBS-4, or NBS-5 expression or activity can be used to treat inflammatory disorders and immune system disorders. The inflammatory and immune disorders include, but are not limited to, chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis), certain viral infections, including HIV, and bacterial infections, including tuberculosis and lepromatous leprosy.

Ischemia is often accompanied by inflammation that causes cell death. Because NBS-2, NBS-3, PYRIN-12/NBS-4, and NBS-5 are expected to play a role in stress-related response, inflammation and apoptosis, NBS-2, NBS-3, PYRIN-12/NBS-4, or NBS-5 polypeptides, nucleic acids, and modulators of NBS-2, NBS-3, PYRIN-12/NBS-4, or NBS-5 expression or activity can be used to treat cell death accompanying inflammatory responses triggered by ischemia.

Invasive infection with Gram-negative bacteria and Gram-positive bacteria often results in septic shock. NBS-2, NBS-3, PYRIN-12/NBS-4, and NBS-5 may recognize and bind components of Gram-negative bacteria and Gram-positive bacteria or other infectious agents (e.g., intracellular parasites), triggering an inflammatory response. Thus, NBS-2, NBS-3, PYRIN-12/NBS-4, and NBS-5 may play a role in innate immune system responses that is similar to that of Toll-like receptor 2 (TLR2), a receptor which has some structural similarity to plant R proteins and IL-1R. TLR2 is a signaling receptor that, in association with CD 14, is activated by LPS in a response that requires LPS-binding protein. The interaction of TLR2 with LPS leads to TLR2 oligomerization and recruitment of IRAK (Yang et al. (1998) Nature 395:284–88; Yang et al (1999) J. Immunol. 163:639–43; and Yoshimura et al. (1999) J. Immunol. 163: 105). Thus, TLR2 is thought to be a direct mediator of signaling by LPS. TLR2 is also thought to mediate cell activation induced by peptidoglycan and lipoteichoic acid, the main stimulatory components of Gram-positive bacteria (Schwandner et al. (1999) J. Biol. Chem. 274:17406–09).

In addition to the aforementioned disorders, NBS-2, NBS-3, PYRIN-12/NBS-4, or NBS-5 polypeptides, nucleic acids, and modulators of NBS-2, NBS-3, PYRIN-12/NBS-4, or NBS-5 expression or activity can be used to treat septic shock and other disorders associated with an innate immune response. For example, NBS-2, NBS-3, PYRIN-12/NBS-4, or NBS-5 may bind to a component of an intracellular infectious agent or a component of an infectious agent that is brought into a cell expressing NBS-2, NBS-3, PYRIN-12/NBS-4, or NBS-5, e.g., a component that enters a cell through a receptor or is expressed by a viral gene.

The invention encompasses methods of diagnosing and treating patients who are suffering from a disorder associated with an abnormal level or rate (undesirably high or undesirably low) of apoptotic cell death, abnormal activity of stress-related pathways of the endoplasmic reticulum (ER), abnormal activity of the Fas/APO-1 receptor complex, abnormal activity of the TNF receptor complex, or abnormal activity of a caspase by administering a compound that modulates the expression of NBS-2, NBS-3, PYRIN-12/NBS-4, or NBS-5 (at the DNA, mRNA or protein level, e.g., by altering mRNA splicing) or by altering the activity of NBS-2, NBS-3, PYRIN-12/NBS-4, or NBS-5. Examples of such compounds include small molecules, antisense nucleic acid molecules, ribozymes, and polypeptides.

Certain disorders are associated with an increased number of surviving cells, which are produced and continue to survive or proliferate when apoptosis is inhibited or occurs at an undesirably low rate. NBS-2, NBS-3, PYRIN-12/NBS-4, or NBS-5 and compounds that modulate the expression or activity of NBS-2, NBS-3, PYRIN-12/NBS-4, or NBS-5 can be used to treat or diagnose such disorders. These disorders include cancer (particularly follicular lymphomas, chronic myelogenous leukemia, melanoma, colon cancer, lung carcinoma, carcinomas associated with mutations in p53, and hormone-dependent tumors such as breast cancer, prostate cancer, and ovarian cancer). Such compounds can also be used to treat infections such as infections by bacteria, fungus, parasites, or viruses (such as those caused by herpesviruses, poxviruses, and adenoviruses). Failure to remove autoimmune cells that arise during development or that develop as a result of somatic mutation during an immune response can result in autoimmune disease. Thus, an autoimmune disorder can be caused by an undesirably low level of apoptosis. Accordingly, NBS-2, NBS-3, PYRIN-12/NBS-4, or NBS-5 and modulators of NBS-2, NBS-3, PYRIN-12/NBS-4, or NBS-5 activity or expression can be used to treat autoimmune disorders (e.g., systemic lupus erythematosis, immune-mediated glomerulonephritis, and arthritis).

Many diseases are associated with an undesirably high rate of apoptosis. NBS-2, NBS-3, PYRIN-12/NBS-4, or NBS-5 and modulators of NBS-2, NBS-3, PYRIN-12/NBS-4, or NBS-5 expression or activity can be used to treat or diagnose such disorders. A wide variety of neurological diseases are characterized by the gradual loss of specific sets of neurons. Such disorders include Alzheimer's disease, Parkinson's disease, amyotrophic lateral sclerosis (ALS), retinitis pigmentosa, spinal muscular atrophy, Huntington's disease, and various forms of cerebellar degeneration. The cell loss in these diseases does not induce an inflammatory response, and apoptosis appears to be the mechanism of cell death. In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses. Two common disorders associated with cell death are myocardial infarction and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis. Additional diseases associated with an undesirably high rate of apoptosis include: ischemic and hypoxic brain injury, traumatic and excitotoxic brain damage, neuronal transplantation, acute bacterial meningitis, kidney ischemia/reperfusion injury, and liver disease. NBS-2, NBS-3, PYRIN-12/NBS-4, or NBS-5 and modulators of NBS-2, NBS-3, PYRIN-12/NBS-4, or NBS-5 may therefore be useful in treating and diagnosing these conditions.

Populations of cells are often depleted in the event of viral infection, with perhaps the most dramatic example being the cell depletion caused by the human immunodeficiency virus (HIV). Surprisingly, most T cells that die during HIV infections do not appear to be infected with HIV. Although a number of explanations have been proposed, recent evidence suggests that stimulation of the CD4 receptor results in the enhanced susceptibility of uninfected T cells to undergo apoptosis.

In addition to the aforementioned disorders, NBS-2, NBS-3, PYRIN-12/NBS-4, or NBS-5 polypeptides, nucleic acids, and modulators of NBS-2, NBS-3, PYRIN-12/NBS-4, or NBS-5 expression or activity can be used to treat disorders of cell signaling and disorders of tissues in which NBS-2, NBS-3, PYRIN-12/NBS-4, or NBS-5 is expressed.

The invention features a nucleic acid molecule which is at least 45% (or 55%, 65%, 75%, 85%, 95%, or 98%) identical to the nucleotide sequence shown in SEQ ID NO:1, SEQ ID NO:3, SEQ ID NO:5, SEQ ID NO:7, SEQ ID NO:12, SEQ ID NO:14, SEQ ID NO:15, SEQ ID NO:17, SEQ ID NO:18, SEQ ID NO:20, SEQ ID NO:21, SEQ ID NO:23, or a complement thereof.

The invention features a nucleic acid molecule which includes a fragment of at least 150 (300, 325, 350, 375, 400, 425, 450, 500, 550, 600, 650, 700, 800, 900, 1000, 1100, 1200, 1300, 1400, 1500, 1600, 1800, 2000, 2250, 2500, 2750, or 3000) nucleotides of the nucleotide sequence shown in SEQ ID NO:1, SEQ ID NO:3, SEQ ID NO:5, SEQ ID NO:7, SEQ ID NO:12, SEQ ID NO:14, SEQ ID NO:15, SEQ ID NO:17, SEQ ID NO:18, SEQ ID NO:20, SEQ ID NO:21, SEQ ID NO:23, or a complement thereof.

The invention also features a nucleic acid molecule that hybridizes to a nucleic acid molecule consisting of the nucleotide sequence of SEQ ID NO:1, SEQ ID NO:3, SEQ ID NO:5, SEQ ID NO:7, SEQ ID NO:12, SEQ ID NO:14, SEQ ID NO:15, SEQ ID NO:17, SEQ ID NO:18, SEQ ID NO:20, SEQ ID NO:21, SEQ ID NO:23, or a complement thereof, under conditions of incubation at 45° C. in 6.0×SSC followed by washing in 0.2×SSC/0.1% SDS at 65° C.

In an embodiment, a NBS-2 nucleic acid molecule has the nucleotide sequence shown in SEQ ID NO:1, SEQ ID NO:12 or SEQ ID NO:14.

Also within the invention is a nucleic acid molecule which encodes a polypeptide consisting of the amino acid sequence of SEQ ID NO:2 or SEQ ID NO:13.

Also within the invention is a nucleic acid molecule which encodes a polypeptide consisting essentially of the amino acid sequence of SEQ ID NO:2 or SEQ ID NO:13.

Also within the invention is a nucleic acid molecule which encodes a fragment of a polypeptide having the amino acid sequence of SEQ ID NO:2 or SEQ ID NO:13.

Also within the invention is a nucleic acid molecule which encodes a polypeptide consisting of a fragment of the amino acid sequence of SEQ ID NO:2 or SEQ ID NO:13, wherein the fragment comprises at least 50, 75, 100, 150, 200, 250, 300 or more contiguous amino acids of the sequence of SEQ ID NO:2 or SEQ ID NO:13.

The invention includes a nucleic acid molecule which encodes a naturally occurring allelic variant of a polypeptide comprising the amino acid sequence of SEQ ID NO:2 or SEQ ID NO:13, wherein the nucleic acid molecule hybridizes to a nucleic acid molecule consisting of SEQ ID NO:1, SEQ ID NO:12 or SEQ ID NO:14 under stringent conditions.

In general, an allelic variant of a gene will be readily identifiable as mapping to the same chromosomal location as the gene.

The invention also includes a nucleic acid molecule encoding a naturally occurring polypeptide, wherein the nucleic acid hybridizes to a nucleic acid molecule consisting of SEQ ID NO:1, SEQ ID NO:12, or SEQ ID NO:14 under stringent conditions (e.g., hybridization in 6× sodium chloride/sodium citrate (SSC) at about 60° C., followed by one or more washes in 0.2×SSC, 0.1% SDS at 65° C.), and wherein the nucleic acid encodes a polypeptide of 978–982 amino acids in length, preferably 980 amino acids. Thus, the invention encompasses a nucleic acid molecule which includes the sequence of the protein coding region of a naturally occurring mRNA (or the corresponding cDNA sequence) that is expressed in a human cell.

Also within the invention are: an isolated NBS-2 protein having an amino acid sequence that is at least about 65%, preferably 75%, 85%, 95%, or 98% identical to the amino acid sequence of SEQ ID NO:2 or SEQ ID NO:13; and an isolated NBS-2 protein having an amino acid sequence that is at least about 65%, preferably 75%, 85%, 95%, or 98% identical to the pyrin domain of SEQ ID NO:2 or SEQ ID NO:13 (e.g., about amino acid residues 8–84 of SEQ ID NO:2 or SEQ ID NO:13); an isolated NBS-2 protein having an amino acid sequence that is at least about 65%, preferably 75%, 85%, 95%, or 98% identical to the NBS domain of SEQ ID NO:2 or SEQ ID NO:13 (e.g., about amino acids 167–583 of SEQ ID NO:2 or 172–482 of SEQ ID NO:13); an isolated NBS-2 protein having an amino acid sequence that is at least about 65%, preferably 75%, 85%, 95%, or 98% identical to the kinase 1a domain of SEQ ID NO:2 or SEQ ID NO:13 (e.g., about amino acids 173–188 of SEQ ID NO:2 or 172–195 of SEQ ID NO:13); an isolated NBS-2 protein having an amino acid sequence that is at least about 65%, preferably 75%, 85%, 95%, or 98% identical to the Motif II domain of SEQ ID NO:2 or SEQ ID NO:13 (e.g., about amino acids 202–231 of SEQ ID NO:13); an isolated NBS-2 protein having an amino acid sequence that is at least about 65%, preferably 75%, 85%, 95%, or 98% identical to the kinase 2 domain of SEQ ID NO:2 or SEQ ID NO:13 (e.g., about amino acids 241–257 of SEQ ID NO:2 or 235–257 of SEQ ID NO:13); an isolated NBS-2 protein having an amino acid sequence that is at least about 65%, preferably 75%, 85%, 95%, or 98% identical to the kinase 3a domain of SEQ ID NO:2 or SEQ ID NO:13 (e.g., about amino acids 300–306 of SEQ ID NO:2 or 279–304 of SEQ ID NO:13); an isolated NBS-2 protein having an amino acid sequence that is at least about 65%, preferably 75%, 85%, 95%, or 98% identical to the Motif V domain of SEQ ID NO:2 or SEQ ID NO:13 (e.g., about amino acids 355–375 of SEQ ID NO:13); an isolated NBS-2 protein having an amino acid sequence that is at least about 65%, preferably 75%, 85%, 95%, or 98% identical to the Motif VI domain of SEQ ID NO:2 or SEQ ID NO:13 (e.g., about amino acids 437–452 of SEQ ID NO:13); an isolated NBS-2 protein having an amino acid sequence that is at least about 65%, preferably 75%, 85%, 95%, or 98% identical to the Motif VII domain of SEQ ID NO:2 or SEQ ID NO:13 (e.g., about amino acids 463–482 of SEQ ID NO:13); an isolated NBS-2 protein having an amino acid sequence that is at least about 65%, preferably 75%, 85%, 95%, or 98% identical to the LRR domain of SEQ ID NO:2 or SEQ ID NO:13 (e.g., about amino acids 629–821 of SEQ ID NO:2 or 673–929 of SEQ ID NO:13); and an isolated NBS-2 protein having an amino acid sequence that is at least about 65%, preferably 75%, 85%, 95%, or 98% identical to one or more of the leucine rich repeats of SEQ ID NO:2 or SEQ ID NO:13 (e.g., about amino acids residues 629–656, 657–684, 685–712, 715–743, 744–770, 772–799, and 800–821 of SEQ ID NO:2 or 673–702, 704–729, 730–756, 760–786, 788–815, 817–843, 845–872, 874–901, and 902–929 of SEQ ID NO:13).

In an embodiment, a NBS-3 nucleic acid molecule has the nucleotide sequence shown in SEQ ID NO:3, SEQ ID NO:15, SEQ ID NO:17, SEQ ID NO:21 or SEQ ID NO:23.

Also within the invention is a nucleic acid molecule which encodes a polypeptide consisting of the amino acid sequence of SEQ ID NO:4, SEQ ID NO:16 or SEQ ID NO:22.

Also within the invention is a nucleic acid molecule which encodes a polypeptide consisting essentially of the amino acid sequence of SEQ ID NO:4, SEQ ID NO:16 or SEQ ID NO:22.

Also within the invention is a nucleic acid molecule which encodes a fragment of a polypeptide having the amino acid sequence of SEQ ID NO:4, SEQ ID NO:16 or SEQ ID NO:22.

Also within the invention is a nucleic acid molecule which encodes a polypeptide consisting of a fragment of the amino acid sequence of SEQ ID NO:4, SEQ ID NO:16 or SEQ ID NO:22, wherein the fragment comprises at least 50, 75, 100, 150, 200, 250, 300 or more contiguous amino acids of the sequence of SEQ ID NO:4, SEQ ID NO:16 or SEQ ID NO:22.

The invention includes a nucleic acid molecule which encodes a naturally occurring allelic variant of a polypeptide comprising the amino acid sequence of SEQ ID NO:4, SEQ ID NO:16, or SEQ ID NO:22, wherein the nucleic acid molecule hybridizes to a nucleic acid molecule consisting of SEQ ID NO:3, SEQ ID NO:15, SEQ ID NO:17, SEQ ID NO:21 or SEQ ID NO:23 under stringent conditions.

The invention also includes a nucleic acid molecule encoding a naturally occurring polypeptide, wherein the nucleic acid hybridizes to a nucleic acid molecule consisting of SEQ ID NO:3, SEQ ID NO:17, or SEQ ID NO:23 under stringent conditions (e.g., hybridization in 6× sodium chloride/sodium citrate (SSC) at about 60° C., followed by one or more washes in 0.2×SSC, 0.1% SDS at 65° C.), and wherein the nucleic acid encodes a polypeptide of 1031–1035 amino acids in length, preferably 1033 amino acids. Thus, the invention encompasses a nucleic acid molecule which includes the sequence of the protein coding region of a naturally occurring mRNA (or the corresponding cDNA sequence) that is expressed in a human cell.

Also within the invention are: an isolated NBS-3 protein having an amino acid sequence that is at least about 65%, preferably 75%, 85%, 95%, or 98% identical to the amino acid sequence of SEQ ID NO:4, SEQ ID NO:16 or SEQ ID NO:22; and an isolated NBS-3 protein having an amino acid sequence that is at least about 65%, preferably 75%, 85%, 95%, or 98% identical to the pyrin domain of SEQ ID NO:4, SEQ ID NO:16, or SEQ ID NO:22 (e.g., about amino acid residues 7–82 of SEQ ID NO:4, 7–82 of SEQ ID NO:16, or 1–92 of SEQ ID NO:22); an isolated NBS-3 protein having an amino acid sequence that is at least about 65%, preferably 75%, 85%, 95%, or 98% identical to the NBS domain of SEQ ID NO:4, SEQ ID NO:16, or SEQ ID NO:22 (e.g., about amino acids 106–538 of SEQ ID NO:4, 111–428 of SEQ ID NO:16, or 148–464 of SEQ ID NO:22); an isolated NBS-3 protein having an amino acid sequence that is at least about 65%, preferably 75%, 85%, 95%, or 98% identical to the kinase 1a domain of SEQ ID NO:4, SEQ ID NO:16, or SEQ ID NO:22 (e.g., about amino acids 112–127 of SEQ ID NO:4, 111–134 of SEQ ID NO:16, or 148–170 of SEQ ID NO:22); an isolated NBS-3 protein having an amino acid sequence that is at least about 65%, preferably 75%, 85%, 95%, or 98% identical to the Motif II domain of SEQ ID NO:4, SEQ ID NO:16, or SEQ ID NO:22 (e.g., about amino acids 142–171 of SEQ ID NO:16 or 177–207 of SEQ ID NO:22); an isolated NBS-3 protein having an amino acid sequence that is at least about 65%, preferably 75%, 85%, 95%, or 98% identical to the kinase 2 domain of SEQ ID NO:4, SEQ ID NO:16, or SEQ ID NO:22 (e.g., about amino acids 181–197 of SEQ ID NO:4, 175–198 of SEQ ID NO:16, or 211–234 of SEQ ID NO:22); an isolated NBS-3 protein having an amino acid sequence that is at least about 65%, preferably 75%, 85%, 95%, or 98% identical to the kinase 3a domain of SEQ ID NO:4, SEQ ID NO:16, or SEQ ID NO:22 (e.g., about amino acids 235–246 of SEQ ID NO:4, 219–244 of SEQ ID NO:16, or 256–280 of SEQ ID NO:22); an isolated NBS-3 protein having an amino acid sequence that is at least about 65%, preferably 75%, 85%, 95%, or 98% identical to the Motif V domain of SEQ ID NO:4, SEQ ID NO:16, or SEQ ID NO:22 (e.g., about amino acids 295–315 of SEQ ID NO:16 or 331–351 of SEQ ID NO:22); an isolated NBS-3 protein having an amino acid sequence that is at least about 65%, preferably 75%, 85%, 95%, or 98% identical to the Motif VI domain of SEQ ID NO:4, SEQ ID NO:16, or SEQ ID NO:22 (e.g., about amino acids 383–398 of SEQ ID NO:16 or 419–434 of SEQ ID NO:22); an isolated NBS-3 protein having an amino acid sequence that is at least about 65%, preferably 75%, 85%, 95%, or 98% identical to the Motif VII domain of SEQ ID NO:4, SEQ ID NO:16, or SEQ ID NO:22 (e.g., about amino acids 409–428 of SEQ ID NO:16 or 445–464 of SEQ ID NO:22); an isolated NBS-3 protein having an amino acid sequence that is at least about 65%, preferably 75%, 85%, 95%, or 98% identical to the leucine rich repeat domain of SEQ ID NO:4, SEQ ID NO:16, or SEQ ID NO 22 (e.g., about amino acids residues 596–623 of SEQ ID NO:4, 596–850 of SEQ ID NO:16, or 632–943 of SEQ ID NO:22); and an isolated NBS-3 protein having an amino acid sequence that is at least about 65%, preferably 75%, 85%, 95%, or 98% identical to one or more of the leucine rich repeats of SEQ ID NO:4, SEQ ID NO:16, or SEQ ID NO:22 (e.g., about amino acids residues 596–623 of SEQ ID NO:4, 596–623, 625–652, 653–679, 681–708, 709–736, 738–765, 766–793, 795–823, and 824–850 of SEQ ID NO:16, or 632–659, 661–687, 717–744, 745–772, 774–801, 831–858, 859–886, 888–915, and 916–943 of SEQ ID NO:22).

In an embodiment, a PYRIN-12/NBS-4 nucleic acid molecule has the nucleotide sequence shown in SEQ ID NO:5, SEQ ID NO:18 or SEQ ID NO:20.

Also within the invention is a nucleic acid molecule which encodes a polypeptide consisting of the amino acid sequence of SEQ ID NO:6 or SEQ ID NO:19.

Also within the invention is a nucleic acid molecule which encodes a polypeptide consisting essentially of the amino acid sequence of SEQ ID NO:6 or SEQ ID NO:19.

Also within the invention is a nucleic acid molecule which encodes a fragment of a polypeptide having the amino acid sequence of SEQ ID NO:6 or SEQ ID NO:19.

Also within the invention is a nucleic acid molecule which encodes a polypeptide consisting of a fragment of the amino acid sequence of SEQ ID NO:6 or SEQ ID NO:19, wherein the fragment comprises at least 50, 75, 100, 150, 200, 250, 300 or more contiguous amino acids of the sequence of SEQ ID NO:6 or SEQ ID NO:19.

The invention includes a nucleic acid molecule which encodes a naturally occurring allelic variant of a polypeptide comprising the amino acid sequence of SEQ ID NO:6 or SEQ ID NO:19, wherein the nucleic acid molecule hybridizes to a nucleic acid molecule consisting of SEQ ID NO:5, SEQ ID NO:18 or SEQ ID NO:20 under stringent conditions.

The invention also includes a nucleic acid molecule encoding a naturally occurring polypeptide, wherein the nucleic acid hybridizes to a nucleic acid molecule consisting of SEQ ID NO:5, SEQ ID NO:18, or SEQ ID NO:20 under stringent conditions (e.g., hybridization in 6× sodium chloride/sodium citrate (SSC) at about 60° C., followed by one or more washes in 0.2×SSC, 0.1% SDS at 65° C.), and wherein the nucleic acid encodes a polypeptide of 1014–1018 amino acids in length, preferably 1016 amino acids. Thus, the invention encompasses a nucleic acid molecule which includes the sequence of the protein coding region of a naturally occurring mRNA (or the corresponding cDNA sequence) that is expressed in a human cell.

Also within the invention are: an isolated PYRIN-12/NBS-4 protein having an amino acid sequence that is at least about 65%, preferably 75%, 85%, 95%, or 98% identical to the amino acid sequence of SEQ ID NO:6 or SEQ ID NO:19; an isolated PYRIN-12/NBS-4 protein having an amino acid sequence that is at least about 65%, preferably 75%, 85%, 95%, or 98% identical to the pyrin domain of SEQ ID NO:6 or SEQ ID NO:19 (e.g., about amino acids 1–90 of SEQ ID NO:19); an isolated PYRIN-12/NBS-4 protein having an amino acid sequence that is at least about 65%, preferably 75%, 85%, 95%, or 98% identical to the NBS domain of SEQ ID NO:6 or SEQ ID NO:19 (e.g., about amino acids 42–521 of SEQ ID NO:6 or 211–532 of SEQ ID NO:19); an isolated PYRIN-12/NBS-4 protein having an amino acid sequence that is at least about 65%, preferably 75%, 85%, 95%, or 98% identical to the kinase 1a domain of SEQ ID NO:6 or SEQ ID NO:19 (e.g., about amino acids 47–62 of SEQ ID NO:6 or 211–234 of SEQ ID NO:19); an isolated PYRIN-12/NBS-4 protein having an amino acid sequence that is at least about 65%, preferably 75%, 85%, 95%, or 98% identical to the Motif II domain of SEQ ID NO:6 or SEQ ID NO:19 (e.g., about amino acids 241–271 of SEQ ID NO:19); an isolated PYRIN-12/NBS-4 protein having an amino acid sequence that is at least about 65%, preferably 75%, 85%, 95%, or 98% identical to the kinase 2 domain of SEQ ID NO:6 or SEQ ID NO:19 (e.g., about amino acids 116–132 of SEQ ID NO:6 or 275–298 of SEQ ID NO:19); an isolated PYRIN-12/NBS-4 protein having an amino acid sequence that is at least about 65%, preferably 75%, 85%, 95%, or 98% identical to the kinase 3a domain of SEQ ID NO:6 or SEQ ID NO:19 (e.g., about amino acids 174–185 of SEQ ID NO:6 or 323–348 of SEQ ID NO:19); an isolated PYRIN-12/NBS-4 protein having an amino acid sequence that is at least about 65%, preferably 75%, 85%, 95%, or 98% identical to the Motif V domain of SEQ ID NO:6 or SEQ ID NO:19 (e.g., about amino acids 399–419 of SEQ ID NO:19); an isolated PYRIN-12/NBS-4 protein having an amino acid sequence that is at least about 65%, preferably 75%, 85%, 95%, or 98% identical to the Motif VI domain of SEQ ID NO:6 or SEQ ID NO:19 (e.g., about amino acids 487–502 of SEQ ID NO:19); an isolated PYRIN-12/NBS-4 protein having an amino acid sequence that is at least about 65%, preferably 75%, 85%, 95%, or 98% identical to the Motif VII domain of SEQ ID NO:6 or SEQ ID NO:19 (e.g., about amino acids 513–532 of SEQ ID NO:19); an isolated PYRIN-12/NBS-4 protein having an amino acid sequence that is at least about 65%, preferably 75%, 85%, 95%, or 98% identical to the leucine rich repeat domain of SEQ ID NO:6 or SEQ ID NO:19 (e.g., about amino acids residues 663–960 of SEQ ID NO:19); and an isolated PYRIN-12/NBS-4 protein having an amino acid sequence that is at least about 65%, preferably 75%, 85%, 95%, or 98% identical to one or more of the leucine rich repeats of SEQ ID NO:6 or SEQ ID NO:19 (e.g., about amino acids residues 663–689, 734–761, 762–789, 791–818, 819–846, 848–875, 876–903, 904–931, and 932–960 of SEQ ID NO:19).

In an embodiment, a NBS-5 nucleic acid molecule has the nucleotide sequence shown in SEQ ID NO:7.

Also within the invention is a nucleic acid molecule which encodes a polypeptide consisting of the amino acid sequence of of SEQ ID NO:8.

Also within the invention is a nucleic acid molecule which encodes a polypeptide consisting essentially of the amino acid sequence of of SEQ ID NO:8.

Also within the invention is a nucleic acid molecule which encodes a fragment of a polypeptide having the amino acid sequence of SEQ ID NO:8.

Also within the invention is a nucleic acid molecule which encodes a polypeptide consisting of a fragment of the amino acid sequence of SEQ ID NO:8, wherein the fragment comprises at least 50, 75, 100, 150, 200, 250, 300 or more contiguous amino acids of the sequence of SEQ ID NO:8.

The invention includes a nucleic acid molecule which encodes a naturally occurring allelic variant of a polypeptide comprising the amino acid sequence of SEQ ID NO:8, wherein the nucleic acid molecule hybridizes to a nucleic acid molecule consisting of SEQ ID NO:7 or the cDNA of ATCC $_{13\ 13\ 13\ 13}$ under stringent conditions.

The invention also includes a nucleic acid molecule encoding a naturally occurring polypeptide, wherein the nucleic acid hybridizes to a nucleic acid molecule consisting of SEQ ID NO:7 under stringent conditions (e.g., hybridization in 6× sodium chloride/sodium citrate (SSC) at about 60° C., followed by one or more washes in 0.2×SSC, 0.1% SDS at 65° C.), and wherein the nucleic acid encodes a polypeptide of 855–861 amino acids in length, preferably 858 amino acids. Thus, the invention encompasses a nucleic acid molecule which includes the sequence of the protein coding region of a naturally occurring mRNA (or the corresponding cDNA sequence) that is expressed in a human cell.

Also within the invention are: an isolated NBS-5 protein having an amino acid sequence that is at least about 65%, preferably 75%, 85%, 95%, or 98% identical to the amino acid sequence of SEQ ID NO:8; an isolated NBS-5 protein having an amino acid sequence that is at least about 65%, preferably 75%, 85%, 95%, or 98% identical to the NBS domain of SEQ ID NO:8 (e.g., about amino acids 38–475 of SEQ ID NO:8); an isolated NBS-5 protein having an amino acid sequence that is at least about 65%, preferably 75%, 85%, 95%, or 98% identical to the kinase 1a domain of SEQ ID NO:8 (e.g., about amino acids 43–58 of SEQ ID NO:8); an isolated NBS-5 protein having an amino acid sequence that is at least about 65%, preferably 75%, 85%, 95%, or 98% identical to the kinase 2 domain of SEQ ID NO:8 (e.g., about amino acids 112–128 of SEQ ID NO:8); an isolated NBS-5 protein having an amino acid sequence that is at least about 65%, preferably 75%, 85%, 95%, or 98% identical to the kinase 3a domain of SEQ ID NO:8 (e.g., about amino acids 166–177 of SEQ ID NO:8); an isolated NBS-5 protein having an amino acid sequence that is at least about 65%, preferably 75%, 85%, 95%, or 98% identical to the LRR domain of SEQ ID NO:8 (e.g., about amino acids 530–840 of SEQ ID NO:8); and an isolated NBS-5 protein having an amino acid sequence that is at least about 65%, preferably 75%, 85%, 95%, or 98% identical to one or more of the leucine rich repeat of SEQ ID NO:8 (e.g., about amino acids residues 530–557, 558–586, 587–614, 615–642, 643–669, 671–698, 699–726, 727–755, 756–783, 784–812, and 813–840 of SEQ ID NO:8).

Also within the invention are: an isolated NBS-2 protein which is encoded by a nucleic acid molecule having a nucleotide sequence that is at least about 65%, preferably 75%, 85%, or 95% identical to SEQ ID NO:1, SEQ ID NO:12 or SEQ ID NO:14; an isolated NBS-2 protein which is encoded by a nucleic acid molecule having a nucleotide sequence at least about 65% preferably 75%, 85%, or 95% identical to the pyrin domain encoding portion of SEQ ID NO:1, SEQ ID NO:12, or SEQ ID NO:14; an isolated NBS-2 protein which is encoded by a nucleic acid molecule having a nucleotide sequence at least about 65% preferably 75%, 85%, or 95% identical to the NBS domain encoding portion of SEQ ID NO:1, SEQ ID NO:12, or SEQ ID NO:14; an isolated NBS-2 protein which is encoded by a nucleic acid molecule having a nucleotide sequence at least about 65% preferably 75%, 85%, or 95% identical to the kinase 1a, Motif II, kinase 2, kinase 3a region, Motif V, Motif VI, or Motif VII encoding portion of SEQ ID NO:1, SEQ ID NO:12, or SEQ ID NO:14; an isolated NBS-2 protein which is encoded by a nucleic acid molecule having a nucleotide sequence at least about 65% preferably 75%, 85%, or 95% identical to the LRR domain encoding portion of SEQ ID NO:1, SEQ ID NO:12, or SEQ ID NO:14 or one or more leucine rich repeat encoding portions of SEQ ID NO:1, SEQ ID NO:12, or SEQ ID NO:14; and an isolated NBS-2 protein which is encoded by a nucleic acid molecule having a nucleotide sequence which hybridizes under stringent hybridization conditions to a nucleic acid molecule having the nucleotide sequence of SEQ ID NO:1, SEQ ID NO:12 or SEQ ID NO:14.

Also within the invention are: an isolated NBS-3 protein which is encoded by a nucleic acid molecule having a nucleotide sequence that is at least about 65%, preferably 75%, 85%, or 95% identical to SEQ ID NO:3, SEQ ID NO:15, SEQ ID NO:17, SEQ ID NO:21 or SEQ ID NO:23; an isolated NBS-3 protein which is encoded by a nucleic acid molecule having a nucleotide sequence at least about 65% preferably 75%, 85%, or 95% identical to the pyrin domain encoding portion of SEQ ID NO:3, SEQ ID NO:15, SEQ ID NO:17, SEQ ID NO:21, or SEQ ID NO:23; an isolated NBS-3 protein which is encoded by a nucleic acid molecule having a nucleotide sequence at least about 65% preferably 75%, 85%, or 95% identical to the NBS domain encoding portion of SEQ ID NO:3, SEQ ID NO:15, SEQ ID NO:17, SEQ ID NO:21, or SEQ ID NO:23; an isolated NBS-3 protein which is encoded by a nucleic acid molecule having a nucleotide sequence at least about 65% preferably 75%, 85%, or 95% identical to the kinase 1a, Motif II, kinase 2, kinase 3a region, Motif V, Motif VI, or Motif VII region encoding portion of SEQ ID NO:3, SEQ ID NO:15, SEQ ID NO:17, SEQ ID NO:21, or SEQ ID NO:23; an isolated NBS-3 protein which is encoded by a nucleic acid molecule having a nucleotide sequence at least about 65% preferably 75%, 85%, or 95% identical to the LRR domain encoding portion of SEQ ID NO:3, SEQ ID NO:15, SEQ ID NO:17, SEQ ID NO:21, or SEQ ID NO:23 or one or more leucine rich repeat encoding portions of SEQ ID NO:3, SEQ ID NO:15, SEQ ID NO:17, SEQ ID NO:21, or SEQ ID NO:23; and an isolated NBS-3 protein which is encoded by a nucleic acid molecule having a nucleotide sequence which hybridizes under stringent hybridization conditions to a nucleic acid molecule having the nucleotide sequence of SEQ ID NO:3, SEQ ID NO:15, SEQ ID NO:17, SEQ ID NO:21 or SEQ ID NO:23.

Also within the invention are: an isolated PYRIN-12/NBS-4 protein which is encoded by a nucleic acid molecule having a nucleotide sequence that is at least about 65%, preferably 75%, 85%, or 95% identical to SEQ ID NO:5, SEQ ID NO:18 or SEQ ID NO:20; an isolated PYRIN-12/NBS-4 protein which is encoded by a nucleic acid molecule having a nucleotide sequence at least about 65% preferably 75%, 85%, or 95% identical to the NBS domain encoding portion of SEQ ID NO:5, SEQ ID NO:18, or SEQ ID NO:20; an isolated PYRIN-12/NBS-4 protein which is encoded by a nucleic acid molecule having a nucleotide sequence at least about 65% preferably 75%, 85%, or 95% identical to the kinase 1a, Motif II, kinase 2, kinase 3a region, Motif V, Motif VI, or Motif VII encoding portion of SEQ ID NO:5, SEQ ID NO:18, or SEQ ID NO:20; an isolated PYRIN-12/NBS-4 protein which is encoded by a nucleic acid molecule having a nucleotide sequence at least about 65% preferably 75%, 85%, or 95% identical to the LRR domain encoding portion of SEQ ID NO:5, SEQ ID NO:18, or SEQ ID NO:20 or one or more leucine rich repeat encoding portions of SEQ ID NO:5, SEQ ID NO:18, or SEQ ID NO:20; and an isolated PYRIN-12/NBS-4 protein which is encoded by a nucleic acid molecule having a nucleotide sequence which hybridizes under stringent hybridization conditions to a nucleic acid molecule having the nucleotide sequence of SEQ ID NO:5, SEQ ID NO:18 or SEQ ID NO:20.

Also within the invention are: an isolated NBS-5 protein which is encoded by a nucleic acid molecule having a nucleotide sequence that is at least about 65%, preferably 75%, 85%, or 95% identical to SEQ ID NO:7; an isolated NBS-5 protein which is encoded by a nucleic acid molecule having a nucleotide sequence at least about 65% preferably 75%, 85%, or 95% identical to the NBS domain encoding portion of SEQ ID NO:7; an isolated NBS-5 protein which is encoded by a nucleic acid molecule having a nucleotide sequence at least about 65% preferably 75%, 85%, or 95% identical to the kinase 1a, kinase 2, or kinase 3a region encoding portion of SEQ ID NO:7; an isolated NBS-5 protein which is encoded by a nucleic acid molecule having a nucleotide sequence at least about 65% preferably 75%, 85%, or 95% identical to the LRR domain encoding portion of SEQ ID NO:7 or one or more leucine rich repeat encoding portions of SEQ ID NO:7; and an isolated NBS-5 protein which is encoded by a nucleic acid molecule having a nucleotide sequence which hybridizes under stringent hybridization conditions to a nucleic acid molecule having the nucleotide sequence of SEQ ID NO:7.

The NBS-2, NBS-3, PYRIN-12/NBS-4, or NBS-5 nucleic acids, polypeptides, and antibodies of the invention may be useful for mapping the location of either the NBS-2, NBS-3, PYRIN-12/NBS-4, or NBS-5 genes.

Another embodiment of the invention features NBS-2, NBS-3, PYRIN-12/NBS-4, or NBS-5 nucleic acid molecules which specifically detect NBS-2, NBS-3, PYRIN-12/NBS-4, or NBS-5 nucleic acid molecules, relative to nucleic acid molecules encoding other members of the NBS/LRR superfamily. For example, in one embodiment, a NBS-2, NBS-3, PYRIN-12/NBS-4, or NBS-5 nucleic acid molecule hybridizes under stringent conditions to a nucleic acid molecule comprising the nucleotide sequence of SEQ ID NO:1, SEQ ID NO:3, SEQ ID NO:5, SEQ ID NO:7, SEQ ID NO:12, SEQ ID NO:14, SEQ ID NO:15, SEQ ID NO:17, SEQ ID NO:18, SEQ ID NO:20, SEQ ID NO:21, SEQ ID NO:23, or a complement thereof. In another embodiment, the NBS-2, NBS-3, PYRIN-12/NBS-4, or NBS-5 nucleic acid molecule is at least 300(350, 400, 450, 500, 550, 600, 650, 700, 800, 900, 1000, 1100, 1200, 1300, 1400, 1500, 1600, 1800, 2000, 2250, 2500, 2750, or 3000) nucleotides in length and hybridizes under stringent conditions to a nucleic acid molecule comprising the nucleotide sequence shown in SEQ ID NO:1, SEQ ID NO:3, SEQ ID NO:5, SEQ ID NO:7, SEQ ID NO:12, SEQ ID NO:14, SEQ ID NO:15, SEQ ID NO:17, SEQ ID NO:18, SEQ ID NO:20, SEQ ID NO:21, SEQ ID NO:23 or a complement thereof. In another embodiment, an isolated NBS-2, NBS-3, PYRIN-12/NBS-4, or NBS-5 nucleic acid molecule comprises the NBS domain encoding portion of SEQ ID NO:1, SEQ ID NO:3, SEQ ID NO:5, SEQ ID NO:7, SEQ ID NO:12, SEQ ID NO:14, SEQ ID NO:15, SEQ ID NO:17, SEQ ID NO:18, SEQ ID NO:20, SEQ ID NO:21, SEQ ID NO:23, or a complement thereof.

In another embodiment, an isolated NBS-2, NBS-3, or PYRIN-12/NBS-4 nucleic acid molecule comprises the pyrin domain encoding portion of SEQ ID NO:1, SEQ ID NO:3, SEQ ID NO:5; SEQ ID NO:7, SEQ ID NO:12, SEQ ID NO:14, SEQ ID NO:15, SEQ ID NO:17, SEQ ID NO:18, SEQ ID NO:20, SEQ ID NO:21, SEQ ID NO:23, or a complement thereof. In another embodiment, an isolated NBS-2, NBS-3, PYRIN-12/NBS-4, or NBS-5 nucleic acid molecule comprises the LRR domain encoding portion of SEQ ID NO:1, SEQ ID NO:3, SEQ ID NO:5, SEQ ID NO:7, SEQ ID NO:12, SEQ ID NO:14, SEQ ID NO:15, SEQ ID NO:17, SEQ ID NO:18, SEQ ID NO:20, SEQ ID NO:21, SEQ ID NO:23, or a complement thereof. In yet another embodiment, the invention provides an isolated nucleic acid molecule which is antisense to the coding strand of a NBS-2, NBS-3, PYRIN-12/NBS-4, or NBS-5 nucleic acid.

Another aspect of the invention provides a vector, e.g., a recombinant expression vector, comprising a NBS-2, NBS-3, PYRIN-12/NBS-4, or NBS-5 nucleic acid molecule of the invention. In another embodiment the invention provides a host cell containing such a vector. The invention also provides a method for producing NBS-2, NBS-3, PYRIN-12/NBS-4, or NBS-5 protein by culturing, in a suitable medium, a host cell of the invention containing a recombinant expression vector such that a NBS-2, NBS-3, PYRIN-12/NBS-4, or NBS-5 protein is produced.

Another aspect of this invention features isolated or recombinant NBS-2, NBS-3, PYRIN-12/NBS-4, or NBS-5 proteins and polypeptides. Preferred NBS-2, NBS-3, PYRIN-12/NBS-4, or NBS-5 proteins and polypeptides possess at least one biological activity possessed by naturally occurring human NBS-2, NBS-3, PYRIN-12/NBS-4, or NBS-5, e.g., (1) the ability to form protein:protein interactions with proteins in an apoptotic and/or inflammatory signaling pathway; (2) the ability to form pyrin domain-pyrin domain interactions with proteins in an apoptotic and/or inflammatory signaling pathway; (3) the ability to bind to and/or hydrolyze a nucleotide, e.g., ATP or GTP; (4) the ability to bind a NBS-2, NBS-3, PYRIN-12/NBS-4, or NBS-5 ligand; and (5) the ability to bind to an intracellular target. Other activities include: (1) modulation of cellular proliferation; (2) modulation of cellular differentiation; (3) modulation of cellular death; (4) modulation of ER-specific apoptosis pathways; (5) modulation of amyloid-β-mediated neurotoxicity; (6) modulation of the NF-kB pathway; and (7) modulation of stress-responsive signaling pathways.

The NBS-2, NBS-3, PYRIN-12/NBS-4, or NBS-5 proteins of the present invention, or biologically active portions thereof, can be operatively linked to a non-NBS-2, NBS-3, PYRIN-12/NBS-4, or NBS-5 polypeptide (e.g., heterologous amino acid sequences) to form NBS-2, NBS-3, PYRIN-12/NBS-4, or NBS-5 fusion proteins, respectively. The invention further features antibodies that specifically bind NBS-2, NBS-3, PYRIN-12/NBS-4, or NBS-5 proteins, such as monoclonal or polyclonal antibodies. In addition, the NBS-2, NBS-3, PYRIN-12/NBS-4, or NBS-5 proteins or biologically active portions thereof can be incorporated into pharmaceutical compositions, which optionally include pharmaceutically acceptable carriers.

In another aspect, the present invention provides a method for detecting the presence of NBS-2, NBS-3, PYRIN-12/NBS-4, or NBS-5 activity or expression in a biological sample by contacting the biological sample with an agent capable of detecting an indicator of NBS-2, NBS-3, PYRIN-12/NBS-4, or NBS-5 activity such that the presence of NBS-2, NBS-3, PYRIN-12/NBS-4, or NBS-5 activity is detected in the biological sample.

In another aspect, the invention provides a method for modulating NBS-2, NBS-3, PYRIN-12/NBS-4, or NBS-5 activity comprising contacting a cell with an agent that modulates (inhibits or stimulates) NBS-2, NBS-3, PYRIN-12/NBS-4, or NBS-5 activity or expression such that NBS-2, NBS-3, PYRIN-12/NBS-4, or NBS-5 activity or expression in the cell is modulated. In one embodiment, the agent is an antibody that specifically binds to NBS-2, NBS-3, PYRIN-12/NBS-4, or NBS-5 protein. In another embodiment, the agent modulates expression of NBS-2, NBS-3, PYRIN-12/NBS-4, or NBS-5 by modulating transcription of a NBS-2, NBS-3, PYRIN-12/NBS-4, or NBS-5 gene, splicing of a NBS-2, NBS-3, PYRIN-12/NBS-4, or NBS-5 mRNA, or translation of a NBS-2, NBS-3, PYRIN-12/NBS-4, or NBS-5 mRNA. In yet another embodiment, the agent is a nucleic acid molecule having a nucleotide sequence that is antisense to the coding strand of the NBS-2, NBS-3, PYRIN-12/NBS-4, or NBS-5 mRNA or the NBS-2, NBS-3, PYRIN-12/NBS-4, or NBS-5 gene.

In one embodiment, the methods of the present invention are used to treat a subject having a disorder characterized by aberrant NBS-2, NBS-3, PYRIN-12/NBS-4, or NBS-5 protein or nucleic acid expression or activity or related to NBS-2, NBS-3, PYRIN-12/NBS-4, or NBS-5 expression or activity by administering an agent which is a NBS-2, NBS-3, PYRIN-12/NBS-4, or NBS-5 modulator to the subject. In one embodiment, the NBS-2, NBS-3, PYRIN-12/NBS-4, or NBS-5 modulator is a NBS-2, NBS-3, PYRIN-12/NBS-4, or NBS-5 protein. In another embodiment the NBS-2, NBS-3, PYRIN-12/NBS-4, or NBS-5 modulator is a NBS-2, NBS-3, PYRIN-12/NBS-4, or NBS-5 nucleic acid molecule. In other embodiments, the NBS-2, NBS-3, PYRIN-12/NBS-4, or NBS-5 modulator is a peptide, peptidomimetic, or other small molecule.

The present invention also provides a diagnostic assay for identifying the presence or absence of a genetic lesion or mutation characterized by at least one of: (i) aberrant modification or mutation of a gene encoding a NBS-2, NBS-3, PYRIN-12/NBS-4, or NBS-5 protein; (ii) mis-regulation of a gene encoding a NBS-2, NBS-3, PYRIN-12/NBS-4, or NBS-5 protein; (iii) aberrant RNA splicing; and (iv) aberrant post-translational modification of a NBS-2, NBS-3, PYRIN-12/NBS-4, or NBS-5 protein, wherein a wild-type form of the gene encodes a protein with a NBS-2, NBS-3, PYRIN-12/NBS-4, or NBS-5 activity.

In another aspect, the invention provides a method for identifying a compound that binds to or modulates the activity of a NBS-2, NBS-3, PYRIN-12/NBS-4, or NBS-5 protein. In general, such methods entail measuring a biological activity of a NBS-2, NBS-3, PYRIN-12/NBS-4, or NBS-5 protein in the presence and absence of a test compound and identifying those compounds that alter the activity of the NBS-2, NBS-3, PYRIN-12/NBS-4, or NBS-5 protein.

The invention also features methods for identifying a compound that modulates the expression of NBS-2, NBS-3, PYRIN-12/NBS-4, or NBS-5 by measuring the expression of NBS-2, NBS-3, PYRIN-12/NBS-4, or NBS-5 in the presence and absence of a compound.

The invention also features methods for identifying a compound that alters (increases or decreases) the binding of NBS-2, NBS-3, PYRIN-12/NBS-4, or NBS-5 (or a pyrin, NBS, or LRR domain containing portion thereof) to another protein (e.g., a NBS-2, NBS-3, PYRIN-12/NBS-4, or NBS-5 protein) or molecule. For example, the method includes measuring the binding of the protein (or polypeptides) to each other in the presence and absence of a test compound and identifying the test compound as a compound that alters binding if the binding in the presence of test compound differs from the binding in the absence of the test compound.

The invention also features a method for identifying a compound that binds to the NBS domain of NBS-2, NBS-3, PYRIN-12/NBS-4, or NBS-5 by measuring the binding of a test compound to a polypeptide comprising the NBS domain of NBS-2, NBS-3, PYRIN-12/NBS-4, or NBS-5. The binding can be measured in the presence of a nucleotide (e.g., an NTP such as ATP) for a competitive binding assay. Alternatively, the binding can be measured in the absence of a nucleotide that binds to the NBS site.

The invention also features methods for treating disorders associated with inappropriate apoptosis (e.g., Alzheimer's diseases or other neurological disorders associated with neuronal apoptosis) by modulating the expression or activity of NBS-2, NBS-3, PYRIN-12/NBS-4, or NBS-5.

Other features and advantages of the invention will be apparent from the following detailed description and claims.

BRIEF DESCRIPTION OF THE DRAWINGS

FIGS. 1A–1D depict the predicted partial cDNA sequence (SEQ ID NO:1) and the predicted partial amino acid sequence (SEQ ID NO:2) of human NBS-2. The open reading frame of NBS-2 extends from nucleotide 1 to nucleotide 2463 of SEQ ID NO:1.

FIG. 4A depicts an alignment of amino acids 176–190 of human NBS-2 (amino acid residues 176–190 of SEQ ID NO:2) with an NB-ARC domain (SEQ ID NO:9) derived from a hidden Markov model.

FIG. 4B depicts an alignment of amino acids 743–770 of human NBS-2 (amino acid residues 743–770 of SEQ ID NO:2) with a consensus leucine rich repeat (SEQ ID NO:10) derived from a hidden Markov model.

FIG. 4C depicts an alignment of amino acids 772–799 of human NBS-2 (amino acid residues 772–799 of SEQ ID NO:2) with a consensus leucine rich repeat (SEQ ID NO:10) derived from a hidden Markov model.

FIGS. 5A–5D depict the predicted partial cDNA sequence (SEQ ID NO:3) and the predicted partial amino acid sequence (SEQ ID NO:4) of human NBS-3. The open reading frame of NBS-3 extends from nucleotide 1 to nucleotide 1893 of SEQ ID NO:3.

FIG. 8 depicts an alignment of amino acids 596–623 of human NBS-3 (amino acid residues 596–623 of SEQ ID NO:4) with a consensus leucine rich repeat (SEQ ID NO:10) derived from a hidden Markov model.

FIGS. 9A–9C depict the predicted partial cDNA sequence (SEQ ID NO:5) and the predicted partial amino acid sequence (SEQ ID NO:6) of human PYRIN-12/NBS-4. The open reading frame of NBS-2 extends from nucleotide 1 to nucleotide 1563 of SEQ ID NO:5.

FIGS. 13A–13E depict the predicted partial cDNA sequence (SEQ ID NO:7) and the predicted partial amino acid sequence (SEQ ID NO:8) of human NBS-5. The open reading frame of NBS-5 extends from nucleotide 2 to nucleotide 2575 of SEQ ID NO:7.

FIG. 16A depicts an alignment of amino acids 530–557 of human NBS-5 (amino acid residues 530–557 of SEQ ID NO:8) with a consensus leucine rich repeat (SEQ ID NO:10) derived from a hidden Markov model.

FIG. 16B depicts an alignment of amino acids 615–642 of human NBS-5 (amino acid residues 615–642 of SEQ ID NO:8) with a consensus leucine rich repeat (SEQ ID NO:10) derived from a hidden Markov model.

FIG. 16C depicts an alignment of amino acids 643–669 of human NBS-5 (amino acid residues 643–669 of SEQ ID NO:8) with a consensus leucine rich repeat (SEQ ID NO:10) derived from a hidden Markov model.

FIG. 16D depicts an alignment of amino acids 699–726 of human NBS-5 (amino acid residues 699–726 of SEQ ID NO:8) with a consensus leucine rich repeat (SEQ ID NO:10) derived from a hidden Markov model.

FIG. 16E depicts an alignment of amino acids 728–755 of human NBS-5 (amino acid residues 728–755 of SEQ ID NO:8) with a consensus leucine rich repeat (SEQ ID NO:10) derived from a hidden Markov model.

FIG. 16F depicts an alignment of amino acids 756–783 of human NBS-5 (amino acid residues 756–783 of SEQ ID NO:8) with a consensus leucine rich repeat (SEQ ID NO:10) derived from a hidden Markov model.

FIG. 16G depicts an alignment of amino acids 785–812 of human NBS-5 (amino acid residues 785–812 of SEQ ID NO:8) with a consensus leucine rich repeat (SEQ ID NO:10) derived from a hidden Markov model.

FIG. 16H depicts an alignment of amino acids 813–840 of human NBS-5 (amino acid residues 813–840 of SEQ ID NO:8) with a consensus leucine rich repeat (SEQ ID NO:10) derived from a hidden Markov model.

FIGS. 17A–17E depict a predicted cDNA sequence (SEQ ID NO:12) and a predicted amino acid sequence (SEQ ID NO:13) of human NBS-2. The open reading frame of NBS-2 extends from nucleotide 59 to nucleotide 2998 of SEQ ID NO:12 (SEQ ID NO:14).

FIGS. 18A–18D depict a predicted cDNA sequence (SEQ ID NO:15) and a predicted amino acid sequence (SEQ ID NO:16) of human NBS-3. The open reading frame of NBS-3 extends from nucleotide 1 to nucleotide 2625 of SEQ ID NO:15 (SEQ ID NO:17).

FIGS. 19A–19E depict a predicted cDNA sequence (SEQ ID NO:18) and a predicted amino acid sequence (SEQ ID NO:19) of human PYRIN-12/NBS-4. The open reading frame of PYRIN-12/NBS-4 extends from nucleotide 1 to nucleotide 3048 of SEQ ID NO:18 (SEQ ID NO:20).

FIGS. 20A–20F depict a predicted cDNA sequence (SEQ ID NO:21) and a predicted amino acid sequence (SEQ ID NO:22) of human NBS-3. The open reading frame of NBS-3 extends from nucleotide 100 to nucleotide 3198 of SEQ ID NO:21 (SEQ ID NO:23).

DETAILED DESCRIPTION OF THE INVENTION

Figure 2:
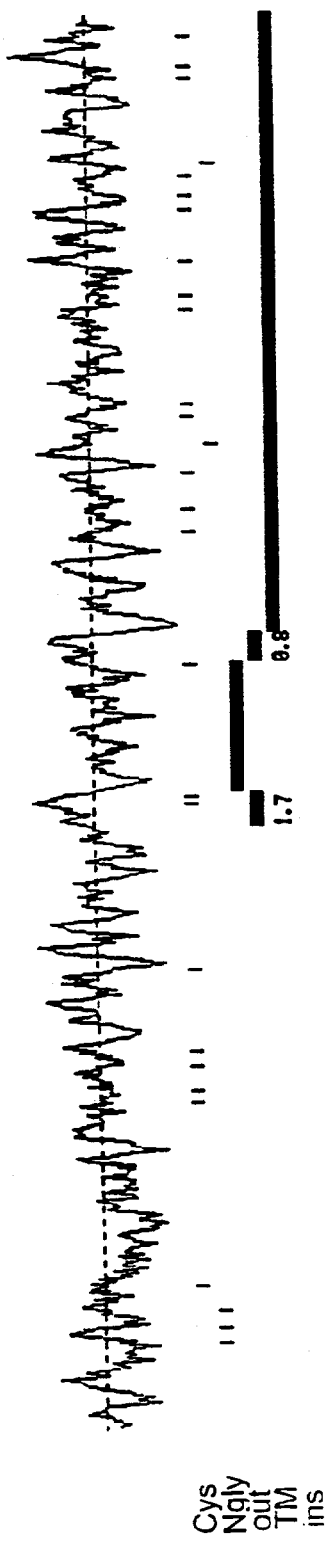
FIG. 2 depicts a hydropathy plot of NBS-2. Relatively hydrophobic residues are above the dashed horizontal line, and relatively hydrophilic residues are below the dashed horizontal line. The cysteine residues (cys) and N-linked glycosylation sites (N-gly) are indicated by short vertical lines just below the hydropathy trace.

The present invention is based, in part, on the identification of a sequence encoding human NBS-2 protein. A nucleotide sequence encoding a human NBS-2 protein is shown in FIGS. 1A–1D (SEQ ID NO:1) and FIGS. 17A–17E (SEQ ID NO:12). A predicted amino acid sequence of NBS-2 protein is also shown in FIGS. 1A–1D (SEQ ID NO:2) and FIGS. 17A–17E (SEQ ID NO:13).

The present invention is also based, in part, on the identification of a sequence encoding human NBS-3 protein. A nucleotide sequence encoding a human NBS-3 protein is shown in FIGS. 5A–5D (SEQ ID NO:3) and FIGS. 18A–18D (SEQ ID NO:15). A predicted amino acid sequence of NBS-3 protein is also shown in FIGS. 5A–5D (SEQ ID NO:4) and FIGS. 18A–18D (SEQ ID NO:16).

The present invention is also based, in part, on the identification of a sequence encoding human PYRIN-12/NBS-4 protein. A nucleotide sequence encoding a human PYRIN-12/NBS-4 protein is shown in FIGS. 9A–9C (SEQ ID NO:5) and FIGS. 19A-19E (SEQ ID NO:18). A predicted amino acid sequence of PYRIN-12/NBS-4 protein is also shown in FIGS. 9A–9C (SEQ ID NO:6) and FIGS. 19A–19E (SEQ ID NO:19).

The present invention is also based, in part, on the identification of a sequence encoding human NBS-5 protein. A nucleotide sequence encoding a human NBS-5 protein is shown in FIGS. 13A–13E (SEQ ID NO:7). A predicted amino acid sequence of NBS-5 protein is also shown in FIGS. 13A–13E (SEQ ID NO:8).

Identification and Characterization of Human NBS-2

A DNA encoding human NBS-2 was identified by a search of the publicly available High Throughput Genome sequencing (HTG) nucleotide database (for information on the HTG database, see ncbi.nlm.nih.gov/HTGS/index.html) using a portion of NBS-1 containing the pyrin domain and nucleotide-binding site (NBS) (amino acids 1–648 of NBS-1; U.S. application Ser. No. 09/506,067, filed Feb. 17, 2000). A sequence encoding a portion of a novel NBS-encoding protein was identified in a 210200 nucleotide BAC clone (GenBank™ Accession Number AC019238). GENSCAN analysis was performed to identify potential adjacent exons. Based on an analysis of the GENSCAN results, eight exons were identified that contain an open reading frame encoding an NBS-containing protein identified as NBS-2.

FIGS. 1A–1D depict the sequence of a 2464 nucleotide DNA (SEQ ID NO:1) encoding a 821 amino acid human NBS-2 protein (SEQ ID NO:2).

The NBS-2 sequence of SEQ ID NO:1 was used to further characterize a NBS-2 cDNA sequence. A search of the Incyte (Palo Alto, Calif.) Life Gold Templates cDNA database was performed using a 5' portion of the NBS-2 sequence of SEQ ID NO:1. This search identified a cDNA fragment (clone number 2344137) that contains the 5' portion of an NBS-2 cDNA. Clone number 2344137 was obtained and sequenced in its entirety. The sequence of this clone contains the cDNA sequence of NBS-2 as represented in SEQ ID NO:12. FIGS. 17A–17E depict the sequence of a NBS-2 cDNA (SEQ ID NO:12), a 980 amino acid NBS-2 protein (SEQ ID NO:13), and the open reading frame encoding NBS-2 (SEQ ID NO:14; nucleotides 59–2998 of SEQ ID NO:12).

The predicted partial exon structure of the genomic sequence of NBS-2 is described in Table 1. Table 1 lists the positions of the predicted NBS-2 exons in the BAC clone (GenBank™ Accession Number AC019238; hereby incorporated by reference). Table 1 also details the positions in SEQ ID NO:1 (predicted cDNA sequence) and the encoded portions of SEQ ID NO:2 (predicted amino acid sequence) that correspond to the individual exons. The NBS-2 gene is in reverse orientation in this BAC clone.

TABLE 1

Predicted Exon of the NBS-2 Gene

| Exon Designation | Position in Accession Number AC019238 | Position in SEQ ID NO:1 | Encoded Portion of SEQ ID NO:2 |
|---|---|---|---|
| 1 | 108431–108155 | 1–277 | 1–93 |
| 2 | 177720–107646 | 278–352 | 93–118 |

TABLE 1-continued

Predicted Exon of the NBS-2 Gene

| Exon Designation | Position in Accession Number AC019238 | Position in SEQ ID NO:1 | Encoded Portion of SEQ ID NO:2 |
|---|---|---|---|
| 3 | 107182–106386 | 353–1149 | 118–383 |
| 4 | 106335–105605 | 1150–1880 | 384–627 |
| 5 | 104874–104761 | 1881–1994 | 627–665 |
| 6 | 103147–102977 | 1995–2165 | 665–722 |
| 7 | 101375–101205 | 2166–2336 | 722–779 |
| 8 | 100455–100328 | 2337–2464 | 779–821 |

Table 2 lists predicted intron positions in the NBS-2 gene (bold residues in Table 2 indicate RNA splicing junctions). The consensus splicing sequences of both the donor and acceptor splice site each comprise sequences that are located in both an intron and an exon. Mutations in the noncoding, intronic sequence of NBS-2 may result in alterations in NBS-2 expression. For example, a mutation that causes either the destruction of a splicing site described in Table 2 or the creation of an aberrant splicing site at a position in a NBS-2 intron (e.g., at a site not used for splicing in the wild type gene) may cause improper splicing of the gene product. This could ultimately result in the translation of a mutant NBS-2 protein that may have an altered activity with respect to the wild type protein product. A mutation in an intron may thus be disease-causing by resulting in the expression of a NBS-2 molecule that either acquires or loses one or more activities possessed by the wild type NBS-2.

TABLE 2

Predicted Introns of the NBS-2 gene

| Intron designation | Position in Accession Number AC019238 | Donor Site Sequence | Acceptor Site Sequence |
|---|---|---|---|
| 1 | 108154–107721 | GTAA | ACAG |
| 2 | 107645–107183 | GTGG | GCAG |
| 3 | 106385–106336 | GTCC | GCAG |
| 4 | 105604–104875 | GTAA | TCAG |
| 5 | 104760–103148 | GTAA | CTAG |
| 6 | 102976–101376 | GTGG | ACAG |
| 7 | 101204–100456 | GTAA | GCAG |

The predicted amino acid sequence of human NBS-2 depicted in SEQ ID NO:2 was compared to amino acid sequences of known proteins and various motifs were identified. The NBS-2 of SEQ ID NO:2 protein includes five N-glycosylation sites (e.g., about amino acid residues 60–63, 69–72, 79–82, 583–586, and 743–746 of SEQ ID NO:2); two cAMP- and cGMP-dependent protein kinase phosphorylation sites (e.g., about amino acid residues 167–170 and 801–804 of SEQ ID NO:2); 12 protein kinase C phosphorylation sites (e.g., about amino acid residues 24–26, 151–153, 165–167, 203–205, 211–213, 300–302, 372–374, 593–595, 646–648, 745–747, 789–791, and 800–802 of SEQ ID NO:2); nine casein kinase II phosphorylation sites (e.g., about amino acid residues 12–15, 44–47, 61–64, 211–214, 222–225, 488–491, 547–550, 561–564, and 789–792 of SEQ ID NO:2); four N-myristoylation sites (e.g., about amino acid residues 181–186, 360–365, 422–427, and 724–729 of SEQ ID NO:2); two amidation sites (e.g., about amino acid residues 50–53 and 683–686 of SEQ ID NO:2); and one ATP/GTP-binding site motif A (P-loop) (e.g., about amino acid residues 178–185 of SEQ ID NO:2).

FIG. 2 depicts a hydropathy plot of the NBS-2 protein of SEQ ID NO:2. Relatively hydrophobic residues are above the dashed horizontal line, and relatively hydrophilic residues are below the dashed horizontal line. The cysteine residues (cys) and N-linked glycosylation sites (N-gly) are indicated by short vertical lines just below the hydropathy trace.

Figure 3:
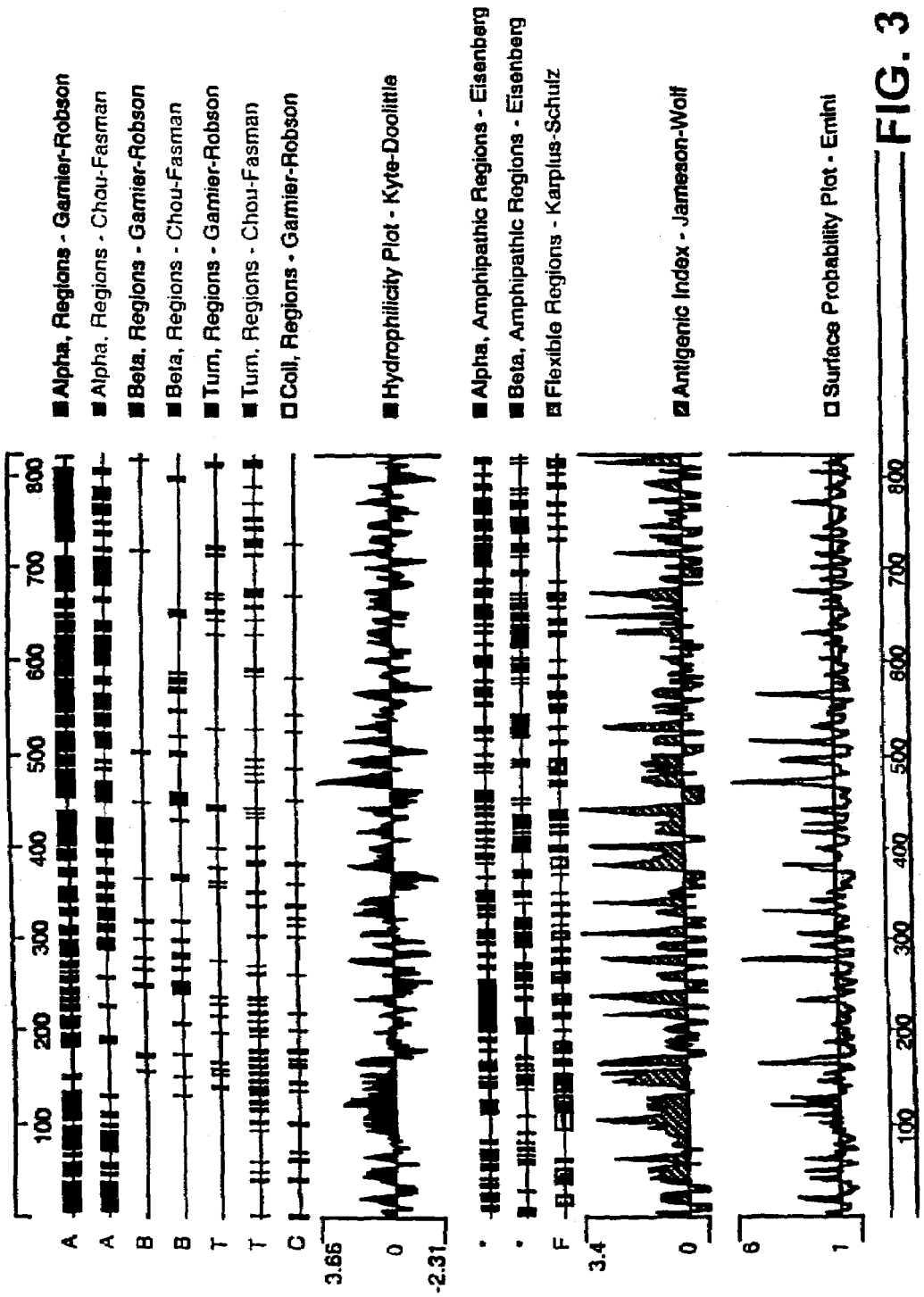
FIG. 3 depicts a plot showing the predicted structural features of NBS-2. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

A plot showing the predicted structural features of the NBS-2 protein of SEQ ID NO:2 is presented in FIG. 3. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

An analysis of the predicted NBS-2 amino acid sequence showed it to contain a pyrin domain (e.g., about amino acid residues 8–84 of SEQ ID NO:2 or SEQ ID NO:13), a nucleotide binding site (NBS; e.g., about amino acid residues 167–583 of SEQ ID NO:2 or 172–482 of SEQ ID NO:13), and several leucine rich repeats (e.g., about amino acid residues 629–656, 657–684, 685–712, 715–743, 744–770, 772–799, and 800–821 of SEQ ID NO:2 or 673–702, 704–729, 730–756, 760–786, 788–815, 817–843, 845–872, 874–901, and 902–929 of SEQ ID NO:13) which form a LRR domain (e.g., about amino acid residues 629–821 of SEQ ID NO:2 or 673–929 of SEQ ID NO:13). Within the predicted NBS there is a kinase 1a domain (Motif I; P-loop) (e.g., about amino acid residues 173–188 of SEQ ID NO:2 or 172–195 of SEQ ID NO:13), a Motif II domain (e.g., about amino acid residues 202–231 of SEQ ID NO:13), a kinase 2 domain (Motif III; Walker B box) (e.g., about amino acid residues 241–257 of SEQ ID NO:2 or 235–257 of SEQ ID NO:13), a kinase 3a domain (Motif IV) (e.g., about amino acid residues 300–306 of SEQ ID NO:2 or 279–304 of SEQ ID NO:13), a Motif V domain (e.g., about amino acid residues 355–375 of SEQ ID NO:13), a Motif VI domain (e.g., about amino acid residues 437–452 of SEQ ID NO:13), and a Motif VII domain (e.g., about amino acid residues 463–482 of SEQ ID NO:13).

FIG. 4A depicts an alignment of amino acids 176–190 of human NBS-2 (amino acid residues 176–190 of SEQ ID NO:2) with a NB-ARC domain derived from a HMM.

FIGS. 4B–C depict alignments of two of the seven leucine rich repeats within the LRR domain of NBS-2 (amino acid residues 743–770 of SEQ ID NO:2 (FIG. 4B) and amino acid residues 772–799 of SEQ ID NO:2 (FIG. 4C)) with a consensus LRR derived from a HMM.

The domain alignments depicted in FIGS. 4A–4C were identified by homology searching using consensus domains derived from hidden Markov models (HMMs). HMMs can be used to perform multiple sequence alignment and very sensitive database searching, using statistical descriptions of a domain's consensus sequence. For more information on HMM searches, see, e.g., hmmer.wustl.edu/. In the alignments of FIGS. 4A–C a single letter amino acid designation at a position on the line between the NBS-2 sequence and the HMM-generated consensus domain sequence indicates an exact match between the two. A "+" in this middle line indicates a conservative substitution at the particular residue of NBS-2. Amino acid residues located in the domains identified by the HMM search may be important for the appropriate functioning of the NBS-2 protein. For this reason, amino acid substitutions with respect to the sequence of SEQ ID NO:2 that are outside of the domains homologous to HMM consensus domains may be less detrimental to the activity of the NBS-2 protein.

Identification and Characterization of Human NBS-3

A DNA encoding human NBS-3 was identified by a search of the publicly available High Throughput Genome sequencing (HTG) nucleotide database (for information on the HTG database, see ncbi.nlm.nih.gov/HTGS/index.html) using a portion of NBS-1 containing the pyrin domain and nucleotide-binding site (NBS) (amino acids 1–648 of NBS-1; U.S. application Ser. No. 09/506,067, filed Feb. 17, 2000). A sequence encoding a portion of a novel NBS-encoding protein was identified in a 119,768 nucleotide BAC clone (GenBank™ Accession Number AC012310) derived from chromosome 19. GENSCAN analysis was performed to identify potential adjacent exons. Based on an analysis of the GENSCAN results, three exons were identified that contain an open reading frame encoding an NBS-containing protein identified as NBS-3.

FIGS. 5A–5D depict the sequence of a 1895 nucleotide DNA (SEQ ID NO:3) encoding a 631 amino acid human NBS-3 protein (SEQ ID NO:4).

The NBS-3 sequence of SEQ ID NO:3 was used to further characterize the NBS-3 coding sequence. A search of the Celera Genomics (Rockville, Md.) genomic database was performed using a pyrin domain-encoding portion of the NBS-3 sequence of SEQ ID NO:3. GENSCAN analysis was performed to identify potential exons. This analysis identified a predicted NBS-3 cDNA sequence represented in SEQ ID NO:15. FIGS. 18A–18D depict the sequence of a predicted NBS-3 cDNA (SEQ ID NO:15), an 875 amino acid NBS-3 protein (SEQ ID NO:16), and an open reading frame encoding NBS-3 (SEQ ID NO:17; nucleotides 1–2625 of SEQ ID NO:15).

A full length NBS-3 cDNA sequence was identified by a search of publicly available databases using the sequence of SEQ ID NO:3. This search identified GenBank™ Accession No. BF797150 as containing a portion of a predicted NBS-3 cDNA. GenBank™ Accession No. BF797150 was obtained and sequenced in its entirety. This sequencing and subsequent analysis identified a predicted NBS-3 cDNA sequence represented in SEQ ID NO:21 and a predicted 1033 amino acid NBS-3 protein represented in SEQ ID NO:22 (see FIGS. 20A–20F). The open reading frame of NBS-3 extends from nucleotide 100 to nucleotide 3198 of SEQ ID NO:21 (SEQ ID NO:23).

The predicted partial exon structure of the genomic sequence of NBS-3 is described in Table 3. Table 3 lists the positions of the predicted NBS-3 exons in the BAC clone (GenBank™ Accession Number AC012310; hereby incorporated by reference). Table 3 also details the positions in SEQ ID NO:3 (predicted cDNA sequence) and the encoded portions of SEQ ID NO:4 (predicted amino acid sequence)

that correspond to the individual exons. The NBS-3 gene is in reverse orientation in this BAC clone.

TABLE 3

Predicted Exons of the NBS-3 Gene

| Exon Designation | Position in Accession Number AC012310 | Position in SEQ ID NO:3 | Encoded Portion of SEQ ID NO:4 |
|---|---|---|---|
| 1 | 74435–74165 | 1–271 | 1–91 |
| 2 | 66481–65020 | 272–1733 | 91–578 |
| 3 | 64265–64104 | 1734–1895 | 578–631 |

Table 4 lists predicted intron positions in the NBS-3 gene (bold residues in Table 4 indicate RNA splicing junctions). The consensus splicing sequences of both the donor and acceptor splice site each comprise sequences that are located in both an intron and an exon. Mutations in the noncoding, intronic sequence of NBS-3 may result in alterations in NBS-3 expression. For example, a mutation that causes either the destruction of a splicing site described in Table 4 or the creation of an aberrant splicing site at a position in a NBS-3 intron (e.g., at a site not used for splicing in the wild type gene) may cause improper splicing of the gene product. This could ultimately result in the translation of a mutant NBS-3 protein that may have an altered activity with respect to the wild type protein product. A mutation in an intron may thus be disease-causing by resulting in the expression of a NBS-3 molecule that either acquires or loses one or more activities possessed by the wild type NBS-3.

TABLE 4

Predicted Introns of the NBS-3 gene

| Intron designation | Position in Accession Number AC012310 | Donor Site Sequence | Acceptor Site Sequence |
|---|---|---|---|
| 1 | 74164–66482 | GTGA | TCAG |
| 2 | 65019–64266 | GTGA | GTAG |

The predicted amino acid sequence of human NBS-3 was compared to amino acid sequences of known proteins and various motifs were identified. The NBS-3 protein of SEQ ID NO:4 includes five N-glycosylation sites (e.g., about amino acid residues 17–20, 160–163, 205–208, 212–215, and 375–378 of SEQ ID NO:4); 12 protein kinase C phosphorylation sites (e.g., about amino acid residues 19–21, 25–27, 121–123, 214–215, 240–242, 405–407, 484–486, 538–540, 557–559, 598–600, 613–615, and 625–627 of SEQ ID NO:4); 12 casein kinase II phosphorylation sites (e.g., about amino acid residues 7–10, 19–22, 48–51, 151–154, 162–169, 329–332, 377–380, 387–390, 405–408, 524–527, 538–541, and 598–601 of SEQ ID NO:4); three N-myristoylation sites (e.g., about amino acid residues 347–352, 368–373, and 461–466 of SEQ ID NO:4); two amidation sites (e.g., about amino acid residues 86–89 and 266–269 of SEQ ID NO:4); one ATP/GTP-binding site motif A (P-loop) (e.g., about amino acid residues 117–124 of SEQ ID NO:4); one leucine zipper pattern (e.g., about amino acid residues 188–209 of SEQ ID NO:4); one copper type II, ascorbate-dependent monooxygenase signature 1 site (e.g., about amino acid residues 505–512 of SEQ ID NO:4); and one ribosomal protein S14 signature (e.g., about amino acid residues 360–382 of SEQ ID NO:4).

Figure 6:
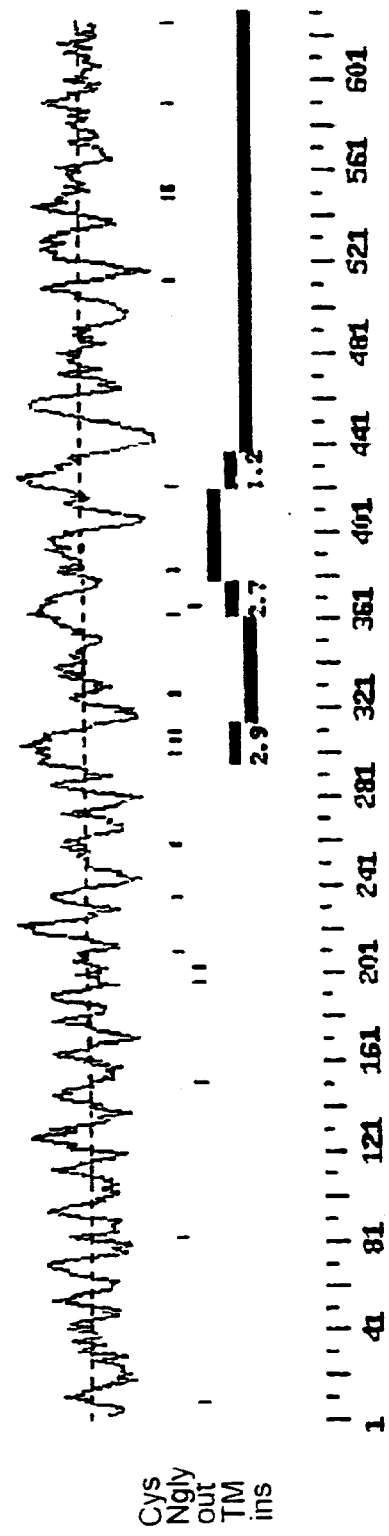
FIG. 6 depicts a hydropathy plot of NBS-3. Relatively hydrophobic residues are above the dashed horizontal line, and relatively hydrophilic residues are below the dashed horizontal line. The cysteine residues (cys) and N-linked glycosylation sites (N-gly) are indicated by short vertical lines just below the hydropathy trace.

FIG. 6 depicts a hydropathy plot of the NBS-3 protein of SEQ ID NO:4. Relatively hydrophobic residues are above the dashed horizontal line, and relatively hydrophilic residues are below the dashed horizontal line. The cysteine residues (cys) and N-linked glycosylation sites (N-gly) are indicated by short vertical lines just below the hydropathy trace.

Figure 7:
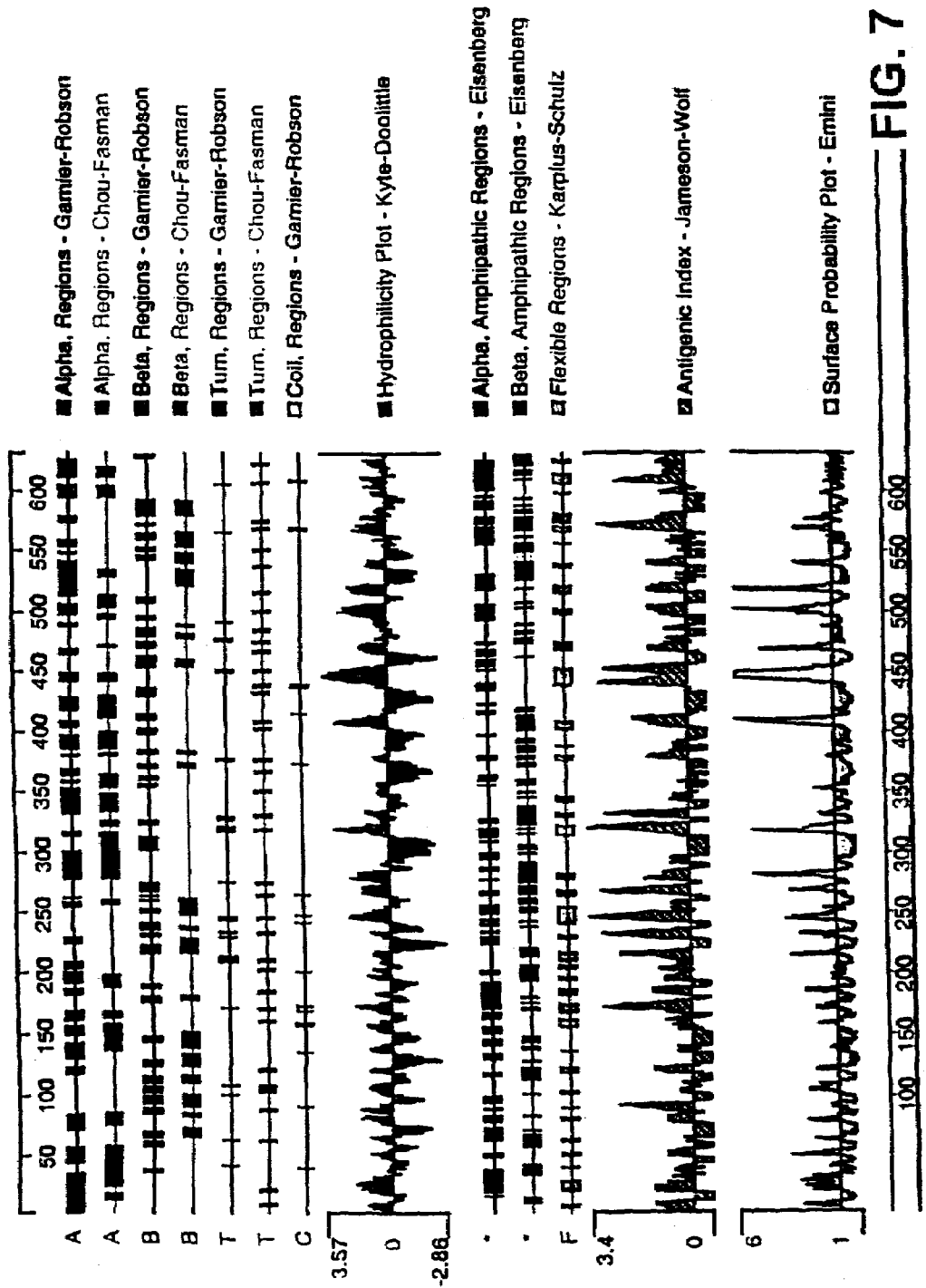
FIG. 7 depicts a plot showing the predicted structural features of NBS-3. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

A plot showing the predicted structural features of the NBS-3 protein of SEQ ID NO:4 is presented in FIG. 7. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

An analysis of the predicted NBS-3 amino acid sequence showed it to contain a pyrin domain (e.g., about amino acid residues 7–82 of SEQ ID NO:4, 7–82 of SEQ ID NO:16, or 1–92 of SEQ ID NO:22), a nucleotide binding site (NBS; e.g., about amino acid residues 106–538 of SEQ ID NO:4, 111–428 of SEQ ID NO:16, or 148–464 of SEQ ID NO:22), and several leucine rich repeats (e.g., about amino acid residues 596–623 of SEQ ID NO:4, 596–623, 625–652, 653–679, 681–708, 709–736, 738–765, 766–793, 795–823, and 824–850 of SEQ ID NO:16, or 632–659, 661–687, 717–744, 745–772, 774–801, 831–858, 859–886, 888–915, and 916–943 of SEQ ID NO:22) which form a LRR domain (e.g., about amino acid residues 596–623 of SEQ ID NO:4, 596–850 of SEQ ID NO:16, or 632–943 of SEQ ID NO:22). Within the predicted NBS there is a kinase 1a domain (Motif I; P-loop) (e.g., about amino acid residues 112–127 of SEQ ID NO:4, 111–134 of SEQ ID NO:16, or 148–170 of SEQ ID NO:22), a Motif II domain (e.g., about amino acid residues 142–171 of SEQ ID NO:16 or 177–207 of SEQ ID NO:22), a kinase 2 domain (Motif III; Walker B box) (e.g., about amino acid residues 181–197 of SEQ ID NO:4, 175–198 of SEQ ID NO:16, or 211–234 of SEQ ID NO:22), a kinase 3a domain (Motif IV) (e.g., about amino acid residues 235–246 of SEQ ID NO:4, 219–244 of SEQ ID NO:16, or 256–280 of SEQ ID NO:22), a Motif V domain (e.g., about amino acid residues 295–315 of SEQ ID NO:16 or 331–351 of SEQ ID NO:22), a Motif VI domain (e.g., about amino acid residues 383–398 of SEQ ID NO:16 or 419–434 of SEQ ID NO:22), and a Motif VII domain (e.g., about amino acid residues 409–428 of SEQ ID NO:16 or 445–464 of SEQ ID NO:22).

FIG. 8 depicts an alignment of a leucine rich repeat within the LRR domain of NBS-3 (amino acid residues 596–623 of SEQ ID NO:4) with a consensus LRR derived from a HMM.

The domain alignment depicted in FIG. 8 was identified by homology searching using consensus domains derived from hidden Markov models (HMMs). In the alignment of FIG. 8 a single letter amino acid designation at a position on the line between the NBS-3 sequence and the HMM-generated consensus domain sequence indicates an exact match between the two. A "+" in this middle line indicates a conservative substitution at the particular residue of NBS-3. Amino acid residues located in the domains identified by the HMM search may be important for the appropriate functioning of the NBS-3 protein. For this reason, amino acid substitutions with respect to the sequence of SEQ ID NO:4 that are outside of the domains homologous to HMM consensus domains may be less detrimental to the activity of the NBS-3 protein.

Identification and Characterization of Human PYRIN-12/NBS-4

A DNA encoding human PYRIN-12/NBS-4 was identified by a search of the publicly available High Throughput Genome sequencing (HTG) nucleotide database (for information on the HTG database, see ncbi.nlm.nih.gov/HTGS/index.html) using a portion of NBS-1 containing the pyrin domain and nucleotide-binding site (NBS) (amino acids 1–648 of NBS-1; U.S. application Ser. No. 09/506,067, filed Feb. 17, 2000). A sequence encoding a portion of a novel NBS-encoding protein was identified in a 119,768 nucleotide BAC clone (GenBank™ Accession Number AC012310) derived from chromosome 19. GENSCAN analysis was performed to identify potential exons. Based on an analysis of the GENSCAN results, one exon was identified that contains an open reading frame encoding an NBS-containing protein identified as PYRIN-12/NBS-4.

FIGS. 9A–9C depict the sequence of a 1566 nucleotide DNA (SEQ ID NO:5) encoding a 521 amino acid human PYRIN-12/NBS-4 protein (SEQ ID NO:6).

The PYRIN-12/NBS-4 sequence of SEQ ID NO:5 was used to further characterize the PYRIN-12/NBS-4 coding sequence. A search of the Celera Genomics (Rockville, Md.) genomic database was performed using a pyrin domain-encoding portion of the PYRIN-12/NBS-4 sequence of SEQ ID NO:5. GENSCAN analysis was performed to identify potential exons. This analysis identified a predicted PYRIN-12/NBS-4 cDNA sequence represented in SEQ ID NO:18. FIGS. 19A–19E depict the sequence of a predicted PYRIN-12/NBS-4 cDNA (SEQ ID NO:18), a 1016 amino acid PYRIN-12/NBS-4 protein (SEQ ID NO:19), and an open reading frame encoding PYRIN-12/NBS-4 (SEQ ID NO:20; nucleotides 1–3048 of SEQ ID NO:18).

The predicted partial exon structure of the genomic sequence of PYRIN-12/NBS-4 is described in Table 5. Table 5 lists the positions of the predicted PYRIN-12/NBS-4 exon in the BAC clone (GenBank™ Accession Number AC012310; hereby incorporated by reference). Table 5 also details the positions in SEQ ID NO:5 (predicted cDNA sequence) and the encoded portions of SEQ ID NO:6 (predicted amino acid sequence) that correspond to the individual exon.

TABLE 5

Predicted Exon of the PYRIN-12/NBS-4 Gene

| Exon Designation | Position in Accession Number AC012310 | Position in SEQ ID NO:5 | Encoded Portion of SEQ ID NO:6 |
|---|---|---|---|
| 1 | 88251–89816 | 1–1566 | 1–521 |

The predicted amino acid sequence of human PYRIN-12/NBS-4 was compared to amino acid sequences of known proteins and various motifs were identified. The PYRIN-12/NBS-4 protein of SEQ ID NO:6 includes five N-glycosylation sites (e.g., about amino acid residues 11–14, 23–26, 39–42, 232–235, and 312–315 of SEQ ID NO:6); five protein kinase C phosphorylation sites (e.g., about amino acid residues 24–26, 179–181, 377–379, 426–428, and 468–470 of SEQ ID NO:6); 12 casein kinase II phosphorylation sites (e.g., about amino acid residues 24–27, 97–100, 118–121, 138–141, 142–145, 204–207, 220–223, 282–285, 320–323, 332–335, 355–358, and 462–465 of SEQ ID NO:6); four N-myristoylation sites (e.g., about amino acid residues 55–60, 146–151, 295–300, and 346–351 of SEQ ID NO:6); and one ATP/GTP-binding site motif A (P-loop) (e.g., about amino acid residues 52–59 of SEQ ID NO:6).

Figures 10, 12:
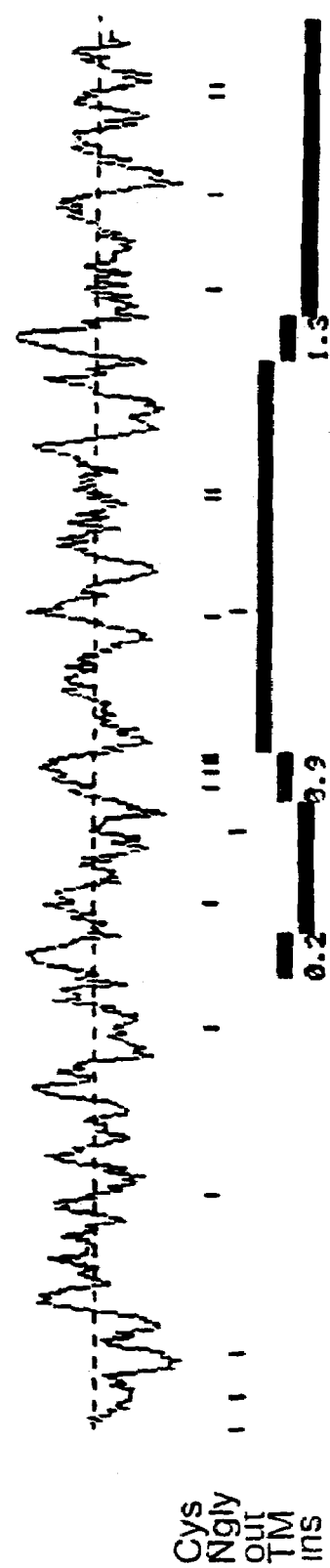
FIG. 10 depicts a hydropathy plot of PYRIN-12/NBS-4. Relatively hydrophobic residues are above the dashed horizontal line, and relatively hydrophilic residues are below the dashed horizontal line. The cysteine residues (cys) and N-linked glycosylation sites (N-gly) are indicated by short vertical lines just below the hydropathy trace.
FIG. 12 depicts an alignment of amino acids 50–79 of human PYRIN-12/NBS-4 (amino acid residues 50–79 of SEQ ID NO:6) with an NB-ARC domain (SEQ ID NO:11) derived from a hidden Markov model.

FIG. 10 depicts a hydropathy plot of the PYRIN-12/NBS-4 protein of SEQ ID NO:6. Relatively hydrophobic residues are above the dashed horizontal line, and relatively hydrophilic residues are below the dashed horizontal line. The cysteine residues (cys) and N-linked glycosylation sites (N-gly) are indicated by short vertical lines just below the hydropathy trace.

Figure 11:
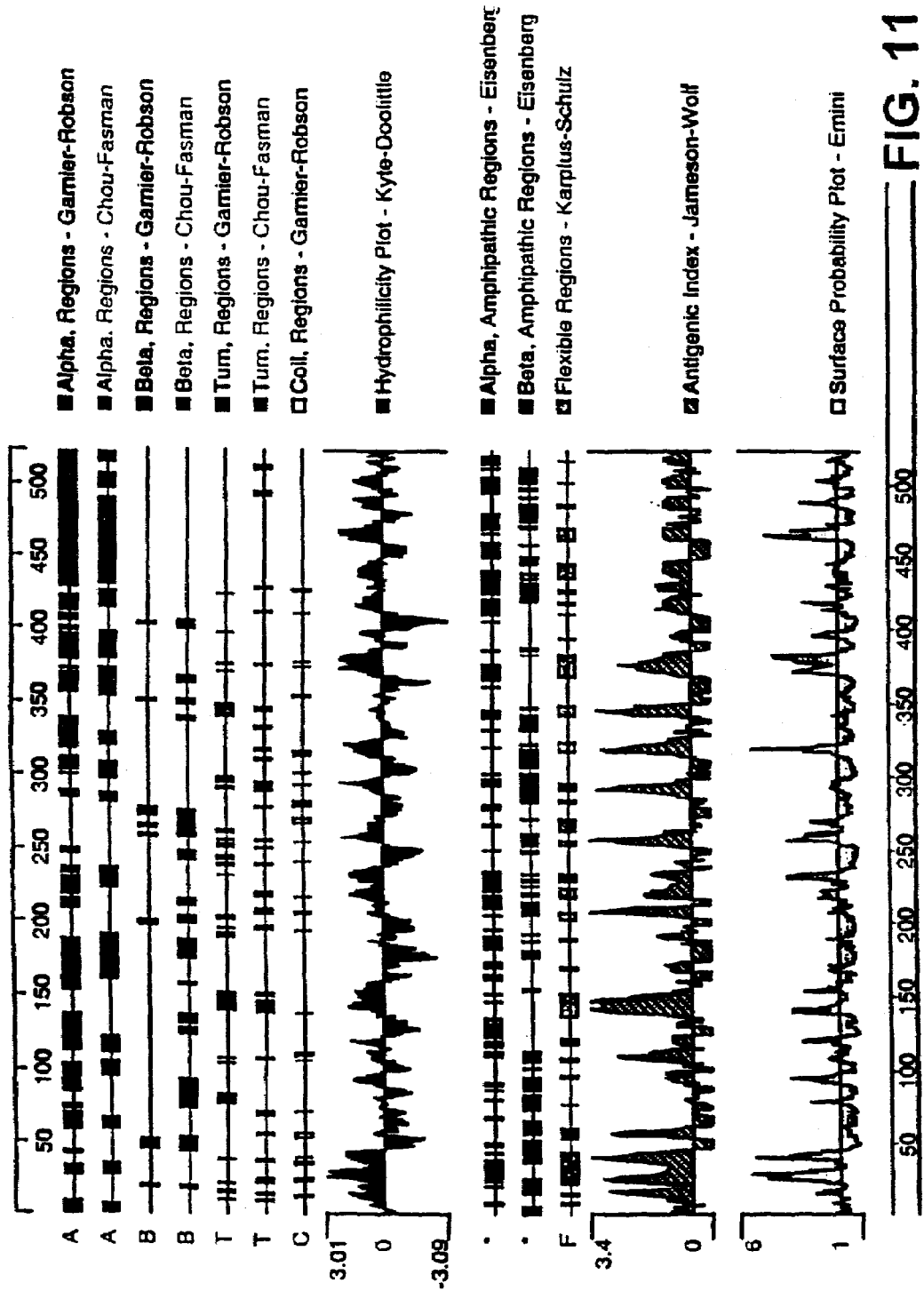
FIG. 11 depicts a plot showing the predicted structural features of PYRIN-12/NBS-4. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

A plot showing the predicted structural features of the PYRIN-12/NBS-4 protein of SEQ ID NO:6 is presented in FIG. 11. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

An analysis of the predicted PYRIN-12/NBS-4 amino acid sequence showed it to contain a pyrin domain (e.g., about amino acid residues 1–90 of SEQ ID NO:19), a nucleotide binding site (NBS; e.g., about amino acid residues 42–521 of SEQ ID NO:6 or 211–532 of SEQ ID NO:19), and several leucine rich repeats (e.g., about amino acid residues 663–689, 734–761, 762–789, 791–818, 819–846, 848–875, 876–903, 904–931, and 932–960 of SEQ ID NO:19) which form a LRR domain (e.g., about amino acid residues 663–960 of SEQ ID NO:19). Within the predicted NBS there is a kinase 1a domain (Motif I; P-loop) (e.g., about amino acid residues 47–62 of SEQ ID NO:6 or 211–234 of SEQ ID NO:19), a Motif II domain (e.g., about amino acid residues 241–271 of SEQ ID NO:19), a kinase 2 domain (Motif III; Walker B box) (e.g., about amino acid residues 116–132 of SEQ ID NO:6 or 275–298 of SEQ ID NO:19), a kinase 3a domain (Motif IV) (e.g., about amino acid residues 174–185 of SEQ ID NO:6 or 323–348 of SEQ ID NO:19), a Motif V domain (e.g., about amino acid residues 399–419 of SEQ ID NO:19), a Motif VI domain (e.g., about amino acid residues 487–502 of SEQ ID NO:19), and a Motif VII domain (e.g., about amino acid residues 513–532 of SEQ ID NO:19).

FIG. 12 depicts an alignment of amino acids 50–79 of human PYRIN-12/NBS-4 (amino acid residues 50–79 of SEQ ID NO:6) with a NB-ARC domain derived from a HMM.

The domain alignment depicted in FIG. 12 was identified by homology searching using consensus domains derived from hidden Markov models (HMMs). In the alignment of FIG. 12 a single letter amino acid designation at a position on the line between the PYRIN-12/NBS-4 sequence and the HMM-generated consensus domain sequence indicates an exact match between the two. A "+" in this middle line indicates a conservative substitution at the particular residue of PYRIN-12/NBS-4. Amino acid residues located in the domains identified by the HMM search may be important for the appropriate functioning of the PYRIN-12/NBS-4 protein. For this reason, amino acid substitutions with respect to the sequence of SEQ ID NO:6 that are outside of the domains homologous to HMM consensus domains may be less detrimental to the activity of the PYRIN-12/NBS-4 protein.

Identification and Characterization of Human NBS-5

A DNA encoding human NBS-5 was identified by a search of the publicly available High Throughput Genome sequencing (HTG) nucleotide database (for information on the HTG database, see ncbi.nlm.nih.gov/HTGS/index.html) using a portion of NBS-1 containing the pyrin domain and nucleotide-binding site (NBS) (amino acids 1–648 of NBS-1; U.S. application Ser. No. 09/506,067, filed Feb. 17, 2000). A sequence encoding a portion of a novel NBS-encoding protein was identified in a 119,768 nucleotide BAC clone (GenBank™ Accession Number AC012310) derived from chromosome 19. GENSCAN analysis was performed to identify potential adjacent exons. Based on an analysis of the GENSCAN results, eight exons were identified that contain an open reading frame encoding an NBS-containing protein identified as NBS-5.

FIGS. 13A–E depict the sequence of a 2575 nucleotide DNA (SEQ ID NO:7) encoding a 858 amino acid human NBS-5 protein (SEQ ID NO:8).

The predicted partial exon structure of the genomic sequence of NBS-5 is described in Table 6. Table 6 lists the positions of the predicted NBS-5 exons in the BAC clone (GenBank™ Accession Number AC012310; hereby incorporated by reference). Table 6 also details the positions in SEQ ID NO:7 (predicted cDNA sequence) and the encoded portions of SEQ ID NO:8 (predicted amino acid sequence) that correspond to the individual exons.

TABLE 6

Predicted Exons of the NBS-5 Gene

| Exon Designation | Position in Accession Number AC012310 | Position in SEQ ID NO:7 | Encoded Portion of SEQ ID NO:8 |
|---|---|---|---|
| 1 | 95919–97454 | 1–1536 | 1–511 |
| 2 | 99591–99752 | 1537–1698 | 511–566 |
| 3 | 100197–100364 | 1699–1866 | 566–622 |
| 4 | 105863–106030 | 1867–2034 | 622–678 |
| 5 | 108983–109153 | 2035–2205 | 678–735 |
| 6 | 115152–115322 | 2206–2376 | 735–792 |
| 7 | 116950–117120 | 2377–2547 | 792–849 |
| 8 | 117238–117265 | 2548–2575 | 849–858 |

Table 7 lists predicted intron positions in the NBS-5 gene (bold residues in Table 7 indicate RNA splicing junctions). The consensus splicing sequences of both the donor and acceptor splice site each comprise sequences that are located in both an intron and an exon. Mutations in the noncoding, intronic sequence of NBS-5 may result in alterations in NBS-5 expression. For example, a mutation that causes either the destruction of a splicing site described in Table 7 or the creation of an aberrant splicing site at a position in a NBS-5 intron (e.g., at a site not used for splicing in the wild type gene) may cause improper splicing of the gene product. This could ultimately result in the translation of a mutant NBS-5 protein that may have an altered activity with respect to the wild type protein product. A mutation in an intron may thus be disease-causing by resulting in the expression of a NBS-5 molecule that either acquires or loses one or more activities possessed by the wild type NBS-5.

TABLE 7

Predicted Introns of the NBS-5 gene

| Intron designation | Position in Accession Number AC012310 | Donor Site Sequence | Acceptor Site Sequence |
|---|---|---|---|
| 1 | 97455–99590 | GTGA | ACAG |
| 2 | 99753–100196 | GTGA | GCAG |
| 3 | 100365–105862 | GTAA | GCAG |
| 4 | 106031–108982 | GTGA | ATAG |
| 5 | 109154–115151 | GTAG | GCAG |
| 6 | 115323–116949 | GTGG | GCAG |
| 7 | 117121–117237 | GTGA | TCAG |

The predicted amino acid sequence of human NBS-5 was compared to amino acid sequences of known proteins and various motifs were identified. The 858 amino acid NBS-5 protein includes five N-glycosylation sites (e.g., about amino acid residues 196–199, 569–572, 650–653, 699–702, and 820–823 of SEQ ID NO:8); one cAMP- and cGMP-dependent protein kinase phosphorylation site (e.g., about amino acid residues 644–647 of SEQ ID NO:8); six protein kinase C phosphorylation sites (e.g., about amino acid residues 5–7, 198–200, 243–245, 491–493, 559–561, and 701–703 of SEQ ID NO:8); 14 casein kinase II phosphorylation sites (e.g., about amino acid residues 8–11, 93–96, 114–117, 125–128, 185–188, 361–364, 430–433, 511–514, 542–545, 600–603, 606–609, 629–632, 719–722, and 782–785 of SEQ ID NO:8); three tyrosine kinase phosphorylation sites (e.g., about amino acid residues 7–15, 69–77, 605–613 of SEQ ID NO:8); seven N-myristoylation sites (e.g., about amino acid residues 51–56, 316–321, 393–398, 435–440, 638–643, 792–797, and 849–854 of SEQ ID NO:8); and one ATP/GTP-binding site motif A (P-loop) (e.g., about amino acid residues 48–55 of SEQ ID NO:8).

Figure 14:
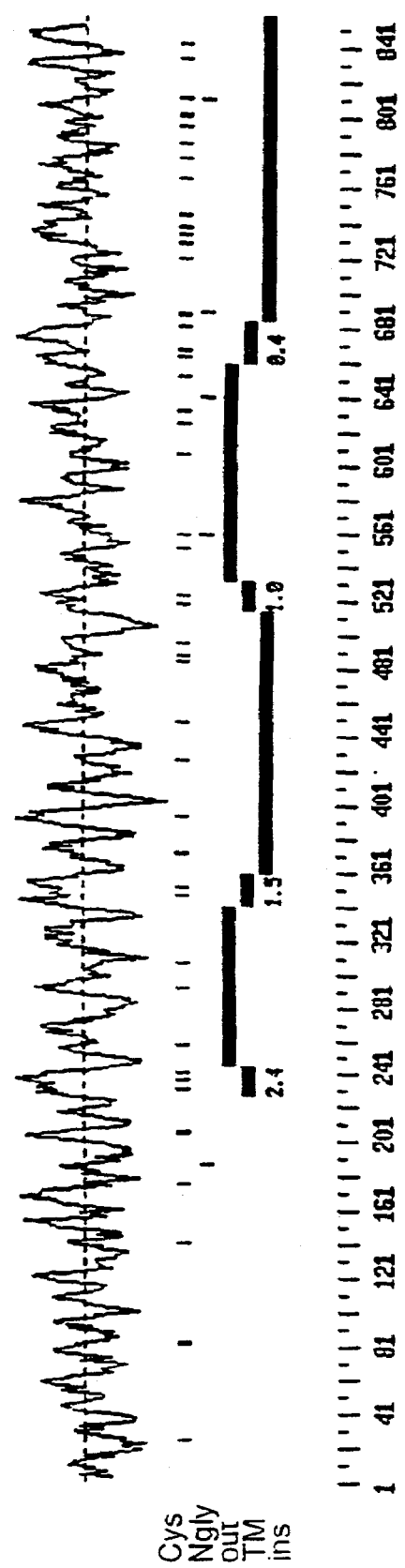
FIG. 14 depicts a hydropathy plot of NBS-5. Relatively hydrophobic residues are above the dashed horizontal line, and relatively hydrophilic residues are below the dashed horizontal line. The cysteine residues (cys) and N-linked glycosylation sites (N-gly) are indicated by short vertical lines just below the hydropathy trace.

FIG. 14 depicts a hydropathy plot of NBS-5. Relatively hydrophobic residues are above the dashed horizontal line, and relatively hydrophilic residues are below the dashed horizontal line. The cysteine residues (cys) and N-linked glycosylation sites (N-gly) are indicated by short vertical lines just below the hydropathy trace.

Figure 15:
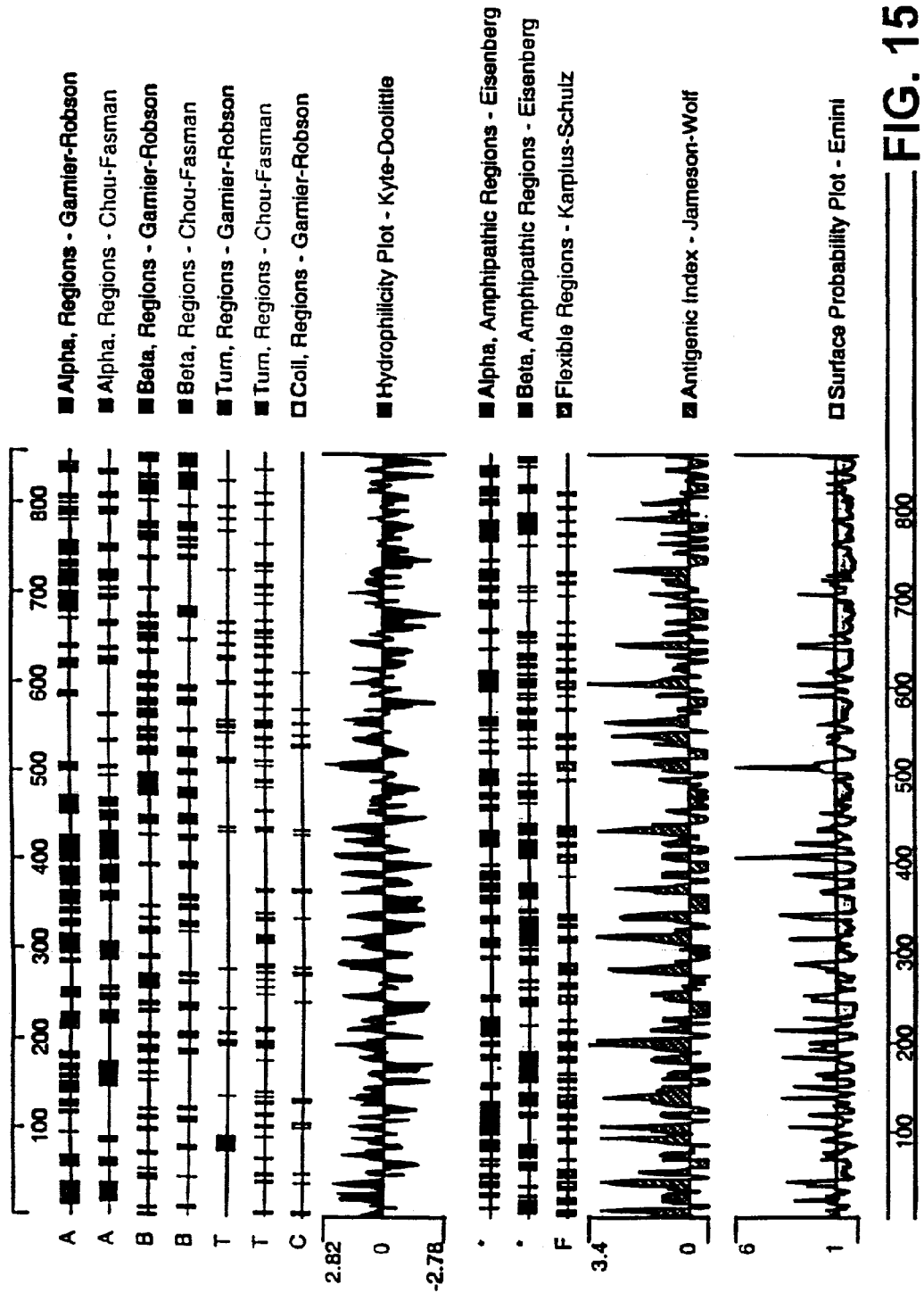
FIG. 15 depicts a plot showing the predicted structural features of NBS-5. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

A plot showing the predicted structural features of NBS-5 is presented in FIG. 15. This figure shows the predicted alpha regions (Garnier-Robson and Chou-Fasman), the predicted beta regions (Garnier-Robson and Chou-Fasman), the predicted turn regions (Garnier-Robson and Chou-Fasman) and the predicted coil regions (Garnier-Robson). Also included in the figure is a hydrophilicity plot (Kyte-Doolittle), the predicted alpha and beta-amphipathic regions (Eisenberg), the predicted flexible regions (Karplus-Schulz), the predicted antigenic index (Jameson-Wolf) and the predicted surface probability plot (Emini).

An analysis of the predicted NBS-5 amino acid sequence showed it to contain a nucleotide binding site (NBS; e.g., about amino acid residues 38–475 of SEQ ID NO:8), and 11 leucine rich repeats (e.g., about amino acid residues 530–557, 558–586, 587–614, 615–642, 643–669, 671–698, 699–726, 727–755, 756–783, 784–812, and 813–840 of SEQ ID NO:8) which form a LRR domain (e.g., about amino acid residues 530–840 of SEQ ID NO:8). Within the predicted NBS there is a kinase 1a domain (P-loop) (e.g., about amino acid residues 43–58 of SEQ ID NO:8), a kinase 2 domain (Walker B box) (e.g., about amino acid residues 112–128 of SEQ ID NO:8), and a kinase 3a domain (e.g., about amino acid residues 166–177 of SEQ ID NO:8).

FIGS. 16A–H depict alignments of eight of the 11 leucine rich repeats within the LRR domain of NBS-5 (amino acid residues 530–557 of SEQ ID NO:8 (FIG. 16A), amino acid residues 615–642 of SEQ ID NO:8 (FIG. 16B), amino acid residues 643–669 of SEQ ID NO:8 (FIG. 16C), amino acid residues 699–726 of SEQ ID NO:8 (FIG. 16D), amino acid residues 728–755 of SEQ ID NO:8 (FIG. 16E), amino acid residues 756–783 of SEQ ID NO:8 (FIG. 16F), amino acid residues 785–812 of SEQ ID NO:8 (FIG. 16G), and amino acid residues 813–840 of SEQ ID NO:8 (FIG. 16H)) with a consensus LRR derived from a HMM.

The domain alignments depicted in FIGS. 16A–16H were identified by homology searching using consensus domains derived from hidden Markov models (HMMs). In the alignments of FIGS. 16A–H a single letter amino acid designation at a position on the line between the NBS-5 sequence and the HMM-generated consensus domain sequence indicates an exact match between the two. A "+" in this middle line indicates a conservative substitution at the particular residue of NBS-5. Amino acid residues located in the domains identified by the HMM search may be important for the appropriate functioning of the NBS-5 protein. For this reason, amino acid substitutions with respect to the sequence of SEQ ID NO:8 that are outside of the domains homologous to HMM consensus domains may be less detrimental to the activity of the NBS-5 protein.

TABLE 8

Summary of Human NBS-2, NBS-3, PYRIN-12/NBS-4, and NBS-5 Sequence Information

| Gene | cDNA | Protein | ORF | FIG. |
|---|---|---|---|---|
| Human NBS-2 | SEQ ID NO:1; | SEQ ID NO:2; | | FIGS. 1A–D; |
| | SEQ ID NO:12 | SEQ ID NO:13 | SEQ ID NO:14 | FIGS. 17A–E |
| Human NBS-3 | SEQ ID NO:3; | SEQ ID NO:4; | | FIGS. 5A–D; |
| | SEQ ID NO:15; | SEQ ID NO:16; | SEQ ID NO:17; | FIGS. 18A–D; |
| | SEQ ID NO:21 | SEQ ID NO:22 | SEQ ID NO:23 | FIGS. 20A–F |
| Human PYRIN-12/ NBS-4 | SEQ ID NO:5; SEQ ID NO:18 | SEQ ID NO:6; SEQ ID NO:19 | SEQ ID NO:20 | FIGS. 9A–C FIGS. 19A–E |
| Human NBS-5 | SEQ ID NO:7 | SEQ ID NO:8 | | FIGS. 13A–E |

TABLE 9

Summary of Domains of NBS-2

| Domain | Location |
|---|---|
| Pyrin domain | about amino acid residues 8–84 of SEQ ID NO:2; about amino acid residues 8–84 of SEQ ID NO:13 |
| NBS domain | about amino acid residues 167–583 of SEQ ID NO:2; about amino acid residues 172–482 of SEQ ID NO:13 |
| Kinase 1a domain (Motif I; P-loop) | about amino acid residues 173–188 of SEQ ID NO:2; about amino acid residues 172–195 of SEQ ID NO:13 |
| Motif II | about amino acid residues 202–231 of SEQ ID NO:13 |
| Kinase 2 domain (Motif III; Walker B box) | about amino acid residues 241–257 of SEQ ID NO:2; about amino acid residues 235–257 of SEQ ID NO:13 |
| Kinase 3a domain (Motif IV) | about amino acid residues 300–306 of SEQ ID NO:2; about amino acid residues 279–304 of SEQ ID NO:13 |

TABLE 9-continued

Summary of Domains of NBS-2

| Domain | Location |
|---|---|
| Motif V | about amino acid residues 355–375 of SEQ ID NO:13 |
| Motif VI | about amino acid residues 437–452 of SEQ ID NO:13 |
| Motif VII | about amino acid residues 463–482 of SEQ ID NO:13 |
| Leucine rich repeats | about amino acids residues 629–656, 657–684, 685–712, 715–743, 744–770, 772–799, and 800–821 of SEQ ID NO:2; about amino acids residues 673–702, 704–729, 730–756, 760–786, 788–815, 817–843, 845–872, 874–901, and 902–929 of SEQ ID NO:13 |
| LRR domain | about amino acid residues 629–821 of SEQ ID NO:2; about amino acid residues 673–929 of SEQ ID NO:13 |

TABLE 10

Summary of Domains of NBS-3

| Domain | Location |
|---|---|
| Pyrin domain | about amino acid residues 7–82 of SEQ ID NO:4; about amino acid residues 7–82 of SEQ ID NO:16; about amino acid residues 1–92 of SEQ ID NO:22 |
| NBS domain | about amino acid residues 106–538 of SEQ ID NO:4; about amino acid residues 111–428 of SEQ ID NO:16; about amino acid residues 148–464 of SEQ ID NO:22 |
| Kinase 1a domain (Motif I; P-loop) | about amino acid residues 112–127 of SEQ ID NO:4; about amino acid residues 111–134 of SEQ ID NO:16; about amino acid residues 148–170 of SEQ ID NO:22 |
| Motif II | about amino acid residues 142–171 of SEQ ID NO:16; about amino acid residues 177–207 of SEQ ID NO:22 |
| Kinase 2 domain (Motif III; Walker B box) | about amino acid residues 181–197 of SEQ ID NO:4; about amino acid residues 175–198 of SEQ ID NO:16; about amino acid residues 211–234 of SEQ ID NO:22 |
| Kinase 3a domain (Motif IV) | about amino acid residues 235–246 of SEQ ID NO:4; about amino acid residues 219–244 of SEQ ID NO:16; about amino acid residues 256–280 of SEQ ID NO:22 |
| Motif V | about amino acid residues 295–315 of SEQ ID NO:16; about amino acid residues 331–351 of SEQ ID NO:22 |
| Motif VI | about amino acid residues 383–398 of SEQ ID NO:16; about amino acid residues 419–434 of SEQ ID NO:22 |
| Motif VII | about amino acid residues 409–428 of SEQ ID NO:16; about amino acid residues 445–464 of SEQ ID NO:22 |
| Leucine rich repeats | about amino acids residues 596–623 of SEQ ID NO:4; about amino acids residues 596–623, 625–652, 653–679, 681–708, 709–736, 738–765, 766–793, 795–823, and 824–850 of SEQ ID NO:16; about amino acid residues 632–659, 661–687, 717–744, 745–772, 774–801, 831–858, 859–886, 888–915, and 916–943 of SEQ ID NO:22 |
| LRR domain | about amino acids residues 596–623 of SEQ ID NO:4; about amino acid residues 596–850 of SEQ ID NO:16; about amino acid residues 632–943 of SEQ ID NO:22 |

TABLE 11

Summary of Domains of PYRIN-12/NBS-4

| Domain | Location |
|---|---|
| Pyrin | about amino acid residues 1–90 of SEQ ID NO:19 |
| NBS domain | about amino acid residues 42–521 of SEQ ID NO:6 about amino acid residues 211–532 of SEQ ID NO:19 |
| Kinase 1a domain (Motif I; P-loop) | about amino acid residues 47–62 of SEQ ID NO:6 about amino acid residues 211–234 of SEQ ID NO:19 |
| Motif II | about amino acid residues 241–271 of SEQ ID NO:19 |
| Kinase 2 domain (Motif III; Walker B box) | about amino acid residues 116–132 of SEQ ID NO:6 about amino acid residues 275–298 of SEQ ID NO:19 |

TABLE 11-continued

Summary of Domains of PYRIN-12/NBS-4

| Domain | Location |
| --- | --- |
| Kinase 3a domain (Motif IV) | about amino acid residues 174–185 of SEQ ID NO:6 about amino acid residues 323–348 of SEQ ID NO:19 |
| Motif V | about amino acid residues 399–419 of SEQ ID NO:19 |
| Motif VI | about amino acid residues 487–502 of SEQ ID NO:19 |
| Motif VII | about amino acid residues 513–532 of SEQ ID NO:19 |
| Leucine rich repeats | about amino acids residues 663–689, 734–761, 762–789, 791–818, 819–846, 848–875, 876–903, 904–931, and 932–960 of SEQ ID NO:19 |
| LRR domain | about amino acid residues 663–960 of SEQ ID NO:19 |

TABLE 12

Summary of Domains of NBS-5

| Domain | Location |
| --- | --- |
| NBS domain | about amino acid residues 38–475 of SEQ ID NO:8 |
| Kinase 1a domain (Motif I; P-loop) | about amino acid residues 43–58 of SEQ ID NO:8 |
| Kinase 2 domain (Motif III; Walker B box) | about amino acid residues 112–128 of SEQ ID NO:8 |
| Kinase 3a domain (Motif IV) | about amino acid residues 166–177 of SEQ ID NO:8 |
| Leucine rich repeats | about amino acids residues 530–557, 558–586, 587–614, 615–642, 643–669, 671–698, 699–726, 727–755, 756–783, 784–812, and 813–840 of SEQ ID NO:8 |
| LRR domain | about amino acids residues 530–840 of SEQ ID NO:8 |

Each of NBS-2, NBS-3, PYRIN-12/NBS-4, and NBS-5 are members of a family of molecules (NBS-2, NBS-3, PYRIN-12/NBS-4, and NBS-5 families, respectively) having certain conserved structural and functional features. The term "family" when referring to the protein and nucleic acid molecules of the invention is intended to mean two or more proteins or nucleic acid molecules having a common structural domain and having sufficient amino acid or nucleotide sequence identity as defined herein. Such family members can be naturally occurring and can be from either the same or different species. For example, a family can contain a first protein of human origin and a homologue of that protein of murine origin, as well as a second, distinct protein of human origin and a murine homologue of that protein. Members of a family may also have common functional characteristics.

Preferred NBS-2, NBS-3, PYRIN-12/NBS-4, or NBS-5 polypeptides of the present invention include an amino acid sequence sufficiently identical to one or more of the following domains: a pyrin domain, and NBS domain, and/or a LRR domain.

As used interchangeably herein a "NBS-2, NBS-3, PYRIN-12/NBS-4, or NBS-5 activity", "biological activity of NBS-2, NBS-3, PYRIN-12/NBS-4, or NBS-5" or "functional activity of NBS-2, NBS-3, PYRIN-12/NBS-4, or NBS-5", refers to an activity exerted by a NBS-2, NBS-3, PYRIN-12/NBS-4, or NBS-5 protein, polypeptide or nucleic acid molecule on a NBS-2, NBS-3, PYRIN-12/NBS-4, or NBS-5 responsive cell as determined in vivo, or in vitro, according to standard techniques. NBS-2, NBS-3, PYRIN-12/NBS-4, or NBS-5 may act as a pro-apoptotic protein or an anti-apoptotic protein (i.e., it might act to decrease or increase apoptosis). A NBS-2, NBS-3, PYRIN-12/NBS-4, or NBS-5 activity can be a direct activity, such as an association with or an enzymatic activity on a second protein or an indirect activity, such as a cellular signaling activity mediated by interaction of the NBS-2, NBS-3, PYRIN-12/NBS-4, or NBS-5 protein with a second protein.

In one embodiment, a NBS-2, NBS-3, PYRIN-12/NBS-4, or NBS-5 activity can include at least one or more of the following activities: (i) the ability to interact with proteins in an apoptotic or inflammatory signaling pathway; (ii) the ability to interact with a NBS-2, NBS-3, PYRIN-12/NBS-4, or NBS-5; (iii) the ability to bind to and/or hydrolyze a nucleotide, e.g., ATP or GTP; (iv) the ability to interact with an intracellular target protein; (v) the ability to interact, directly or indirectly, with one or more proteins having a pyrin domain, a CARD domain, or other domain associated with apoptotic or inflammatory signaling; (vi) the ability to modulate, directly or indirectly, the activity of a caspase, e.g., caspase-9; (vii) the ability to modulate of ER-specific apoptosis pathways; (viii) the ability to modulate, directly or indirectly, the activity of NF-kB; (ix) the ability to modulate, directly or indirectly, Apaf-1; (x) the ability to modulate apoptosis and/or inflammation; (xi) the ability to interact, directly or indirectly, with a Bcl-2 family member; (xii) the ability to modulate, directly or indirectly, the activity of a stress activated kinase (e.g., JNK/p38); and (xiii) the ability to modulate, directly or indirectly, phosphorylation of CHOP (GADD 153). NBS-2, NBS-3, PYRIN-12/NBS-4, or NBS-5 nucleic acids and polypeptides as well as modulators of activity or expression of NBS-2, NBS-3, PYRIN-12/NBS-4, or NBS-5 might be used to modulate an Apaf-1 signaling pathway.

Accordingly, another embodiment of the invention features isolated NBS-2, NBS-3, PYRIN-12/NBS-4, or NBS-5 proteins and polypeptides having a NBS-2, NBS-3, PYRIN-12/NBS-4, or NBS-5 activity.

Various aspects of the invention are described in further detail in the following subsections.

I. Isolated Nucleic Acid Molecules

One aspect of the invention pertains to isolated nucleic acid molecules that encode NBS-2, NBS-3, PYRIN-12/NBS-4, or NBS-5 proteins or biologically active portions thereof, as well as nucleic acid molecules sufficient for use as hybridization probes to identify NBS-2, NBS-3, PYRIN-12/NBS-4, or NBS-5-encoding nucleic acids (e.g., NBS-2, NBS-3, PYRIN-12/NBS-4, or NBS-5 mRNA) and fragments for use as PCR primers for the amplification or mutation of NBS-2, NBS-3, PYRIN-12/NBS-4, or NBS-5 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences (preferably protein encoding sequences) that which naturally flank the nucleic acid (i.e., sequences located at the 5' and 3' ends of the nucleic acid) in the genomic DNA of the organism from which the nucleic acid is derived. For example, in various embodiments, the isolated NBS-2, NBS-3, PYRIN-12/NBS-4, or NBS-5 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3, SEQ ID NO:5, SEQ ID NO:7, SEQ ID NO:12, SEQ ID NO:14, SEQ ID NO:15, SEQ ID NO:17, SEQ ID NO:18, SEQ ID NO:20, SEQ ID NO:21, SEQ ID NO:23, or a complement of any of these nucleotide sequences, can be isolated using standard molecular biology techniques and the sequence information provided herein. Using all or portion of the nucleic acid sequences of SEQ ID NO:1, SEQ ID NO:3, SEQ ID NO:5, SEQ ID NO:7, SEQ ID NO:12, SEQ ID NO:14, SEQ ID NO:15, SEQ ID NO:17, SEQ ID NO:18, SEQ ID NO:20, SEQ ID NO:21 or SEQ ID NO:23 as a hybridization probe, NBS-2, NBS-3, PYRIN-12/NBS-4, or NBS-5 nucleic acid molecules can be isolated using standard hybridization and cloning techniques (e.g., as described in Sambrook et al., eds., Molecular Cloning: A Laboratory Manual. 2nd, ed., Cold Spring Harbor Laboratory, Cold Spring Harbor Laboratory Press, Cold Spring Harbor, N.Y., 1989).

A nucleic acid of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to NBS-2, NBS-3, PYRIN-12/NBS-4, or NBS-5 nucleotide sequences can be prepared by standard synthetic techniques, e.g., using an automated DNA synthesizer.

In another embodiment, an isolated nucleic acid molecule of the invention comprises a nucleic acid molecule which is a complement of the nucleotide sequence shown in SEQ ID NO:1, SEQ ID NO:3, SEQ ID NO:5, SEQ ID NO:7, SEQ ID NO:12, SEQ ID NO:14, SEQ ID NO:15, SEQ ID NO:17, SEQ ID NO:18, SEQ ID NO:20, SEQ ID NO:21 or SEQ ID NO:23, or a portion thereof. A nucleic acid molecule which is complementary to a given nucleotide sequence is one which is sufficiently complementary to the given nucleotide sequence that it can hybridize to the given nucleotide sequence thereby forming a stable duplex.

Moreover, the nucleic acid molecule of the invention can comprise only a portion of a nucleic acid sequence encoding NBS-2, NBS-3, PYRIN-12/NBS-4, or NB S-5, for example, a fragment which can be used as a probe or primer or a fragment encoding a biologically active portion of NBS-2, NBS-3, PYRIN-12/NBS-4, or NBS-5. The nucleotide sequence determined from the cloning of the NBS-2, NBS-3, PYRIN-12/NBS-4, or NBS-5 gene allows for the generation of probes and primers designed for use in identifying and/or cloning NBS-2, NBS-3, PYRIN-12/NBS-4, or NBS-5 homologues in other cell types, e.g., from other tissues, as well as NBS-2, NBS-3, PYRIN-12/NBS-4, or NBS-5 homologues and orthologs from other mammals. The probe/primer typically comprises substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense sequence of SEQ ID NO:1, SEQ ID NO:3, SEQ ID NO:5, SEQ ID NO:7, SEQ ID NO:12, SEQ ID NO:14, SEQ ID NO:15, SEQ ID NO:17, SEQ ID NO:18, SEQ ID NO:20, SEQ ID NO:21, SEQ ID NO:23, or of a naturally occurring mutant of one of SEQ ID NO:1, SEQ ID NO:3, SEQ ID NO:5, SEQ ID NO:7, SEQ ID NO:12, SEQ ID NO:14, SEQ ID NO:15, SEQ ID NO:17, SEQ ID NO:18, SEQ ID NO:20, SEQ ID NO:21 or SEQ ID NO:23.

Probes based on the NBS-2, NBS-3, PYRIN-12/NBS-4, or NBS-5 nucleotide sequence can be used to detect transcripts or genomic sequences encoding the same or similar proteins. The probe comprises a label group attached thereto, e.g., a radioisotope, a fluorescent compound, an enzyme, or an enzyme co-factor. Such probes can be used as a part of a diagnostic test kit for identifying allelic variants and orthologs of the NBS-2, NBS-3, PYRIN-12/NBS-4, or NBS-5 proteins of the present invention, identifying cells or tissue which mis-express a NBS-2, NBS-3, PYRIN-12/NBS-4, or NBS-5 protein, such as by measuring a level of a NBS-2, NBS-3, PYRIN-12/NBS-4, or NBS-5-encoding nucleic acid in a sample of cells from a subject, e.g., detecting NBS-2, NBS-3, PYRIN- 12/NBS-4, or NBS-5 mRNA levels or determining whether a genomic NBS-2, NBS-3, PYRIN-12/NBS-4, or NBS-5 gene has been mutated or deleted.

A nucleic acid fragment encoding a "biologically active portion" of NBS-2, NBS-3, PYRIN-12/NBS-4, or NBS-5 can be prepared by isolating a portion of SEQ ID NO:1, SEQ ID NO:3, SEQ ID NO:5, SEQ ID NO:7, SEQ ID NO:12, SEQ ID NO:14, SEQ ID NO:15, SEQ ID NO:17, SEQ ID NO:18, SEQ ID NO:20, SEQ ID NO:21 or SEQ ID NO:23, which encodes a polypeptide having a NBS-2, NBS-3, PYRIN-12/NBS-4, or NBS-5 biological activity, expressing the encoded portion of NBS-2, NBS-3, PYRIN-12/NBS-4, or NBS-5 protein (e.g., by recombinant expression in vitro) and assessing the activity of the encoded portion of NBS-2, NBS-3, PYRIN-12/NBS-4, or NBS-5.

The invention further encompasses nucleic acid molecules that differ from the nucleotide sequence of SEQ ID NO:1, SEQ ID NO:3, SEQ ID NO:5, SEQ ID NO:7, SEQ ID NO:12, SEQ ID NO:14, SEQ ID NO:15, SEQ ID NO:17, SEQ ID NO:18, SEQ ID NO:20 and SEQ ID NO:21, SEQ ID NO:23 due to degeneracy of the genetic code and thus encode the same NBS-2, NBS-3, PYRIN-12/NBS-4, or NBS-5 protein as that encoded by the nucleotide sequence shown in SEQ ID NO:1, SEQ ID NO:3, SEQ ID NO:5, SEQ ID NO:7, SEQ ID NO:12, SEQ ID NO:14, SEQ ID NO:15, SEQ ID NO:17, SEQ ID NO:18, SEQ ID NO:20, SEQ ID NO:21 or SEQ ID NO:23.

In addition to the NBS-2, NBS-3, PYRIN-12/NBS-4, or NBS-5 nucleotide sequences shown in SEQ ID NO:1, SEQ ID NO:3, SEQ ID NO:5, SEQ ID NO:7, SEQ ID NO:12, SEQ ID NO:14, SEQ ID NO:15, SEQ ID NO:17, SEQ ID NO:18, SEQ ID NO:20, SEQ ID NO:21 and SEQ ID NO:23, it will be appreciated by those skilled in the art that DNA sequence polymorphisms that lead to changes in the amino acid sequences of NBS-2, NBS-3, PYRIN-12/NBS-4, or NBS-5 may exist within a population (e.g., the human population). Such genetic polymorphism in the NBS-2, NBS-3, PYRIN-12/NBS-4, or NBS-5 gene may exist among individuals within a population due to natural allelic variation. As used herein, the terms "gene" and "recombinant gene" refer to nucleic acid molecules comprising an open reading frame encoding a NBS-2, NBS-3, PYRIN-12 NBS-4, or NBS-5 protein, preferably a mammalian NBS-2, NBS-3, PYRIN-12 NBS-4, or NBS-5 protein. Such natural allelic variations can typically result in 1–5% variance in the nucleotide sequence of the NBS-2, NBS-3, PYRIN-12/NBS-4, or NBS-5 gene. Any and all such nucleotide variations and resulting amino acid polymorphisms in NBS-2, NBS-3, PYRIN-12/NBS-4, or NBS-5 that are the result of natural allelic variation and that do not alter the functional activity of NBS-2, NBS-3, PYRIN-12/NBS-4, or NBS-5 are intended to be within the scope of the invention. Thus, e.g., 1%, 2%, 3%, 4%, or 5% of the amino acids in NBS-2, NBS-3, PYRIN-12/NBS-4, or NBS-5 (e.g., 1, 2, 3, 4, 5, 6, 8, 10, 15, or 17 amino acids) are replaced by another amino acid, preferably by conservative substitution.

Moreover, nucleic acid molecules encoding NBS-2, NBS-3, PYRIN-12/NBS-4, or NBS-5 proteins from other species (NBS-2, NBS-3, PYRIN-12/NBS-4, or NBS-5 orthologs/homologues), which have a nucleotide sequence which differs from that of a NBS-2, NBS-3, PYRIN-12/NBS-4, or NBS-5 disclosed herein, are intended to be within the scope of the invention.

Accordingly, in another embodiment, an isolated nucleic acid molecule of the invention is at least 150 (300, 325, 350, 375, 400, 425, 450, 500, 550, 600, 650, 700, 800, 900, 1000, 1100, 1200, 1300, 1400, 1500, 1600, 1800, 2000, 2250, or 2500) nucleotides in length and hybridizes under stringent conditions to the nucleic acid molecule comprising the nucleotide sequence, preferably the coding sequence, of SEQ ID NO:1, SEQ ID NO:3, SEQ ID NO:5, SEQ ID NO:7, SEQ ID NO:12, SEQ ID NO:14, SEQ ID NO:15, SEQ ID NO:17, SEQ ID NO:18, SEQ ID NO:20, SEQ ID NO:21 or SEQ ID NO:23.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1–6.3.6. An, non-limiting example of stringent hybridization conditions are hybridization in 6× sodium chloride/sodium citrate (SSC) at about 45° C., followed by one or more washes in 0.2×SSC, 0.1% SDS at 50–65° C. (e.g., 50° C. or 60° C. or 65° C.). Preferably, the isolated nucleic acid molecule of the invention that hybridizes under stringent conditions corresponds to a naturally-occurring nucleic acid molecule. As used herein, a "naturally-occurring" nucleic acid molecule refers to an RNA or DNA molecule having a nucleotide sequence that occurs in a human cell in nature (e.g., encodes a natural protein).

In addition to naturally-occurring allelic variants of the NBS-2, NBS-3, PYRIN-12/NBS-4, or NBS-5 sequence that may exist in the population, the skilled artisan will further appreciate that changes can be introduced by mutation into the nucleotide sequence of SEQ ID NO:1, SEQ ID NO:3, SEQ ID NO:5, SEQ ID NO:7, SEQ ID NO:12, SEQ ID NO:14, SEQ ID NO:15, SEQ ID NO:17, SEQ ID NO:18, SEQ ID NO:20, SEQ ID NO:21 or SEQ ID NO:23, thereby leading to changes in the amino acid sequence of the encoded protein without altering the functional ability of the protein. For example, one can make nucleotide substitutions leading to amino acid substitutions at "non-essential" amino acid residues. A "non-essential" amino acid residue is a residue that can be altered from the wild-type sequence of NBS-2, NBS-3, PYRIN-12/NBS-4, or NBS-5 protein without altering the biological activity, whereas an "essential" amino acid residue is required for biological activity. For example, amino acid residues that are conserved among the NBS-2, NBS-3, PYRIN-12/NBS-4, or NBS-5, proteins of various species are predicted to be particularly unamenable to alteration.

For example, preferred NBS-2, NBS-3, PYRIN-12/NBS-4, or NBS-5 proteins of the present invention contain at least one domain identified herein. Such conserved domains are less likely to be amenable to mutation. Other amino acid residues, however, (e.g., those that are not conserved or only semi-conserved among NBS-2, NBS-3, PYRIN-12/NBS-4, or NBS-5 of various species) may not be essential for activity and thus are likely to be amenable to alteration.

Accordingly, another aspect of the invention pertains to nucleic acid molecules encoding NBS-2, NBS-3, PYRIN-12/NBS-4, or NBS-5 proteins that contain changes in amino acid residues that are not essential for activity. Such NBS-2, NBS-3, PYRIN-12/NBS-4, or NBS-5 proteins differ in amino acid sequence from SEQ ID NO:2, SEQ ID NO:4, SEQ ID NO:6, SEQ ID NO:8, SEQ ID NO:13, SEQ ID NO:16, SEQ ID NO:19, or SEQ ID NO:22 and yet retain biological activity. In one embodiment, the isolated nucleic acid molecule includes a nucleotide sequence encoding a protein that includes an amino acid sequence that is at least about 45% identical, 65%, 75%, 85%, 95%, or 98% identical to the amino acid sequence of SEQ ID NO:2, SEQ ID NO:4, SEQ ID NO:6, SEQ ID NO:8, SEQ ID NO:13, SEQ ID NO:16, SEQ ID NO:19, or SEQ ID NO:22. An isolated nucleic acid molecule encoding a NBS-2, NBS-3, PYRIN-12/NBS-4, or NBS-5 protein having a sequence which differs from that of SEQ ID NO:1, SEQ ID NO:3, SEQ ID NO:5, SEQ ID NO:7, SEQ ID NO:12, SEQ ID NO:14, SEQ ID NO:15, SEQ ID NO:17, SEQ ID NO:18, SEQ ID NO:20, SEQ ID NO:21 or SEQ ID NO:23 can be created by introducing one or more nucleotide substitutions, additions or deletions into the nucleotide sequence of NBS-2, NBS-3, PYRIN-12/NBS-4, or NBS-5 (SEQ ID NO:1, SEQ ID NO:3, SEQ ID NO:5, SEQ ID NO:7, SEQ ID NO:12, SEQ ID NO:14, SEQ ID NO:15, SEQ ID NO:17, SEQ ID NO:18, SEQ ID NO:20, SEQ ID NO:21 or SEQ ID NO:23 such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted nonessential amino acid residues. Thus, for example, 1%, 2%, 3%, 5%, or 10% of the amino acids can be replaced by conservative substitution. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in NBS-2, NBS-3, PYRIN-12/NBS-4, or NBS-5 is preferably replaced with another amino acid residue from the same side chain family. Alternatively, mutations can be introduced randomly along all or part of a NBS-2, NBS-3, PYRIN-12/NBS-4, or NBS-5 coding sequence, such as by saturation mutagenesis, and the resultant mutants can be screened for NBS-2, NBS-3, PYRIN-12/NBS-4, or NBS-5 biological activity to identify mutants that retain activity. Following mutagenesis, the encoded protein can be expressed recombinantly and the activity of the protein can be determined.

In an embodiment, a mutant NBS-2, NBS-3, PYRIN-12/NBS-4, or NBS-5 protein can be assayed for: (1) the ability to form protein:protein interactions with proteins in the apoptotic signaling pathway; (2) the ability to bind a NBS-2, NBS-3, PYRIN-12/NBS-4, or NBS-5 ligand; or (3) the ability to bind to an intracellular target protein.

The present invention encompasses antisense nucleic acid molecules, i.e., molecules which are complementary to a sense nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire NBS-2, NBS-3, PYRIN-12/NBS-4, or NBS-5 coding strand, or to only a portion thereof, e.g., all or part of the protein coding region (or open reading frame). An antisense nucleic acid molecule can be antisense to a noncoding region of the coding strand of a nucleotide sequence encoding NBS-2, NBS-3, PYRIN-12/NBS-4, or NBS-5. The noncoding regions ("5' and 3' untranslated regions") are the 5' and 3' sequences that flank the coding region and are not translated into amino acids. Given the coding strand sequences encoding NBS-2, NBS-3, PYRIN-12/NBS-4, or NBS-5 disclosed herein, antisense nucleic acids of the invention can be designed according to the rules of Watson and Crick base pairing. The antisense nucleic acid molecule can be complementary to the entire coding region of NBS-2, NBS-3, PYRIN-12/NBS-4, or NBS-5 mRNA, but more preferably is an oligonucleotide which is antisense to only a portion of the coding or noncoding region of NBS-2, NBS-3, PYRIN-12/NBS-4, or NBS-5 mRNA. For example, the antisense oligonucleotide can be complementary to the region surrounding the translation start site of NBS-2, NBS-3, PYRIN-12/NBS-4, or NBS-5 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-aino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a NBS-2, NBS-3, PYRIN-12/NBS-4, or NBS-5 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An antisense nucleic acid molecule of the invention can be administered by direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids. Res. 15:6625–6641). The antisense nucleic acid molecule can also comprise a 2'-o-methylribonucleotide (Inoue et al. (1987) Nucleic Acids Res. 15:6131–6148) or a chimeric RNA-DNA analogue (Inoue et al. (1987) FEBS Lett. 215:327–330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585–591)) can be used to catalytically cleave NBS-2, NBS-3, PYRIN-12/NBS-4, or NBS-5 mRNA transcripts to thereby inhibit translation of NBS-2, NBS-3, PYRIN-12/NBS-4, or NBS-5 mRNA. A ribozyme having specificity for a NBS-2, NBS- 3, PYRIN-12/NBS-4, or NBS-5-encoding nucleic acid can be designed based upon the nucleotide sequence of a NBS-2, NBS-3, PYRIN-12/NBS-4, or NBS-5 cDNA disclosed herein. For example, a derivative of a Tetrahymena L-19 IVS RNA can be constructed in which the nucleotide sequence of the active site is complementary to the nucleotide sequence to be cleaved in a NBS-2, NBS-3, PYRIN-12/NBS-4, or NBS-5-encoding mRNA. See, e.g., Cech et al. U.S. Pat. No. 4,987,071; and Cech et al. U.S. Pat. No. 5,116,742. Alternatively, NBS-2, NBS-3, PYRIN-12/NBS-4, or NBS-5 mRNA can be used to select a catalytic RNA having a specific ribonuclease activity from a pool of RNA molecules. See, e.g., Bartel and Szostak (1993) Science 261:1411–1418.

The invention also encompasses nucleic acid molecules which form triple helical structures. For example, NBS-2, NBS-3, PYRIN-12/NBS-4, or NBS-5 gene expression can be inhibited by targeting nucleotide sequences complementary to the regulatory region of the NBS-2, NBS-3, PYRIN-12/NBS-4, or NBS-5 (e.g., the NBS-2, NBS-3, PYRIN-12/NBS-4, or NBS-5 promoter and/or enhancers) to form triple helical structures that prevent transcription of the NBS-2, NBS-3, PYRIN-12/NBS-4, or NBS-5 gene in target cells. See generally, Helene (1991) Anticancer Drug Des. 6(6): 569–84; Helene (1992) Ann. N.Y. Acad. Sci. 660:27–36; and Maher (1992) Bioassays 14(12):807–15.

In embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) Bioorganic & Medicinal Chemistry 4(1):5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. (1996) Proc. Natl. Acad. Sci. USA 93:14670–675.

PNAs of NBS-2, NBS-3, PYRIN-12/NBS-4, or NBS-5 can be used for therapeutic and diagnostic applications. For example, PNAs can be used as antisense or antigene agents for sequence-specific modulation of gene expression by, e.g., inducing transcription or translation arrest or inhibiting replication. PNAs of NBS-2, NBS-3, PYRIN-12/NBS-4, or NBS-5 can also be used, e.g., in the analysis of single base pair mutations in a gene by, e.g., PNA directed PCR clamping; as artificial restriction enzymes when used in combination with other enzymes, e.g., S1 nucleases (Hyrup (1996) supra; or as probes or primers for DNA sequence and hybridization (Hyrup (1996) supra; Perry-O'Keefe et al. (1996) Proc. Natl. Acad. Sci. USA 93: 14670–675).

In another embodiment, PNAs of NBS-2, NBS-3, PYRIN-12/NBS-4, or NBS-5 can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of NBS-2, NBS-3, PYRIN-12/NBS-4, or NBS-5 can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) supra). The synthesis of PNA-DNA chimeras can be performed as described in Hyrup (1996) supra and Finn et al. (1996) Nucleic Acids Research 24(17):3357–63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag et al. (1989) Nucleic Acid Res. 17:5973–88). PNA monomers are then coupled in a stepwise manner to produce a chimeric molecule with a 5' PNA segment and a 3' DNA segment (Finn et al. (1996) Nucleic Acids Research 24(17):3357–63).

Alternatively, chimeric molecules can be synthesized with a 5' DNA segment and a 3' PNA segment (Peterser et al. (1975) Bioorganic Med. Chem. Lett. 5:1119–11124).

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553–6556; Lemaitre et al. (1987) Proc. Natl. Acad. Sci. USA 84:648–652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) Bio/Techniques 6:958–976) or intercalating agents (see, e.g., Zon (1988) Pharm. Res. 5:539–549). To this end, the oligonucleotide may be conjugated to another molecule, e.g., a peptide, hybridization triggered cross-linking agent, transport agent, hybridization-triggered cleavage agent, etc.

II. Isolated NBS-2, NBS-3, PYRIN-12/NBS-4, or NBS-5 Proteins and Anti-NBS-2, NBS-3, PYRIN-12/NBS-4, or NBS-5 Antibodies.

One aspect of the invention pertains to isolated NBS-2, NBS-3, PYRIN-12/NBS-4, or NBS-5 proteins, and biologically active portions thereof, as well as polypeptide fragments suitable for use as immunogens to raise anti-NBS-2, NBS-3, PYRIN-12/NBS-4, or NBS-5 antibodies. In one embodiment, native NBS-2, NBS-3, PYRIN-12/NBS-4, or NBS-5 proteins can be isolated from cells or tissue sources by an appropriate purification scheme using standard protein purification techniques. In another embodiment, NBS-2, NBS-3, PYRIN-12/NBS-4, or NBS-5 proteins are produced by recombinant DNA techniques. Alternative to recombinant expression, a NBS-2, NBS-3, PYRIN-12/NBS-4, or NBS-5 protein or polypeptide can be synthesized chemically using standard peptide synthesis techniques.

An "isolated" or "purified" protein or biologically active portion thereof is substantially free of cellular material or other contaminating proteins from the cell or tissue source from which the NBS-2, NBS-3, PYRIN-12/NBS-4, or NBS-5 protein is derived, or substantially free from chemical precursors or other chemicals when chemically synthesized. The language "substantially free of cellular material" includes preparations of NBS-2, NBS-3, PYRIN-12/NBS-4, or NBS-5 protein in which the protein is separated from cellular components of the cells from which it is isolated or recombinantly produced. Thus, NBS-2, NBS-3, PYRIN-12/NBS-4, or NBS-5 protein that is substantially free of cellular material includes preparations of NBS-2, NBS-3, PYRIN-12/NBS-4, or NBS-5 protein having less than about 30%, 20%, 10%, or 5% (by dry weight) of non-NBS-2, NBS-3, PYRIN-12/NBS-4, or NBS-5 protein (also referred to herein as a "contaminating protein"). When the NBS-2, NBS-3, PYRIN-12/NBS-4, or NBS-5 protein or biologically active portion thereof is recombinantly produced, it is also preferably substantially free of culture medium, i.e., culture medium represents less than about 20%, 10%, or 5% of the volume of the protein preparation. When NBS-2, NBS-3, PYRIN-12/NBS-4, or NBS-5 protein is produced by chemical synthesis, it is preferably substantially free of chemical precursors or other chemicals, i.e., it is separated from chemical precursors or other chemicals which are involved in the synthesis of the protein. Accordingly such preparations of NBS-2, NBS-3, PYRIN-12/NBS-4, or NBS-5 protein have less than about 30%, 20%, 10%, 5% (by dry weight) of chemical precursors or non-NBS-2, NBS-3, PYRIN-12/NBS-4, or NBS-5 chemicals.

Biologically active portions of a NBS-2, NBS-3, PYRIN-12/NBS-4, or NBS-5 protein include peptides comprising amino acid sequences sufficiently identical to or derived from the amino acid sequence of the NBS-2, NBS-3, PYRIN-12/NBS-4, or NBS- 5 protein (e.g., the amino acid sequence shown in SEQ ID NO:2, SEQ ID NO:4, SEQ ID NO:6, SEQ ID NO:8, SEQ ID NO:13, SEQ ID NO:16, SEQ ID NO:19, or SEQ ID NO:22), which include less amino acids than the full length NBS-2, NBS-3, PYRIN-12/NBS-4, or NBS-5 protein, and exhibit at least one activity of a NBS-2, NBS-3, PYRIN-12/NBS-4, or NBS-5 protein. Typically, biologically active portions comprise a domain or motif with at least one activity of the NBS-2, NBS-3, PYRIN-12/NBS-4, or NBS-5 protein. A biologically active portion of a NBS-2, NBS-3, PYRIN-12/NBS-4, or NBS-5 protein can be a polypeptide which is, for example, 10, 25, 50, 72, 100, 125, 150, 175, 200, 225, 250, 272, 300, 325, 350, 375, 400, 425, 450 or more amino acids in length. Preferred biologically active polypeptides include one or more identified NBS-2, NBS-3, PYRIN-12/NBS-4, or NBS-5 structural domains, e.g., the NBS domain.

Moreover, other biologically active portions, in which other regions of the protein are deleted, can be prepared by recombinant techniques and evaluated for one or more of the functional activities of a native NBS-2, NBS-3, PYRIN-12/NBS-4, or NBS-5 protein.

Human NBS-2, NBS-3, PYRIN-12/NBS-4, and NBS-5 proteins have the amino acid sequences of SEQ ID NO:2, SEQ ID NO:4, SEQ ID NO:6, SEQ ID NO:8, SEQ ID NO:13, SEQ ID NO:16, SEQ ID NO:19, or SEQ ID NO:22. Other useful NBS-2, NBS-3, PYRIN-12/NBS-4, or NBS-5 proteins are substantially identical to SEQ ID NO:2, SEQ ID NO:4, SEQ ID NO:6, SEQ ID NO:8, SEQ ID NO:13, SEQ ID NO:16, SEQ ID NO:19, or SEQ ID NO:22 and retain the functional activity of the protein of SEQ ID NO:2, SEQ ID NO:4, SEQ ID NO:6, SEQ ID NO:8, SEQ ID NO:13, SEQ ID NO:16, SEQ ID NO:19, or SEQ ID NO:22, yet differ in amino acid sequence due to natural allelic variation or mutagenesis.

A useful NBS-2, NBS-3, PYRIN-12/NBS-4, or NBS-5 protein is a protein which includes an amino acid sequence at least about 45%, preferably 55%, 65%, 75%, 85%, 95%, or 99% identical to the amino acid sequence of SEQ ID NO:2, SEQ ID NO:4, SEQ ID NO:6, SEQ ID NO:8, SEQ ID NO:13, SEQ ID NO:16, SEQ ID NO:19, or SEQ ID NO:22, and retains the functional activity of the NBS-2, NBS-3, PYRIN-12/NBS-4, or NBS-5 protein of SEQ ID NO:2, SEQ ID NO:4, SEQ ID NO:6, SEQ ID NO:8, SEQ ID NO:13, SEQ ID NO:16, SEQ ID NO:19, or SEQ ID NO:22.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions×100).

The determination of percent homology between two sequences can be accomplished using a mathematical algorithm. A preferred, non-limiting example of a mathematical algorithm utilized for the comparison of two sequences is the algorithm of Karlin and Altschul (1990) Proc. Nat'l Acad. Sci. USA 87:2264–2268, modified as in Karlin and Altschul (1993) Proc. Nat'l Acad. Sci. USA 90:5873–5877. Such an algorithm is incorporated into the NBLAST and XBLAST programs of Altschul, et al. (1990) J. Mol. Biol. 215:403–410. BLAST nucleotide searches can be performed with the NBLAST program, score=100, wordlength=12 to obtain nucleotide sequences similar or homologous to NBS-2, NBS-3, PYRIN-12/NBS-4, or NBS-5 nucleic acid molecules of the invention. To obtain gapped alignments for comparison purposes, Gapped BLAST can be utilized as described in Altschul et al. (1997) Nucleic Acids Res. 25:3389–3402. When utilizing BLAST and Gapped BLAST programs, the default parameters of the respective programs (e.g., XBLAST and NBLAST) can be used. See ncbi.nlm.nih.gov. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. When utilizing the ALIGN program for comparing nucleic acid sequences, a gap length penalty of 12, and a gap penalty of 4 can be used. Another preferred example of a mathematical algorithm utilized for the comparison of sequences is the Needleman and Wunsch (J. Mol. Biol. (48):444–453 (1970)) algorithm which has been incorporated into the GAP program in the GCG software package (available at gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at gcg.com), using a NWSgapdna.CMP matrix and a gap weight of 40, 50, 60, 70, or 80 and a length weight of 1, 2, 3, 4, 5, or 6.

The percent identity between two sequences can be determined using techniques similar to those described above, with or without allowing gaps. In calculating percent identity, typically exact matches are counted.

The invention also provides NBS-2, NBS-3, PYRIN-12/NBS-4, or NBS-5 chimeric or fusion proteins. As used herein, a NBS-2, NBS-3, PYRIN-12/NBS-4, or NBS-5 "chimeric protein" or "fusion protein" comprises a NBS-2, NBS-3, PYRIN-12/NBS-4, or NBS-5 polypeptide operatively linked to a non-NBS-2, NBS-3, PYRIN-12/NBS-4, or NBS-5 polypeptide. A "NBS-2, NBS-3, PYRIN-12/NBS-4, or NBS-5 polypeptide" refers to a polypeptide having an amino acid sequence corresponding to all or a portion (preferably a biologically active portion) of a NBS-2, NBS-3, PYRIN-12/NBS-4, or NBS-5, whereas a "non-NBS-2, NBS-3, PYRIN-12/NBS-4, or NBS-5 polypeptide" refers to a polypeptide having an amino acid sequence corresponding to a protein which is not substantially identical to the NBS-2, NBS-3, PYRIN-12/NBS-4, or NBS-5 protein, e.g., a protein which is different from the NBS-2, NBS-3, PYRIN-12/NBS-4, or NBS-5 proteins and which is derived from the same or a different organism. Within the fusion protein, the term "operatively linked" is intended to indicate that the NBS-2, NBS-3, PYRIN-12/NBS-4, or NBS-5 polypeptide and the non-NBS-2, NBS-3, PYRIN-12/NBS-4, or NBS-5 polypeptide are fused in-frame to each other. The heterologous polypeptide can be fused to the N-terminus or C-terminus of the NBS-2, NBS-3, PYRIN-12/NBS-4, or NBS-5 polypeptide.

One useful fusion protein is a GST fusion protein in which the NBS-2, NBS-3, PYRIN-12/NBS-4, or NBS-5 sequences are fused to the C-terminus of the GST sequences. Such fusion proteins can facilitate the purification of recombinant NBS-2, NBS-3, PYRIN-12/NBS-4, or NBS-5. In another embodiment, the fusion protein contains a signal sequence from another protein. In certain host cells (e.g., mammalian host cells), expression and/or secretion of NBS-2, NBS-3, PYRIN-12/NBS-4, or NBS-5 can be increased through use of a heterologous signal sequence. For example, the gp67 secretory sequence of the baculovirus envelope protein can be used as a heterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Molecular cloning, Sambrook et al, second edition, Cold spring harbor laboratory press, 1989) and the protein A secretory signal (Pharmacia Biotech; Piscataway, N.J.).

In yet another embodiment, the fusion protein is a NBS-2, NBS-3, PYRIN-12/NBS-4, or NBS-5-immunoglobulin fusion protein in which all or part of NBS-2, NBS-3, PYRIN-12/NBS-4, or NBS-5 is fused to sequences derived from a member of the immunoglobulin protein family. The NBS-2, NBS-3, PYRIN-12/NBS-4, or NBS- 5-immunoglobulin fusion proteins of the invention can be incorporated into pharmaceutical compositions and administered to a subject to inhibit an interaction between a NBS-2, NBS-3, PYRIN-12/NBS-4, or NBS-5 ligand and a NBS-2, NBS-3, PYRIN-12/NBS-4, or NBS-5 protein on the surface of a cell, to thereby suppress NBS-2, NBS-3, PYRIN-12/NBS-4, or NBS-5-mediated signal transduction in vivo. The NBS-2, NBS-3, PYRIN-12/NBS-4, or NBS-5-immunoglobulin fusion proteins can be used to affect the bioavailability of a NBS-2, NBS-3, PYRIN-12/NBS-4, or NBS-5 cognate ligand. Inhibition of the NBS-2, NBS-3, PYRIN-12/NBS-4, or NBS-5 ligand/NBS-2, NBS-3, PYRIN-12/NBS-4, or NBS-5 interaction may be useful therapeutically for both the treatment of proliferative and differentiative disorders, as well as modulating (e.g., promoting or inhibiting) cell survival. Moreover, the NBS-2, NBS-3, PYRIN-12/NBS-4, or NBS-5-immunoglobulin fusion proteins of the invention can be used as immunogens to produce anti-NBS-2, NBS-3, PYRIN-12/NBS-4, or NBS-5 antibodies in a subject, to purify NBS-2, NBS-3, PYRIN-12/NBS-4, or NBS-5 ligands and in screening assays to identify molecules which inhibit the interaction of NBS-2, NBS-3, PYRIN-12/NBS-4, or NBS-5 with a NBS-2, NBS-3, PYRIN-12/NBS-4, or NBS-5 ligand.

Preferably, a NBS-2, NBS-3, PYRIN-12/NBS-4, or NBS-5 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Current Protocols in Molecular Biology, Ausubel et al. eds., John Wiley & Sons: 1992). Moreover, many expression vectors are commercially available that already encode a fusion moiety (e.g., a GST polypeptide). A NBS-2, NBS-3, PYRIN-12/NBS-4, or NBS-5-encoding nucleic acid can be cloned into such an expression vector such that the fusion moiety is linked in-frame to the NBS-2, NBS-3, PYRIN-12/NBS-4, or NBS-5 protein.

The present invention also pertains to variants of the NBS-2, NBS-3, PYRIN-12/NBS-4, or NBS-5 proteins which function as either NBS-2, NBS-3, PYRIN-12/NBS-4, or NBS-5 agonists (mimetics) or as NBS-2, NBS-3, PYRIN-12/NBS-4, or NBS-5 antagonists. Variants of the NBS-2, NBS-3, PYRIN-12/NBS-4, or NBS-5 proteins can be generated by mutagenesis, e.g., discrete point mutation or truncation of the NBS-2, NBS-3, PYRIN-12/NBS-4, or NBS-5 proteins. An agonist of the NBS-2, NBS-3, PYRIN-12/NBS-4, or NBS-5 protein can retain substantially the same, or a subset, of the biological activities of the naturally occurring form of the NBS-2, NBS-3, PYRIN-12/NBS-4, or NBS-5 protein. An antagonist of the NBS-2, NBS-3, PYRIN-12/NBS-4, or NBS-5 protein can inhibit one or more of the activities of the naturally occurring form of the NBS-2, NBS-3, PYRIN-12/NBS-4, or NBS-5 protein by, for example, competitively binding to a downstream or upstream member of a cellular signaling cascade which includes the NBS-2, NBS-3, PYRIN-12/NBS-4, or NBS-5 protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the NBS-2, NBS-3, PYRIN-12/NBS-4, or NBS-5 proteins.

Variants of the NBS-2, NBS-3, PYRIN-12/NBS-4, or NBS-5 protein which function as either NBS-2, NBS-3, PYRIN-12/NBS-4, or NBS-5 agonists (mimetics) or as NBS-2, NBS-3, PYRIN-12/NBS-4, or NBS-5 antagonists can be identified by screening combinatorial libraries of mutants, e.g., truncation mutants of the NBS-2, NBS-3, PYRIN-12/NBS-4, or NBS-5 protein for NBS-2, NBS-3, PYRIN-12/NBS-4, or NBS-5 protein agonist or antagonist activity. In one embodiment, a variegated library of NBS-2, NBS-3, PYRIN-12/NBS-4, or NBS-5 variants is generated by combinatorial mutagenesis at the nucleic acid level and is encoded by a variegated gene library. A variegated library of NBS-2, NBS-3, PYRIN-12/NBS-4, or NBS-5 variants can be produced by, for example, enzymatically ligating a mixture of synthetic oligonucleotides into gene sequences such that a degenerate set of potential NBS-2, NBS-3, PYRIN-12/NBS-4, or NBS-5 sequences is expressible as individual polypeptides, or alternatively, as a set of larger fusion proteins (e.g., for phage display) containing the set of NBS-2, NBS-3, PYRIN-12/NBS-4, or NBS-5 sequences therein. There are a variety of methods which can be used to produce libraries of potential NBS-2, NBS-3, PYRIN-12/NBS-4, or NBS-5 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential NBS-2, NBS-3, PYRIN-12/NBS-4, or NBS-5 sequences. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

Useful fragments of NBS-2, NBS-3, PYRIN-12/NBS-4, or NBS-5, include fragments comprising or consisting of a domain or subdomain described herein, e.g., LRR or NBS or pyrin domain.

In addition, libraries of fragments of the NBS-2, NBS-3, PYRIN-12/NBS-4, or NBS-5 protein coding sequence can be used to generate a variegated population of NBS-2, NBS-3, PYRIN-12/NBS-4, or NBS-5 fragments for screening and subsequent selection of variants of a NBS-2, NBS-3, PYRIN-12/NBS-4, or NBS-5 protein. In one embodiment, a library of coding sequence fragments can be generated by treating a double stranded PCR fragment of a NBS-2, NBS-3, PYRIN-12/NBS-4, or NBS-5 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the NBS-2, NBS-3, PYRIN-12/NBS-4, or NBS-5 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of NBS-2, NBS-3, PYRIN-12/NBS-4, or NBS-5 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify NBS-2, NBS-3, PYRIN-12/NBS-4, or NBS-5 variants (Arkin and Yourvan (1992) Proc. Natl. Acad. Sci. USA 89:7811–7815; Delgrave et al. (1993) Protein Engineering 6(3):327–331).

An isolated NBS-2, NBS-3, PYRIN-12/NBS-4, or NBS-5 protein, or a portion or fragment thereof, can be used as an immunogen to generate antibodies that bind NBS-2, NBS-3, PYRIN-12/NBS-4, or NBS-5 using standard techniques for polyclonal and monoclonal antibody preparation. The full-length NBS-2, NBS-3, PYRIN-12/NBS-4, or NBS-5 protein can be used or, alternatively, the invention provides antigenic peptide fragments of NBS-2, NBS-3, PYRIN-12/NBS-4, or NBS-5 for use as immunogens. The antigenic peptide of NBS-2, NBS-3, PYRIN-12/NBS-4, or NBS-5 comprises at least 8 (preferably 10, 15, 20, or 30) amino acid residues of the amino acid sequence shown in SEQ ID NO:2, SEQ ID NO:4, SEQ ID NO:6, SEQ ID NO:8, SEQ ID NO:13, SEQ ID NO:16, SEQ ID NO:19, or SEQ ID NO:22 and encompasses an epitope of NBS-2, NBS-3, PYRIN-12/NBS-4, or NBS-5 such that an antibody raised against the peptide forms a specific immune complex with NBS-2, NBS-3, PYRIN-12/NBS-4, or NBS-5.

Useful antibodies include antibodies which bind to a domain or subdomain of NBS-2, NBS-3, PYRIN-12/NBS-4, or NBS-5 described herein (e.g., a LRR or NBS or pyrin domain).

Preferred epitopes encompassed by the antigenic peptide are regions of NBS-2, NBS-3, PYRIN-12/NBS-4, or NBS-5 that are located on the surface of the protein, e.g., hydrophilic regions. Other important criteria include a preference for a terminal sequence, high antigenic index (e.g., as predicted by Jameson-Wolf algorithm), ease of peptide synthesis (e.g., avoidance of prolines); and high surface probability (e.g., as predicted by the Emini algorithm; FIGS. 3, 7, 11, and 15).

A NBS-2, NBS-3, PYRIN-12/NBS-4, or NBS-5 immunogen typically is used to prepare antibodies by immunizing a suitable subject, (e.g., rabbit, goat, mouse or other mammal) with the immunogen. An appropriate immunogenic preparation can contain, for example, recombinantly expressed NBS-2, NBS-3, PYRIN-12/NBS-4, or NBS-5 protein or a chemically synthesized NBS-2, NBS-3, PYRIN-12/NBS-4, or NBS-5 polypeptide. The preparation can further include an adjuvant, such as Freund's complete or incomplete adjuvant, or similar immunostimulatory agent. Immunization of a suitable subject with an immunogenic NBS-2, NBS-3, PYRIN-12/NBS-4, or NBS-5 preparation induces a polyclonal anti-NBS-2, NBS-3, PYRIN-12/NBS-4, or NBS-5 antibody response.

Accordingly, another aspect of the invention pertains to anti-NBS-2, NBS-3, PYRIN-12/NBS-4, or NBS-5 antibodies. The term "antibody" as used herein refers to immunoglobulin molecules and immunologically active portions of immunoglobulin molecules, i.e., molecules that contain an antigen binding site which specifically binds an antigen, such as NBS-2, NBS-3, PYRIN-12/NBS-4, or NBS-5. A molecule which specifically binds to NBS-2, NBS-3, PYRIN-12/NBS-4, or NBS-5 is a molecule which binds NBS-2, NBS-3, PYRIN-12/NBS-4, or NBS-5, but does not substantially bind other molecules in a sample, e.g., a biological sample, which naturally contains NBS-2, NBS-3, PYRIN-12/NBS-4, or NBS-5. Examples of immunologically active portions of immunoglobulin molecules include F(ab) and F(ab')2 fragments which can be generated by treating the antibody with an enzyme such as pepsin. The invention provides polyclonal and monoclonal antibodies that bind NBS-2, NBS-3, PYRIN-12/NBS-4, or NBS-5. The term "monoclonal antibody" or "monoclonal antibody composition", as used herein, refers to a population of antibody molecules that contain only one species of an antigen binding site capable of immunoreacting with a particular epitope of NBS-2, NBS-3, PYRIN-12/NBS-4, or NBS-5. A monoclonal antibody composition thus typically displays a single binding affinity for a particular NBS-2, NBS-3, PYRIN-12/NBS-4, or NBS-5 protein with which it immunoreacts.

Polyclonal anti-NBS-2, NBS-3, PYRIN-12/NBS-4, or NBS-5 antibodies can be prepared as described above by immunizing a suitable subject with a NB S-2, NBS-3, PYRIN-12/NBS-4, or NBS-5 immunogen. The anti-NBS-2, NBS-3, PYRIN-12/NBS-4, or NBS-5 antibody titer in the immunized subject can be monitored over time by standard techniques, such as with an enzyme linked immunosorbent assay (ELISA) using immobilized NBS-2, NBS-3, PYRIN-12/NBS-4, or NBS-5. If desired, the antibody molecules directed against NBS-2, NBS-3, PYRIN-12/NBS-4, or NBS-5 can be isolated from the mammal (e.g., from the blood) and further purified by well-known techniques, such as protein A chromatography to obtain the IgG fraction. At an appropriate time after immunization, e.g., when the anti-NBS-2, NBS-3, PYRIN-12/NBS-4, or NBS-5 antibody titers are highest, antibody-producing cells can be obtained from the subject and used to prepare monoclonal antibodies by standard techniques, such as the hybridoma technique originally described by Kohler and Milstein (1975) Nature 256:495–497, the human B cell hybridoma technique (Kozbor et al. (1983) Immunol Today 4:72), the EBV-hybridoma technique (Cole et al. (1985), Monoclonal Antibodies and Cancer Therapy, Alan R. Liss, Inc., pp. 77–96) or trioma techniques. The technology for producing various antibodies monoclonal antibody hybridomas is well known (see generally Current Protocols in Immunology (1994) Coligan et al. (eds.) John Wiley & Sons, Inc., New York, N.Y.). Briefly, an immortal cell line (typically a myeloma) is fused to lymphocytes (typically splenocytes) from a mammal immunized with a NBS-2, NBS-3, PYRIN-12/NBS-4, or NBS-5 immunogen as described above, and the culture supernatants of the resulting hybridoma cells are screened to identify a hybridoma producing a monoclonal antibody that binds NBS-2, NBS-3, PYRIN-12/NBS-4, or NBS-5.

Any of the many well known protocols used for fusing lymphocytes and immortalized cell lines can be applied for the purpose of generating an anti-NBS-2, NBS-3, PYRIN-12/NBS-4, or NBS-5 monoclonal antibody (see, e.g., Current Protocols in Immunology, supra; Galfre et al. (1977) Nature 266:55052; R. H. Kenneth, in Monoclonal Antibodies: A New Dimension In Biological Analyses, Plenum Publishing Corp., New York, N.Y. (1980); and Lerner (1981) Yale J. Biol. Med., 54:387–402). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS 1/1-Ag4-1, P3-x63-Ag8.653 or Sp2/O-Ag14 myeloma lines. These myeloma lines are available from ATCC (Manassas. VA). Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind NBS-2, NBS-3, PYRIN-12/NBS-4, or NBS-5, e.g., using a standard ELISA assay.

Alternative to preparing monoclonal antibody-secreting hybridomas, a monoclonal anti-NBS-2, NBS-3, PYRIN-12/NBS-4, or NBS-5 antibody can be identified and isolated by screening a recombinant combinatorial immunoglobulin library (e.g., an antibody phage display library) with NBS-2, NBS-3, PYRIN-12/NBS-4, or NBS-5 to thereby isolate immunoglobulin library members that bind NBS-2, NBS-3, PYRIN-12/NBS-4, or NBS-5. Kits for generating and screening phage display libraries are commercially available (e.g., the Pharmacia Recombinant Phage Antibody System, Catalog No. 27-9400-01; and the Stratagene SurfZAP Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology 9:1370–1372; Hay et al. (1992) Hum. Antibod. Hybridomas 3:81–85; Huse et al. (1989) Science 246:1275–1281; Griffiths et al. (1993) EMBO J. 12:725–734.

Additionally, recombinant anti-NBS-2, NBS-3, PYRIN-12/NBS-4, or NBS-5 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) Science 240:1041–1043; Liu et al. (1987) Proc. Natl. Acad. Sci. USA 84:3439–3443; Liu et al. (1987) J. Immunol. 139:3521–3526; Sun et al. (1987) Proc. Natl. Acad. Sci. USA 84:214–218; Nishimura et al. (1987) Canc. Res. 47:999–1005; Wood et al. (1985) Nature 314:446–449; and Shaw et al. (1988) J. Natl. Cancer Inst. 80:1553–1559); Morrison, (1985) Science 229:1202–1207; Oi et al. (1986) Bio/Techniques 4:214; U.S. Pat. No. 5,225,539; Jones et al. (1986) Nature 321:552–525; Verhoeyan et al. (1988) Science 239:1534; and Beidler et al. (1988) J. Immunol. 141:4053–4060.

An anti-NBS-2, NBS-3, PYRIN-12/NBS-4, or NBS-5 antibody (e.g., monoclonal antibody) can be used to isolate NBS-2, NBS-3, PYRIN-12/NBS-4, or NBS-5 by standard techniques, such as affinity chromatography or immunoprecipitation. An anti-NBS-2, NBS-3, PYRIN-12/NBS-4, or NBS-5 antibody can facilitate the purification of natural NBS-2, NBS-3, PYRIN-12/NBS-4, or NBS-5 from cells and of recombinantly produced NBS-2, NBS-3, PYRIN-12/NBS-4, or NBS-5 expressed in host cells. Moreover, an anti-NBS-2, NBS-3, PYRIN-12/NBS-4, or NBS-5 antibody can be used to detect NBS-2, NBS-3, PYRIN-12/NBS-4, or NBS-5 protein (e.g., in a cellular lysate or cell supernatant) in order to evaluate the abundance and pattern of expression of the NBS-2, NBS-3, PYRIN-12/NBS-4, or NBS-5 protein. Anti-NBS-2, NBS-3, PYRIN-12/NBS-4, or NBS-5 antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator; or, biological response modifiers such as, for example, lymphokines, interleukin-1 (IL-1), interleukin-2 (IL-2), interleukin-6 (IL-6), granulocyte macrophase colony stimulating factor (GM-CSF), granulocyte colony stimulating factor (G-CSF), or other growth factors.

Techniques for conjugating such therapeutic moiety to antibodies are well known, see, e.g., Arnon et al., "Monoclonal Antibodies for Immunotargeting of Drugs in Cancer Therapy", in Monoclonal Antibodies and Cancer Therapy, Reisfeld et al. (eds.), pp. 243–56 (Alan R. Liss, Inc. 1985); Hellstrom et al., "Antibodies for Drug Delivery", in Controlled Drug Delivery (2nd Ed.), Robinson et al. (eds.), pp. 623–53 (Marcel Dekker, Inc. 1987); Thorpe, "Antibody Carriers of Cytotoxic Agents in Cancer Therapy: A Review", in Monoclonal Antibodies'84: Biological and Clinical Applications, Pinchera et al. (eds.), pp. 475–506 (1985); "Analysis, Results, and Future Prospective of The Therapeutic Use of Radiolabeled Antibody In Cancer Therapy", in Monoclonal Antibodies for Cancer Detection and Therapy, Baldwin et al. (eds.), pp. 303–16 (Academic Press 1985), and Thorpe et al., "The Preparation and Cytotoxic Properties of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

In addition, antibodies of the invention, either conjugated or not conjugated to a therapeutic moiety, can be administered together or in combination with a therapeutic moiety such as a cytotoxin, a therapeutic agent or a radioactive metal ion. The order of administration of the antibody and therapeutic moiety can vary. For example, in some embodiments, the antibody is administered concurrently (through the same or different delivery devices, e.g., syringes) with the therapeutic moiety. Alternatively, the antibody can be administered separately and prior to the therapeutic moiety. Still alternatively, the therapeutic moiety is administered separately and prior to the antibody. In many embodiments, these administration regimens will be continued for days, months or years.

Another aspect of the invention relates to a method for inducing an immunological response in a mammal which comprises inoculating the mammal with a NBS-2, NBS-3, PYRIN-12/NBS-4, or NBS-5 polypeptide, adequate to produce antibody and/or T cell immune response to protect the animal from the diseases hereinbefore mentioned, amongst others. Yet another aspect of the invention relates to a method of inducing immunological response in a mammal which comprises, delivering a NBS-2, NBS-3, PYRIN-12/NBS-4, or NBS-5 polypeptide via a vector directing expression of the polynucleotide and coding for the polypeptide in vivo in order to induce such an immunological response to produce antibody to protect the animal from diseases.

A further aspect of the invention relates to an immunological/vaccine formulation (composition) which, when introduced into a mammalian host, induces an immunological response in that mammal to a NBS-2, NBS-3, PYRIN-12/NBS-4, or NBS-5 polypeptide of the present invention wherein the composition comprises a polypeptide or polynucleotide of NBS-2, NBS-3, PYRIN-12/NBS-4, or NBS-5. The vaccine formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

III. Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exist in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. This skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a work processing test file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or a target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration formed upon the folding of the target motif. There are a variety of target motifs know in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of know algorithms are disclosed publicly and a variety of commercially available software for conducting search means are and can be used in the computer-based systems of the present invention. Examples of such software include, but is not limited to, MacPattern (EMBL), BLASTIN and BLASTX (NCBIA).

For example, software that implements the BLAST (Altschul et al. (1990) *J. of Mol. Biol.* 215:403–410) and BLAZE (Brutlag et al. (1993) *Comp. Chem.* 17:203–207) search algorithms on a Sybase system can be used to identify open reading frames (ORFs) of the sequences of the invention which contain homology to ORFs or proteins from other libraries. Such ORFs are protein-encoding fragments and are useful in producing commercially important proteins such as enzymes used in various reactions and in the production of commercially useful metabolites.

IV. Recombinant Expression Vectors and Host Cells

Another aspect of the invention pertains to vectors, preferably expression vectors, containing a nucleic acid encoding NBS-2, NBS-3, PYRIN-12/NBS-4, or NBS-5 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operatively linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., NBS-2, NBS-3, PYRIN-12/NBS-4, or NBS-5 proteins, mutant forms of NBS-2, NBS-3, PYRIN-12/NBS-4, or NBS-5, fusion proteins, etc.).

The recombinant expression vectors of the invention can be designed for expression of NBS-2, NBS-3, PYRIN-12/NBS-4, or NBS-5 in prokaryotic or eukaryotic cells, e.g., bacterial cells such as E. coli, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion E. coli expression vectors include pTrc (Amann et al., (1988) Gene 69:301–315) and pET 11d (Studier et al., Gene Expression Technology: Methods in Enzymology 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident ë prophage harboring a T7 gn1 gene under the transcriptional control of the lacUV5 promoter.

One strategy to maximize recombinant protein expression in E. coli is to express the protein in a bacterial having an impaired capacity to proteolytically cleave the recombinant protein (Gottesman, Gene Expression Technology: Methods in Enzymology 185, Academic Press, San Diego, Calif. (1990) 119–128). Another strategy is to alter the nucleic acid sequence of the nucleic acid to be inserted into an expression vector so that the individual codons for each amino acid are those preferentially utilized in E. coli (Wada et al. (1992) Nucleic Acids Res. 20:2111–2118). Such alteration of nucleic acid sequences of the invention can be carried out by standard DNA synthesis techniques.

In another embodiment, the NBS-2, NBS-3, PYRIN-12/NBS-4, or NBS-5 expression vector is a yeast expression vector. Examples of vectors for expression in yeast S. cerivisae include pYepSec1 (Baldari et al. (1987) EMBO J. 6:229–234), pMFa (Kurjan and Herskowitz, (1982) Cell 30:933–943), pJRY88 (Schultz et al. (1987) Gene 54:113–123), pYES2 (Invitrogen Corporation, San Diego, Calif.), pGBT9 (Clontech, Palo Alto, Calif.), pGAD10 (Clontech, Palo Alto, Calif.), pYADE4 and pYGAE2 and pYPGE2 (Brunelli and Pall, (1993) Yeast 9:1299–1308), pYPGE15 (Brunelli and Pall, (1993) Yeast 9:1309–1318), pACTII (Dr. S. E. Elledge, Baylor College of Medicine), and picZ (In Vitrogen Corp, San Diego, Calif.). Alternatively, NBS-2, NBS-3, PYRIN-12/NBS-4, or NBS-5 can be expressed in insect cells using baculovirus expression vectors. Baculovirus vectors available for expression of proteins in cultured insect cells (e.g., Sf 9 cells) include the pAc series (Smith et al. (1983) Mol. Cell Biol. 3:2156–2165) and the pVL series (Lucklow and Summers (1989) Virology 170:31–39).

In yet another embodiment, a nucleic acid of the invention is expressed in mammalian cells using a mammalian expression vector. Examples of mammalian expression vectors include pCDM8 (Seed (1987) Nature 329:840), pCI (Promega), and pMT2PC (Kaufman et al. (1987) EMBO J. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al. (supra).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268–277), lymphoid-specific promoters (Calame and Eaton (1988) Adv. Immunol. 43:235–275), in particular promoters of T cell receptors (Winoto and Baltimore (1989) EMBO J. 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) Proc. Natl. Acad. Sci. USA 86:5473–5477), pancreas-specific promoters (Edlund et al. (1985) Science 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) Science 249:374–379) and the α-fetoprotein promoter (Campes and Tilghman (1989) Genes Dev. 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to NBS-2, NBS-3, PYRIN-12/NBS-4, or NBS-5 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (Reviews—Trends in Genetics, Vol. 1(1) 1986).

Another aspect of the invention pertains to host cells into which a recombinant expression vector of the invention or isolated nucleic acid molecule of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, NBS-2, NBS-3, PYRIN-12/NBS-4, or NBS-5 protein can be expressed in bacterial cells such as E. coli, insect cells, yeast or mammalian cells (such as Chinese hamster ovary cells (CHO) or COS cells). Other suitable host cells are known to those skilled in the art.

Vector DNA or an isolated nucleic acid molecule of the invention can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In some cases vector DNA is retained by the host cell. In other cases the host cell does not retain vector DNA and retains only an isolated nucleic acid molecule of the invention carried by the vector. In some cases, and isolated nucleic acid molecule of the invention is used to transform a cell without the use of a vector.

In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding NBS-2, NBS-3, PYRIN-12/NBS-4, or NBS-5 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a NBS-2, NBS-3, PYRIN-12/NBS-4, or NBS-5 protein. Accordingly, the invention further provides methods for producing NBS-2, NBS-3, PYRIN-12/NBS-4, or NBS-5 protein using the host cells of the invention. In one embodiment, the method comprises culturing the host cell of the invention (into which a recombinant expression vector or isolated nucleic acid molecule encoding NBS-2, NBS-3, PYRIN-12/NBS-4, or NBS-5 has been introduced) in a suitable medium such that NBS-2, NBS-3, PYRIN-12/NBS-4, or NBS-5 protein is produced. In another embodiment, the method further comprises isolating NBS-2, NBS-3, PYRIN-12/NBS-4, or NBS-5 from the medium or the host cell.

NBS-2, NBS-3, PYRIN-12/NBS-4, and NBS-5 nucleic acid molecules can be used in viral gene delivery systems for gene therapy, e.g., adenoviral or retroviral gene delivery systems.

NBS-2, NBS-3, PYRIN-12/NBS-4, and NBS-5 nucleic acid molecules can also be used in non-viral gene delivery systems for gene therapy. Thus, another aspect of the invention pertains to non-viral gene delivery systems, such as plasmid-based gene delivery systems. Non-viral gene delivery systems are described in detail by Huang et al. ((1999) Nonviral Vectors for Gene Therapy, Academic Press, San Diego, Calif.). Nonviral vectors have several potential advantages over their viral counterparts, including: reduced immunogenicity; low acute toxicity; simplicity; and ease of large scale production. Nonviral vectors can be delivered as naked DNA, by bioballistic bombardment, and in various complexes, including liposome/DNA complexes (lipoplexes), polymer/DNA complexes (polyplexes), and liposome/polymer/DNA complexes (lipopolyplexes). Nonviral vectors may be administered by various routes, e.g., intravenous injection, peritoneal injection, intramuscular injection, subcutaneous injection, intratracheal injection, and aerosolization.

Naked DNA (i.e. free from association with, e.g., transfection-facilitating proteins, viral particles, liposomal formulations, charged lipids and calcium phosphate precipitating), can be expressed at its injection site or at a remote site. For example, naked DNA can be injected directly into skeletal muscle, liver, heart muscle, and tumor tissue. For systemic administration, plasmid DNA may need to be protected from degradation by endonucleases during delivery from the site of administration to the site of gene expression.

Bioballistic bombardment, also known as gene gun, allows for the penetration of target cells in vitro, ex vivo, or in vivo. In this technique, DNA-coated gold particles are accelerated to a high velocity by an electric arc generated by a high voltage discharge. The method is effective for a variety of organ types, including skin, liver, muscle, spleen, and pancreas. The gene gun transfer method is not dependent upon specific cell surface receptors, cell cycle status, or the size of the DNA vector. Useful gene gun devices include the Accell® (PowderJect Vaccines, Inc.) and the Helios™ (Bio-Rad). These devices create a compressed shock wave of helium gas, accelerating DNA-coated gold (or tungsten) particles to high speed, whereby the particles have sufficient momentum to penetrate a target tissue.

Lipoplexes are typically made up of three components: a cationic lipid, a neutral colipid, and plasmid DNA that encodes one or more genes of interest. Commonly used cationic lipids include DOTMA, DMRIE, DC-chol, DOTAP, DMRIE, DDAB, DODAB/C, DOGS, DOSPA, SAINT-n, DOSPER, DPPES, DORIE, GAP-DLRIE, and DOTIM. Dioleoyl (DO) and dimyristoyl (DM) chains are thought to be especially effective for gene delivery. Cationic lipids are typically composed of a positively charged headgroup, a hydrophobic lipid anchor, and a linker that connects the headgroup and anchor. Catioinc lipids used in lipoplexes can be divided into two broad classes: those that use cholesterol as the lipid anchor and those that use diacyl chains of varying lengths and extent of saturation. The number of protonatable amines on the headgroup may affect transfection activity, with multivalent headgroups being generally more active than monovalent headgroups. The linker can be made of a variety of chemical structures, e.g., ether, amide, carbamate, amine, urea, ester, and peptide bonds. Neutral colipids of lipoplexes commonly include DOPE, DOPC, and cholesterol. Generally, DOPE is used as the neutral colipid with catioinc lipids that are based on cholesterol (e.g., DC-chol, GL-67) and cholesterol is used as the neutral colipid with cationic lipids that harbor diacyl chains as the hydrophobic anchor (e.g., DOTAP, DOTIM).

Polyplexes are formed when cationic polymers are mixed with DNA. Cationic polymers used to from polyplexes are of two general types: linear polymers such as polylysine and spermine; and the branched chain, spherical, or globular polycations such as polyethyleneimine and dendrimers. Lipopolyplexes are formed by the incorporation of polylysine into a lipoplex to form ternary complexes. DNA can be complexed with a natural biopolymer, e.g., gelatin or chitosan, functioning as a gene carrier to form nanospheres. Such biodegradable nanospheres have several advantages, including the coencapsulation of bioactive agents, e.g. nucleic acids and drugs, and the sustained release of the DNA. Gelatin-DNA or chitosan-DNA nanospheres are synthesized by mixing the DNA solution with an aqueous solution of gelatin or chitosan.

The effectiveness nonviral vectors may be enhanced by conjugation to ligands that direct the vector either to a particular cell type or to a particular location within a cell. Antibodies and other site-specific proteins can be attached to a vector, e.g., on the surface of the vector or incorporated in the membrane. Following injection, these vectors bind efficiently and specifically to a target site. With respect to liposomes, ligands to a cell surface receptor can be incorporated into the surface of a liposome by covalently modifying the ligand with a lipid group and adding it during the formation of liposomes. The following classes of ligands can be incorporated into the nonviral DNA delivery complexes of the invention in order to make them more effective for gene delivery: (1) peptides, e.g., peptides having a specific cell surface receptor so that complexes will be targeted to specific cells bearing the receptor; (2) nuclear localization signals, e.g., to promote efficient entry of DNA into the nucleus; (3) pH-sensitive ligands, to encourage endosomal escape; (4) steric stabilizing agents, to prevent destabilization of the complexes after introduction into the biological milieu. Gene chemistry approaches, e.g. peptide nucleic acids, can be used to couple ligands to DNA to improve the in vivo bioavailability and expression of the DNA.

In plasmid-based, non-viral gene delivery systems it is often useful to link a polypeptide (e.g., an antibody), nucleic acid molecule, or other compound to the gene delivery plasmid such that the polypeptide, nucleic acid molecule or other compound remains associated with the plasmid following intracellular delivery in a manner that does not interfere with the transcriptional activity of the plasmid. This can be accomplished using an appropriate biotin-conjugated peptide nucleic acid (PNA) clamp. A sequence complementary to the biotin-conjugated PNA clamp is inserted into the gene delivery plasmid. The biotin-conjugated PNA will bind essentially irreversibly to the complementary sequence inserted into the plasmid. A polypeptide, nucleic acid molecule or other compound of interest can be conjugated to streptavidin. The streptavidin conjugate can bind to the biotin-PNA clamp bound to the plasmid. In this manner, a polypeptide, nucleic acid molecule or other compound can be bound to a gene delivery plasmid such that the polypeptide, nucleic acid molecule or other compound remains bound to the plasmid even within a cell. Importantly, the PNA clamp-binding site in the plasmid must be chosen so as not to interfere with a needed promoter/enhancer or coding region or otherwise disrupt the expression of the gene in the plasmid. An alternative approach employs a maleimide-conjugated PNA clamp. Polypeptides, nucleic acid molecules and other compounds containing a free thiol residue may be conjugated directly to the maleimide-PNA-DNA hybrid. As with the biotin-conjugated method, this conjugation does not disturb the transcriptional activity of the plasmid if the PNA-binding site is chosen to be in a region of the plasmid not essential for gene activity. Both of these approaches are described in detail by Zelphati et al. ((2000) BioTechniques 28:304–315).

The host cells of the invention can also be used to produce nonhuman transgenic animals. For example, in one embodiment, a host cell of the invention is a fertilized oocyte or an embryonic stem cell into which NBS-2, NBS-3, PYRIN-12/NBS-4, or NBS-5-coding sequences have been introduced. Such host cells can then be used to create non-human transgenic animals in which exogenous NBS-2, NBS-3, PYRIN-12/NBS-4, or NBS-5 sequences have been introduced into their genome or homologous recombinant animals in which endogenous NBS-2, NBS-3, PYRIN-12/NBS-4, or NBS-5 sequences have been altered. Such animals are useful for studying the function and/or activity of NBS-2, NBS-3, PYRIN-12/NBS-4, or NBS-5 and for identifying and/or evaluating modulators of NBS-2, NBS-3, PYRIN-12/NBS-4, or NBS-5 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous NBS-2, NBS-3, PYRIN-12/NBS-4, or NBS-5 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing NBS-2, NBS-3, PYRIN-12/NBS-4, or NBS-5-encoding nucleic acid into the male pronuclei of a fertilized oocyte, e.g., by microinjection, retroviral infection, and allowing the oocyte to develop in a pseudopregnant female foster animal. The NBS-2, NBS-3, PYRIN-12/NBS-4, or NBS-5 cDNA sequence, e.g., that of SEQ ID NO:1, SEQ ID NO:3, SEQ ID NO:5, SEQ ID NO:7, SEQ ID NO:12, SEQ ID NO:14, SEQ ID NO:15, SEQ ID NO:17, SEQ ID NO:18 or SEQ ID NO:20 can be introduced as a transgene into the genome of a non-human animal. Alternatively, a nonhuman homolog or ortholog of the human NBS-2, NBS-3, PYRIN-12/NBS-4, or NBS-5 gene, such as a mouse NBS-2, NBS-3, PYRIN-12/NBS-4, or NBS-5 gene, can be isolated based on hybridization to the human NBS-2, NBS-3, PYRIN-12/

NBS-4, or NBS-5 cDNA and used as a transgene. Intronic sequences and polyadenylation signals can also be included in the transgene to increase the efficiency of expression of the transgene. A tissue-specific regulatory sequence(s) can be operably linked to the NBS-2, NBS-3, PYRIN-12/NBS-4, or NBS-5 transgene to direct expression of NBS-2, NBS-3, PYRIN-12/NBS-4, or NBS-5 protein to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the NBS-2, NBS-3, PYRIN-12/NBS-4, or NBS-5 transgene in its genome and/or expression of NBS-2, NBS-3, PYRIN-12/NBS-4, or NBS-5 mRNA in tissues or cells of the animals. A transgenic founder animal can then be used to breed additional animals carrying the transgene. Moreover, transgenic animals carrying a transgene encoding NBS-2, NBS-3, PYRIN-12/NBS-4, or NBS-5 can further be bred to other transgenic animals carrying other transgenes.

To create an homologous recombinant animal, a vector is prepared which contains at least a portion of a NBS-2, NBS-3, PYRIN-12/NBS-4, or NBS-5 gene (e.g., a human or a non-human homolog of the NBS-2, NBS-3, PYRIN-12/NBS-4, or NBS-5 gene, e.g., a murine NBS-2, NBS-3, PYRIN-12/NBS-4, or NBS-5 gene) into which a deletion, addition or substitution has been introduced to thereby alter, e.g., functionally disrupt, the NBS-2, NBS-3, PYRIN-12/NBS-4, or NBS-5 gene. In an embodiment, the vector is designed such that, upon homologous recombination, the endogenous NBS-2, NBS-3, PYRIN-12/NBS-4, or NBS-5 gene is functionally disrupted (i.e., no longer encodes a functional protein; also referred to as a "knock out" vector). Alternatively, the vector can be designed such that, upon homologous recombination, the endogenous NBS-2, NBS-3, PYRIN-12/NBS-4, or NBS-5 gene is mutated or otherwise altered but still encodes functional protein (e.g., the upstream regulatory region can be altered to thereby alter the expression of the endogenous NBS-2, NBS-3, PYRIN-12/NBS-4, or NBS-5 protein). In the homologous recombination vector, the altered portion of the NBS-2, NBS-3, PYRIN-12/NBS-4, or NBS-5 gene is flanked at its 5' and 3' ends by additional nucleic acid of the NBS-2, NBS-3, PYRIN-12/NBS-4, or NBS-5 gene to allow for homologous recombination to occur between the exogenous NBS-2, NBS-3, PYRIN-12/NBS-4, or NBS-5 gene carried by the vector and an endogenous NBS-2, NBS-3, PYRIN-12/NBS-4, or NBS-5 gene in an embryonic stem cell. The additional flanking NBS-2, NBS-3, PYRIN-12/NBS-4, or NBS-5 nucleic acid is of sufficient length for successful homologous recombination with the endogenous gene. Typically, several kilobases of flanking DNA (both at the 5' and 3' ends) are included in the vector (see, e.g., Thomas and Capecchi (1987) Cell 51:503 for a description of homologous recombination vectors). The vector is introduced into an embryonic stem cell line (e.g., by electroporation) and cells in which the introduced NBS-2, NBS-3, PYRIN-12/NBS-4, or NBS-5 gene has homologously recombined with the endogenous NBS-2, NBS-3, PYRIN-12/NBS-4, or NBS-5 gene are selected (see, e.g., Li et al. (1992) Cell 69:915). The selected cells are then injected into a blastocyst of an animal (e.g., a mouse) to form aggregation chimeras (see, e.g., Bradley in Teratocarcinomas and Embryonic Stem Cells: A Practical Approach, Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) Current Opinion in Bio/Technology 2:823–829 and in PCT Publication Nos. WO 90/11354, WO 91/01140, WO 92/0968, and WO 93/04169.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232–6236. Another example of a recombinase system is the FLP recombinase system of Saccharomyces cerevisiae (O'Gorman et al. (1991) Science 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) Nature 385:810–813 and PCT Publication Nos. WO 97/07668 and WO 97/07669. In brief, a cell, e.g., a somatic cell, from the transgenic animal can be isolated and induced to exit the growth cycle and enter Go phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

In another embodiment, the expression characteristics of an endogenous NBS-2, NBS-3, PYRIN-12/NBS-4, or NBS-5 gene within a cell line or microorganism may be modified by inserting a heterologous DNA regulatory element into the genome of a stable cell line or cloned microorganism such that the inserted regulatory element is operatively linked with the endogenous NBS-2, NBS-3, PYRIN-12/NBS-4, or NBS-5 gene. For example, an endogenous NBS-2, NBS-3, PYRIN-12/NBS-4, or NBS-5 which is normally "transcriptionally silent," i.e. a NBS-2, NBS-3, PYRIN-12/NBS-4, or NBS-5 gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous NBS-2, NBS-3, PYRIN-12/NBS-4, or NBS-5 gene may be activated by insertion of a promiscuous regulatory element that works across cell types.

A heterologous regulatory element may be inserted into a stable cell line or cloned microorganism, such that it is operatively linked with an endogenous NBS-2, NBS-3, PYRIN-12/NBS-4, or NBS-5 gene, using techniques, such as targeted homologous recombination, which are well known to those of skill in the art, and described e.g., in Chappel, U.S. Pat. No. 5,272,071; PCT publication No. WO 91/06667, published May 16, 1991.

V. Pharmaceutical Compositions

The NBS-2, NBS-3, PYRIN-12/NBS-4, or NBS-5 nucleic acid molecules, NBS-2, NBS-3, PYRIN-12/NBS-4, or NBS-5 proteins, and anti-NBS-2, NBS-3, PYRIN-12/NBS-4, or NBS-5 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of the invention. Such methods comprise formulating a pharmaceutically acceptable carrier with an agent which modulates expression or activity of a polypeptide or nucleic acid of the invention. Such compositions can further include additional active agents. Thus, the invention further includes methods for preparing a pharmaceutical composition by formulating a pharmaceutically acceptable carrier with an agent which modulates expression or activity of a polypeptide or nucleic acid of the invention and one or more additional active compounds.

The agent which modulates expression or activity may, for example, be a small molecule. For example, such small molecules include peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight les than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a NBS-2, NBS-3, PYRIN-12/NBS-4, or NBS-5 protein or anti-NBS-2, NBS-3, PYRIN-12/NBS-4, or NBS-5 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of protein, polypeptide, or antibody can include a single treatment or, preferably, can include a series of treatments.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) J. Acquired Immune Deficiency Syndromes and Human Retrovirology 14:193).

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The gene therapy vectors of the invention can be either viral or non-viral. Examples of plasmid-based, non-viral vectors are discussed in Huang et al. (1999) Nonviral Vectors for Gene Therapy (supra). A modified plasmid is one example of a non-viral gene delivery system. Peptides, proteins (including antibodies), and oligonucleotides may be stably conjugated to plasmid DNA by methods that do not interfere with the transcriptional activity of the plasmid (Zelphati et al. (2000) BioTechniques 28:304–315). The attachment of proteins and/or oligonucleotides may influence the delivery and trafficking of the plasmid and thus render it a more effective pharmaceutical composition.

The pharmaceutical compositions can be included in a container, pack, or dispenser together with instructions for administration.

VI. Uses and Methods of the Invention

The nucleic acid molecules, proteins, protein homologues, and antibodies described herein can be used in one or more of the following methods: a) screening assays; b) detection assays (e.g., chromosomal mapping, tissue typing, forensic biology), c) predictive medicine (e.g., diagnostic assays, prognostic assays, monitoring clinical trials, and pharmacogenomics); and d) methods of treatment (e.g., therapeutic and prophylactic). A NBS-2, NBS-3, PYRIN-12/NBS-4, or NBS-5 protein interacts with other cellular proteins and can thus be used for (i) regulation of cellular proliferation; (ii) regulation of cellular differentiation; and (iii) regulation of cell survival. The isolated nucleic acid molecules of the invention can be used to express NBS-2, NBS-3, PYRIN-12/NBS-4, or NBS-5 protein (e.g., via a recombinant expression vector in a host cell in gene therapy applications), to detect NBS-2, NBS-3, PYRIN-12/NBS-4, or NBS-5 mRNA (e.g., in a biological sample) or a genetic lesion in a NBS-2, NBS-3, PYRIN-12/NBS-4, or NBS-5 gene, and to modulate NBS-2, NBS-3, PYRIN-12/NBS-4, or NBS-5 activity. In addition, the NBS-2, NBS-3, PYRIN-12/NBS-4, or NBS-5 proteins can be used to screen drugs or compounds which modulate the NBS-2, NBS-3, PYRIN-12/NBS-4, or NBS-5 activity or expression as well as to treat disorders characterized by insufficient or excessive production of NBS-2, NBS-3, PYRIN-12/NBS-4, or NBS-5 protein or production of NBS-2, NBS-3, PYRIN-12/NBS-4, or NBS-5 protein forms which have decreased or aberrant activity compared to NBS-2, NBS-3, PYRIN-12/NBS-4, or NBS-5 wild type protein. In addition, the anti-NBS-2, NBS-3, PYRIN-12/NBS-4, or NBS-5 antibodies of the invention can be used to detect and isolate NBS-2, NBS-3, PYRIN-12/NBS-4, or NBS-5 proteins and modulate NBS-2, NBS-3, PYRIN-12/NBS-4, or NBS-5 activity.

This invention further pertains to novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to NBS-2, NBS-3, PYRIN-12/NBS-4, or NBS-5 proteins or biologically active portions thereof or have a stimulatory or inhibitory effect on, for example, NBS-2, NBS-3, PYRIN-12/NBS-4, or NBS-5 expression or NBS-2, NBS-3, PYRIN-12/NBS-4, or NBS-5 activity. Examples of biologically active portions of human NBS-2, NBS-3, PYRIN-12/NBS-4, or NBS-5 are domains described herein, such as a pyrin domain, an NBS domain (or a motif of an NBS domain), and a LRR domain (or a leucine rich repeat of a LRR domain).

Among the screening assays provided by the invention are screening to identify molecules that prevent the interaction of NBS-2, NBS-3, PYRIN-12/NBS-4, or NBS-5 with another protein or biological molecule and screening to identify a competitive inhibitor of the binding of a nucleotide to the nucleotide binding site of NBS-2, NBS-3, PYRIN-12/NBS-4, or NBS-5. Such assays can employ full-length NBS-2, NBS-3, PYRIN-12/NBS-4, or NBS-5 or a portion of NBS-2, NBS-3, PYRIN-12/NBS-4, or NBS-5, e.g., a domain defined herein.

Molecules that bind to and/or after the activity of an NBS domain of NBS-2, NBS-3, PYRIN-12/NBS-4, or NBS-5 may be useful for modulating the activity of NBS-2, NBS-3, PYRIN-12/NBS-4, or NBS-5. For example, molecules can be tested for their ability to modulate, e.g., antagonize, the hydrolysis of an NTP, e.g., ATP, by the NBS domain (or a fragment of an NBS domain such as an NBS motif described herein) of NBS-2, NBS-3, PYRIN-12/NBS-4, or NBS-5. Methods of detecting the hydrolysis of a NTP by a protein containing a nucleotide-binding site are described in, for example, Li et al. (1996) J. Biol. Chem. 271:28463–28468 and Gadsby et al. (1999) Physiol. Rev. 79:S77–S107.

A purified protein containing an NBS domain of NBS-2, NBS-3, PYRIN-12/NBS-4, or NBS-5 can be evaluated for its ability to mediate NTPase activity in vitro. The assay can be performed in the presence of a test compound to determine the ability of the test compound to modulate the NTPase activity of the purified protein. In addition, or alternatively, the purified protein used in an NTPase activity assay can be a variant or a fragment of NBS-2, NBS-3, PYRIN-12/NBS-4, or NBS-5, and the assay can be performed to determine the NTPase activity of the fragment or variant.

In one example, an NBS domain can be assayed for its ability to hydrolyze ATP. ATPase activity can measured as the production of $[\alpha^{32}\text{-P}]\text{ADP}$ from $[\alpha^{32}\text{-P}]\text{ATP}$, using polyethyleneimine-cellulose chromatography for separation of the nucleotides. The assay can be carried out in a 15 µl reaction mixture containing 50 mM Tris, 50 mM NaCl, pH 7.5, 2 mM MgCl$_2$, 10% glycerol, 0.5 mM CHAPS, and 8 µCi of $[\alpha^{32}\text{-P}]\text{ATP}$. Reaction mixtures are incubated at 30° C. and are stopped by the addition of 5 µl of 10% SDS. One µl samples are spotted on a polyethyleneimine-cellulose plate and developed in 1 M formic acid, 0.5 M LiCl. The location and quantitation of the radiolabeled ATP and ADP can determined with a Molecular Dynamics PhosphorImager. Data can be analyzed using the ImageQuant software package (Molecular Dynamics). See, e.g., Li et al. (1996) J. Biol. Chem. 271:28463–28468 for additional details on methods detecting ATPase activity by nucleotide binding site-containing proteins and variants thereof. Thin layer chromatography techniques similar to those described above can also be used for the measurement of NTPase activity such as GTPase activity (see, e.g., Gout et al. (1993) Cell 75:25–36).

Screening assays can be used to identify molecules that bind to and/or modulate the activity of a pyrin domain or a LRR domain of a NBS-2, NBS-3, PYRIN-12/NBS-4, or NBS-5 protein, fragment, or variant thereof.

Screening assays can also be used to identify molecules which modulate a NBS-2, NBS-3, PYRIN-12/NBS-4, or NBS-5 mediated increase in transcription of genes having an AP-1 or NF-κB binding site. For example, expression of a reporter gene under the control of NF-κB (or AP-1) is measured in the presence and absence of a candidate molecule and in the presence and absence of NBS-2, NBS-3, PYRIN-12/NBS-4, or NBS-5 to identify those molecules which alter expression of the reporter in a NBS-2, NBS-3, PYRIN-12/NBS-4, or NBS-5 dependent manner. In addition, screening assays can be used to identify molecules that modulate a NBS-2, NBS-3, PYRIN-12/NBS-4, or NBS-5 mediated increase in CHOP phosphorylation. For example, the expression of a reporter gene under the control of CHOP is measured in the presence and absence of a candidate small molecule and in the presence and absence of NBS-2, NBS-3, PYRIN-12/NBS-4, or NBS-5 to identify those molecules that alter expression of the reporter in a NBS-2, NBS-3, PYRIN-12/NBS-4, or NBS-5 dependent manner. A screening assay can be carried out to identify molecules which modulate the NBS-2, NBS-3, PYRIN-12/NBS-4, or NBS-5 mediated increase in CHOP phosphorylation. For example, CHOP phosphorylation is measured in the presence and absence of a candidate molecule and in the presence and absence of NBS-2, NBS-3, PYRIN-12/NBS-4, or NBS-5. Phosphorylation of CHOP can be measured using an antibody which binds to phosphorylated CHOP, but not to non-phosphorylated CHOP.

In one embodiment, the invention provides assays for screening candidate or test compounds which bind to or modulate the activity of a NBS-2, NBS-3, PYRIN-12/NBS-4, or NBS-5 proteins or polypeptides or biologically active portions thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145). Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds may be presented in solution (e.g., Houghten (1992) Bio/Techniques 13:412–421), or on beads (Lam (1991) Nature 354:82–84), chips (Fodor (1993) Nature 364:555–556), bacteria (U.S. Pat. No. 5,223,409), spores (U.S. Pat. Nos. 5,571,698; 5,403,484; and 5,223,409), plasmids (Cull et al. (1992) Proc. Natl. Acad. Sci. USA 89:1865–1869) or on phage (Scott and Smith (1990) Science 249:386–390; Devlin (1990) Science 249:404–406; Cwirla et al. (1990) Proc. Natl. Acad. Sci. 87:6378–6382; and Felici (1991) J. Mol. Biol. 222:301–310).

In one embodiment, an assay is one in which a polypeptide of the invention, or a biologically active portion thereof, is contacted with a test compound and the ability of the test compound to bind to the polypeptide determined. Determining the ability of the test compound to bind to the polypeptide can be accomplished, for example, by coupling the test compound with a radioisotope or enzymatic label such that binding of the test compound to the polypeptide or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

Determining the ability of the test compound to modulate the activity of NBS-2, NBS-3, PYRIN-12/NBS-4, or NBS-5 or a biologically active portion thereof can be accomplished, for example, by determining the ability of the NBS-2, NBS-3, PYRIN-12/NBS-4, or NBS-5 protein to bind to or interact with a NBS-2, NBS-3, PYRIN-12/NBS-4, or NBS-5 target molecule. As used herein, a "target molecule" is a molecule with which a NBS-2, NBS-3, PYRIN-12/NBS-4, or NBS-5 protein binds or interacts in nature, for example, a molecule associated with the internal surface of a cell membrane or a cytoplasmic molecule. A NBS-2, NBS-3, PYRIN-12/NBS-4, or NBS-5 target molecule can be a non-NBS-2, NBS-3, PYRIN-12/NBS-4, or NBS-5 molecule or a NBS-2, NBS-3, PYRIN-12/NBS-4, or NBS-5 protein or polypeptide of the present invention. In one embodiment, a NBS-2, NBS-3, PYRIN-12/NBS-4, or NBS-5 target molecule is a component of an apoptotic signal transduction pathway. The target, for example, can be a second intracellular protein which has catalytic activity or a protein which facilitates the association of downstream signaling molecules with NBS-2, NBS-3, PYRIN-12/NBS-4, or NBS-5. In particular the target can be another protein having a pyrin domain (or a pyrin domain containing fragment thereof).

Determining the ability of the test compound to modulate the activity of NBS-2, NBS-3, PYRIN-12/NBS-4, or NBS-5 or a biologically active portion thereof can be accomplished, for example, by determining the ability of the NBS-2, NBS-3, PYRIN-12/NBS-4, or NBS-5 protein to bind to or interact with any of the specific proteins listed in the previous paragraph as NBS-2, NBS-3, PYRIN-12/NBS-4, or NBS-5 target molecules. In another embodiment, NBS-2, NBS-3, PYRIN-12/NBS-4, or NBS-5 target molecules include all proteins that bind to a NBS-2, NBS-3, PYRIN-12/NBS-4, or NBS-5 protein or a fragment thereof in a two-hybrid system binding assay which can be used without undue experimentation to isolate such proteins from cDNA or genomic two-hybrid system libraries. The binding assays described in this section can be cell-based or cell free (described subsequently).

Determining the ability of the NBS-2, NBS-3, PYRIN-12/NBS-4, or NBS-5 protein to bind to or interact with a NBS-2, NBS-3, PYRIN-12/NBS-4, or NBS-5 target molecule can be accomplished by one of the methods described above for determining direct binding. In an embodiment, determining the ability of the NBS-2, NBS-3, PYRIN-12/NBS-4, or NBS-5 protein to bind to or interact with a NBS-2, NBS-3, PYRIN-12/NBS-4, or NBS-5 target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a NBS-2, NBS-3, PYRIN-12/NBS-4, or NBS-5-responsive regulatory element operatively linked to a nucleic acid encoding a detectable marker, e.g. luciferase), or detecting a cellular response, for example, cell survival, cellular differentiation, or cell proliferation. The activity of a target molecule can be monitored by assaying the caspase 9-mediated apoptosis cellular response or caspase 9 enzymatic activity. In addition, and in another embodiment, genes induced by NBS-2, NBS-3, PYRIN-12/NBS-4, or NBS-5 expression can be identified by expressing NBS-2, NBS-3, PYRIN-12/NBS-4, or NBS-5 in a cell line and conducting a transcriptional profiling experiment wherein the mRNA expression patterns of the cell line transformed with an empty expression vector and the cell line transformed with a NBS-2, NBS-3, PYRIN-12/NBS-4, or NBS-5 expression vector are compared. The promoters of genes induced by NBS-2, NBS-3, PYRIN-12/NBS-4, or NBS-5 expression can be operatively linked to reporter genes suitable for screening such as luciferase, secreted alkaline phosphatase, or beta-galactosidase and the resulting constructs could be introduced into appropriate expression vectors. A recombinant cell line containing NBS-2, NBS-3, PYRIN-12/NBS-4, or NBS-5 and transfected with an expression vector containing a NBS-2, NBS-3, PYRIN-12/NBS-4, or NBS-5 responsive promoter operatively linked to a reporter gene can be used to identify test compounds that modulate NBS-2, NBS-3, PYRIN-12/NBS-4, or NBS-5 activity by assaying the expression of the reporter gene in response to contacting the recombinant cell line with test compounds. NBS-2, NBS-3, PYRIN-12/NBS-4, or NBS-5 agonists can be identified as increasing the expression of the reporter gene and NBS-2, NBS-3, PYRIN-12/NBS-4, or NBS-5 antagonists can be identified as decreasing the expression of the reporter gene.

In another embodiment of the invention, the ability of a test compound to modulate the activity of NBS-2, NBS-3, PYRIN-12/NBS-4, or NBS-5, or biologically active portions thereof can be determined by assaying the ability of the test compound to modulate NBS-2, NBS-3, PYRIN-12/NBS-4, or NBS-5-dependent pathways or processes where the NBS-2, NBS-3, PYRIN-12/NBS-4, or NBS-5 target proteins that mediate the NBS-2, NBS-3, PYRIN-12/NBS-4, or NBS-5 effect are known or unknown. Potential NBS-2, NBS-3, PYRIN-12/NBS-4, or NBS-5-dependent pathways or processes include, but are not limited to, the modulation of cellular signal transduction pathways and their related second messenger molecules (e.g., intracellular Ca2+, diacylglycerol, IP3, cAMP etc.), cellular enzymatic activities, cellular responses (e.g., cell survival, cellular differentiation, or cell proliferation), or the induction or repression of cellular or heterologous mRNAs or proteins. NBS-2, NBS-3, PYRIN-12/NBS-4, or NBS-5-dependent pathways or processes could be assayed by standard cell-based or cell free assays appropriate for the specific pathway or process under study. In another embodiment, cells cotransfected with NBS-2, NBS-3, PYRIN-12/NBS-4, or NBS-5 and a NF-κB luciferase reporter gene could be contacted with a test compound and test compounds that block NBS-2, NBS-3, PYRIN-12/NBS-4, or NBS-5 activity could be identified by their reduction of NBS-2, NBS-3, PYRIN-12/NBS-4, or NBS-5-dependent NF-κB pathway luciferase reporter gene expression. Test compounds that agonize NBS-2, NBS-3, PYRIN-12/NBS-4, or NBS-5 would be expected to increase reporter gene expression. In another embodiment, NBS-2, NBS-3, PYRIN-12/NBS-4, or NBS-5 could be expressed in a cell line and the recombinant NBS-2, NBS-3, PYRIN-12/NBS-4, or NBS-5-expressing cell line could be contacted with a test compound. Test compounds that inhibit NBS-2, NBS-3, PYRIN-12/NBS-4, or NBS-5 activity could be identified by their reduction of NBS-2, NBS-3, PYRIN-12/NBS-4, or NBS-5-depended NF-κB pathway stimulation as measured by the assay of a NF-κB pathway reporter gene, NF-κB nuclear localization, IκB phosphorylation or proteolysis, or other standard assays for NF-κB pathway activation known to those skilled in the art.

In yet another embodiment, an assay of the present invention is a cell-free assay comprising contacting a NBS-2, NBS-3, PYRIN-12/NBS-4, or NBS-5 protein or biologically active portion thereof with a test compound and determining the ability of the test compound to bind to the NBS-2, NBS-3, PYRIN-12/NBS-4, or NBS-5 protein or biologically active portion thereof. Binding of the test compound to the NBS-2, NBS-3, PYRIN-12/NBS-4, or NBS-5 protein can be determined either directly or indirectly as described above. In one embodiment, a competitive binding assay includes contacting the NBS-2, NBS-3, PYRIN-12/NBS-4, or NBS-5 protein or biologically active portion thereof with a compound known to bind NBS-2, NBS-3, PYRIN-12/NBS-4, or NBS-5 to form an assay mixture, contacting the assay mixture with a test compound, and determining the ability of the test compound to interact with a NBS-2, NBS-3, PYRIN-12/NBS-4, or NBS-5 protein, wherein determining the ability of the test compound to interact with a NBS-2, NBS-3, PYRIN-12/NBS-4, or NBS-5 protein comprises determining the ability of the test compound to preferentially bind to NBS-2, NBS-3, PYRIN-12/NBS-4, or NBS-5 or biologically active portion thereof as compared to the known binding compound.

In another embodiment, an assay is a cell-free assay comprising contacting NBS-2, NBS-3, PYRIN-12/NBS-4, or NBS-5 protein or biologically active portion thereof with a test compound and determining the ability of the test compound to modulate (e.g., stimulate or inhibit) the activity of the NBS-2, NBS-3, PYRIN-12/NBS-4, or NBS-5 protein or biologically active portion thereof. Determining the ability of the test compound to modulate the activity of NBS-2, NBS-3, PYRIN-12/NBS-4, or NBS-5 can be accomplished, for example, by determining the ability of the NBS-2, NBS-3, PYRIN-12/NBS-4, or NBS-5 protein to bind to or interact with a NBS-2, NBS-3, PYRIN-12/NBS-4, or NBS-5 target molecule by one of the methods described above for determining direct binding. In an alternative embodiment, determining the ability of the test compound to modulate the activity of NBS-2, NBS-3, PYRIN-12/NBS-4, or NBS-5 can be accomplished by determining the ability of the NBS-2, NBS-3, PYRIN-12/NBS-4, or NBS-5 protein to further modulate a NBS-2, NBS-3, PYRIN-12/NBS-4, or NBS-5 target molecule. For example, the catalytic/enzymatic activity of the target molecule on an appropriate substrate can be determined as previously described.

In yet another embodiment, the cell-free assay comprises contacting the NBS-2, NBS-3, PYRIN-12/NBS-4, or NBS-5 protein or biologically active portion thereof with a known compound which binds NBS-2, NBS-3, PYRIN-12/NBS-4, or NBS-5 to form an assay mixture, contacting the assay mixture with a test compound, and determining the ability of the test compound to interact with a NBS-2, NBS-3, PYRIN-12/NBS-4, or NBS-5 protein, wherein determining the ability of the test compound to interact with a NBS-2, NBS-3, PYRIN-12/NBS-4, or NBS-5 protein comprises determining the ability of the NBS-2, NBS-3, PYRIN-12/NBS-4, or NBS-5 protein to preferentially bind to or modulate the activity of a NBS-2, NBS-3, PYRIN-12/NBS-4, or NBS-5 target molecule. The cell-free assays of the present invention are amenable to use of either the soluble form or a membrane-associated form of NBS-2, NBS-3, PYRIN-12/NBS-4, or NBS-5. A membrane-associated form of NBS-2, NBS-3, PYRIN-12/NBS-4, or NBS-5 refers to NBS-2, NBS-3, PYRIN-12/NBS-4, or NBS-5 that interacts with a membrane-bound target molecule. In the case of cell-free assays comprising the membrane-associated form of NBS-2, NBS-3, PYRIN-12/NBS-4 or NBS-5, it may be desirable to utilize a solubilizing agent such that the membrane-associated form of NBS-2, NBS-3, PYRIN-12/NBS-4, or NBS-5 is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either NBS-2, NBS-3, PYRIN-12/NBS-4, or NBS-5 or its target molecule to facilitate separation of complexed from uncomplexed forms of one or both of the proteins, as well as to accommodate automation of the assay. Binding of a test compound to NBS-2, NBS-3, PYRIN-12/NBS-4, or NBS-5, or interaction of NBS-2, NBS-3, PYRIN-12/NBS-4, or NBS-5 with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/NBS-2, NBS-3, PYRIN-12/NBS-4, or NBS-5 fusion proteins or glutathione-S-transferase/target fusion proteins can be adsorbed onto glutathione sepharose beads (Sigma Chemical; St. Louis, Mo.) or glutathione derivatized microtitre plates, which are then combined with the test compound and either the non-adsorbed target protein or NBS-2, NBS-3, PYRIN-12/NBS-4, or NBS-5 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of NBS-2, NBS-3, PYRIN-12/NBS-4, or NBS-5 binding or activity determined using standard techniques. In an alternative embodiment, MYC or HA epitope tag NBS-2, NBS-3, PYRIN-12/NBS-4, or NBS-5 fusion proteins or MYC or HA epitope tag target fusion proteins can be adsorbed onto anti-MYC or anti-HA antibody coated microbeads or onto anti-MYC or anti-HA antibody coated microtitre plates, which are then combined with the test compound or the test compound and either the non-adsorbed target protein or NBS-2, NBS-3, PYRIN-12/NBS-4, or NBS-5 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of NBS-2, NBS-3, PYRIN-12/NBS-4, or NBS-5 binding or activity determined using standard techniques.

Other techniques for immobilizing proteins on matrices can also be used in the screening assays of the invention. For example, NBS-2, NBS-3, PYRIN-12/NBS-4, or NBS-5 or its target molecule can be immobilized utilizing conjugation of biotin and streptavidin. Biotinylated NBS-2, NBS-3, PYRIN-12/NBS-4, or NBS-5 target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with NBS-2, NBS-3, PYRIN-12/NBS-4, or NBS-5 or target molecules but which do not interfere with binding of the protein to its target molecule can be derivatized to the wells of the plate, and unbound target or protein trapped in the wells by antibody conjugation. Methods for detecting such complexes, in addition to those described above for the GST-immobilized complexes and epitope tag immobilized complexes, include immunodetection of complexes using antibodies reactive with the NBS-2, NBS-3, PYRIN-12/NBS-4, or NBS-5 or target molecule, as well as enzyme-linked assays which rely on detecting an enzymatic activity associated with the NBS-2, NBS-3, PYRIN-12/NBS-4, or NBS-5 or a target molecule.

In another embodiment, modulators of NBS-2, NBS-3, PYRIN-12/NBS-4, or NBS-5 expression are identified in a method in which a cell is contacted with a candidate compound and the expression of the NBS-2, NBS-3, PYRIN-12/NBS-4, or NBS-5 promoter, mRNA or protein in the cell is determined. The level of expression of NBS-2, NBS-3, PYRIN-12/NBS-4, or NBS-5 mRNA or protein in the presence of the candidate compound is compared to the level of expression of NBS-2, NBS-3, PYRIN-12/NBS-4, or NBS-5 mRNA or protein in the absence of the candidate compound. The candidate compound can then be identified as a modulator of NBS-2, NBS-3, PYRIN-12/NBS-4, or NBS-5 expression based on this comparison. For example, when expression of NBS-2, NBS-3, PYRIN-12/NBS-4, or NBS-5 mRNA or protein is greater (statistically significantly greater) in the presence of the candidate compound than in its absence, the candidate compound is identified as a stimulator of NBS-2, NBS-3, PYRIN-12/NBS-4, or NBS-5 mRNA or protein expression. Alternatively, when expression of NBS-2, NBS-3, PYRIN-12/NBS-4, or NBS-5 mRNA or protein is less (statistically significantly less) in the presence of the candidate compound than in its absence, the candidate compound is identified as an inhibitor of NBS-2, NBS-3, PYRIN-12/NBS-4, or NBS-5 mRNA or protein expression. The level of NBS-2, NBS-3, PYRIN-12/NBS-4, or NBS-5 mRNA or protein expression in the cells can be determined by methods described herein for detecting NBS-2, NBS-3, PYRIN-12/NBS-4, or NBS-5 mRNA or protein. The activity of the NBS-2, NBS-3, PYRIN-12/NBS-4, or NBS-5 promoter can be assayed by linking the NBS-2, NBS-3, PYRIN-12/NBS-4, or NBS-5 promoter to a reporter gene such as luciferase, secreted alkaline phosphatase, or beta-galactosidase and introducing the resulting construct into an appropriate vector, transfecting a host cell line, and measuring the activity of the reporter gene in response to test compounds.

In yet another aspect of the invention, the NBS-2, NBS-3, PYRIN-12/NBS-4, or NBS-5 proteins can be used as "bait proteins" in a two-hybrid assay (for a discussion of a mammalian two-hybrid assay, see e.g., Hosfield and Chang (1999) *Strategies Newsletter* 2(2):62–65) or three hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Bio/Techniques 14:920–924; Iwabuchi et al. (1993) Oncogene 8:1693–1696; and PCT Publication No. WO 94/10300), to identify other proteins, which bind to or interact with NBS-2, NBS-3, PYRIN-12/NBS-4, or NBS-5 ("NBS-2, NBS-3, PYRIN-12/NBS-4, or NBS-5-binding proteins" or "NBS-2, NBS-3, PYRIN-12/NBS-4, or NBS-5-bp") and modulate NBS-2, NBS-3, PYRIN-12/NBS-4, or NBS-5 activity. Such NBS-2, NBS-3, PYRIN-12/NBS-4, or NBS-5-binding proteins are also likely to be involved in the propagation of signals by the NBS-2, NBS-3, PYRIN-12/NBS-4, or NBS-5 proteins as, for example, upstream or downstream elements of the NBS-2, NBS-3, PYRIN-12/NBS-4, or NBS-5 pathway.

The two-hybrid system is based on the modular nature of most transcription factors, which consist of separable DNA-binding and activation domains. Briefly, the assay utilizes two different DNA constructs. In one construct, the gene that codes for NBS-2, NBS-3, PYRIN-12/NBS-4, or NBS-5 is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a NBS-2, NBS-3, PYRIN-12/NBS-4, or NBS-5-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with NBS-2, NBS-3, PYRIN-12/NBS-4, or NBS-5.

In an embodiment of the invention, the ability of a test compound to modulate the activity of NBS-2, NBS-3, PYRIN-12/NBS-4, or NBS-5, or a biologically active portion thereof can be determined by assaying the ability of the test compound to block the binding of NBS-2, NBS-3, PYRIN-12/NBS-4, or NBS-5 to its target proteins in a yeast or mammalian two-hybrid system assay. This assay could be automated for high throughput drug screening purposes. In another embodiment of the invention, NBS-2, NBS-3, PYRIN-12/NBS-4, or NBS-5 and a target protein could be configured in the reverse two-hybrid system (Vidal et al. (1996) Proc. Natl. Acad. Sci. USA 93:10321–6 and Vidal et al. (1996) Proc. Natl. Acad. Sci. USA 93:10315–20) designed specifically for efficient drug screening. In the reverse two-hybrid system, inhibition of a NBS-2, NBS-3, PYRIN-12/NBS-4, or NBS-5 physical interaction with a target protein would result in induction of a reporter gene in contrast to the normal two-hybrid system where inhibition of NBS-2, NBS-3, PYRIN-12/NBS-4, or NBS-5 physical interaction with a target protein would lead to reporter gene repression. The reverse two-hybrid system is preferred for drug screening because reporter gene induction is more easily assayed than report gene repression.

Alternative embodiments of the invention are proteins found to physically interact with proteins that bind to NBS-2, NBS-3, PYRIN-12/NBS-4, or NBS-5. NBS-2, NBS-3, PYRIN-12/NBS-4, or NBS-5 interactors could be configured into two-hybrid system baits and used in two-hybrid screens to identify additional members of the NBS-2, NBS-3, PYRIN-12/NBS-4, or NBS-5 pathway. The interactors of NBS-2, NBS-3, PYRIN- 12/NBS-4, or NBS-5 interactors identified in this way could be useful targets for therapeutic intervention in NBS-2, NBS-3, PYRIN-12/NBS-4, or NBS-5 related diseases and pathologies and an assay of their enzymatic or binding activity could be useful for the identification of test compounds that modulate NBS-2, NBS-3, PYRIN-12/NBS-4, or NBS-5 activity.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. Accordingly, NBS-2, NBS-3, PYRIN-12/NBS-4, or NBS-5 nucleic acid molecules described herein or fragments thereof, can be used to map the location of NBS-2, NBS-3, PYRIN-12/NBS-4, or NBS-5 genes on a chromosome. The mapping of the NBS-2, NBS-3, PYRIN-12/NBS-4, or NBS-5 sequences to chromosomes is an important first step in correlating these sequences with genes associated with disease.

Briefly, NBS-2, NBS-3, PYRIN-12/NBS-4, or NBS-5 genes can be mapped to chromosomes by preparing PCR primers (preferably 15–25 bp in length) from the NBS-2, NBS-3, PYRIN-12/NBS-4, or NBS-5 sequences. Computer analysis of NBS-2, NBS-3, PYRIN-12/NBS-4, or NBS-5 sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the NBS-2, NBS-3, PYRIN-12/NBS-4, or NBS-5 sequences will yield an amplified fragment. Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio et al. (1983) Science 220:919–924). Somatic cell hybrids containing only fragments of human chromosomes can also be produced using human chromosomes with translocations and deletions.

PCR mapping of somatic cell hybrids is a rapid procedure for assigning a particular sequence to a particular chromosome. Three or more sequences can be assigned per day using a single thermal cycler. Using the NBS-2, NBS-3, PYRIN-12/NBS-4, or NBS-5 sequences to design oligonucleotide primers, sublocalization can be achieved with panels of fragments from specific chromosomes. Other mapping strategies which can similarly be used to map a NBS-2, NBS-3, PYRIN-12/NBS-4, or NBS-5 sequence to its chromosome include in situ hybridization (described in Fan et al. (1990) Proc. Natl. Acad. Sci. USA 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., (Human Chromosomes: A Manual of Basic Techniques (Pergamon Press, New York, 1988)).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) Nature, 325:783–787.

Moreover, differences in the DNA sequences between individuals affected and unaffected with a disease associated with the NBS-2, NBS-3, PYRIN-12/NBS-4, or NBS-5 gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

A NBS-2, NBS-3, PYRIN-12/NBS-4, or NBS-5 polypeptide and fragments and sequences thereof and antibodies specific thereto can be used to map the location of the gene encoding the polypeptide on a chromosome. This mapping can be carried out by specifically detecting the presence of the polypeptide in members of a panel of somatic cell hybrids between cells of a first species of animal from which the protein originates and cells from a second species of animal and then determining which somatic cell hybrid(s) expresses the polypeptide and noting the chromosome(s) from the first species of animal that it contains. For examples of this technique, see Pajunen et al. (1988) Cytogenet. Cell Genet. 47:37–41 and Van Keuren et al. (1986) Hum. Genet. 74:34–40. Alternatively, the presence of the NBS-2, NBS-3, PYRIN-12/NBS-4, or NBS-5 polypeptide in the somatic cell hybrids can be determined by assaying an activity or property of the polypeptide, for example, enzymatic activity, as described in Bordelon-Riser et al. (1979) Somatic Cell Genetics 5:597–613 and Owerbach et al. (1978) Proc. Natl. Acad. Sci. USA 75:5640–5644.

2. Tissue Typing

The NBS-2, NBS-3, PYRIN-12/NBS-4, or NBS-5 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the NBS-2, NBS-3, PYRIN-12/NBS-4, or NBS-5 sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The NBS-2, NBS-3, PYRIN-12/NBS-4, or NBS-5 sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of NBS-2, NBS-3, PYRIN-12/NBS-4, or NBS-5 can comfortably provide positive individual identification with a panel of perhaps 10 to 1,000 primers which each yield a noncoding amplified sequence of 100 bases. If predicted coding sequences, such as those in SEQ ID NO:1, SEQ ID NO:3, SEQ ID NO:5, SEQ ID NO:7, SEQ ID NO:12, SEQ ID NO:14, SEQ ID NO:15, SEQ ID NO:17, SEQ ID NO:18, SEQ ID NO:20, or SEQ ID NO:23 are used, a more appropriate number of primers for positive individual identification would be 500–2,000.

If a panel of reagents from NBS-2, NBS-3, PYRIN-12/NBS-4, or NBS-5 sequences described herein is used to generate a unique identification database for an individual, those same reagents can later be used to identify tissue from that individual. Using the unique identification database, positive identification of the individual, living or dead, can be made from extremely small tissue samples.

3. Use of Partial Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of NBS-2, NBS-3, PYRIN-12/NBS-4, or NBS-5 are particularly appropriate for this use as greater numbers of polymorphisms occur in the noncoding regions, making it easier to differentiate individuals using this technique. Examples of polynucleotide reagents include the NBS-2, NBS-3, PYRIN-12/NBS-4, or NBS-5 sequences or portions thereof, e.g., fragments derived from the noncoding regions of NBS-2, NBS-3, PYRIN-12/NBS-4, or NBS-5 which have a length of at least 20 or 30 bases.

The sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such NBS-2, NBS-3, PYRIN-12/NBS-4, or NBS-5 probes can be used to identify tissue by species and/or by organ type.

In a similar fashion, these reagents, e.g., NBS-2, NBS-3, PYRIN-12/NBS-4, or NBS-5 primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining NBS-2, NBS-3, PYRIN-12/NBS-4, or NBS-5 protein and/or nucleic acid expression as well as NBS-2, NBS-3, PYRIN-12/NBS-4, or NBS-5 activity, in the context of a biological sample (e.g., blood, serum, cells, tissue) to thereby determine whether an individual is afflicted with a disease or disorder, or is at risk of developing a disorder, associated with aberrant NBS-2, NBS-3, PYRIN-12/NBS-4, or NBS-5 expression or activity. The invention also provides for prognostic (or predictive) assays for determining whether an individual is at risk of developing a disorder associated with NBS-2, NBS-3, PYRIN-12/NBS-4, or NBS-5 protein, nucleic acid expression or activity. For example, mutations in a NBS-2, NBS-3, PYRIN-12/NBS-4, or NBS-5 gene can be assayed in a biological sample. Such assays can be used for prognostic or predictive purpose to thereby prophylactically treat an individual prior to the onset of a disorder characterized by or associated with NBS-2, NBS-3, PYRIN-12/NBS-4, or NBS-5 protein, nucleic acid expression or activity.

Another aspect of the invention provides methods for determining NBS-2, NBS-3, PYRIN-12/NBS-4, or NBS-5 protein, nucleic acid expression or NBS-2, NBS-3, PYRIN-12/NBS-4, or NBS-5 activity in an individual to thereby select appropriate therapeutic or prophylactic agents for that individual (referred to herein as "pharmacogenomics").

Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.).

Yet another aspect of the invention pertains to monitoring the influence of agents (e.g., drugs or other compounds) on the expression or activity of NBS-2, NBS-3, PYRIN-12/NBS-4, or NBS-5 in clinical trials.

These and other agents are described in further detail in the following sections.

1. Diagnostic Assays

An exemplary method for detecting the presence or absence of NBS-2, NBS-3, PYRIN-12/NBS-4, or NBS-5 in a biological sample involves obtaining a biological sample from a test subject and contacting the biological sample with a compound or an agent capable of detecting NBS-2, NBS-3, PYRIN-12/NBS-4, or NBS-5 protein or nucleic acid (e.g., mRNA, genomic DNA) that encodes NBS-2, NBS-3, PYRIN-12/NBS- 4, or NBS-5 protein such that the presence of NBS-2, NBS-3, PYRIN-12/NBS-4, or NBS-5 is detected in the biological sample. An agent for detecting NBS-2, NBS-3, PYRIN-12/NBS-4, or NBS-5 mRNA or genomic DNA is a labeled nucleic acid probe capable of hybridizing to NBS-2, NBS-3, PYRIN-12/NBS-4, or NBS-5 mRNA or genomic DNA. The nucleic acid probe can be, for example, the nucleic acid of SEQ ID NO:1, SEQ ID NO:3, SEQ ID NO:5, SEQ ID NO:7, SEQ ID NO:12, SEQ ID NO:14, SEQ ID NO:15, SEQ ID NO:17, SEQ ID NO:18, SEQ ID NO:20, SEQ ID NO:21, SEQ ID NO:23, or a portion thereof, such as an oligonucleotide of at least 15, 30, 50, 100, 250, 500, 750, 1000, 1250, or 1500 nucleotides in length and sufficient to specifically hybridize under stringent conditions to mRNA or genomic DNA. Other suitable probes for use in the diagnostic assays of the invention are described herein.

An agent for detecting NBS-2, NBS-3, PYRIN-12/NBS-4, or NBS-5 protein can be an antibody capable of binding to NBS-2, NBS-3, PYRIN-12/NBS-4, or NBS-5 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells, biological fluids, and stool samples isolated from a subject, as well as tissues, cells and fluids present within a subject. That is, the detection method of the invention can be used to detect NBS-2, NBS-3, PYRIN-12/NBS-4, or NBS-5 mRNA, protein, or genomic DNA in a biological sample in vitro as well as in vivo. For example, in vitro techniques for detection of NBS-2, NBS-3, PYRIN-12/NBS-4, or NBS-5 mRNA include Northern hybridizations and in situ hybridizations. In vitro techniques for detection of NBS-2, NBS-3, PYRIN-12/NBS-4, or NBS-5 protein include enzyme linked immunosorbent assays (ELISAs), Western blots, immunoprecipitations and immunofluorescence. In vitro techniques for detection of NBS-2, NBS-3, PYRIN-12/NBS-4, or NBS-5 genomic DNA include Southern hybridizations. Furthermore, in vivo techniques for detection of NBS-2, NBS-3, PYRIN-12/NBS-4, or NBS-5 protein include introducing into a subject a labeled anti-NBS-2, NB S-3, PYRIN-12/NBS-4, or NBS-5 antibody. For example, the antibody can be labeled with a radioactive marker whose presence and location in a subject can be detected by standard imaging techniques.

Stool samples may be analyzed using various in vitro techniques, including techniques directed to analysis of DNA, RNA, or protein in the sample (Machiels et al. (2000) BioTechniques 28:286–290).

In one embodiment, the biological sample contains protein molecules from the test subject. Alternatively, the biological sample can contain mRNA molecules from the test subject or genomic DNA molecules from the test subject. A biological sample is a peripheral blood leukocyte sample isolated by conventional means from a subject.

In another embodiment, the methods further involve obtaining a control biological sample from a control subject, contacting the control sample with a compound or agent capable of detecting NBS-2, NBS-3, PYRIN-12/NBS-4, or NBS-5 protein, mRNA, or genomic DNA, such that the presence of NBS-2, NBS-3, PYRIN-12/NBS-4, or NBS-5 protein, mRNA or genomic DNA is detected in the biological sample, and comparing the presence of NBS-2, NBS-3, PYRIN-12/NBS-4, or NBS-5 protein, mRNA or genomic DNA in the control sample with the presence of NBS-2, NBS-3, PYRIN-12/NBS-4, or NBS-5 protein, mRNA or genomic DNA in the test sample.

The invention also encompasses kits for detecting the presence of NBS-2, NBS-3, PYRIN-12/NBS-4, or NBS-5 in a biological sample (a test sample). Such kits can be used to determine if a subject is suffering from or is at increased risk of developing a disorder associated with aberrant expression of NBS-2, NBS-3, PYRIN-12/NBS-4, or NBS-5 (e.g., an immunological disorder). For example, the kit can comprise a labeled compound or agent capable of detecting NBS-2, NBS-3, PYRIN-12/NBS-4, or NBS-5 protein or mRNA in a biological sample and means for determining the amount of NBS-2, NBS-3, PYRIN-12/NBS-4, or NBS-5 in the sample (e.g., an anti-NBS-2, NBS-3, PYRIN-12/NBS-4, or NBS-5 antibody or an oligonucleotide probe which binds to DNA encoding NBS-2, NBS-3, PYRIN-12/NBS-4, or NBS-5, e.g., SEQ ID NO:1, SEQ ID NO:3, SEQ ID NO:5, SEQ ID NO:7, SEQ ID NO:12, SEQ ID NO:14, SEQ ID NO:15, SEQ ID NO:17, SEQ ID NO:18, SEQ ID NO:20, SEQ ID NO:21, or SEQ ID NO:23). Kits may also include instruction for observing that the tested subject is suffering from or is at risk of developing a disorder associated with aberrant expression of NBS-2, NBS-3, PYRIN-12/NBS-4, or NBS-5 if the amount of NBS-2, NBS-3, PYRIN-12/NBS-4, or NBS-5 protein or mRNA is above or below a normal level.

For antibody-based kits, the kit may comprise, for example: (1) a first antibody (e.g., attached to a solid support) which binds to NBS-2, NBS-3, PYRIN-12/NBS-4, or NBS-5 protein; and, optionally, (2) a second, different antibody which binds to NBS-2, NBS-3, PYRIN-12/NBS-4, or NBS-5 protein or the first antibody and is conjugated to a detectable agent. For oligonucleotide-based kits, the kit may comprise, for example: (1) a oligonucleotide, e.g., a detectably labeled oligonucleotide, which hybridizes to a NBS-2, NBS-3, PYRIN-12/NBS-4, or NBS-5 nucleic acid sequence or (2) a pair of primers useful for amplifying a NBS-2, NBS-3, PYRIN-12/NBS-4, or NBS-5 nucleic acid molecule.

The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of NBS-2, NBS-3, PYRIN-12/NBS-4, or NBS-5.

2. Prognostic Assays

The methods described herein can furthermore be utilized as diagnostic or prognostic assays to identify subjects having or at risk of developing a disease or disorder associated with aberrant NBS-2, NBS-3, PYRIN-12/NBS-4, or NBS-5 expression or activity. For example, the assays described herein, such as the preceding diagnostic assays or the following assays, can be utilized to identify a subject having or at risk of developing a disorder associated with NBS-2, NBS-3, PYRIN-12/NBS-4, or NBS-5 protein, nucleic acid expression or activity. Alternatively, the prognostic assays can be utilized to identify a subject having or at risk for developing such a disease or disorder. Thus, the present invention provides a method in which a test sample is obtained from a subject and NBS-2, NBS-3, PYRIN-12/NBS-4, or NBS-5 protein or nucleic acid (e.g., mRNA, genomic DNA) is detected, wherein the presence of NBS-2, NBS-3, PYRIN-12/NBS-4, or NBS-5 protein or nucleic acid is diagnostic for a subject having or at risk of developing a disease or disorder associated with aberrant NBS-2, NBS-3, PYRIN-12/NBS-4, or NBS-5 expression or activity. As used herein, a "test sample" refers to a biological sample obtained from a subject of interest. For example, a test sample can be a biological fluid (e.g., serum), cell sample, tissue, or stool sample. Stool samples may be analyzed using various in vitro techniques, including techniques directed to analysis of DNA, RNA, or protein in the sample (Machiels et al. (2000) BioTechniques 28:286–290). Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant NBS-2, NBS-3, PYRIN-12/NBS-4, or NBS-5 expression or activity. For example, such methods can be used to determine whether a subject can be effectively treated with a specific agent or class of agents (e.g., agents of a type which decrease NBS-2, NBS-3, PYRIN-12/NBS-4, or NBS-5 activity). Thus, the present invention provides methods for determining whether a subject can be effectively treated with an agent for a disorder associated with aberrant NBS-2, NBS-3, PYRIN-12/NBS-4, or NBS-5 expression or activity in which a test sample is obtained and NBS-2, NBS-3, PYRIN-12/NBS-4, or NBS-5 protein or nucleic acid is detected (e.g., wherein the presence of NBS-2, NBS-3, PYRIN-12/NBS-4, or NBS-5 protein or nucleic acid is diagnostic for a subject that can be administered the agent to treat a disorder associated with aberrant NBS-2, NBS-3, PYRIN-12/NBS-4, or NBS-5 expression or activity).

The methods of the invention can also be used to detect genetic lesions or mutations in a NBS-2, NBS-3, PYRIN-12/NBS-4, or NBS-5 gene, thereby determining if a subject with the lesioned gene is at risk for a disorder characterized by aberrant cell proliferation and/or differentiation. In preferred embodiments, the methods include detecting, in a sample of cells from the subject, the presence or absence of a genetic lesion characterized by at least one of an alteration affecting the integrity of a gene encoding a NBS-2, NBS-3, PYRIN-12/NBS-4, or NBS-5-protein, or the mis-expression of the NBS-2, NBS-3, PYRIN-12/NBS-4, or NBS-5 gene. For example, such genetic lesions can be detected by ascertaining the existence of at least one of 1) a deletion of one or more nucleotides from a NBS-2, NBS-3, PYRIN-12/NBS-4, or NBS-5 gene; 2) an addition of one or more nucleotides to a NBS-2, NBS-3, PYRIN-12/NBS-4, or NBS-5 gene; 3) a substitution of one or more nucleotides of a NBS-2, NBS-3, PYRIN-12/NBS-4, or NBS-5 gene; 4) a chromosomal rearrangement of a NBS-2, NBS-3, PYRIN-12/NBS-4, or NBS-5 gene; 5) an alteration in the level of a messenger RNA transcript of a NBS-2, NBS-3, PYRIN-12/NBS-4, or NBS-5 gene; 6) aberrant modification of a NBS-2, NBS-3, PYRIN-12/NBS-4, or NBS-5 gene, such as of the methylation pattern of the genomic DNA; 7) the presence of a non-wild type splicing pattern of a messenger RNA transcript of a NBS-2, NBS-3, PYRIN-12/NBS-4, or NBS-5 gene (e.g., caused by a mutation in a splice donor or splice acceptor site); 8) a non-wild type level of a NBS-2, NBS-3, PYRIN-12/NBS-4, or NBS-5-protein; 9) allelic loss of a NBS-2, NBS-3, PYRIN-12/NBS-4, or NBS-5 gene; and 10) inappropriate post-translational modification of a NBS-2, NBS-3, PYRIN-12/NBS-4, or NBS-5-protein. As described herein, there are a large number of assay techniques known in the art which can be used for detecting lesions in a NBS-2, NBS-3, PYRIN-12/NBS-4, or NBS-5 gene. A biological sample is a peripheral blood leukocyte sample isolated by conventional means from a subject.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1994) Proc. Natl. Acad. Sci. USA 91:360–364), the latter of which can be particularly useful for detecting point mutations in the NBS-2, NBS-3, PYRIN-12/NBS-4, or NBS-5 gene (see, e.g., Abravaya et al. (1995) Nucleic Acids Res. 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a NBS-2, NBS-3, PYRIN-12/NBS-4, or NBS-5 gene under conditions such that hybridization and amplification of the NBS-2, NBS-3, PYRIN-12/NBS-4, or NBS-5-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) Proc. Natl. Acad. Sci. USA 87:1874–1878), transcriptional amplification system (Kwoh, et al. (1989) Proc. Natl. Acad. Sci. USA 86:1173–1177), Q-Beta Replicase (Lizardi et al. (1988) Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a NBS-2, NBS-3, PYRIN-12/NBS-4, or NBS-5 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in NBS-2, NBS-3, PYRIN-12/NBS-4, or NBS-5 can be identified by hybridizing a sample and control nucleic acids, e.g., DNA or RNA, to high density arrays containing hundreds or thousands of oligonucleotides probes (Cronin et al. (1996) Human Mutation 7:244–255; Kozal et al. (1996) Nature Medicine 2:753–759). For example, genetic mutations in NBS-2, NBS-3, PYRIN-12/NBS-4, or NBS-5 can be identified in two-dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the NBS-2, NBS-3, PYRIN-12/NBS-4, or NBS-5 gene and detect mutations by comparing the sequence of the sample NBS-2, NBS-3, PYRIN-12/NBS-4, or NBS-5 with the corresponding wild-type (control) sequence. Examples of sequencing reactions include those based on techniques developed by Maxam and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Bio/Techniques 19:448), including sequencing by mass spectrometry (see, e.g., PCT Publication No. WO 94/16101; Cohen et al. (1996) Adv. Chromatogr. 36:127–162; and Griffin et al. (1993) Appl. Biochem. Biotechnol. 38:147–159).

Other methods for detecting mutations in the NBS-2, NBS-3, PYRIN-12/NBS-4, or NBS-5 gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes of formed by hybridizing (labeled) RNA or DNA containing the wild-type NBS-2, NBS-3, PYRIN-12/NBS-4, or NBS-5 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al (1988) Proc. Natl. Acad Sci USA 85:4397; Saleeba et al (1992) Methods Enzymol. 217:286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in NBS-2, NBS-3, PYRIN-12/NBS-4, or NBS-5 cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15:1657–1662). According to an exemplary embodiment, a probe based on a NBS-2, NBS-3, PYRIN-12/NBS-4, or NBS-5 sequence, e.g., a wild-type NBS-2, NBS-3, PYRIN-12/NBS-4, or NBS-5 sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in NBS-2, NBS-3, PYRIN-12/NBS-4, or NBS-5 genes. For example, single strand conformation polymorphism (SSCP) may be used to detect differences in electrophoretic mobility between mutant and wild type nucleic acids (Orita et al. (1989) Proc Natl. Acad. Sci USA: 86:2766, see also Cotton (1993) Mutat. Res. 285:125–144; and Hayashi (1992) Genet Anal Tech Appl 9:73–79). Single-stranded DNA fragments of sample and control NBS-2, NBS-3, PYRIN-12/NBS-4, or NBS-5 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In an embodiment, the subject method utilizes heteroduplex analysis to separate double stranded heteroduplex molecules on the basis of changes in electrophoretic mobility (Keen et al. (1991) Trends Genet 7:5).

In yet another embodiment, the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) Proc. Natl. Acad. Sci USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437–2448) or at the extreme 3' end of one primer where, under appropriate conditions, mismatch can prevent, or reduce polymerase extension (Prossner (1993) Tibtech 11:238). In addition, it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a NBS-2, NBS-3, PYRIN-12/NBS-4, or NBS-5 gene.

Furthermore, any cell type or tissue, preferably peripheral blood leukocytes, in which NBS-2, NBS-3, PYRIN-12/NBS-4, or NBS-5 is expressed may be utilized in the prognostic assays described herein.

3. Pharmacogenomics

Agents, or modulators which have a stimulatory or inhibitory effect on NBS-2, NBS-3, PYRIN-12/NBS-4, or NBS-5 activity (e.g., NBS-2, NBS-3, PYRIN-12/NBS-4, or NBS-5 gene expression) as identified by a screening assay described herein can be administered to individuals to treat (prophylactically or therapeutically) disorders (e.g., a neurodegenerative disease such as Alzheimer's disease) associated with aberrant NBS-2, NBS-3, PYRIN-12/NBS-4, or NBS-5 activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of NBS-2, NBS-3, PYRIN-12/NBS-4, or NBS-5 protein, expression of NBS-2, NBS-3, PYRIN-12/NBS-4, or NBS-5 nucleic acid, or mutation content of NBS-2, NBS-3, PYRIN-12/NBS-4, or NBS-5 genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) Clin. Chem. 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM exhibit no therapeutic response, as demonstrated for the analgesic effect of codeine mediated by its CYP2D6-formed metabolite morphine. The other extreme are the so-called ultra-rapid metabolizers who do not respond to standard doses. Recently, the molecular basis of ultra-rapid metabolism has been identified to be due to CYP2D6 gene amplification.

Thus, the activity of NBS-2, NBS-3, PYRIN-12/NBS-4, or NBS-5 protein, expression of NBS-2, NBS-3, PYRIN-12/NBS-4, or NBS-5 nucleic acid, or mutation content of NBS-2, NBS-3, PYRIN-12/NBS-4, or NBS-5 genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a NBS-2, NBS-3, PYRIN-12/NBS-4, or NBS-5 modulator, such as a modulator identified by one of the exemplary screening assays described herein.

4. Monitoring of Effects During Clinical Trials

Monitoring the influence of agents (e.g., drugs, compounds) on the expression or activity of NBS-2, NBS-3, PYRIN-12/NBS-4, or NBS-5 (e.g., the ability to modulate aberrant cell proliferation and/or differentiation) can be applied not only in basic drug screening, but also in clinical trials. For example, the effectiveness of an agent determined by a screening assay as described herein to increase NBS-2, NBS-3, PYRIN-12/NBS-4, or NBS-5 gene expression, protein levels, or upregulate NBS-2, NBS-3, PYRIN-12/NBS-4, or NBS-5 activity, can be monitored in clinical trails of subjects exhibiting decreased NBS-2, NBS-3, PYRIN-12/NBS-4, or NBS-5 gene expression, protein levels, or downregulated NBS-2, NBS-3, PYRIN-12/NBS-4, or NBS-5 activity. Alternatively, the effectiveness of an agent determined by a screening assay to decrease NBS-2, NBS-3, PYRIN-12/NBS-4, or NBS-5 gene expression, protein levels, or downregulated NBS-2, NBS-3, PYRIN-12/NBS-4, or NBS-5 activity, can be monitored in clinical trials of subjects exhibiting increased NBS-2, NBS-3, PYRIN-12/NBS-4, or NBS-5 gene expression, protein levels, or upregulated NBS-2, NBS-3, PYRIN-12/NBS-4, or NBS-5 activity. In such clinical trials, the expression or activity of NBS-2, NBS-3, PYRIN-12/NBS-4, or NBS-5 and, preferably, other genes that have been implicated in, for example, a cellular proliferation disorder can be used as a "read out" or markers of the immune responsiveness of a particular cell.

For example, and not by way of limitation, genes, including NBS-2, NBS-3, PYRIN-12/NBS-4, or NBS-5, that are modulated in cells by treatment with an agent (e.g., compound, drug or small molecule) which modulates NBS-2, NBS-3, PYRIN-12/NBS-4, or NBS-5 activity (e.g., identified in a screening assay as described herein) can be identified. Thus, to study the effect of agents on cellular proliferation disorders, for example, in a clinical trial, cells can be isolated and RNA prepared and analyzed for the levels of expression of NBS-2, NBS-3, PYRIN-12/NBS-4, or NBS-5 and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of NBS-2, NBS-3, PYRIN-12/NBS-4, or NBS-5 or other genes. In this way, the gene expression pattern can serve as a marker, indicative of the physiological response of the cells to the agent. Accordingly, this response state may be determined before, and at various points during, treatment of the individual with the agent.

In an embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a NBS-2, NBS-3, PYRIN-12/NBS-4, or NBS-5 protein, mRNA, or genomic DNA in the preadministration sample; (iii) obtaining one or more post-administration samples from the subject; (iv) detecting the level of expression or activity of the NBS-2, NBS-3, PYRIN-12/NBS-4, or NBS-5 protein, mRNA, or genomic DNA in the post-administration samples; (v) comparing the level of expression or activity of the NBS-2, NBS-3, PYRIN-12/NBS-4, or NBS-5 protein, mRNA, or genomic DNA in the pre-administration sample with the NBS-2, NBS-3, PYRIN-12/NBS-4, or NBS-5 protein, mRNA, or genomic DNA in the post administration sample or samples; and (vi) altering the administration of the agent to the subject accordingly. For example, increased administration of the agent may be desirable to increase the expression or activity of NBS-2, NBS-3, PYRIN-12/NBS-4, or NBS-5 to higher levels than detected, i.e., to increase the effectiveness of the agent. Alternatively, decreased administration of the agent may be desirable to decrease expression or activity of NBS-2, NBS-3, PYRIN-12/NBS-4, or NBS-5 to lower levels than detected, i.e., to decrease the effectiveness of the agent.

5. Transcriptional Profiling

The NBS-2, NBS-3, PYRIN-12/NBS-4, or NBS-5 nucleic acid molecules described herein, including small oligonucleotides, can be used in transcriptionally profiling. For example, these nucleic acids can be used to examine the expression of NBS-2, NBS-3, PYRIN-12/NBS-4, or NBS-5 in normal tissue or cells and in tissue or cells subject to a disease state, e.g., tissue or cells derived from a patient having a disease of interest or cultured cells which model or reflect a disease state of interest, e.g., cells of a cultured tumor cell line. By measuring expression of NBS-2, NBS-3, PYRIN-12/NBS-4, or NBS-5, together or individually, a profile of expression in normal and disease states can be developed. This profile can be used diagnostically and to examine the effectiveness of a therapeutic regime.

C. Methods of Treatment

The present invention provides for both prophylactic and therapeutic methods of treating a subject at risk of (or susceptible to) a disorder or having a disorder associated with aberrant NBS-2, NBS-3, PYRIN-12/NBS-4, or NBS-5 expression or activity, examples of which are provided herein.

1. Prophylactic Methods

In one aspect, the invention provides a method for preventing in a subject, a disease or condition associated with an aberrant NBS-2, NBS-3, PYRIN-12/NBS-4, or NBS-5 expression or activity, by administering to the subject an agent which modulates NBS-2, NBS-3, PYRIN-12/NBS-4, or NBS-5 expression or at least one NBS-2, NBS-3, PYRIN-12/NBS-4, or NBS-5 activity. Subjects at risk for a disease which is caused or contributed to by aberrant NBS-2, NBS-3, PYRIN-12/NBS-4, or NBS-5 expression or activity can be identified by, for example, any or a combination of diagnostic or prognostic assays as described herein. Administration of a prophylactic agent can occur prior to the manifestation of symptoms characteristic of the NBS-2, NBS-3, PYRIN-12/NBS-4, or NBS-5 aberrancy, such that a disease or disorder is prevented or, alternatively, delayed in its progression. Depending on the type of NBS-2, NBS-3, PYRIN-12/NBS-4, or NBS-5 aberrancy, for example, a NBS-2, NBS-3, PYRIN-12/NBS-4, or NBS-5 agonist or NBS-2, NBS-3. PYRIN-12/NBS-4, or NBS-5 antagonist agent can be used for treating the subject. The appropriate agent can be determined based on screening assays described herein.

2. Therapeutic Methods

Another aspect of the invention pertains to methods of modulating NBS-2, NBS-3, PYRIN-12/NBS-4, or NBS-5 expression or activity for therapeutic purposes. The modulatory method of the invention involves contacting a cell with an agent that modulates one or more of the activities of NBS-2, NBS-3, PYRIN-12/NBS-4, or NBS-5 protein activity associated with the cell. An agent that modulates NBS-2, NBS-3, PYRIN-12/NBS-4, or NBS-5 protein activity can be an agent as described herein, such as a nucleic acid or a protein, a naturally-occurring cognate ligand of a NBS-2, NBS-3, PYRIN-12/NBS-4, or NBS-5 protein, a peptide, a NBS-2, NBS-3, PYRIN-12/NBS-4, or NBS-5 peptidomimetic, or other small molecule. In one embodiment, the agent stimulates one or more of the biological activities of NBS-2, NBS-3, PYRIN-12/NBS-4, or NBS-5 protein. Examples of such stimulatory agents include active NBS-2, NBS-3, PYRIN-12/NBS-4, or NBS-5 protein and a nucleic acid molecule encoding NBS-2, NBS-3, PYRIN-12/NBS-4, or NBS-5 that has been introduced into the cell. In another embodiment, the agent inhibits one or more of the biological activities of NBS-2, NBS-3, PYRIN-12/NBS-4, or NBS-5 protein. Examples of such inhibitory agents include antisense NBS-2, NBS-3, PYRIN-12/NBS-4, or NBS-5 nucleic acid molecules and anti-NBS-2, NBS-3, PYRIN-12/NBS-4, or NBS-5 antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a NBS-2, NBS-3, PYRIN-12/NBS-4, or NBS-5 protein or nucleic acid molecule or a disorder related to NBS-2, NBS-3, PYRIN-12/NBS-4, or NBS-5 expression or activity. In one embodiment, the method involves administering an agent (e.g., an agent identified by a screening assay described herein), or combination of agents that modulates (e.g., upregulates or downregulates) NBS-2, NBS-3, PYRIN-12/NBS-4, or NBS-5 expression or activity. In another embodiment, the method involves administering a NBS-2, NBS-3, PYRIN-12/NBS-4, or NBS-5 protein or nucleic acid molecule as therapy to compensate for reduced or aberrant NBS-2, NBS-3, PYRIN-12/NBS-4, or NBS-5 expression or activity. Stimulation of NBS-2, NBS-3, PYRIN-12/NBS-4, or NBS-5 activity is desirable in situations in which NBS-2, NBS-3, PYRIN-12/NBS-4, or NBS-5 is abnormally downregulated and/or in which increased NBS-2, NBS-3, PYRIN-12/NBS-4, or NBS-5 activity is likely to have a beneficial effect. Conversely, inhibition of NBS-2, NBS-3, PYRIN-12/NBS-4, or NBS-5 activity is desirable in situations in which NBS-2, NBS-3, PYRIN-12/NBS-4, or NBS-5 is abnormally upregulated, e.g., in myocardial infarction, and/or in which decreased NBS-2, NBS-3, PYRIN-12/NBS-4, or NBS-5 activity is likely to have a beneficial effect.

This invention is further illustrated by the following examples which should not be construed as limiting. The contents of all references, patents and published patent applications cited throughout this application are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

The invention claimed is:

1. An isolated nucleic acid molecule encoding a polypeptide comprising the amino acid sequence of SEQ ID NO:19.

2. The isolated nucleic acid molecule of claim 1, wherein the polypeptide consists of the amino acid sequence of SEQ ID NO:19.

3. An isolated nucleic acid molecule encoding a polypeptide comprising at least 100 contiguous amino acids of the amino acid sequence of SEQ ID NO:19 wherein said polypeptide comprises the pyrin domain of PYRIN-12/NBS-4 (amino acid residues 1–90 of SEQ ID NO:19) and binds a nucleotide.

4. An isolated nucleic acid molecule comprising at least 300 contiguous nucleotides of the nucleotide sequence of SEQ ID NO:18 wherein the nucleotide sequence encodes a polypeptide which comprises the pyrin domain of PYRIN-12/NBS-4 (amino acid residues 1–90 of SEQ ID NO:19) and binds a nucleotide.

5. The nucleic acid molecule of claim 1, wherein the nucleic acid molecule comprises the nucleotide sequence of SEQ ID NO:18.

6. An isolated nucleic acid molecule encoding a fusion protein containing at least one domain selected from the group consisting of:
   a) an NBS domain of PYRIN-12/NBS-4 (amino acid residues 42–521 of SEQ ID NO:6 or 211–532 of SEQ ID NO:19);
   b) a pyrin domain of PYRIN-12/NBS-4 (amino acid residues 1–90 of SEQ ID NO:19); and
   c) a leucine rich repeat domain of PYRIN-12/NBS-4 (amino acid residues 663–960 of SEQ ID NO:19);
operably linked to a non-PYRIN-12/NBS-4 polypeptide, wherein the fusion protein has an PYRIN-12/NBS-4 activity.

7. An isolated nucleic acid molecule that hybridizes to a nucleic acid molecule consisting of the nucleotide sequence of SEQ ID NO:18 under conditions of incubation at 45° C. in 6.0×SSC followed by washing in 0.2×SSC/0.1% SDS at 65° C., wherein said nucleic acid molecule has a nucleic acid sequence which encodes an allelic variant of PYRIN-12/NBS-4 (SEQ ID NO:19) and the variant binds a nucleotide.

8. The isolated nucleic acid molecule of claim 1, further comprising vector nucleic acid sequences.

9. A host cell containing the nucleic acid molecule of claim 1.

10. A method for producing a polypeptide comprising the amino acid sequence of SEQ ID NO:19, the method comprising culturing the host cell of claim 9 under conditions in which the polypeptide is expressed.

11. The nucleic acid molecule of claim 4, wherein the nucleic acid molecule has a nucleotide sequence which further encodes the NBS domain of PYRIN-12/NBS-4 211–532 of SEQ ID NO:19).

12. The nucleic acid molecule of claim 11 further encoding a heterologous polypeptide.

13. The isolated nucleic acid molecule of claim 11, further comprising vector nucleic acid sequences.

14. The nucleic acid molecule of claim 6, wherein the nucleic acid molecule has a nucleotide sequence which encodes the pyrin domain of PYRIN-12/NBS-4 (amino acids 1–90 of SEQ ID NO:19).

15. The nucleic acid molecule of claim 6, wherein the nucleic acid molecule has a nucleotide sequence which encodes the LRR domain of PYRIN-12/NBS-4 (amino acids 663–960 of SEQ ID NO:19).

16. An isolated nucleic acid molecule comprising SEQ ID NO:20.

17. An isolated nucleic acid molecule encoding a polypeptide consisting of the amino acid sequence of SEQ ID NO:6.

18. An isolated nucleic acid molecule consisting of SEQ ID NO:5, or a complement thereof.

19. An isolated nucleic acid molecule encoding a polypeptide which has at least 95% identity to PYRIN-12/NBS-4 (SEQ ID NO:19), wherein the polypeptide binds a nucleotide.

20. The isolated nucleic acid molecule of claim 19, wherein the nucleic acid molecule encodes a polypeptide with at least 98% identity to PYRIN-12/NBS-4 (SEQ ID NO:19).

21. The isolated nucleic acid molecule of claim 19, further comprising vector nucleic acid sequences.

22. A host cell containing the nucleic acid molecule of claim 19.

23. A method for producing a polypeptide comprising an amino acid sequence which is at least 95% identical to SEQ ID NO:19, wherein the polypeptide binds a nucleotide, the method comprising culturing the host cell of claim 22 under conditions in which the polypeptide is expressed.

24. The isolated nucleic acid molecule of claim 1, wherein the nucleic acid molecule further encodes a non-PYRIN-12/NBS-4 polypeptide operably linked to SEQ ID NO:19.

* * * * *

SEQUENCE LISTING

<160> NUMBER OF SEQ ID NOS: 31

<210> SEQ ID NO 1
<211> LENGTH: 221
<212> TYPE: PRT
<213> ORGANISM: Artificial Sequence
<220> FEATURE:

<223> OTHER INFORMATION: Description of Artificial Sequence: fusion of
    sequence for a part of human rydocan and a part of human
    fibroblast growth factor 1

<400> SEQUENCE: 1

```
Met Ala Pro Ala Arg Leu Phe Ala Leu Leu Leu Phe Phe Val Gly Gly
 1               5                  10                  15

Val Ala Glu Ser Ile Arg Glu Thr Glu Val Ile Asp Pro Gln Asp Leu
            20                  25                  30

Leu Glu Gly Arg Tyr Phe Ser Gly Ala Leu Pro Asp Asp Glu Asp Val
        35                  40                  45

Val Gly Pro Gly Gln Glu Ser Asp Asp Phe Glu Leu Ser Gly Ser Gly
    50                  55                  60

Asp Leu Asp Asp Leu Glu Asp Ser Met Ile Gly Pro Glu Val Val His
65                  70                  75                  80

Pro Leu Val Pro Leu Asp Ala Asn Tyr Lys Lys Pro Lys Leu Leu Tyr
                85                  90                  95

Cys Ser Asn Gly Gly His Phe Leu Arg Ile Leu Pro Asp Gly Thr Val
            100                 105                 110

Asp Gly Thr Arg Asp Arg Ser Asp Gln His Ile Gln Leu Gln Leu Ser
        115                 120                 125

Ala Glu Ser Val Gly Glu Val Tyr Ile Lys Ser Thr Glu Thr Gly Gln
    130                 135                 140

Tyr Leu Ala Met Asp Thr Asp Gly Leu Leu Tyr Gly Ser Gln Thr Pro
145                 150                 155                 160

Asn Glu Glu Cys Leu Phe Leu Glu Arg Leu Glu Glu Asn His Tyr Asn
                165                 170                 175

Thr Tyr Ile Ser Lys Lys His Ala Glu Lys Asn Trp Phe Val Gly Leu
            180                 185                 190

Lys Lys Asn Gly Ser Cys Lys Arg Gly Pro Arg Thr His Tyr Gly Gln
        195                 200                 205

Lys Ala Ile Leu Phe Leu Pro Leu Pro Val Ser Ser Asp
    210                 215                 220
```

<210> SEQ ID NO 2
<211> LENGTH: 663
<212> TYPE: DNA
<213> ORGANISM: Artificial Sequence
<220> FEATURE:
<223> OTHER INFORMATION: Description of Artificial Sequence: fusion of
    sequence for a part of human rydocan and a part of human
    fibroblast growth factor 1
<221> NAME/KEY: CDS
<222> LOCATION: (1)..(663)

<400> SEQUENCE: 2

```
atg gcc ccc gcc cgt ctg ttc gcg ctg ctg ctg ttc ttc gta ggc gga    48
Met Ala Pro Ala Arg Leu Phe Ala Leu Leu Leu Phe Phe Val Gly Gly
 1               5                  10                  15 gtc gcc gag tcg atc cga gag act gag gtc atc gac ccc cag gac ctc    96
Val Ala Glu Ser Ile Arg Glu Thr Glu Val Ile Asp Pro Gln Asp Leu
            20                  25                  30 cta gaa ggc cga tac ttc tcc gga gcc cta cca gac gat gag gat gta   144
Leu Glu Gly Arg Tyr Phe Ser Gly Ala Leu Pro Asp Asp Glu Asp Val
        35                  40                  45 gtg ggg ccc ggg cag gaa tct gat gac ttt gag ctg tct ggc tct gga   192
Val Gly Pro Gly Gln Glu Ser Asp Asp Phe Glu Leu Ser Gly Ser Gly
    50                  55                  60 gat ctg gat gac ttg gaa gac tcc atg atc ggc cct gaa gtt gtc cat   240
```

```
Asp Leu Asp Asp Leu Glu Asp Ser Met Ile Gly Pro Glu Val Val His
 65                  70                  75                  80 ccc ttg gtg cct cta gat gct aat tac aag aag ccc aaa ctc ctc tac     288
Pro Leu Val Pro Leu Asp Ala Asn Tyr Lys Lys Pro Lys Leu Leu Tyr
                 85                  90                  95 tgt agc aac ggg ggc cac ttc ctg agg atc ctt ccg gat ggc aca gtg     336
Cys Ser Asn Gly Gly His Phe Leu Arg Ile Leu Pro Asp Gly Thr Val
            100                 105                 110 gat ggg aca agg gac agg agc gac cag cac att cag ctg cag ctc agt     384
Asp Gly Thr Arg Asp Arg Ser Asp Gln His Ile Gln Leu Gln Leu Ser
        115                 120                 125 gcg gaa agc gtg ggg gag gtg tat ata aag agt acc gag act ggc cag     432
Ala Glu Ser Val Gly Glu Val Tyr Ile Lys Ser Thr Glu Thr Gly Gln
    130                 135                 140 tac ttg gcc atg gac acc gac ggg ctt tta tac ggc tca cag aca cca     480
Tyr Leu Ala Met Asp Thr Asp Gly Leu Leu Tyr Gly Ser Gln Thr Pro
145                 150                 155                 160 aat gag gaa tgt ttg ttc ctg gaa agg ctg gag gag aac cat tac aac     528
Asn Glu Glu Cys Leu Phe Leu Glu Arg Leu Glu Glu Asn His Tyr Asn
                165                 170                 175 acc tat ata tcc aag aag cat gca gag aag aat tgg ttt gtt ggc ctc     576
Thr Tyr Ile Ser Lys Lys His Ala Glu Lys Asn Trp Phe Val Gly Leu
            180                 185                 190 aag aag aat ggg agc tgc aaa cgc ggt cct cgg act cac tat ggc cag     624
Lys Lys Asn Gly Ser Cys Lys Arg Gly Pro Arg Thr His Tyr Gly Gln
        195                 200                 205 aaa gca atc ttg ttt ctc ccc ctg cca gtc tct tct gat                 663
Lys Ala Ile Leu Phe Leu Pro Leu Pro Val Ser Ser Asp
    210                 215                 220

<210> SEQ ID NO 3
<211> LENGTH: 175
<212> TYPE: PRT
<213> ORGANISM: Artificial Sequence
<220> FEATURE:
<223> OTHER INFORMATION: Description of Artificial Sequence: fusion of
      sequence for a part of mouse fibroblast growth factor 6 and
      a part of human fibroblast growth factor 1

<400> SEQUENCE: 3

Met Ser Arg Gly Ala Gly Arg Val Gln Gly Thr Leu Gln Ala Leu Val
 1               5                  10                  15

Phe Leu Gly Val Leu Val Gly Met Val Val Pro Ser Pro Ala Gly Ala
                20                  25                  30

Arg Ala Asn Gly Thr Leu Leu Asp Ala Asn Tyr Lys Lys Pro Lys Leu
            35                  40                  45

Leu Tyr Cys Ser Asn Gly Gly His Phe Leu Arg Ile Leu Pro Asp Gly
        50                  55                  60

Thr Val Asp Gly Thr Arg Asp Arg Ser Asp Gln His Ile Gln Leu Gln
 65                  70                  75                  80

Leu Ser Ala Glu Ser Val Gly Glu Val Tyr Ile Lys Ser Thr Glu Thr
                85                  90                  95

Gly Gln Tyr Leu Ala Met Asp Thr Asp Gly Leu Leu Tyr Gly Ser Gln
            100                 105                 110

Thr Pro Asn Glu Glu Cys Leu Phe Leu Glu Arg Leu Glu Glu Asn His
        115                 120                 125

Tyr Asn Thr Tyr Ile Ser Lys Lys His Ala Glu Lys Asn Trp Phe Val
    130                 135                 140

Gly Leu Lys Lys Asn Gly Ser Cys Lys Arg Gly Pro Arg Thr His Tyr
```

```
                145                 150                 155                 160
Gly Gln Lys Ala Ile Leu Phe Leu Pro Leu Pro Val Ser Ser Asp
                165                 170                 175

<210> SEQ ID NO 4
<211> LENGTH: 525
<212> TYPE: DNA
<213> ORGANISM: Artificial Sequence
<220> FEATURE:
<223> OTHER INFORMATION: Description of Artificial Sequence: fusion of
      sequence for a part of mouse fibroblast growth factor 6 and
      a part of human fibroblast growth factor 1
<221> NAME/KEY: CDS
<222> LOCATION: (1)..(525)

<400> SEQUENCE: 4 atg tcc cgg gga gca gga cgt gtt cag ggc acg ctg cag gct ctc gtc       48
Met Ser Arg Gly Ala Gly Arg Val Gln Gly Thr Leu Gln Ala Leu Val
  1               5                  10                  15 ttc tta ggc gtc cta gtg ggc atg gtg gtg ccc tca cct gcc ggc gcc       96
Phe Leu Gly Val Leu Val Gly Met Val Val Pro Ser Pro Ala Gly Ala
                20                  25                  30 cgc gcc aac ggc acg cta ctg gac gct aat tac aag aag ccc aaa ctc      144
Arg Ala Asn Gly Thr Leu Leu Asp Ala Asn Tyr Lys Lys Pro Lys Leu
            35                  40                  45 ctc tac tgt agc aac ggg ggc cac ttc ctg agg atc ctt ccg gat ggc      192
Leu Tyr Cys Ser Asn Gly Gly His Phe Leu Arg Ile Leu Pro Asp Gly
        50                  55                  60 aca gtg gat ggg aca agg gac agg agc gac cag cac att cag ctg cag      240
Thr Val Asp Gly Thr Arg Asp Arg Ser Asp Gln His Ile Gln Leu Gln
 65                  70                  75                  80 ctc agt gcg gaa agc gtg ggg gag gtg tat ata aag agt acc gag act      288
Leu Ser Ala Glu Ser Val Gly Glu Val Tyr Ile Lys Ser Thr Glu Thr
                 85                  90                  95 ggc cag tac ttg gcc atg gac acc gac ggg ctt tta tac ggc tca cag      336
Gly Gln Tyr Leu Ala Met Asp Thr Asp Gly Leu Leu Tyr Gly Ser Gln
            100                 105                 110 aca cca aat gag gaa tgt ttg ttc ctg gaa agg ctg gag gag aac cat      384
Thr Pro Asn Glu Glu Cys Leu Phe Leu Glu Arg Leu Glu Glu Asn His
        115                 120                 125 tac aac acc tat ata tcc aag aag cat gca gag aag aat tgg ttt gtt      432
Tyr Asn Thr Tyr Ile Ser Lys Lys His Ala Glu Lys Asn Trp Phe Val
    130                 135                 140 ggc ctc aag aag aat ggg agc tgc aaa cgc ggt cct cgg act cac tat      480
Gly Leu Lys Lys Asn Gly Ser Cys Lys Arg Gly Pro Arg Thr His Tyr
145                 150                 155                 160 ggc cag aaa gca atc ttg ttt ctc ccc ctg cca gtc tct tct gat          525
Gly Gln Lys Ala Ile Leu Phe Leu Pro Leu Pro Val Ser Ser Asp
                165                 170                 175

<210> SEQ ID NO 5
<211> LENGTH: 181
<212> TYPE: PRT
<213> ORGANISM: Artificial Sequence
<220> FEATURE:
<223> OTHER INFORMATION: Description of Artificial Sequence: fusion of
      sequence for a part of mouse fibroblast growth factor 6,
      a part of human fibroblast growth factor 1 and an artificial
      sequence

<400> SEQUENCE: 5

Met Ser Arg Gly Ala Gly Arg Val Gln Gly Thr Leu Gln Ala Leu Val
  1               5                  10                  15
```

US 7,034,135 B2

```
        Phe Leu Gly Val Leu Val Gly Met Val Val Pro Ser Pro Ala Gly Ala
                        20                  25                  30

Arg Ala Gln Gly Thr Leu Leu Asp Ala Asn Tyr Lys Lys Pro Lys Leu
                    35                  40                  45

Leu Tyr Cys Ser Asn Gly Gly His Phe Leu Arg Ile Leu Pro Asp Gly
                50                  55                  60

Thr Val Asp Gly Thr Arg Asp Arg Ser Asp Gln His Ile Gln Leu Gln
        65                  70                  75                  80

Leu Ser Ala Glu Ser Val Gly Glu Val Tyr Ile Lys Ser Thr Glu Thr
                        85                  90                  95

Gly Gln Tyr Leu Ala Met Asp Thr Asp Gly Leu Leu Tyr Gly Ser Gln
                    100                 105                 110

Thr Pro Asn Glu Glu Cys Leu Phe Leu Glu Arg Leu Glu Glu Ala Ala
                    115                 120                 125

Thr Pro Ala Pro Asn His Tyr Asn Thr Tyr Ile Ser Lys Lys His Ala
                130                 135                 140

Glu Lys Asn Trp Phe Val Gly Leu Lys Lys Asn Gly Ser Cys Lys Arg
        145                 150                 155                 160

Gly Pro Arg Thr His Tyr Gly Gln Lys Ala Ile Leu Phe Leu Pro Leu
                        165                 170                 175

Pro Val Ser Ser Asp
                    180

<210> SEQ ID NO 6
<211> LENGTH: 543
<212> TYPE: DNA
<213> ORGANISM: Artificial Sequence
<220> FEATURE:
<223> OTHER INFORMATION: Description of Artificial Sequence: fusion of
      sequence for a part of mouse fibroblast growth factor 6,
      a part of human fibroblast growth factor 1 and an artificial
      sequence
<221> NAME/KEY: CDS
<222> LOCATION: (1)..(543)

<400> SEQUENCE: 6 atg tcc cgg gga gca gga cgt gtt cag ggc acg ctg cag gct ctc gtc     48
Met Ser Arg Gly Ala Gly Arg Val Gln Gly Thr Leu Gln Ala Leu Val
1               5                   10                  15 ttc tta ggc gtc cta gtg ggc atg gtg gtg ccc tca cct gcc ggc gcc     96
Phe Leu Gly Val Leu Val Gly Met Val Val Pro Ser Pro Ala Gly Ala
                20                  25                  30 cgc gcc caa ggc acg cta ctg gac gct aat tac aag aag ccc aaa ctc    144
Arg Ala Gln Gly Thr Leu Leu Asp Ala Asn Tyr Lys Lys Pro Lys Leu
            35                  40                  45 ctc tac tgt agc aac ggg ggc cac ttc ctg agg atc ctt ccg gat ggc    192
Leu Tyr Cys Ser Asn Gly Gly His Phe Leu Arg Ile Leu Pro Asp Gly
        50                  55                  60 aca gtg gat ggg aca agg gac agg agc gac cag cac att cag ctg cag    240
Thr Val Asp Gly Thr Arg Asp Arg Ser Asp Gln His Ile Gln Leu Gln
65                  70                  75                  80 ctc agt gcg gaa agc gtg ggg gag gtg tat ata aag agt acc gag act    288
Leu Ser Ala Glu Ser Val Gly Glu Val Tyr Ile Lys Ser Thr Glu Thr
                85                  90                  95 ggc cag tac ttg gcc atg gac acc gac ggg ctt tta tac ggc tca cag    336
Gly Gln Tyr Leu Ala Met Asp Thr Asp Gly Leu Leu Tyr Gly Ser Gln
            100                 105                 110 aca cca aat gag gaa tgt ttg ttc ctg gaa agg ctg gag gag gct gct    384
Thr Pro Asn Glu Glu Cys Leu Phe Leu Glu Arg Leu Glu Glu Ala Ala
        115                 120                 125
```

| | | | | | | | | | | | | | | |
|---|---|---|---|---|---|---|---|---|---|---|---|---|---|---|
| act | cca | gct | cca | aac | cat | tac | aac | acc | tat | ata | tcc | aag | aag | cat | gca | 432 |
| Thr | Pro | Ala | Pro | Asn | His | Tyr | Asn | Thr | Tyr | Ile | Ser | Lys | Lys | His | Ala |
| | 130 | | | | 135 | | | | | 140 | | | | |

| | | | | | | | | | | | | | | | | |
|---|---|---|---|---|---|---|---|---|---|---|---|---|---|---|---|---|
| gag | aag | aat | tgg | ttt | gtt | ggc | ctc | aag | aag | aat | ggg | agc | tgc | aaa | cgc | 480 |
| Glu | Lys | Asn | Trp | Phe | Val | Gly | Leu | Lys | Lys | Asn | Gly | Ser | Cys | Lys | Arg |
| 145 | | | | 150 | | | | | 155 | | | | | 160 |

| | | | | | | | | | | | | | | | | |
|---|---|---|---|---|---|---|---|---|---|---|---|---|---|---|---|---|
| ggt | cct | cgg | act | cac | tat | ggc | cag | aaa | gca | atc | ttg | ttt | ctc | ccc | ctg | 528 |
| Gly | Pro | Arg | Thr | His | Tyr | Gly | Gln | Lys | Ala | Ile | Leu | Phe | Leu | Pro | Leu |
| | | | | 165 | | | | | 170 | | | | | 175 |

| | | | | |
|---|---|---|---|---|---|
| cca | gtc | tct | tct | gat | 543 |
| Pro | Val | Ser | Ser | Asp |
| | | | 180 |

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:primer for
    PCR

<400> SEQUENCE: 7
ttgtcgaccc accatggccc ccgcccgtct                              30

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:primer for
    PCR

<400> SEQUENCE: 8
ttgatatcta gaggcaccaa gggatg                                  26

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence:primer for
    PCR

<400> SEQUENCE: 9
gcgtcgacag cgctaattac aagaagccca aactc                        35

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence:primer for
    PCR

<400> SEQUENCE: 10
ccgaattcga attctttaat cagaagagac tgg                          33

<210> SEQ ID NO 11
<211> LENGTH: 64
<212> TYPE: DNA
<213> ORGANISM: Artificial Sequence
<220> FEATURE:
<223> OTHER INFORMATION: Description of Artificial Sequence:primer for
    PCR

<400> SEQUENCE: 11

-continued

```
gcgtcgaccc accatgtccc ggggagcagg acgtgttcag ggcacgctgc aggctctcgt      60
cttc                                                                  64
```

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence:primer for
      PCR

<400> SEQUENCE: 12

```
gcgatatcca gtagcgtgcc gttggcgcg                                       29
```

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence:primer for
      PCR

<400> SEQUENCE: 13

```
gcgtcgaccc accatgtc                                                   18
```

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence:primer for
      PCR

<400> SEQUENCE: 14

```
gcgatatcca gtagcgtgcc ttgggcgcg                                       29
```

<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence:primer for
      PCR

<400> SEQUENCE: 15

```
gctggaggag gctgctactc cagctccaaa ccattaca                             38
```

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:primer for
      PCR

<400> SEQUENCE: 16

```
gccgctctag aactagtgga t                                               21
```

<210> SEQ ID NO 17
<211> LENGTH: 200
<212> TYPE: PRT
<213> ORGANISM: Artificial Sequence
<220> FEATURE:
<223> OTHER INFORMATION: Description of Artificial Sequence: fusion of
      sequence for a part of human ryudocan and a part of human
      fibroblast growth factor 1

<400> SEQUENCE: 17

```
Met Ala Pro Ala Arg Leu Phe Ala Leu Leu Leu Phe Phe Val Gly Gly
1               5                   10                  15

Val Ala Glu Ser Ile Arg Glu Thr Glu Val Ile Asp Pro Gln Asp Leu
            20                  25                  30

Leu Glu Gly Arg Tyr Phe Ser Gly Ala Leu Pro Asp Asp Glu Asp Val
        35                  40                  45

Val Gly Pro Gly Gln Glu Ser Asp Asp Phe Glu Leu Ser Gly Ser Gly
    50                  55                  60

Asp Ala Asn Tyr Lys Lys Pro Lys Leu Leu Tyr Cys Ser Asn Gly Gly
65                  70                  75                  80

His Phe Leu Arg Ile Leu Pro Asp Gly Thr Val Asp Gly Thr Arg Asp
                85                  90                  95

Arg Ser Asp Gln His Ile Gln Leu Gln Leu Ser Ala Glu Ser Val Gly
            100                 105                 110

Glu Val Tyr Ile Lys Ser Thr Glu Thr Gly Gln Tyr Leu Ala Met Asp
        115                 120                 125

Thr Asp Gly Leu Leu Tyr Gly Ser Gln Thr Pro Asn Glu Glu Cys Leu
    130                 135                 140

Phe Leu Glu Arg Leu Glu Glu Asn His Tyr Asn Thr Tyr Ile Ser Lys
145                 150                 155                 160

Lys His Ala Glu Lys Asn Trp Phe Val Gly Leu Lys Lys Asn Gly Ser
                165                 170                 175

Cys Lys Arg Gly Pro Arg Thr His Tyr Gly Gln Lys Ala Ile Leu Phe
            180                 185                 190

Leu Pro Leu Pro Val Ser Ser Asp
        195                 200
```

```
<210> SEQ ID NO 18
<211> LENGTH: 600
<212> TYPE: DNA
<213> ORGANISM: Artificial Sequence
<220> FEATURE:
<223> OTHER INFORMATION: Description of Artificial Sequence: fusion of
      sequence for a part of human ryudocan and a part of human
      fibroblast growth factor 1
<221> NAME/KEY: CDS
<222> LOCATION: (1)..(600)
```

<400> SEQUENCE: 18

```
atg gcc ccc gcc cgt ctg ttc gcg ctg ctg ctg ttc ttc gta ggc gga       48
Met Ala Pro Ala Arg Leu Phe Ala Leu Leu Leu Phe Phe Val Gly Gly
1               5                   10                  15 gtc gcc gag tcg atc cga gag act gag gtc atc gac ccc cag gac ctc       96
Val Ala Glu Ser Ile Arg Glu Thr Glu Val Ile Asp Pro Gln Asp Leu
            20                  25                  30 cta gaa ggc cga tac ttc tcc gga gcc cta cca gac gat gag gat gta      144
Leu Glu Gly Arg Tyr Phe Ser Gly Ala Leu Pro Asp Asp Glu Asp Val
        35                  40                  45 gtg ggg ccc ggg cag gaa tct gat gac ttt gag ctg tct ggc tct gga      192
Val Gly Pro Gly Gln Glu Ser Asp Asp Phe Glu Leu Ser Gly Ser Gly
    50                  55                  60 gat gct aat tac aag aag ccc aaa ctc ctc tac tgt agc aac ggg ggc      240
Asp Ala Asn Tyr Lys Lys Pro Lys Leu Leu Tyr Cys Ser Asn Gly Gly
65                  70                  75                  80 cac ttc ctg agg atc ctt ccg gat ggc aca gtg gat ggg aca agg gac      288
His Phe Leu Arg Ile Leu Pro Asp Gly Thr Val Asp Gly Thr Arg Asp
                85                  90                  95
```

```
agg agc gac cag cac att cag ctg cag ctc agt gcg gaa agc gtg ggg      336
Arg Ser Asp Gln His Ile Gln Leu Gln Leu Ser Ala Glu Ser Val Gly
            100                 105                 110 gag gtg tat ata aag agt acc gag act ggc cag tac ttg gcc atg gac      384
Glu Val Tyr Ile Lys Ser Thr Glu Thr Gly Gln Tyr Leu Ala Met Asp
        115                 120                 125 acc gac ggg ctt tta tac ggc tca cag aca cca aat gag gaa tgt ttg      432
Thr Asp Gly Leu Leu Tyr Gly Ser Gln Thr Pro Asn Glu Glu Cys Leu
130                 135                 140 ttc ctg gaa agg ctg gag gag aac cat tac aac acc tat ata tcc aag      480
Phe Leu Glu Arg Leu Glu Glu Asn His Tyr Asn Thr Tyr Ile Ser Lys
145                 150                 155                 160 aag cat gca gag aag aat tgg ttt gtt ggc ctc aag aag aat ggg agc      528
Lys His Ala Glu Lys Asn Trp Phe Val Gly Leu Lys Lys Asn Gly Ser
            165                 170                 175 tgc aaa cgc ggt cct cgg act cac tat ggc cag aaa gca atc ttg ttt      576
Cys Lys Arg Gly Pro Arg Thr His Tyr Gly Gln Lys Ala Ile Leu Phe
        180                 185                 190 ctc ccc ctg cca gtc tct tct gat                                      600
Leu Pro Leu Pro Val Ser Ser Asp
        195                 200
```

<210> SEQ ID NO 19
<211> LENGTH: 200
<212> TYPE: PRT
<213> ORGANISM: Artificial Sequence
<220> FEATURE:
<223> OTHER INFORMATION: Description of Artificial Sequence: fusion of
      sequence for a part of human ryudocan mutant and a part of human
      fibroblast growth factor 1

<400> SEQUENCE: 19

```
Met Ala Pro Ala Arg Leu Phe Ala Leu Leu Leu Phe Phe Val Gly Gly
 1               5                  10                  15

Val Ala Glu Ser Ile Arg Glu Thr Glu Val Ile Asp Pro Gln Asp Leu
            20                  25                  30

Leu Glu Gly Arg Tyr Phe Ser Gly Ala Leu Ser Asp Asp Glu Asp Val
        35                  40                  45

Val Gly Pro Gly Gln Glu Ser Asp Asp Phe Glu Leu Ser Gly Ser Gly
    50                  55                  60

Asp Ala Asn Tyr Lys Lys Pro Lys Leu Leu Tyr Cys Ser Asn Gly Gly
65                  70                  75                  80

His Phe Leu Arg Ile Leu Pro Asp Gly Thr Val Asp Gly Thr Arg Asp
                85                  90                  95

Arg Ser Asp Gln His Ile Gln Leu Gln Leu Ser Ala Glu Ser Val Gly
            100                 105                 110

Glu Val Tyr Ile Lys Ser Thr Glu Thr Gly Gln Tyr Leu Ala Met Asp
        115                 120                 125

Thr Asp Gly Leu Leu Tyr Gly Ser Gln Thr Pro Asn Glu Glu Cys Leu
    130                 135                 140

Phe Leu Glu Arg Leu Glu Glu Asn His Tyr Asn Thr Tyr Ile Ser Lys
145                 150                 155                 160

Lys His Ala Glu Lys Asn Trp Phe Val Gly Leu Lys Lys Asn Gly Ser
                165                 170                 175

Cys Lys Arg Gly Pro Arg Thr His Tyr Gly Gln Lys Ala Ile Leu Phe
            180                 185                 190

Leu Pro Leu Pro Val Ser Ser Asp
        195                 200
```

-continued

```
<210> SEQ ID NO 20
<211> LENGTH: 600
<212> TYPE: DNA
<213> ORGANISM: Artificial Sequence
<220> FEATURE:
<223> OTHER INFORMATION: Description of Artificial Sequence: fusion of
      sequence for a part of human ryudocan mutant and a part of human
      fibroblast growth factor 1
<221> NAME/KEY: CDS
<222> LOCATION: (1)..(600)

<400> SEQUENCE: 20 atg gcc ccc gcc cgt ctg ttc gcg ctg ctg ctg ttc ttc gta ggc gga         48
Met Ala Pro Ala Arg Leu Phe Ala Leu Leu Leu Phe Phe Val Gly Gly
  1               5                  10                  15 gtc gcc gag tcg atc cga gag act gag gtc atc gac ccc cag gac ctc         96
Val Ala Glu Ser Ile Arg Glu Thr Glu Val Ile Asp Pro Gln Asp Leu
             20                  25                  30 cta gaa ggc cga tac ttc tcc gga gcc cta tca gac gat gag gat gta        144
Leu Glu Gly Arg Tyr Phe Ser Gly Ala Leu Ser Asp Asp Glu Asp Val
         35                  40                  45 gtg ggg ccc ggg cag gaa tct gat gac ttt gag ctg tct ggc tct gga        192
Val Gly Pro Gly Gln Glu Ser Asp Asp Phe Glu Leu Ser Gly Ser Gly
     50                  55                  60 gat gct aat tac aag aag ccc aaa ctc ctc tac tgt agc aac ggg ggc        240
Asp Ala Asn Tyr Lys Lys Pro Lys Leu Leu Tyr Cys Ser Asn Gly Gly
 65                  70                  75                  80 cac ttc ctg agg atc ctt ccg gat ggc aca gtg gat ggg aca agg gac        288
His Phe Leu Arg Ile Leu Pro Asp Gly Thr Val Asp Gly Thr Arg Asp
                 85                  90                  95 agg agc gac cag cac att cag ctg cag ctc agt gcg gaa agc gtg ggg        336
Arg Ser Asp Gln His Ile Gln Leu Gln Leu Ser Ala Glu Ser Val Gly
            100                 105                 110 gag gtg tat ata aag agt acc gag act ggc cag tac ttg gcc atg gac        384
Glu Val Tyr Ile Lys Ser Thr Glu Thr Gly Gln Tyr Leu Ala Met Asp
        115                 120                 125 acc gac ggg ctt tta tac ggc tca cag aca cca aat gag gaa tgt ttg        432
Thr Asp Gly Leu Leu Tyr Gly Ser Gln Thr Pro Asn Glu Glu Cys Leu
    130                 135                 140 ttc ctg gaa agg ctg gag gag aac cat tac aac acc tat ata tcc aag        480
Phe Leu Glu Arg Leu Glu Glu Asn His Tyr Asn Thr Tyr Ile Ser Lys
145                 150                 155                 160 aag cat gca gag aag aat tgg ttt gtt ggc ctc aag aag aat ggg agc        528
Lys His Ala Glu Lys Asn Trp Phe Val Gly Leu Lys Lys Asn Gly Ser
                165                 170                 175 tgc aaa cgc ggt cct cgg act cac tat ggc cag aaa gca atc ttg ttt        576
Cys Lys Arg Gly Pro Arg Thr His Tyr Gly Gln Lys Ala Ile Leu Phe
            180                 185                 190 ctc ccc ctg cca gtc tct tct gat                                        600
Leu Pro Leu Pro Val Ser Ser Asp
        195                 200

<210> SEQ ID NO 21
<211> LENGTH: 254
<212> TYPE: PRT
<213> ORGANISM: Artificial Sequence
<220> FEATURE:
<223> OTHER INFORMATION: Description of Artificial Sequence: fusion of
      sequence for a part of human ryudocan and a part of human
      fibroblast growth factor 1

<400> SEQUENCE: 21
```

```
Met Ala Pro Ala Arg Leu Phe Ala Leu Leu Leu Phe Phe Val Gly Gly
 1               5                  10                  15

Val Ala Glu Ser Ile Arg Glu Thr Glu Val Ile Asp Pro Gln Asp Leu
             20                  25                  30

Leu Glu Gly Arg Tyr Phe Ser Gly Ala Leu Pro Asp Asp Glu Asp Val
         35                  40                  45

Val Gly Pro Gly Gln Glu Ser Asp Asp Phe Glu Leu Ser Gly Ser Gly
 50                  55                  60

Asp Leu Asp Asp Leu Glu Asp Ser Met Ile Gly Pro Glu Val Val His
 65                  70                  75                  80

Pro Leu Val Pro Leu Asp Asn His Ile Pro Glu Arg Ala Gly Ser Gly
                 85                  90                  95

Ser Gln Val Pro Thr Glu Pro Lys Lys Leu Glu Glu Asn Glu Val Ile
                100                 105                 110

Pro Lys Arg Ile Ser Pro Val Ala Asn Tyr Lys Lys Pro Lys Leu Leu
            115                 120                 125

Tyr Cys Ser Asn Gly Gly His Phe Leu Arg Ile Leu Pro Asp Gly Thr
        130                 135                 140

Val Asp Gly Thr Arg Asp Arg Ser Asp Gln His Ile Gln Leu Gln Leu
145                 150                 155                 160

Ser Ala Glu Ser Val Gly Glu Val Tyr Ile Lys Ser Thr Glu Thr Gly
                165                 170                 175

Gln Tyr Leu Ala Met Asp Thr Asp Gly Leu Leu Tyr Gly Ser Gln Thr
            180                 185                 190

Pro Asn Glu Glu Cys Leu Phe Leu Glu Arg Leu Glu Glu Asn His Tyr
        195                 200                 205

Asn Thr Tyr Ile Ser Lys Lys His Ala Glu Lys Asn Trp Phe Val Gly
210                 215                 220

Leu Lys Lys Asn Gly Ser Cys Lys Arg Gly Pro Arg Thr His Tyr Gly
225                 230                 235                 240

Gln Lys Ala Ile Leu Phe Leu Pro Leu Pro Val Ser Ser Asp
            245                 250

<210> SEQ ID NO 22
<211> LENGTH: 762
<212> TYPE: DNA
<213> ORGANISM: Artificial Sequence
<220> FEATURE:
<223> OTHER INFORMATION: Description of Artificial Sequence: fusion of
      sequence for a part of human ryudocan and a part of human
      fibroblast growth factor 1
<221> NAME/KEY: CDS
<222> LOCATION: (1)..(762)

<400> SEQUENCE: 22 atg gcc ccc gcc cgt ctg ttc gcg ctg ctg ctg ttc ttc gta ggc gga    48
Met Ala Pro Ala Arg Leu Phe Ala Leu Leu Leu Phe Phe Val Gly Gly
 1               5                  10                  15 gtc gcc gag tcg atc cga gag act gag gtc atc gac ccc cag gac ctc    96
Val Ala Glu Ser Ile Arg Glu Thr Glu Val Ile Asp Pro Gln Asp Leu
             20                  25                  30 cta gaa ggc cga tac ttc tcc gga gcc cta cca gac gat gag gat gta   144
Leu Glu Gly Arg Tyr Phe Ser Gly Ala Leu Pro Asp Asp Glu Asp Val
         35                  40                  45 gtg ggg ccc ggg cag gaa tct gat gac ttt gag ctg tct ggc tct gga   192
Val Gly Pro Gly Gln Glu Ser Asp Asp Phe Glu Leu Ser Gly Ser Gly
 50                  55                  60 gat ctg gat gac ttg gaa gac tcc atg atc ggc cct gaa gtt gtc cat   240
Asp Leu Asp Asp Leu Glu Asp Ser Met Ile Gly Pro Glu Val Val His
```

-continued

```
Asp Leu Asp Asp Leu Glu Asp Ser Met Ile Gly Pro Glu Val Val His
 65                  70                  75                  80 ccc ttg gtg cct cta gat aac cat atc cct gag agg gca ggg tct ggg      288
Pro Leu Val Pro Leu Asp Asn His Ile Pro Glu Arg Ala Gly Ser Gly
                 85                  90                  95 agc caa gtc ccc acc gaa ccc aag aaa cta gag gag aat gag gtt atc      336
Ser Gln Val Pro Thr Glu Pro Lys Lys Leu Glu Glu Asn Glu Val Ile
            100                 105                 110 ccc aag aga atc tca ccc gtt gct aat tac aag aag ccc aaa ctc ctc      384
Pro Lys Arg Ile Ser Pro Val Ala Asn Tyr Lys Lys Pro Lys Leu Leu
        115                 120                 125 tac tgt agc aac ggg ggc cac ttc ctg agg atc ctt ccg gat ggc aca      432
Tyr Cys Ser Asn Gly Gly His Phe Leu Arg Ile Leu Pro Asp Gly Thr
    130                 135                 140 gtg gat ggg aca agg gac agg agc gac cag cac att cag ctg cag ctc      480
Val Asp Gly Thr Arg Asp Arg Ser Asp Gln His Ile Gln Leu Gln Leu
145                 150                 155                 160 agt gcg gaa agc gtg ggg gag gtg tat ata aag agt acc gag act ggc      528
Ser Ala Glu Ser Val Gly Glu Val Tyr Ile Lys Ser Thr Glu Thr Gly
                165                 170                 175 cag tac ttg gcc atg gac acc gac ggg ctt tta tac ggc tca cag aca      576
Gln Tyr Leu Ala Met Asp Thr Asp Gly Leu Leu Tyr Gly Ser Gln Thr
            180                 185                 190 cca aat gag gaa tgt ttg ttc ctg gaa agg ctg gag gag aac cat tac      624
Pro Asn Glu Glu Cys Leu Phe Leu Glu Arg Leu Glu Glu Asn His Tyr
        195                 200                 205 aac acc tat ata tcc aag aag cat gca gag aag aat tgg ttt gtt ggc      672
Asn Thr Tyr Ile Ser Lys Lys His Ala Glu Lys Asn Trp Phe Val Gly
    210                 215                 220 ctc aag aag aat ggg agc tgc aaa cgc ggt cct cgg act cac tat ggc      720
Leu Lys Lys Asn Gly Ser Cys Lys Arg Gly Pro Arg Thr His Tyr Gly
225                 230                 235                 240 cag aaa gca atc ttg ttt ctc ccc ctg cca gtc tct tct gat               762
Gln Lys Ala Ile Leu Phe Leu Pro Leu Pro Val Ser Ser Asp
                245                 250
```

<210> SEQ ID NO 23
<211> LENGTH: 281
<212> TYPE: PRT
<213> ORGANISM: Artificial Sequence
<220> FEATURE:
<223> OTHER INFORMATION: Description of Artificial Sequence: fusion of
      sequence for a part of human ryudocan and a part of human
      fibroblast growth factor 1

<400> SEQUENCE: 23

```
Met Ala Pro Ala Arg Leu Phe Ala Leu Leu Phe Phe Val Gly Gly
  1               5                  10                  15

Val Ala Glu Ser Ile Arg Glu Thr Glu Val Ile Asp Pro Gln Asp Leu
                 20                  25                  30

Leu Glu Gly Arg Tyr Phe Ser Gly Ala Leu Pro Asp Asp Glu Asp Val
             35                  40                  45

Val Gly Pro Gly Gln Glu Ser Asp Asp Phe Glu Leu Ser Gly Ser Gly
         50                  55                  60

Asp Leu Asp Asp Leu Glu Asp Ser Met Ile Gly Pro Glu Val Val His
 65                  70                  75                  80

Pro Leu Val Pro Leu Asp Asn His Ile Pro Glu Arg Ala Gly Ser Gly
                 85                  90                  95

Ser Gln Val Pro Thr Glu Pro Lys Lys Leu Glu Glu Asn Glu Val Ile
            100                 105                 110
```

```
Pro Lys Arg Ile Ser Pro Val Glu Glu Ser Glu Asp Val Ser Asn Lys
        115                 120                 125

Val Ser Met Ser Ser Thr Val Gln Gly Ser Asn Ile Phe Glu Arg Thr
    130                 135                 140

Glu Val Ala Asn Tyr Lys Lys Pro Lys Leu Leu Tyr Cys Ser Asn Gly
145                 150                 155                 160

Gly His Phe Leu Arg Ile Leu Pro Asp Gly Thr Val Asp Gly Thr Arg
                165                 170                 175

Asp Arg Ser Asp Gln His Ile Gln Leu Gln Leu Ser Ala Glu Ser Val
            180                 185                 190

Gly Glu Val Tyr Ile Lys Ser Thr Glu Thr Gly Gln Tyr Leu Ala Met
        195                 200                 205

Asp Thr Asp Gly Leu Leu Tyr Gly Ser Gln Thr Pro Asn Glu Glu Cys
    210                 215                 220

Leu Phe Leu Glu Arg Leu Glu Glu Asn His Tyr Asn Thr Tyr Ile Ser
225                 230                 235                 240

Lys Lys His Ala Glu Lys Asn Trp Phe Val Gly Leu Lys Lys Asn Gly
                245                 250                 255

Ser Cys Lys Arg Gly Pro Arg Thr His Tyr Gly Gln Lys Ala Ile Leu
            260                 265                 270

Phe Leu Pro Leu Pro Val Ser Ser Asp
        275                 280

<210> SEQ ID NO 24
<211> LENGTH: 843
<212> TYPE: DNA
<213> ORGANISM: Artificial Sequence
<220> FEATURE:
<223> OTHER INFORMATION: Description of Artificial Sequence: fusion of
      sequence for a part of human ryudocan and a part of human
      fibroblast growth factor 1
<221> NAME/KEY: CDS
<222> LOCATION: (1)..(843)

<400> SEQUENCE: 24 atg gcc ccc gcc cgt ctg ttc gcg ctg ctg ctg ttc ttc gta ggc gga        48
Met Ala Pro Ala Arg Leu Phe Ala Leu Leu Leu Phe Phe Val Gly Gly
1               5                   10                  15 gtc gcc gag tcg atc cga gag act gag gtc atc gac ccc cag gac ctc        96
Val Ala Glu Ser Ile Arg Glu Thr Glu Val Ile Asp Pro Gln Asp Leu
            20                  25                  30 cta gaa ggc cga tac ttc tcc gga gcc cta cca gac gat gag gat gta       144
Leu Glu Gly Arg Tyr Phe Ser Gly Ala Leu Pro Asp Asp Glu Asp Val
        35                  40                  45 gtg ggg ccc ggg cag gaa tct gat gac ttt gag ctg tct ggc tct gga       192
Val Gly Pro Gly Gln Glu Ser Asp Asp Phe Glu Leu Ser Gly Ser Gly
    50                  55                  60 gat ctg gat gac ttg gaa gac tcc atg atc ggc cct gaa gtt gtc cat       240
Asp Leu Asp Asp Leu Glu Asp Ser Met Ile Gly Pro Glu Val Val His
65                  70                  75                  80 ccc ttg gtg cct cta gat aac cat atc cct gag agg gca ggg tct ggg       288
Pro Leu Val Pro Leu Asp Asn His Ile Pro Glu Arg Ala Gly Ser Gly
                85                  90                  95 agc caa gtc ccc acc gaa ccc aag aaa cta gag gag aat gag gtt atc       336
Ser Gln Val Pro Thr Glu Pro Lys Lys Leu Glu Glu Asn Glu Val Ile
            100                 105                 110 ccc aag aga atc tca ccc gtt gaa gag agt gag gat gtg tcc aac aag       384
Pro Lys Arg Ile Ser Pro Val Glu Glu Ser Glu Asp Val Ser Asn Lys
        115                 120                 125
```

```
gtg tca atg tcc agc act gtg cag ggc agc aac atc ttt gag aga acg      432
Val Ser Met Ser Ser Thr Val Gln Gly Ser Asn Ile Phe Glu Arg Thr
    130                 135                 140 gag gtc gct aat tac aag aag ccc aaa ctc ctc tac tgt agc aac ggg      480
Glu Val Ala Asn Tyr Lys Lys Pro Lys Leu Leu Tyr Cys Ser Asn Gly
145                 150                 155                 160 ggc cac ttc ctg agg atc ctt ccg gat ggc aca gtg gat ggg aca agg      528
Gly His Phe Leu Arg Ile Leu Pro Asp Gly Thr Val Asp Gly Thr Arg
                165                 170                 175 gac agg agc gac cag cac att cag ctg cag ctc agt gcg gaa agc gtg      576
Asp Arg Ser Asp Gln His Ile Gln Leu Gln Leu Ser Ala Glu Ser Val
            180                 185                 190 ggg gag gtg tat ata aag agt acc gag act ggc cag tac ttg gcc atg      624
Gly Glu Val Tyr Ile Lys Ser Thr Glu Thr Gly Gln Tyr Leu Ala Met
        195                 200                 205 gac acc gac ggg ctt tta tac ggc tca cag aca cca aat gag gaa tgt      672
Asp Thr Asp Gly Leu Leu Tyr Gly Ser Gln Thr Pro Asn Glu Glu Cys
    210                 215                 220 ttg ttc ctg gaa agg ctg gag gag aac cat tac aac acc tat ata tcc      720
Leu Phe Leu Glu Arg Leu Glu Glu Asn His Tyr Asn Thr Tyr Ile Ser
225                 230                 235                 240 aag aag cat gca gag aag aat tgg ttt gtt ggc ctc aag aag aat ggg      768
Lys Lys His Ala Glu Lys Asn Trp Phe Val Gly Leu Lys Lys Asn Gly
                245                 250                 255 agc tgc aaa cgc ggt cct cgg act cac tat ggc cag aaa gca atc ttg      816
Ser Cys Lys Arg Gly Pro Arg Thr His Tyr Gly Gln Lys Ala Ile Leu
            260                 265                 270 ttt ctc ccc ctg cca gtc tct tct gat                                  843
Phe Leu Pro Leu Pro Val Ser Ser Asp
        275                 280

<210> SEQ ID NO 25
<211> LENGTH: 172
<212> TYPE: PRT
<213> ORGANISM: Artificial Sequence
<220> FEATURE:
<223> OTHER INFORMATION: Description of Artificial Sequence: fusion of
      sequence for a part of mouse fibroblast growth factor 6 and
      a part of human fibroblast growth factor 1

<400> SEQUENCE: 25

Met Ser Arg Gly Ala Gly Arg Val Gln Gly Thr Leu Gln Ala Leu Val
1               5                   10                  15

Phe Leu Gly Val Leu Val Gly Met Val Val Pro Ser Pro Ala Gly Ala
            20                  25                  30

Arg Ala Asn Gly Ser Ala Asn Tyr Lys Lys Pro Lys Leu Leu Tyr Cys
        35                  40                  45

Ser Asn Gly Gly His Phe Leu Arg Ile Leu Pro Asp Gly Thr Val Asp
    50                  55                  60

Gly Thr Arg Asp Arg Ser Asp Gln His Ile Gln Leu Gln Leu Ser Ala
65                  70                  75                  80

Glu Ser Val Gly Glu Val Tyr Ile Lys Ser Thr Glu Thr Gly Gln Tyr
                85                  90                  95

Leu Ala Met Asp Thr Asp Gly Leu Leu Tyr Gly Ser Gln Thr Pro Asn
            100                 105                 110

Glu Glu Cys Leu Phe Leu Glu Arg Leu Glu Glu Asn His Tyr Asn Thr
        115                 120                 125

Tyr Ile Ser Lys Lys His Ala Glu Lys Asn Trp Phe Val Gly Leu Lys
    130                 135                 140
```

```
Lys Asn Gly Ser Cys Lys Arg Gly Pro Arg Thr His Tyr Gly Gln Lys
145                 150                 155                 160

Ala Ile Leu Phe Leu Pro Leu Pro Val Ser Ser Asp
                165                 170
```

<210> SEQ ID NO 26
<211> LENGTH: 516
<212> TYPE: DNA
<213> ORGANISM: Artificial Sequence
<220> FEATURE:
<223> OTHER INFORMATION: Description of Artificial Sequence: fusion of
      sequence for a part of mouse fibroblast growth factor 6 and
      a part of human fibroblast growth factor 1
<221> NAME/KEY: CDS
<222> LOCATION: (1)..(516)

<400> SEQUENCE: 26

```
atg tcc cgg gga gca gga cgt gtt cag ggc acg ctg cag gct ctc gtc        48
Met Ser Arg Gly Ala Gly Arg Val Gln Gly Thr Leu Gln Ala Leu Val
1               5                   10                  15 ttc tta ggc gtc cta gtg ggc atg gtg gtg ccc tca cct gcc ggc gcc        96
Phe Leu Gly Val Leu Val Gly Met Val Val Pro Ser Pro Ala Gly Ala
            20                  25                  30 cgc gcc aac ggc tcg gct aat tac aag aag ccc aaa ctc ctc tac tgt       144
Arg Ala Asn Gly Ser Ala Asn Tyr Lys Lys Pro Lys Leu Leu Tyr Cys
        35                  40                  45 agc aac ggg ggc cac ttc ctg agg atc ctt ccg gat ggc aca gtg gat       192
Ser Asn Gly Gly His Phe Leu Arg Ile Leu Pro Asp Gly Thr Val Asp
    50                  55                  60 ggg aca agg gac agg agc gac cag cac att cag ctg cag ctc agt gcg       240
Gly Thr Arg Asp Arg Ser Asp Gln His Ile Gln Leu Gln Leu Ser Ala
65                  70                  75                  80 gaa agc gtg ggg gag gtg tat ata aag agt acc gag act ggc cag tac       288
Glu Ser Val Gly Glu Val Tyr Ile Lys Ser Thr Glu Thr Gly Gln Tyr
                85                  90                  95 ttg gcc atg gac acc gac ggg ctt tta tac ggc tca cag aca cca aat       336
Leu Ala Met Asp Thr Asp Gly Leu Leu Tyr Gly Ser Gln Thr Pro Asn
            100                 105                 110 gag gaa tgt ttg ttc ctg gaa agg ctg gag gag aac cat tac aac acc       384
Glu Glu Cys Leu Phe Leu Glu Arg Leu Glu Glu Asn His Tyr Asn Thr
        115                 120                 125 tat ata tcc aag aag cat gca gag aag aat tgg ttt gtt ggc ctc aag       432
Tyr Ile Ser Lys Lys His Ala Glu Lys Asn Trp Phe Val Gly Leu Lys
    130                 135                 140 aag aat ggg agc tgc aaa cgc ggt cct cgg act cac tat ggc cag aaa       480
Lys Asn Gly Ser Cys Lys Arg Gly Pro Arg Thr His Tyr Gly Gln Lys
145                 150                 155                 160 gca atc ttg ttt ctc ccc ctg cca gtc tct tct gat                       516
Ala Ile Leu Phe Leu Pro Leu Pro Val Ser Ser Asp
                165                 170
```

<210> SEQ ID NO 27
<211> LENGTH: 210
<212> TYPE: PRT
<213> ORGANISM: Artificial Sequence
<220> FEATURE:
<223> OTHER INFORMATION: Description of Artificial Sequence: fusion of
      sequence for a part of mouse fibroblast growth factor 6 and
      a part of human fibroblast growth 1

<400> SEQUENCE: 27

```
Met Ser Arg Gly Ala Gly Arg Val Gln Gly Thr Leu Gln Ala Leu Val
1               5                   10                  15
```

-continued

```
Phe Leu Gly Val Leu Val Gly Met Val Val Pro Ser Pro Ala Gly Ala
             20                  25                  30

Arg Ala Asn Gly Thr Leu Leu Asp Ser Arg Gly Trp Gly Thr Leu Leu
         35                  40                  45

Ser Arg Ser Arg Ala Gly Leu Ala Gly Glu Ile Ser Gly Val Asn Trp
 50                  55                  60

Glu Ser Gly Tyr Leu Val Gly Ile Lys Arg Gln Ala Asn Tyr Lys Lys
 65                  70                  75                  80

Pro Lys Leu Leu Tyr Cys Ser Asn Gly Gly His Phe Leu Arg Ile Leu
                 85                  90                  95

Pro Asp Gly Thr Val Asp Gly Thr Arg Asp Arg Ser Asp Gln His Ile
            100                 105                 110

Gln Leu Gln Leu Ser Ala Glu Ser Val Gly Glu Val Tyr Ile Lys Ser
        115                 120                 125

Thr Glu Thr Gly Gln Tyr Leu Ala Met Asp Thr Asp Gly Leu Leu Tyr
    130                 135                 140

Gly Ser Gln Thr Pro Asn Glu Glu Cys Leu Phe Leu Glu Arg Leu Glu
145                 150                 155                 160

Glu Asn His Tyr Asn Thr Tyr Ile Ser Lys Lys His Ala Glu Lys Asn
                165                 170                 175

Trp Phe Val Gly Leu Lys Lys Asn Gly Ser Cys Lys Arg Gly Pro Arg
            180                 185                 190

Thr His Tyr Gly Gln Lys Ala Ile Leu Phe Leu Pro Leu Pro Val Ser
        195                 200                 205

Ser Asp
    210

<210> SEQ ID NO 28
<211> LENGTH: 630
<212> TYPE: DNA
<213> ORGANISM: Artificial Sequence
<220> FEATURE:
<223> OTHER INFORMATION: Description of Artificial Sequence: fusion of
      sequence for a part of mouse fibroblast growth factor 6 and
      a part of human fibroblast growth 1
<221> NAME/KEY: CDS
<222> LOCATION: (1)..(630)

<400> SEQUENCE: 28 atg tcc cgg gga gca gga cgt gtt cag ggc acg ctg cag gct ctc gtc      48
Met Ser Arg Gly Ala Gly Arg Val Gln Gly Thr Leu Gln Ala Leu Val
 1               5                  10                  15 ttc tta ggc gtc cta gtg ggc atg gtg gtg ccc tca cct gcc ggc gcc      96
Phe Leu Gly Val Leu Val Gly Met Val Val Pro Ser Pro Ala Gly Ala
             20                  25                  30 cgc gcc aac ggc acg cta ctg gac tcc aga ggc tgg ggc acc ctc ttg     144
Arg Ala Asn Gly Thr Leu Leu Asp Ser Arg Gly Trp Gly Thr Leu Leu
         35                  40                  45 tcc agg tct cga gct ggg cta gct gga gag att tcg ggt gtg aat tgg     192
Ser Arg Ser Arg Ala Gly Leu Ala Gly Glu Ile Ser Gly Val Asn Trp
 50                  55                  60 gaa agc ggc tat ttg gtg ggc att aag cga cag gct aat tac aag aag     240
Glu Ser Gly Tyr Leu Val Gly Ile Lys Arg Gln Ala Asn Tyr Lys Lys
 65                  70                  75                  80 ccc aaa ctc ctc tac tgt agc aac ggg ggc cac ttc ctg agg atc ctt     288
Pro Lys Leu Leu Tyr Cys Ser Asn Gly Gly His Phe Leu Arg Ile Leu
                 85                  90                  95 ccg gat ggc aca gtg gat ggg aca agg gac agg agc gac cag cac att     336
```

```
                Pro Asp Gly Thr Val Asp Gly Thr Arg Asp Arg Ser Asp Gln His Ile
                        100                 105                 110 cag ctg cag ctc agt gcg gaa agc gtg ggg gag gtg tat ata aag agt          384
Gln Leu Gln Leu Ser Ala Glu Ser Val Gly Glu Val Tyr Ile Lys Ser
            115                 120                 125 acc gag act ggc cag tac ttg gcc atg gac acc gac ggg ctt tta tac          432
Thr Glu Thr Gly Gln Tyr Leu Ala Met Asp Thr Asp Gly Leu Leu Tyr
    130                 135                 140 ggc tca cag aca cca aat gag gaa tgt ttg ttc ctg gaa agg ctg gag          480
Gly Ser Gln Thr Pro Asn Glu Glu Cys Leu Phe Leu Glu Arg Leu Glu
145                 150                 155                 160 gag aac cat tac aac acc tat ata tcc aag aag cat gca gag aag aat          528
Glu Asn His Tyr Asn Thr Tyr Ile Ser Lys Lys His Ala Glu Lys Asn
                165                 170                 175 tgg ttt gtt ggc ctc aag aag aat ggg agc tgc aaa cgc ggt cct cgg          576
Trp Phe Val Gly Leu Lys Lys Asn Gly Ser Cys Lys Arg Gly Pro Arg
            180                 185                 190 act cac tat ggc cag aaa gca atc ttg ttt ctc ccc ctg cca gtc tct          624
Thr His Tyr Gly Gln Lys Ala Ile Leu Phe Leu Pro Leu Pro Val Ser
    195                 200                 205 tct gat                                                                   630
Ser Asp
    210
```

<210> SEQ ID NO 29
<211> LENGTH: 180
<212> TYPE: PRT
<213> ORGANISM: Artificial Sequence
<220> FEATURE:
<223> OTHER INFORMATION: Description of Artificial Sequence: fusion of
      sequence for a part of mouse fibroblast growth factor 6,
      a part of human fibroblast growth factor 1 and an artificial
      sequence

<400> SEQUENCE: 29

```
Met Ser Arg Gly Ala Gly Arg Val Gln Gly Thr Leu Gln Ala Leu Val
1               5                   10                  15

Phe Leu Gly Val Leu Val Gly Met Val Val Pro Ser Pro Ala Gly Ala
            20                  25                  30

Arg Ala Asn Gly Thr Leu Leu Asp Ala Asn Tyr Lys Lys Pro Lys Leu
        35                  40                  45

Leu Tyr Cys Ser Asn Gly Gly His Phe Leu Arg Ile Leu Pro Asp Gly
    50                  55                  60

Thr Val Asp Gly Thr Arg Asp Arg Ser Asp Gln His Ile Gln Leu Gln
65                  70                  75                  80

Leu Ser Ala Glu Ser Val Gly Glu Val Tyr Ile Lys Ser Thr Glu Thr
                85                  90                  95

Gly Gln Tyr Leu Ala Met Asp Thr Asp Gly Leu Leu Tyr Gly Ser Gln
            100                 105                 110

Thr Pro Asn Glu Glu Cys Leu Phe Leu Glu Arg Leu Glu Glu Asn Ala
        115                 120                 125

Thr Pro Ala Pro His Tyr Asn Thr Tyr Ile Ser Lys Lys His Ala Glu
    130                 135                 140

Lys Asn Trp Phe Val Gly Leu Lys Lys Asn Gly Ser Cys Lys Arg Gly
145                 150                 155                 160

Pro Arg Thr His Tyr Gly Gln Lys Ala Ile Leu Phe Leu Pro Leu Pro
                165                 170                 175

Val Ser Ser Asp
            180
```

<210> SEQ ID NO 30
<211> LENGTH: 540
<212> TYPE: DNA
<213> ORGANISM: Artificial Sequence
<220> FEATURE:
<223> OTHER INFORMATION: Description of Artificial Sequence: fusion of
    sequence for a part of mouse fibroblast growth factor 6,
    a part of human fibroblast growth factor 1 and an artificial
    sequence
<221> NAME/KEY: CDS
<222> LOCATION: (1)..(540)

<400> SEQUENCE: 30

```
atg tcc cgg gga gca gga cgt gtt cag ggc acg ctg cag gct ctc gtc      48
Met Ser Arg Gly Ala Gly Arg Val Gln Gly Thr Leu Gln Ala Leu Val
 1               5                  10                  15 ttc tta ggc gtc cta gtg ggc atg gtg gtg ccc tca cct gcc ggc gcc      96
Phe Leu Gly Val Leu Val Gly Met Val Val Pro Ser Pro Ala Gly Ala
             20                  25                  30 cgc gcc aac ggc acg cta ctg gac gct aat tac aag aag ccc aaa ctc     144
Arg Ala Asn Gly Thr Leu Leu Asp Ala Asn Tyr Lys Lys Pro Lys Leu
         35                  40                  45 ctc tac tgt agc aac ggg ggc cac ttc ctg agg atc ctt ccg gat ggc     192
Leu Tyr Cys Ser Asn Gly Gly His Phe Leu Arg Ile Leu Pro Asp Gly
     50                  55                  60 aca gtg gat ggg aca agg gac agg agc gac cag cac att cag ctg cag     240
Thr Val Asp Gly Thr Arg Asp Arg Ser Asp Gln His Ile Gln Leu Gln
 65                  70                  75                  80 ctc agt gcg gaa agc gtg ggg gag gtg tat ata aag agt acc gag act     288
Leu Ser Ala Glu Ser Val Gly Glu Val Tyr Ile Lys Ser Thr Glu Thr
                 85                  90                  95 ggc cag tac ttg gcc atg gac acc gac ggg ctt tta tac ggc tca cag     336
Gly Gln Tyr Leu Ala Met Asp Thr Asp Gly Leu Leu Tyr Gly Ser Gln
            100                 105                 110 aca cca aat gag gaa tgt ttg ttc ctg gaa agg ctg gag gag aac gct     384
Thr Pro Asn Glu Glu Cys Leu Phe Leu Glu Arg Leu Glu Glu Asn Ala
        115                 120                 125 act cca gct cca cat tac aac acc tat ata tcc aag aag cat gca gag     432
Thr Pro Ala Pro His Tyr Asn Thr Tyr Ile Ser Lys Lys His Ala Glu
    130                 135                 140 aag aat tgg ttt gtt ggc ctc aag aag aat ggg agc tgc aaa cgc ggt     480
Lys Asn Trp Phe Val Gly Leu Lys Lys Asn Gly Ser Cys Lys Arg Gly
145                 150                 155                 160 cct cgg act cac tat ggc cag aaa gca atc ttg ttt ctc ccc ctg cca     528
Pro Arg Thr His Tyr Gly Gln Lys Ala Ile Leu Phe Leu Pro Leu Pro
                165                 170                 175 gtc tct tct gat                                                     540
Val Ser Ser Asp
            180
```

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:primer for
    PCR

<400> SEQUENCE: 31
aacaaaagct gggtaccggg                                                20